US008206904B2

(12) United States Patent
Allawi et al.

(10) Patent No.: US 8,206,904 B2
(45) Date of Patent: Jun. 26, 2012

(54) DETECTION OF NUCLEIC ACIDS

(75) Inventors: Hatim T. Allawi, Madison, WI (US); Victor Lyamichev, Madison, WI (US)

(73) Assignee: Third Wave Technologies, Inc., Madison, WI (US)

(*) Notice: Subject to any disclaimer, the term of this patent is extended or adjusted under 35 U.S.C. 154(b) by 0 days.

(21) Appl. No.: 11/809,567

(22) Filed: Jun. 1, 2007

(65) Prior Publication Data
US 2008/0131890 A1 Jun. 5, 2008

Related U.S. Application Data

(63) Continuation-in-part of application No. 10/740,256, filed on Dec. 18, 2003, now Pat. No. 7,851,150, and a continuation-in-part of application No. 11/266,723, filed on Nov. 3, 2005, now abandoned.

(60) Provisional application No. 60/434,518, filed on Dec. 18, 2002, provisional application No. 60/443,814, filed on Jan. 30, 2003, provisional application No. 60/624,626, filed on Nov. 3, 2004, provisional application No. 60/810,078, filed on Jun. 1, 2006.

(51) Int. Cl.
*C12Q 1/68* (2006.01)

(52) U.S. Cl. ........................................... 435/6.1

(58) Field of Classification Search .................. None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,011,769 A | 4/1991 | Duck | |
| 5,118,801 A | 6/1992 | Lizardi et al. | |
| 5,124,246 A | 6/1992 | Urdea | |
| 5,210,015 A | 5/1993 | Gelfand et al. | |
| 5,215,899 A | 6/1993 | Dattagupta | |
| 5,270,163 A | 12/1993 | Gold et al. | |
| 5,288,609 A | 2/1994 | Engelhardt | |
| 5,403,711 A | 4/1995 | Walder | |
| 5,474,796 A | 12/1995 | Brennan | |
| 5,494,810 A | 2/1996 | Barany et al. | |
| 5,538,848 A | 7/1996 | Livak | |
| 5,607,834 A | 3/1997 | Bagwell | |
| 5,614,402 A | 3/1997 | Dahlberg | |
| 5,624,802 A | 4/1997 | Urdea | |
| 5,660,988 A | 8/1997 | Duck | |
| 5,710,264 A | 1/1998 | Urdea | |
| 5,770,365 A | 6/1998 | Lane et al. | |
| 5,792,614 A | 8/1998 | Western et al. | |
| 5,795,763 A | 8/1998 | Dahlberg | |
| 5,843,669 A | 12/1998 | Kaiser | |
| 5,846,717 A | 12/1998 | Brow | |
| 5,849,481 A | 12/1998 | Urdea | |
| 5,851,770 A | 12/1998 | Babon et al. | |
| 5,858,659 A | 1/1999 | Sapolsky | |
| 5,866,336 A | 2/1999 | Nazarenko et al. | |
| 5,882,867 A | 3/1999 | Ullman et al. | |
| 5,914,230 A | 6/1999 | Liu et al. | |
| 5,919,626 A | 7/1999 | Shi | |
| 5,925,525 A | 7/1999 | Fodor | |
| 5,952,174 A | 9/1999 | Nikiforov | |
| 5,958,692 A | 9/1999 | Cotton | |
| 5,968,740 A | 10/1999 | Fodor et al. | |
| 5,985,551 A | 11/1999 | Brennan | |
| 5,985,557 A | 11/1999 | Prudent | |
| 5,985,563 A | 11/1999 | Hyldig-Nielsen et al. | |
| 5,994,069 A * | 11/1999 | Hall et al. ................... 435/6.18 |
| 6,001,311 A | 12/1999 | Brennan | |
| 6,001,567 A | 12/1999 | Brow | |
| 6,001,983 A | 12/1999 | Benner | |
| 6,013,170 A | 1/2000 | Meade | |
| 6,017,696 A | 1/2000 | Heller | |
| 6,025,133 A | 2/2000 | Stull et al. | |
| 6,027,889 A | 2/2000 | Barany et al. | |
| 6,045,996 A | 4/2000 | Cronin | |
| 6,051,380 A | 4/2000 | Sosnowski | |
| 6,063,573 A | 5/2000 | Kayyem | |
| 6,068,818 A | 5/2000 | Ackley | |
| 6,090,543 A | 7/2000 | Prudent et al. | |
| 6,110,677 A | 8/2000 | Western | |
| 6,110,684 A | 8/2000 | Kemper | |
| 6,121,001 A | 9/2000 | Western | |
| 6,143,495 A | 11/2000 | Lizardi | |
| 6,150,097 A | 11/2000 | Tyagi | |
| 6,183,960 B1 | 2/2001 | Lizardi | |
| 6,194,149 B1 | 2/2001 | Neri | |
| 6,210,884 B1 | 4/2001 | Lizardi | |

(Continued)

FOREIGN PATENT DOCUMENTS

EP 427073 5/1999

(Continued)

OTHER PUBLICATIONS

Chen et al (Nucl. Acids Res. 33(20): e179, Nov. 27, 2005).* pp. 1-4 of Supplementary Data for Chen et al (Nucl. Acids Res. 33(20): e179, Nov. 27, 2005).*
Drosten et al. (J Clin Microbiol. Jul. 2002;40(7):2323-30).*
Allawi, et al. "Thermodynamics and NMR of internal G.T mismatches in DNA" Biochemistry 36: 10581-94 (1997).
Ambros, et al. "microRNAs: Tiny Regulators with Great Potential" Cell, 2001, pp. 823-826, vol. 107.
Anderson, et al. Quantitative Filter Hybridization, in Nucleic Acid Hybridization (1985).
Azhayeva, et al. "Looped oligonucleotides form stable hybrid complexes with a single-strained DNA," NAR 23: 1170-1176 (1995).
Barany "Genetic disease detection and DNA amplification using cloned thermostable ligase" Proc Natl Acad Sci U S A. Jan. 1, 1991 vol. 88(1) pp. 189-193.
Calin, et al. "Frequent deletions and down-regulation of micro- RNA genes miR15 and miR16 at 13q14 in chronic lymphocytic leukemia" Proc Natl Acad Sci USA, 99, 15524-15529 (2002).
Chen, et al. "Real-time quantification of microRNAs by stem-loop RT-PCR" Nucl. Acids Res. 33(20): e179, Nov. 27, 2005, pp. 1-9.
Chomczynski, et al. "Single-step method of RNA isolation by acid guanidinium thiocyanate-phenol-chloroform extraction" Anal. Biochem. 162: 156-156 (1987).
Cullen, et al. "RNA interference: antiviral defense and genetic tool" Nature Immunology, 3: 597-599 (2002).
Dearruda, et al. "Invader technology for DNA and RNA analysis: principles and applications" Expert Review of Molecular Diagnostics, Sep. 2002, pp. 487-496, vol. 2(5).

(Continued)

Primary Examiner — Christopher M. Babic
(74) Attorney, Agent, or Firm — Casimir Jones, S.C.

(57) ABSTRACT

The present invention relates to compositions and methods for the detection and characterization of small nucleic acid molecules (e.g., RNA (e.g., small RNAs such as micro RNAs (miRNAs) and small interfering RNAs (siRNAs)) and other short nucleic acid molecules). More particularly, the present invention relates to methods for the detection and quantification of RNA expression. The present invention further provides for the detection of miRNA and siRNA variants.

20 Claims, 56 Drawing Sheets

U.S. PATENT DOCUMENTS

| | | | |
|---|---|---|---|
| 6,221,583 B1 | 4/2001 | Kayyem | |
| 6,235,502 B1 | 5/2001 | Weissman et al. | |
| 6,248,229 B1 | 6/2001 | Meade | |
| 6,291,187 B1 | 9/2001 | Kingsmore et al. | |
| 6,316,229 B1 | 11/2001 | Lizardi | |
| 6,344,329 B1 | 2/2002 | Lizardi | |
| 6,348,314 B1 | 2/2002 | Prudent | |
| 6,355,437 B1 | 3/2002 | Neri | |
| 6,358,691 B1 | 3/2002 | Neri | |
| 6,410,278 B1 | 6/2002 | Notomi et al. | |
| 6,458,535 B1 | 10/2002 | Hall | |
| 6,709,815 B1 | 3/2004 | Dong et al. | |
| 6,872,816 B1 | 3/2005 | Hall | |
| 6,875,572 B2 | 4/2005 | Prudent | |
| 6,913,881 B1 | 7/2005 | Aizenstein | |
| 7,011,944 B2 | 3/2006 | Prudent | |
| 7,045,289 B2 | 5/2006 | Allawi | |
| 7,060,436 B2 | 6/2006 | Lyamichev | |
| 7,150,982 B2 | 12/2006 | Allawi | |
| 2003/0104378 A1* | 6/2003 | Allawi et al. | 435/6 |
| 2003/0148519 A1 | 8/2003 | Engelke | |
| 2003/0219784 A1* | 11/2003 | Ip et al. | 435/6 |
| 2005/0074788 A1 | 4/2005 | Dahlberg et al. | |
| 2005/0266418 A1* | 12/2005 | Chen et al. | 435/6 |
| 2005/0272075 A1 | 12/2005 | Jacobsen et al. | |
| 2006/0019258 A1 | 1/2006 | Yeakley et al. | |
| 2006/0147955 A1* | 7/2006 | Allawi et al. | 435/6 |

FOREIGN PATENT DOCUMENTS

| | | |
|---|---|---|
| WO | WO97/27214 | 7/1997 |
| WO | WO98/23774 | 6/1998 |
| WO | WO98/42873 | 10/1998 |
| WO | WO98/50403 | 11/1998 |
| WO | WO99/67641 | 12/1999 |
| WO | WO00/39587 | 7/2000 |
| WO | WO01/57256 | 8/2001 |
| WO | WO01/90337 | 11/2001 |
| WO | WO01/98537 | 12/2001 |
| WO | WO02/070755 | 9/2002 |
| WO | WO2004/057017 | 7/2004 |
| WO | WO2006/050499 | 5/2006 |

OTHER PUBLICATIONS

Doty, et al. "Strand Separation and Specific Recombination in Deoxyribonucleic Acids: Physical Chemical Studies" Proc. Natl. Acad. Sci. USA 46:461 (1960).

Eis, et al. "An Invasive Cleavage Assay for Direct Quantitation of Specific RNAs" Nature Biotechnology, 2001, pp. 673-676, vol. 19.

Elbashir, et al. "Functional anatomy of siRNAs for mediating efficient RNAi in *Drosophila melanogaster* embryo lysate" EMBO J. 20: 6877-6888 (2001).

Francois, et al. "Recognition and cleavage of hairpin structures in nucleic acids by oligodeoxynucleotides," Nucl Acids Res. vol. 22, pp. 3943-3950 (1994).

Grishok, et al. "Genes and mechanisms related to RNA interference regulate expression of the small temporal RNAs that control *C. elegans* developmental timing" (2001) Cell 106, 23-34.

Hall, et al. "Sensitive detection of DNA polymorphisms by the serial invasive signal amplification reaction" Proc Natl Acad Sci U S A. Jul. 18, 2000;97(15):8272-7.

Harborth, et al., "Identification of essential genes in cultured mammalian cells using small interfering RNAs" Journal of Cell Science, 114: 4557-4565 (2001).

Hardenbol, et al. "Multiplexed genotyping with sequence-tagged molecular inversion probes" Nat Biotechnol. Jun. 2003;21(6):673-8.

Humphreys, et al. "MicroRNAs control translation initiation by inhibiting eukaryotic initiation factor 4E/cap and poly (A) tail function" Proc Natl Acad Sci USA 102, 16961-16966 (2005).

Hutvagner, et al. "A cellular function for the RNA-interference enzyme Dicer in the maturation of the let-7 small temporal RNA" (2001) Science 293, 834-838.

Kaiser, et al. "A comparison of eubacterial and archaeal structure-specific 5'-exonuclease" J. Biol. Chem. vol. 274, pp. 21387-21394 (1999).

Ketting, et al. "Dicer functions in RNA interference and in synthesis of small RNA involved in developmental timing in *C. elegans*" (2001) Genes Dev. 15, 2654-2659.

Khvorova, et al. "Functional siRNAs and miRNAs exhibit strand bias" Cell 115: 209-216 (2003).

Kong, et al. "Synthesis and duplex stability of oligonucleotides containing cytosine-thymine analogues" Nucleic Acids Res. 1989, 17, 10373-10383.

Kong, et al. "Synthesis of oligodeoxyribonucleotides containing degenerate bases and their use as primers in the polymerase chain reaction" Nucleic Acids Res., 1992, 20, 5149-5152.

Krichevsky, et al. "A microRNA array reveals extensive regulation of microRNAs during brain development" RNA, vol. 9, pp. 1274-1281 (2003).

Lagos-Quintana, et al. "Identification of novel genes coding for small expressed RNAs" (2001) Science 294, 853-858.

Lau, et al. An Abundant Class of Tiny RNAs with Probable Regulatory Roles in *Caenorhabditis elegans*. Science. Oct. 26, 2001. vol. 294: pp. 858-862.

Ledford, et al. "A multi-site study for detection of the factor V (Leiden) mutation from genomic DNA using a homogeneous invader microtiter plate fluorescence resonance energy transfer(FRET) assay" J Mol Diagn. May 2, 2000 (2):97-104.

Lee, et al. "An extensive class of small RNAs in *Caenorhabditis elegans*" (2001)Science 294,862-864.

Lyamichev, et al. "Polymorphism identification and quantitative detection of genomic DNA by invasive cleavage of oligonucleotide probes" Nat Biotechnol. Mar. 1999, vol. 17(3) p. 292-6.

Lyamichev, et al. "Structure-specific endonucleolytic cleavage of nucleic acids by eubacterial DNA polymerases" Science May 7, 1993, vol. 260 (5109, pp. 778-783.

Marmur, et al. "Strand Separation and Specific Recombination in Deoxyribonucleic Acids: Biological Studies" Proc. Natl. Acad. Sci. USA 46:453 (1960).

Marras, et al. "Multiplex detection of single-nucleotide variations using molecular beacons" Genet Anal. Feb. 1999;14 (5-6):151-6).

Morris, et al. Rapid reverse transcription-PCR detection of hepatitis C virus RNA in serum by using the TaqMan fluorogenic detection system J Clin Microbiol. Dec. 1996; 34(12):2933-6.

Moss "RNA interference: It's a small RNA world" Current Biology, 2001, pp. R772-R775, vol. 11.

Moss "MicroRNAs: hidden in the genome" (2002) Curr. Biol. vol. 12, pp. R138-R140.

Pasquinelli, et al. "Conservation of the sequence and temporal expression of let-7 heterochronic regulatory RNA" (2000) Nature 408:86-9.

Patel, et al. "Formation of chimeric DNA primer extension products by template switching onto an annealed downstream oligonucleotide" Proc Natl Acad Sci U S A. Apr. 2, 1996;93(7):2969-74.

Paul, et al. "Effective expression of small interfering RNA in human cells" Nature Biotechnology 20: 505-508 (2002).

Pillai, et al. "Inhibition of translational initiation by Let-7 MicroRNA in human cells" Science 309, 1573-1576 (2005).

Reynaldo, et al. "The kinetics of oligonucleotide replacements" J. Mol. Biol. 97: 511-520 (2000).

Santalucia "A unified view of polymer, dumbbell, and oligonucleotide DNA nearest-neighbor thermodynamics" Proc Natl Acad Sci U S A. Feb. 17, 1998;95(4):1460-5.

Schweitzer, et al. "Aromatic Nonpolar Nucleosides as Hydroophobic Isosteres of Pyrimidine and Purine Nucleosides" J. Org. Chem., 1994, 59, 7238-7242.

Schweitzer, et al. "Hydrophobic, Non-Hydrogen-Bonding Bases and Base Pairs in DNA" J. Am. Chem. Soc., 1995, 117, 1863-1872.

Thomas, et al. "Amplification of padlock probes for DNA diagnostics by cascade rolling circle amplification or the polymerase chain reaction" Arch Pathol Lab Med. Dec. 1999;123(12):1170-6.

Wu, et al. "The ligation amplification reaction (LAR)—amplification of specific DNA sequences using sequential rounds of template-dependent ligation" Genomics. May 1989;4(4):560-9.

Allawi, et al. "Quantitation of microRNAs using a modified Invader assay" RNA, Cold Spring Harbor Laboratory Prss, Woodbury, NY, vol. 10, 2004, pp. 1153-1161.

* cited by examiner

Figure 4

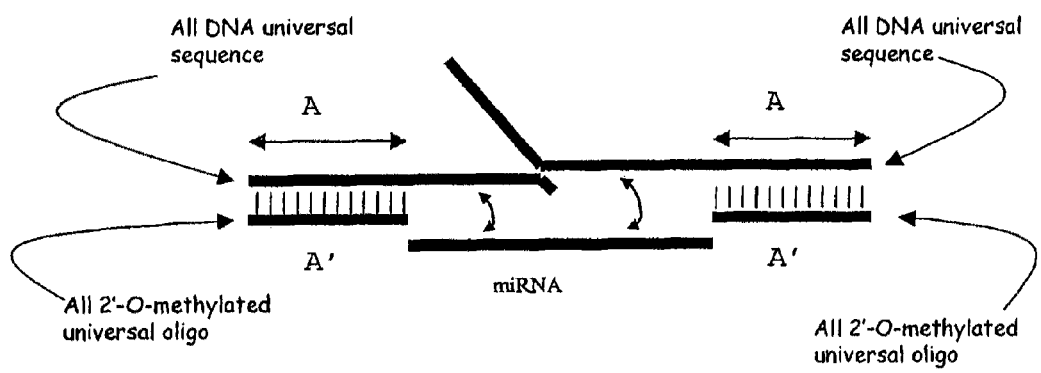

A = Universal sequence that is added to the 3' and 5' of probes and INVADER oligonucleotides, respectively.
From 5' to 3', the probe is composed of the 5'-flap, the miRNA complementary region, and the DNA universal sequence "A".
The INVADER oligonucleotide from 5' to 3', is composed of the DNA universal sequence "A" and an miRNA complementary region.

A' = 2'-O-methyl universal oligonucleotide that compliments the sequence "A" and is added to kits as a standard oligonucleotide.

FIG. 5

| SEQ ID NO | Target | Oligo type | Sequence (5'-3') |
| --- | --- | --- | --- |
| SEQ ID NO:1 | human let-7 miRNA | Invader oligo | ggcacuuuugccAACTATACAACCG |
| SEQ ID NO:2 | human let-7 miRNA | probe oligo | CCGTCGCTGCGTTACTACCTCAcgacguuuucgucg |
| SEQ ID NO:3 | human let-7 miRNA | arrestor oligo | cgacgaaacgucgugaggguaguaacgcag |
| SEQ ID NO:4 | human let-7 miRNA | miRNA | ugaggguaguaagguuguauaguu |
| SEQ ID NO:5 | human let-7 miRNA | Invader oligo | ggcacuuuugccAACTATACAACT |
| SEQ ID NO:6 | human let-7 miRNA | probe oligo | CCGTCGCTGCGTCTACTACCTCAcgacguuuucgucg |
| SEQ ID NO:7 | human let-7 miRNA | arrestor oligo | cgacgaaacgucgugagguaguagacgcag |
| SEQ ID NO:8 | human let-7 miRNA | Invader oligo | ggcacuuuugccAACTATACAAT |
| SEQ ID NO:9 | human let-7 miRNA | probe oligo | AACGAGGCGCACCCTACTACCTCAcgacguuuucgucg |
| SEQ ID NO:10 | human let-7 miRNA | arrestor oligo | cgacgaaacgucgugaggguagugggcucg |
| SEQ ID NO:11 | human miR-1 | Invader oligo | ggcagcuuuugcugccCTCCATACTTCTC |
| SEQ ID NO:12 | human miR-1 | probe oligo | AACGAGGCGCACTTACATTCCAcgagccuuuuggcucg |
| SEQ ID NO:13 | human miR-1 | arrestor oligo | cgagcaaaggcucgugaauguaaacgcg |
| SEQ ID NO:14 | human miR-1 | miRNA | uggaauguaaagaaguauguu |
| SEQ ID NO:15 | human miR-1 | Invader oligo | ggcagcuuuugcugccCTCCATACTTCC |
| SEQ ID NO:16 | human miR-1 | probe oligo | AACGAGGCGCACTTTACATTCCAcgagccuuuuggcucg |
| SEQ ID NO:17 | human miR-1 | arrestor oligo | cgagccaaaggcucgugaauguaaagucg |
| SEQ ID NO:18 | human miR-1 | Invader oligo | ggcagcuuuugcugccCTCCATACTTT |
| SEQ ID NO:19 | human miR-1 | probe oligo | AACGAGGCGCACCTTTACATTCCAcgagccuuuuggcucg |
| SEQ ID NO:20 | human miR-1 | arrestor oligo | cgagccaaaggcucgugaauguaaaggucgc |
| SEQ ID NO:21 | FAM FRET | FRET probe | Yca-cXt-gct-tcg-tgg |
| SEQ ID NO:22 | SRT | Secondary Reaction template | CCA GGA AGC AGC AAG TGA CGC AGC GAC ggu |
| SEQ ID NO:23 | human let-7 miRNA | Invader oligo | ggcacuuuugcugccaacTATACAAT |
| SEQ ID NO:24 | human let-7c miRNA | miRNA | uuggauguucgauauggagu |
| SEQ ID NO:25 | human let-7e miRNA | miRNA | ugguacuuugaugauauggagu |
| SEQ ID NO:26 | human let-7f miRNA | miRNA | uuguauaguuagauugauggagu |
| SEQ ID NO:27 | human miR-135 | Invader oligo | ccgagcgaaagcucggTTCACATAGGAATC |
| SEQ ID NO:28 | human miR-135 | probe oligo | AACGAGGCGCACAAAAGCCATAcgagccgaaaggcucg |
| SEQ ID NO:29 | human miR-135 | arrestor oligo | cgagccuuucgccuauggcuuuuugugcgc |
| SEQ ID NO:30 | human miR-135 | Invader oligo | ccgagcgaaagcucggTTCACATAGGAAC |
| SEQ ID NO:31 | human miR-135 | probe oligo | AACGAGGCGCACTAAAAGCCATAcgagccgaaaggcucg |
| SEQ ID NO:32 | human miR-135 | arrestor oligo | cgagcgaaagcucggTTCACATAGGAC |
| SEQ ID NO:33 | human miR-135 | Invader oligo | cgagcgaaagcucggTTCACATAGGAC |
| SEQ ID NO:34 | human miR-135 | probe oligo | AACGAGGCGCACATAAAAGCCATAAAAAGCCGAAAGGCUCG |
| SEQ ID NO:35 | human miR-135 | arrestor oligo | cgagccuuucgccuuugguuuuugauugcgc |
| SEQ ID NO:36 | human miR-135 | Invader oligo | ccgagcgaaagcucggTTCACATAGGC |
| SEQ ID NO:37 | human miR-135 | probe oligo | AACGAGGCGCACAATAAAAGCCATAcgagccgaaaggcucg |
| SEQ ID NO:38 | human miR-135 | arrestor oligo | cgagccuuucggcuuugguuauggcuuuauaugugcg |

Design Optimization 1496-87-01R

Design Optimization 1496-78-01 R

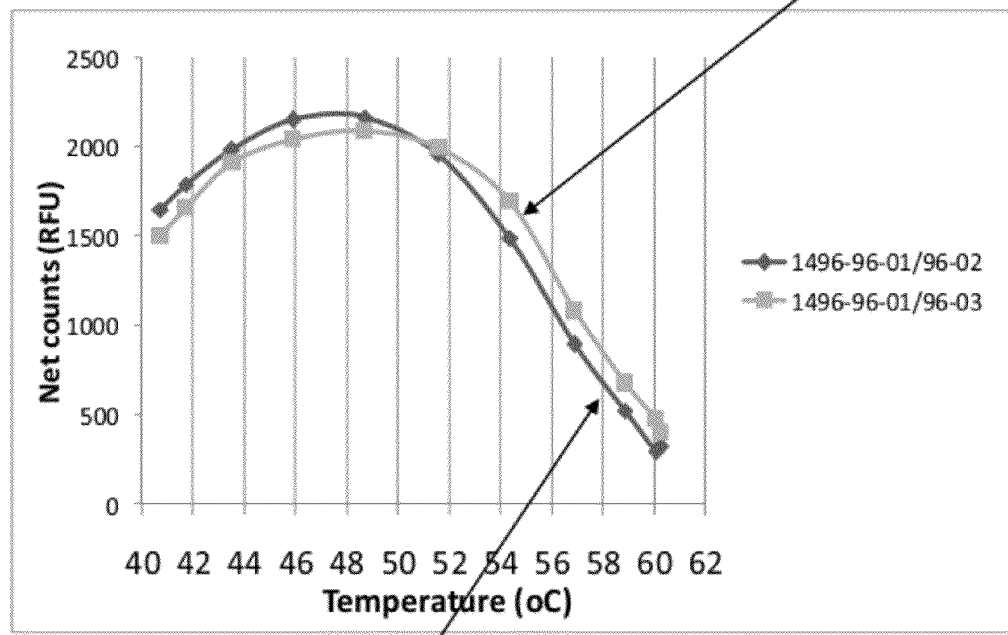
FIGURE 6C Design Optimization
2'-O-methyl only at stacking region of invader
1496-96-01 R
2'-O-methylation of invader extends into the miRNA base pairing region Design Optimization FIGURE 8
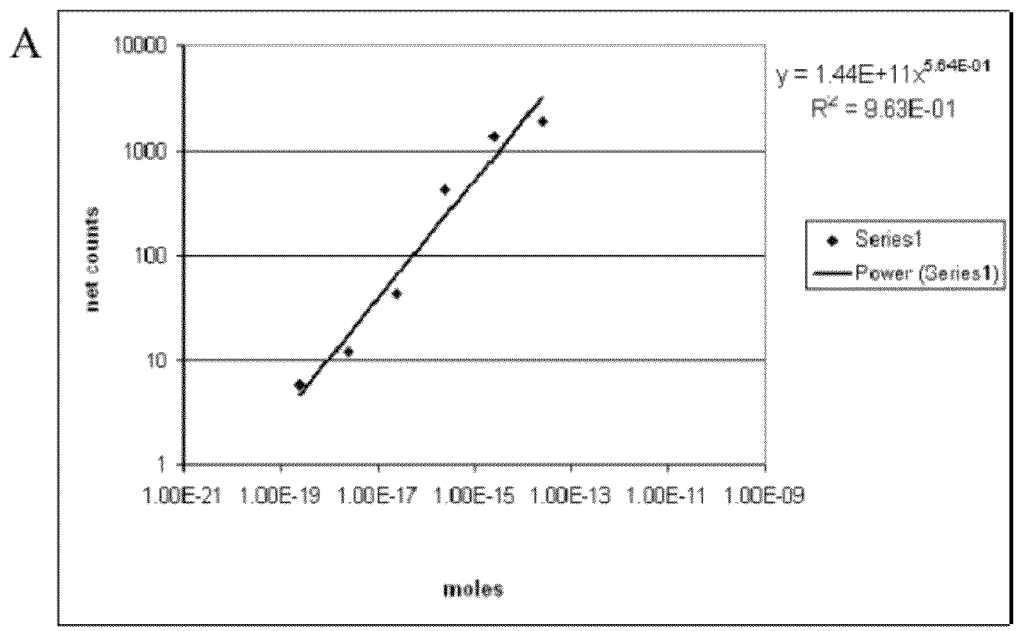
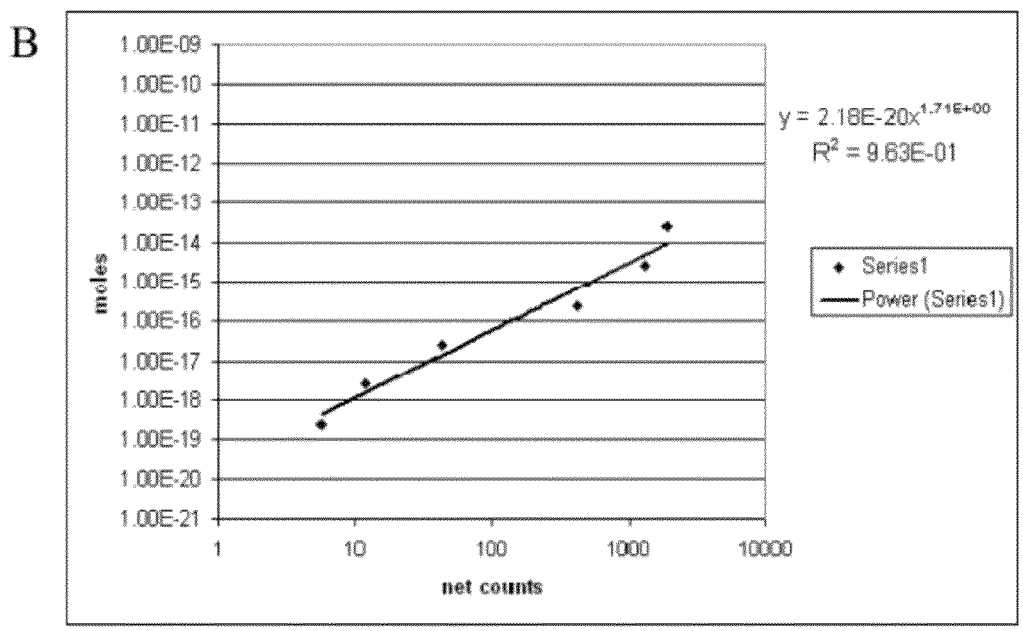

FIGURE 9
CROSS CREATIVITY LET-7
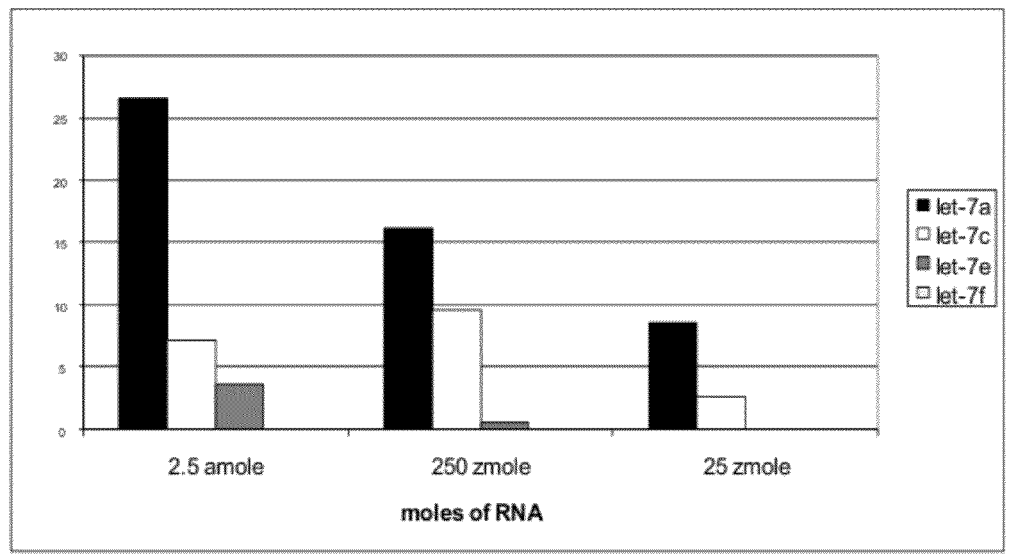
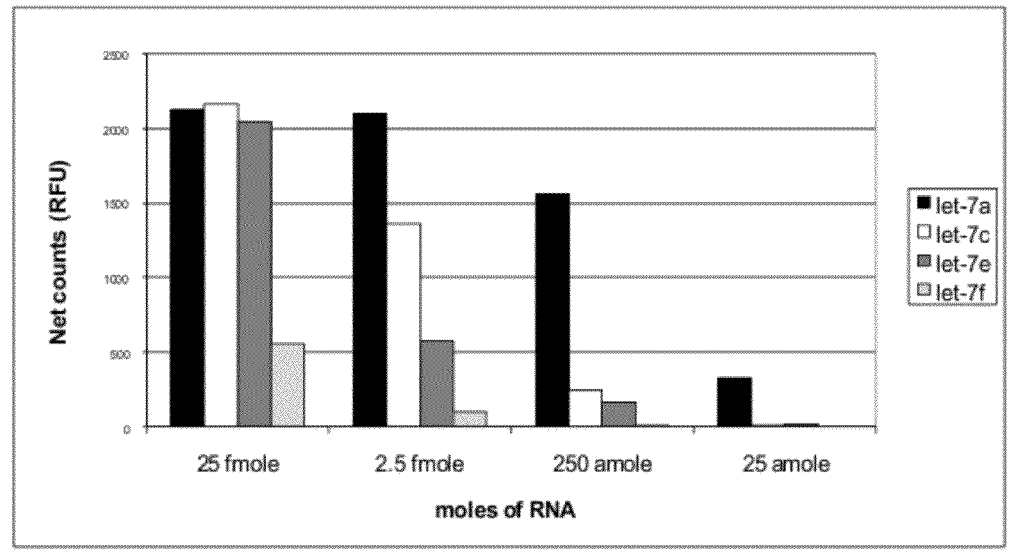

Figure 11
LOD let-7 (1496-78-01R) using Cleavase 12
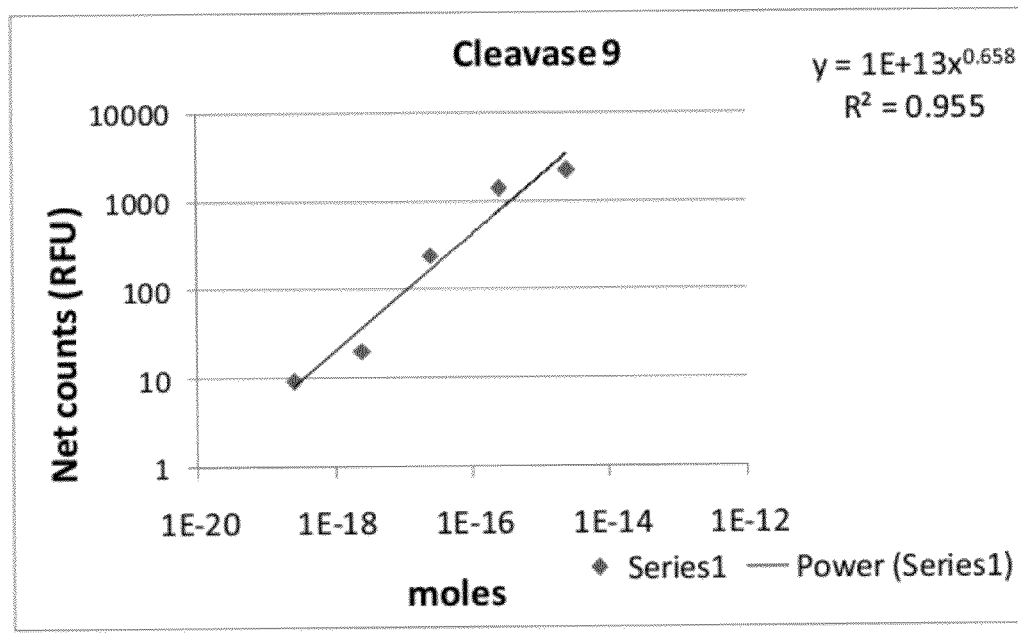
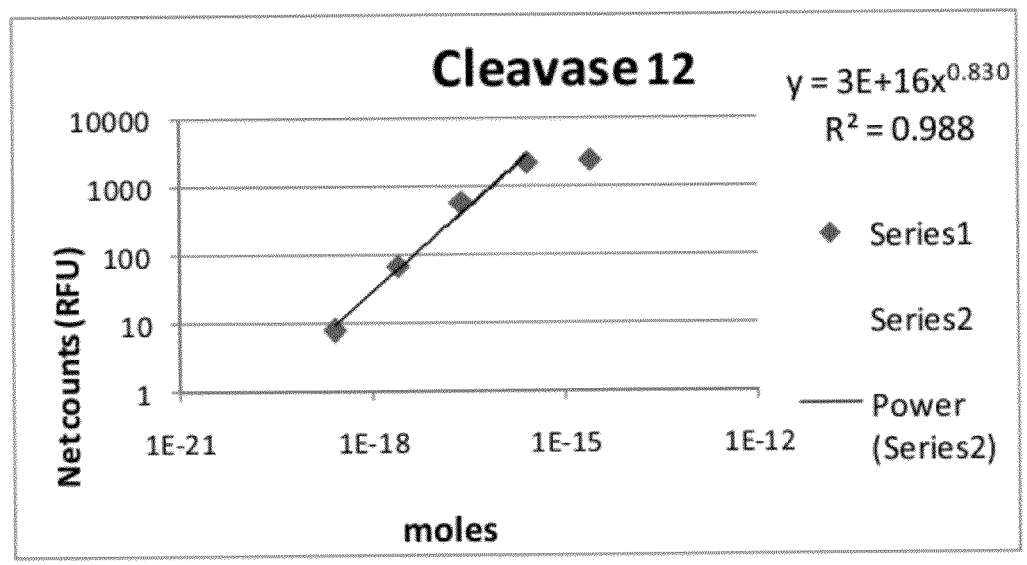

FIGURE 12

FIGURE 18
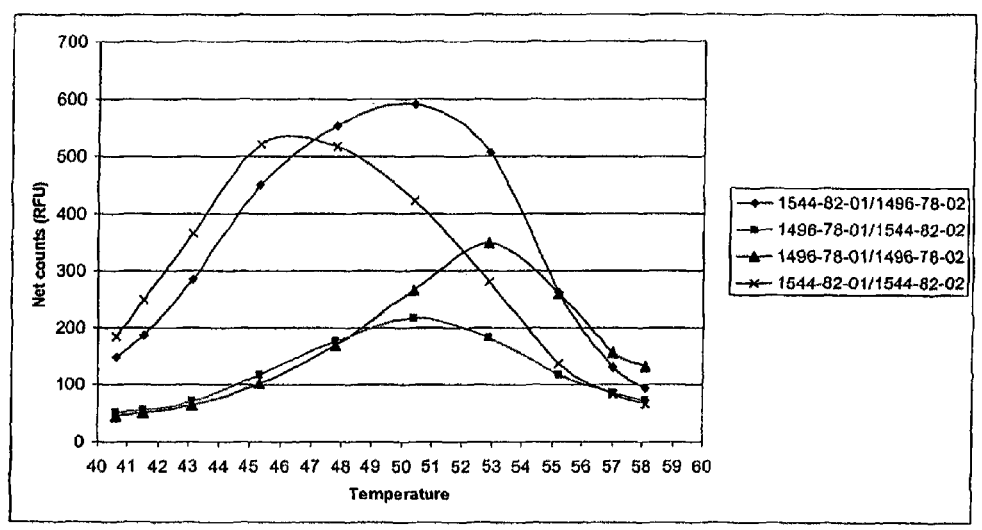
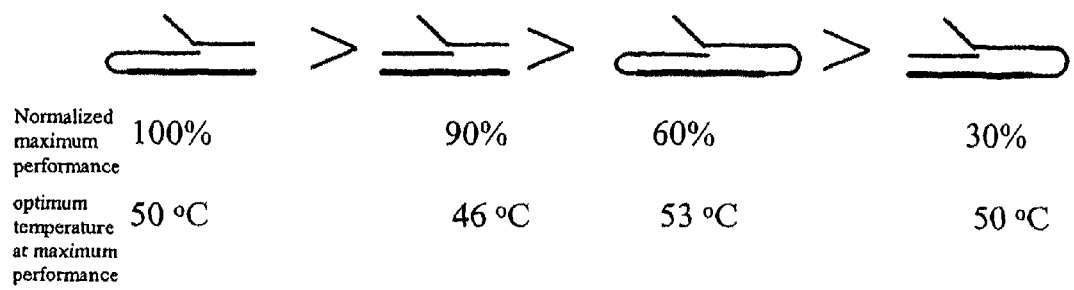
| Normalized maximum performance | 100% | 90% | 60% | 30% |
| --- | --- | --- | --- | --- |
| optimum temperature at maximum performance | 50 °C | 46 °C | 53 °C | 50 °C |

Fig. 19
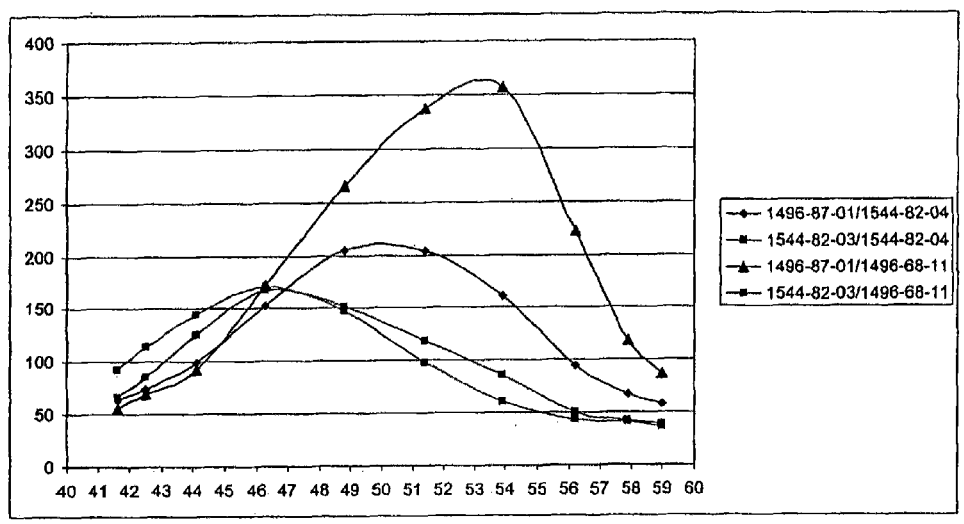
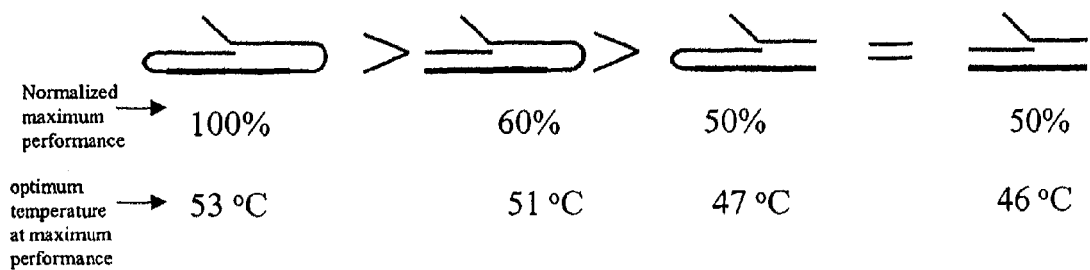
| | | | |
|---|---|---|---|
| Normalized maximum performance → 100% | 60% | 50% | 50% |
| optimum temperature at maximum performance → 53 °C | 51 °C | 47 °C | 46 °C |

Fig. 24

```
                5'-CCGTCGCTGCGT
SEQ ID NO:73                   CTACTACCTCAcgac g  t        SEQ ID NO:115
      t gtgccAACTATACAACT-3'            | | | | |       t
    t    | | | | |                              gctgc    t
     t                                                 t
      t cacgg
        UUGAUAUGUUGGAUGAUGGAGU
             SEQ ID NO:4
```

```
                5'-CCGTCGCTGCGT
SEQ ID NO:124                   CTACTACCTCAcgac g  t       SEQ ID NO:116
      t  gtgccAACTATACAACT-3'           | | | | | |     t
    t    | | | | | |                           Tgctgc   t
     t                                                 t
      t cacggt
        UUGAUAUGUUGGAUGAUGGAGU
             SEQ ID NO:4
```

```
                5'-CCGTCGCTGCGT
SEQ ID NO:125                   CTACTACCTCAcgac g  t       SEQ ID NO:117
      t  gtgccAACTATACAACT-3'           | | | |         t
    t    | | | |                              -ctgc     t
     t                                                 t
      t cacg-
        UUGAUAUGUUGGAUGAUGGAGU
             SEQ ID NO:4
```

FIGURE 31

Let-7a

```
          CCGTCGCTGCGT
                      CTACTACCTCA-NH2        1544-82-01
                      |||||||||||
          UCGGUUGAUAUGUUGGAUGAUGGAGU
        U |||||||||||||||x
2343-28-01  C  GCCAACTATACAACT
           G
```

| | |
|---|---|
| CCGTCGCTGCGTCTACTACCTCA/3AmMC7/ | 1544-82-01 |
| mGmGmCmUmUmCmGmGmCmCAACTATACAACT | 2343-28-01 |
| mUmGmAmGmGmUmAmGmUmAmGmAmCmGmCmAmG | 1581-63-01 |

Let-7f

```
          CCGTCGCTGCGT
                      CTACTACCTCA-NH2        1544-82-01
                      |||||||||||
          UCGGUUGAUAUGUUAGAUGAUGGAGU
        U |||||||||||||||x
2343-28-02  C  GCCAACTATACAATT
           G
```

| | |
|---|---|
| CCGTCGCTGCGTCTACTACCTCA/3AmMC7/ | 1544-82-01 |
| mGmGmCmUmUmCmGmGmCmCAACTATACAATT | 2343-28-02 |
| mUmGmAmGmGmUmAmGmUmAmGmAmCmGmCmAmG | 1581-63-01 |

Let-7c

```
          CCGTCGCTGCGT
                      CTACTACCTCA-NH2        1544-82-01
                      |||||||||||
          UCGGUUGGUAUGUUGGAUGAUGGAGU
        U |||||||||||||||x
2343-28-03  C  GCCAACCATACAACT
           G
```

| | |
|---|---|
| CCGTCGCTGCGTCTACTACCTCA/3AmMC7/ | 1544-82-01 |
| mGmGmCmUmUmCmGmGmCmCAACCATACAACT | 2343-28-03 |
| mUmGmAmGmGmUmAmGmUmAmGmAmCmGmCmAmG | 1581-63-01 |

FIGURE 31
Continued

Let-7e

```
          CCGTCGCTGCGT
                      CTCCTACCTCAGGC U U   2343-28-04
                      ||||||||||||||
             U CGGUGAUAUGUUGGAGGAUGGAGUCCG   C
2343-28-05 U  ||||||||||||x                  G
           C G GCCACTATACAACT
```

CCGTCGCTGCGTCTCCTACCTCAmGmGmCmUmUmCmGmGmCmC    2343-28-04
mGmGmCmUmUmCmGmGmCmCACTATACAACT    2343-28-05
mUmGmAmGmGmUmAmGmGmAmGmAmCmGmCmAmG    2343-28-06

--- miR-15

```
          AACGAGGCGCAC
                      ATGTGCTGCTAGCC U U   2343-28-07
                      ||||||||||||||      C
             U CGGGTGTTTGGTAATACACGACGATCGG
2343-28-08 U  ||||||||||||x                G
           C G GCCCACAAACCATTC
```

AACGAGGCGCACATGTGCTGCTAmGmGmCmUmUmCmGmGmCmC    2343-28-07
mGmGmCmUmUmCmGmGmCmCCACAAACCATTC    2343-28-08
mUmAmGmCmAmGmCmAmCmAmUmGmUmGmCmC    2343-28-09

--- miR-16

```
          AACGAGGCGCAC
                      TACGTGCTGCTAGCC U U
                      |||||||||||||||     2343-28-10
             U CGGGCGGTTATAAATGCACGACGATCGG C
2343-28-11 U  ||||||||||||x                G
           C G GCCCGCCAATATTG
```

AACGAGGCGCACTACGTGCTGCTAmGmGmCmUmUmCmGmGmCmC    2343-28-10
mGmGmCmUmUmCmGmGmCmCCGCCAATATTG    2343-28-11
mUmAmGmCmAmGmCmAmCmGmUmAmGmUmGmCmC    2343-28-12

FIGURE 41

```
miR-15a miRVADER Designs                              ER38 Arm4
                                          GCAGGCACC-5'     ER24 Arm3
                                        GAGGCGCAG-5'
         2343-67-04   3'-NH2-TATTACCA
         2343-67-03   3'-NH2-TGTATTACCA
                             |||||||||
              5'-TAGCAGCACATAATGGTTTGTG-3'
              ||||||||                    ||||||
    5'-GTGCTCAGCCAGGTAGCAGCAC         AAACACCCGATGCACAGAACCATCGG-5'   2343-67-01
    2343-03-06                        AAACACGCGACCTGGCAC-5'           2343-67-02
```

```
miR-16 miRVADER Designs                               ER38 Arm4
                                          GCAGGCACC-5'     ER24 Arm3
                                        GAGGCGCAG-5'
         2343-67-07   3'-NH2-CATTTATA
         2343-67-06   3'-NH2-TGCATTTATA
                             |||||||||
              5'-TAGCAGCACGTAAATATTGGCG-3'
              ||||||||                    ||||||
    5'-GTGCTCAGCCAGGTAGCAGCAC         AACCGCCCGATGCACAGAACCATCGG-5'   2343-03-05
    2343-03-06                        AACCGCGCGACCTGGCAC-5'           2343-67-05
```

```
miR-155 miRVADER Designs                              ER38 Arm4
                                          GCAGGCACC-5'     ER24 Arm3
                                        GAGGCGCAG-5'
         2343-67-12   3'-NH2-TAGCACTA
         2343-67-11   3'-NH2-ATTAGCACTA
                             |||||||||
              5'-TTAATGCTAATCGTGATAGGGG-3'
              ||||||||                    ||||||
    5'-GTGCTCAGCCAGGTTAATGCTA          ATCCCCCCGATGCACAGAACCATCGG-5'  2343-67-08
    2343-67-10                         ATCCCCGCGACCTGGCAC-5'          2343-67-09
```

```
Let-7c miRVADER Designs                               ER38 Arm4
                                          GCAGGCACC-5'     ER24 Arm3
                                        GAGGCGCAG-5'
         2343-67-15   3'-NH2-TCCAACAT
         2343-14-08   3'-NH2-CATCCAACAT
                             |||||||||
              5'-TGAGGTAGTAGGTTGTATGGTT-3'
              ||||||||                    ||T|||
    5'-GTGCTCAGCCAGGTGAGGTAGT          TACCAACCGATGCACAGAACCATCGG-5'  2343-67-13
    2343-16-01                         TACCAAGCGACCTGGCAC-5'          2343-67-14
```

Stackers to use with linear RT primer

5'-mCmGmCmTmGmGmAmCmCmGmTmG-3'    2343-67-34
5'-mCmGmCmTmGmGmAmCmCmGmT-3'      2343-67-35

FIGURE 41
Continued

```
Let-7E miRVADER Designs                        ╲5'  ←──────── ER38 Arm4
                                         GCAGGCACC-5' ←────── ER24 Arm3
                                       GAGGCGCAG-5'
    2343-67-20        3'-NH2-TCCAACA
    2343-67-19      3'-NH2-CCTCCAACAG
                              |||||||||
                    5'-TGAGGTAGGAGGTTGTATAGT-3'
                         ||||||||T                |||||||
    5'-GTGCTCAGCCAGGTGAGGTAGG       ATATCACCGATGCACAGAACCATCGG-5'  2343-67-16
    2343-67-18                      ATATCAGCGACCTGGCAC-5'          2343-67-17
```

```
Let-7F miRVADER Designs                        ╲5'  ←──────── ER38 Arm4
                                         GCAGGCACC-5' ←────── ER24 Arm3
                                       GAGGCGCAG-5'
    2343-67-23        3'-NH2-TCTAACAT
    2343-67-22      3'-NH2-CATCTAACAT
                              |||||||||
                    5'-TGAGGTAGTAGATTGTATAGTT-3'
                         ||||||||                ||||||
    5'-GTGCTCAGCCAGGTGAGGTAGT        TATCAACCGATGCACAGAACCATCGG-5'  2343-03-01
    2343-16-01                       TATCAAGCGACCTGGCAC-5'          2343-67-21
```

```
miR-20a miRVADER Designs                       ╲5'  ←──────── ER38 Arm4
                                         GCAGGCACC-5' ←────── ER24 Arm3
                                       GAGGCGCAG-5'
    2343-67-27        3'-NH2-TATCACGT
    2343-67-26      3'-NH2-AATATCACGT
                              |||||||||
                    5'-TAAAGTGCTTATAGTGCAGGTAG-3'
                         ||||||||                ||||||
    5'-GTGCTCAGCCAGGTAAAGTGCT        TCCATCCCGATGCACAGAACCATCGG-5'  2343-67-24
    2343-67-33                       TCCATCGCGACCTGGCAC-5'          2343-67-25
```

```
miR-427 miRVADER Designs                       ╲5'  ←──────── ER38 Arm4
                                         GCAGGCACC-5' ←────── ER24 Arm3
                                       GAGGCGCAG-5'
    2343-67-32        3'-NH2-GACAAAAC
    2343-67-31      3'-NH2-AGGACAAAAC
                              |||||||||
                    5'-AAAGTGCTTCCTGTTTTGGGCAT-3'
                         ||||||||                ||||||
    5'-GTGCTCAGCCAGGAAAGTGCTT        CCCGTACCGATGCACAGAACCATCGG-5'  2343-67-28
    2343-67-30                       CCCGTAGCGACCTGGCAC-5'          2343-67-29
```

FIGURE 42
Continued
Let-7a
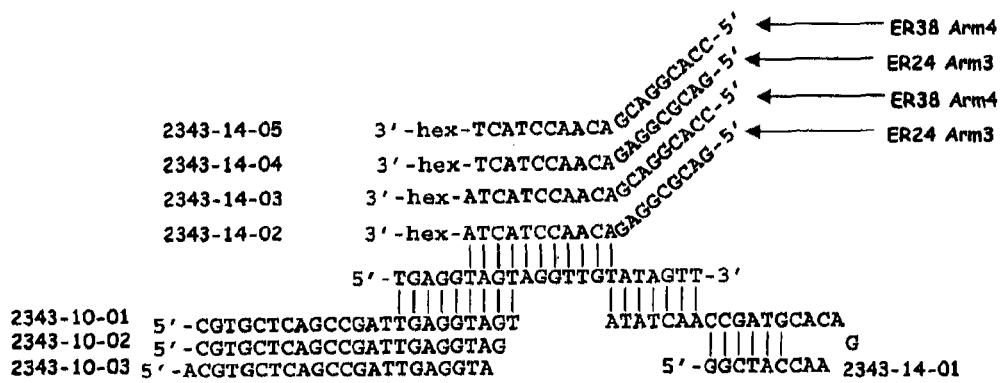
| 1- | 7 base RT primer |
| --- | --- |
| 2- | 11 mer and 10mer probes with Arms 3 &4 |
| 3- | 4, 3, and 2 base overlap with PCR primer |
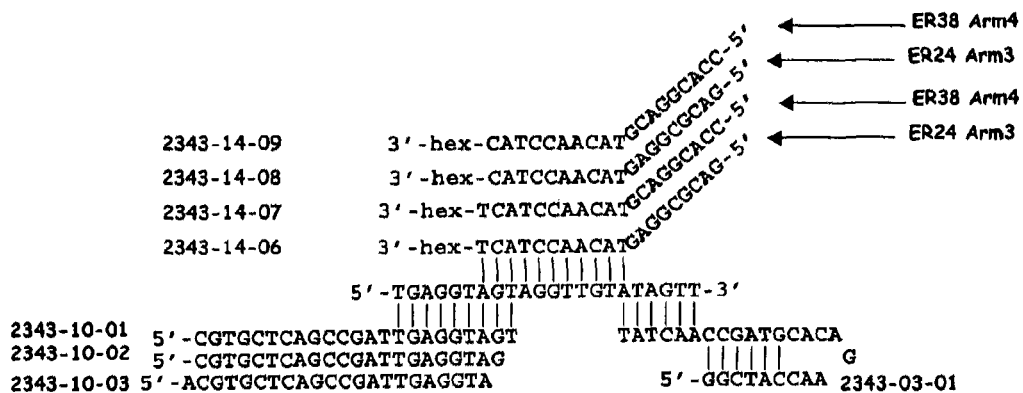
| 1- | 6 base RT primer |
| --- | --- |
| 2- | 11 mer and 10mer probes with Arms 3 &4 |
| 3- | 3, 2, and 1 base overlap with PCR primer |

FIGURE 43A

| SEQ ID NO: | Code Number | Function | Sequence | Notes |
|---|---|---|---|---|
| 144 | 1107-10-02 | 2nd Rxn. Temp. | CAGCGAAGCAAGTGACGCAKGGAGaGaGaU | m=2'-O-Methyl |
| 145 | 1496-78-02 | Invader | mGmGmCmAmCmUmUmUmUmAmUmCmCmCAACTACTACAACT | m=2'-O-Methyl |
| 146 | 1544-82-01 | Primary Probe | CCGTCGCTGCGTCTACTACCTCA/3AmM/ | NH2=Amino |
| 147 | 1544-82-01 | Primary Probe | CCGTCGCTGCGTCTACTACCTCA-NH2 | NH2=Amino |
| 148 | 1581-63-01 | Arrestor | mUmGmAmGmGmUmAmGmUmAmGmAmCmGmCmAmGmCmAmAmG | m=2'-O-Methyl |
| 149 | 1716-94-1 | Primary Probe | 5'--GACGCGGAGTACAACCTAC-HEX | hex=hexanediol |
| 150 | 1716-94-10 | Primary Probe | 5'--GACGCGGAGTACAACCTAC-NH2 | NH2=Amino |
| 151 | 1716-94-11 | Primary Probe | 5'--CCACGCGAGTACAACCT-NH2 | NH2=Amino |
| 152 | 1716-94-2 | Primary Probe | 5'-GACGCGGAGATACAACCTAC-HEX | hex=hexanediol |
| 153 | 1716-94-3 | RT/Primer/Invader | 5'-CACGGTCCAGRGAACTAT | hex=hexanediol |
| 154 | 1716-94-5 | RT/Primer/Invader | 5'-CACGGTCCAGRGAACTA | hex=hexanediol |
| 155 | 1716-94-6 | PCR Primer | 5'-CCAGTGCGATGAGGTAGTA | hex=hexanediol |
| 156 | 1716-94-8 | Stacker | 5'--CCGTGGACGGTG-HEX-3' | hex=hexanediol |
| 157 | 1716-94-9 | Stacker | 5'--TCGGCACTGG-HEX | hex=hexanediol |
| 158 | 1716-96-4 | PCR F. Primer | 5'--CTAAATGGAACGATACAG | |
| 159 | 1716-96-5 | Primary Probe | 5'--CGGCGGTCCTCGATCCTTGCG-NH2 | NH2=Amino |
| 160 | 1716-96-8 | RT/Primer/Invader | 5'-GCTTCACGAATTTGCGTGT | |
| 161 | 1796-53-01 | Primary Probe | ccgccgagatcaaCTAATCTTCTCTGTAT-NH2 | NH2=Amino |
| 162 | 1796-53-02 | Invader | CATCCTTGCCCAGGGGCCATGA | |
| 163 | 1796-53-03 | Arrestor | mAmUmAmCmAmGmAmAmGmAmAmUmUmAmGmCmUmGmAmUmC | m=2'-O-Methyl |
| 164 | 1796-59-01 | U6 RNA Target | rUrUrArUrArGrCrArUrArGrArArGrUrArGrUrArGrCrArGrCrGrCrCrCrUrGrCrGrCrArGrGrArUrGrUrUrU | r=ribose (RNA) |
| 165 | 23-181 | FRET Cassette | YCTCYTCTCAGTGG | y = Red dye and x = Z28 |
| 166 | 23-182 | FRET Cassette | YCACYTGCTTCGTGG | Y = 6FAM, X=Z28 quencher |
| 167 | 23-183 | 2nd Rxn. Temp. | CGCAGTGAGAATGAGGTGATCCTGCmGmGmU | m=2'-O-Methyl |
| 168 | 23-204 | FRET Cassette | YTCTYAGCCGGTTTTCCGGCTGACGTCCGTGGCCT | Y=FAM, X=Z28 |
| 169 | 23-210 | FRET Cassette | YTCTYAGCCGGTTTTCCGGCTGAGACTCCGTGGCCGT | Y=FAM, X=Z28 |
| 170 | 23-211 | FRET Cassette | YTCTYAGCCCTTTTCGGGCCGAGAGACGTGCGTGGCCT | Y=RED, X=Z28 |
| 171 | 2343-03-01 | RT/Primer/Invader | GGCTACCAAGACACGTAGCGAACAT | Hairpin Forming |
| 172 | 2343-03-02 | PCR F. Primer | CGTGCTCAAGCCGATTGAGGTAGTAG | |
| 173 | 2343-03-03 | Primary Probe | GGACGCCGAGTACACACCTACC-hex | hex=hexanediol |
| 174 | 2343-03-05 | RT/Primer/Invader | GGCTACCAACACACCGTAGCCCGCCAA | Hairpin Forming |
| 175 | 2343-03-06 | PCR F. Primer | CGTGCTCAGCGATTAGCAGCAC | |
| 176 | 2343-03-07 | Primary Probe | GGACGCGGAGATATTTACGTGCTG | |
| 177 | 2343-10-01 | PCR F. Primer | CGTGCTCAGCCGATTGAGGTAGT | |

FIGURE 43B

| SEQ ID NO: | Code Number | Function | Sequence | Notes |
|---|---|---|---|---|
| 178 | 2343-10-02 | PCR F. Primer | CGTGCTCAGCCGATTGAGGTAG | |
| 179 | 2343-10-03 | PCR F. Primer | ACGTGCTCAGCCGATTGAGGTA | |
| 180 | 2343-10-04 | Primary Probe | CCACGGACGTACAACCTACTACC-hex | hex=hexanediol |
| 181 | 2343-10-05 | PCR F. Primer | CGTGCTCAGCCGATTAGCAGCA | |
| 182 | 2343-10-06 | PCR F. Primer | CGTGCTCAGCCGATTAGCAGC | |
| 183 | 2343-10-07 | Primary Probe | GCCACGGACGATATTTACGTGCTG-hex | hex=hexanediol |
| 184 | 2343-14-01 | RT/Primer/Invader | GGCTACCAAGACACGTAGCCAACTATA | |
| 185 | 2343-14-02 | Primary Probe | GACGCGGAGACAACCTACTA-hex | hex=hexanediol |
| 186 | 2343-14-03 | Primary Probe | CCACGGACGACAACCTACTA-hex | hex=hexanediol |
| 187 | 2343-14-04 | Primary Probe | GACGCGGAGACAACCTACT-hex | hex=hexanediol |
| 188 | 2343-14-05 | Primary Probe | CCACGGACGACAACCTACT-hex | hex=hexanediol |
| 189 | 2343-14-06 | Primary Probe | GACGCGGGATTACAACCTACT-hex | hex=hexanediol |
| 190 | 2343-14-07 | Primary Probe | CCACGGACGATACAACCTACT-hex | hex=hexanediol |
| 191 | 2343-14-08 | Primary Probe | GACGCGGAGTACAACCTAC-hex | hex=hexanediol |
| 192 | 2343-14-09 | Primary Probe | CCACGGACGTACAACCTAC-hex | hex=hexanediol |
| 193 | 2343-16-01 | PCR F. Primer | GTGCTCAGCCAGGTGAGGTAGT | |
| 194 | 2343-23-01 | FRET Cassette | YCACXTCGAACGTCG | Y = 6FAM, X = Z28 quencher |
| 195 | 2343-23-02 | | CGAAGGTTCGAAGTGGAGGCGTGACmGmGmU | m=2'-O-Methyl |
| 196 | 2343-25-01 | Primary Probe | CCGTCACGCGTCCTACTACCTCA-NH2 | NH2=Amino |
| 197 | 2343-25-02 | Arrestor | mUmGmAmAmGmCmUmAmGmUmAmAmUmAmGmCmAmCmGmCmG | m=2'-O-Methyl |
| 198 | 2343-25-03 | Arrestor | mUmAmAmGmCmUmAmGmUmAmAmUmAmAmGmCmAmCmGmCmG | m=2'-O-Methyl |
| 199 | 2343-25-04 | | mUmGmAmAmGmCmUmAmGmUmUmAmAmUmAmGmCmAmCmGmCmG | m=2'-O-Methyl |
| 200 | 2343-25-05 | | CCGTCACGCCTCATGTGCTCATAmAmUmAmCmUmAmUmUmAmCmAmCmG | m=2'-O-Methyl |
| 201 | 2343-28-01 | Invader | mUmAmAmGmCmAmUmAmAmGmAmUmAmUmAmGCAACT | m=2'-O-Methyl |
| 202 | 2343-28-02 | Invader | mUmAmAmGmCmUmUmAmCmGmAmCmUmAmAmUmAGCAACAAT | m=2'-O-Methyl |
| 203 | 2343-28-03 | Invader | mUmGmAmCmAmCmUmAmUmAmCmGmAmCmUmAmAmCCATACAACT | m=2'-O-Methyl |
| 204 | 2343-28-04 | Primary Probe | CCGTGCTCGAGTCTCCTACCTCAmAmGmCmAmUmUmCmAmCmCmC | m=2'-O-Methyl |
| 205 | 2343-28-05 | Invader | mUmAmCmGmAmCmUmAmAmUmAmGCAmUmCmAmAmCmGmCmG | m=2'-O-Methyl |
| 206 | 2343-28-06 | Arrestor | mUmGmAmAmGmCmAmCmGmCmGmAmCmGmAmAmGmCmAmAmG | m=2'-O-Methyl |
| 207 | 2343-28-07 | Primary Probe | AACGAGGGCGACATGTGCTGCTAmAmGmCmCmUmUmCmGmCmG | m=2'-O-Methyl |
| 208 | 2343-28-08 | Invader | mUmGmAmCmUmCmGmCmGmAmAmCmUmUmCmGmCmGmCmG | m=2'-O-Methyl |
| 209 | 2343-28-09 | Arrestor | mUmAmAmGmCmUmAmGmCmAmAmUmAmGCACAAACCATTC | m=2'-O-Methyl |
| 210 | 2343-28-10 | Primary Probe | AACGAGGCGACTACGTGCTGCTAmAmGmCmCmUmUmCmGmCmG | m=2'-O-Methyl |
| 211 | | | | |

FIGURE 43C

| SEQ ID NO: | Code Number | Function | Sequence | Notes |
|---|---|---|---|---|
| 212 | 2343-28-11 | Invader | mGmCmCmUmCmGmCmCmCCGCCAATATTG | m=2'-O-Methyl |
| 213 | 2343-28-12 | Arrestor | mUmAmCmAmCmAmGmCmGmUmAmGmUmGmCmC | m=2'-O-Methyl |
| 214 | 2343-28-13 | Primary Probe | AACGAGGCACCGGTCTCAGGGAmGmCmUmUmCmCmCGmCmC | m=2'-O-Methyl |
| 215 | 2343-28-14 | Invader | mGmCmCmUmCmGmCmCmCTCAAAGTTAGA | m=2'-O-Methyl |
| 216 | 2343-28-15 | Arrestor | mUmCmCmUmGmAmAmGmAmAmCmCmAmGmCmC | m=2'-O-Methyl |
| 217 | 2343-28-16 | Primary Probe | CCGTCGCTGCGTAATAAGCACTTTAmGmAmGmUmCmGmCmGmC | m=2'-O-Methyl |
| 218 | 2343-28-17 | Invader | mGmCmCmUmCmGmCmCmCTACCTGCACC | m=2'-O-Methyl |
| 219 | 2343-28-18 | Arrestor | mUmAmAmAmGmUmGmCmUmUmAmUmAmCmGmCmAmG | m=2'-O-Methyl |
| 220 | 2343-28-20 | Primary Probe | CCGTCGCTGCGTGATTAGCATTAAmAmGmCmUmUmCmGmCmGmC | m=2'-O-Methyl |
| 221 | 2343-28-21 | Invader | mGmCmCmUmCmGmCmCmCCCCTATCACC | m=2'-O-Methyl |
| 222 | 2343-28-22 | Arrestor | mUmUmAmAmAmUmGmCmUmAmAmUmCmAmCmGmCmAmG | m=2'-O-Methyl |
| 223 | 2343-30-01 | Primary Probe | AAGACGCACCACCTAATCTCTCTCTGTAT/3AmM-6/ | |
| 224 | 2343-30-01 | Primary Probe | AAGACGCAGCACCTAATCTCTCTCTGTAT-NH2 | NH2=Amino |
| 225 | 2343-30-02 | FRET Cassette | TCTCATGCATAGTXCG | y = Red dye and x = Z28 |
| 226 | 2343-30-03 | 2nd Rxn. Temp. | mAmCmAmUmCmAmUmGmAmAmGmAmUmAmCmCmUmG | m=2'-O-Methyl |
| 227 | 2343-30-04 | Arrestor | mAmUmAmCmAmGmAmGmAmGmAmGmAmUmUmAmGmGmUmGmC | m=2'-O-Methyl |
| 228 | 2343-32-01 | Primary Probe | CCGTCGCTGCGTAGGAAGCACTTTAmGmAmGmUmCmGmCmGmC | m=2'-O-Methyl |
| 229 | 2343-32-02 | Invader | mGmCmCmUmCmGmCmCmCATGCCCAAAACG | m=2'-O-Methyl |
| 230 | 2343-32-03 | Arrestor | mAmAmAmGmUmGmCmUmUmCmCmUmAmCmGmCmAmG | m=2'-O-Methyl |
| 231 | 2343-32-04 | Target | /5Phos/rArArArGrUrGrCrUrUrCrCrUrGrUrUrUrGrGrCrArU | r=ribose (RNA) |
| 232 | 2343-60-01 | | CCGTCGCTGCGTCTATAAGACATTTAmGmAmGmUmCmUmCmGmCmGmC | m=2'-O-Methyl |
| 233 | 2343-60-02 | | mGmCmAmAmAmCmUmGmCmAmUmGmCmAmCmCTGCAT | m=2'-O-Methyl |
| 234 | 2343-60-03 | | CCAGGACGACGACCATTAT/3AmM/ | |
| 235 | 2343-60-04 | | AACGAGGCCGCACCGAAGCACTTTAmGmAmGmCmUmUmCmGmCmGmC | m=2'-O-Methyl |
| 236 | 2343-60-05 | | mGmCmAmAmAmCmUmGmCmCmUmCmGmCmCmATGCCCAAACAA | m=2'-O-Methyl |
| 237 | 2343-60-06 | | mAmUmAmGmCmGmCmUmGmCmUmUmCmCmUmGmCmCmC | m=2'-O-Methyl |
| 238 | 2343-67-01 | RT/Primer/Invader | GGCTACCAAGACACGTAGCCCACAAA | Hairpin Forming |
| 239 | 2343-67-02 | RT/Primer/Invader | CACGGTCCAGCGCACAAA | Requires Stacker 2343-67-34 |
| 240 | 2343-67-03 | Primary Probe | GACGCGGAGACCATTAGT/3AmM/ | |
| 241 | 2343-67-04 | Primary Probe | CCACGGACGACGATTAT/3AmM/ | |
| 242 | 2343-67-05 | RT/Primer/Invader | CACGGTCCAGCGCGCAA | Requires Stacker 2343-67-34 |
| 243 | 2343-67-06 | Primary Probe | GACGCGGGATATTTACGT/3AmM/ | |
| 244 | 2343-67-07 | Primary Probe | GACGCGGAGATATTTAC/3AmM/ | |
| 245 | 2343-67-08 | RT/Primer/Invader | GGCTACCAAGACAAGTAGCCCCCTA | Hairpin Forming |
| 246 | 2343-67-09 | RT/Primer/Invader | CACGGTCCAGCGCCCCTA | Requires Stacker 2343-67-34 |
| 247 | 2343-67-10 | PCR F. Primer | GTGTCTAGCCAGGTTAATGCTA | |

FIGURE 43D

| SEQ ID NO: | Code Number | Function | Sequence | Notes |
|---|---|---|---|---|
| 248 | 2343-67-11 | Primary Probe | GACGCGGAGATCACGATTA/3AmM/ | |
| 249 | 2343-67-12 | Primary Probe | GACGCGGAGATCACGAT/3AmM/ | |
| 250 | 2343-67-13 | RT/Primer/Invader | GGCTACCAAGACACGTAGCCAACCAT | Hairpin Forming |
| 251 | 2343-67-14 | RT/Primer/Invader | CACGGTCCAGGACCAT | Requires Stacker 2343-67-34 |
| 252 | 2343-67-16 | RT/Primer/Invader | GGCTACCAAGACACGTAGCCACTATA | Hairpin Forming |
| 253 | 2343-67-17 | RT/Primer/Invader | CACGGTCCAGGACGACTATA | Requires Stacker 2343-67-34 |
| 254 | 2343-67-18 | PCR F. Primer | GTGCTCAGCCAGGTGAGGTAGG | |
| 255 | 2343-67-19 | Primary Probe | GACGCGGAGACAACCTCC/3AmM/ | |
| 256 | 2343-67-20 | Primary Probe | CCACGGACGACAACCT/3AmM/ | |
| 257 | 2343-67-21 | RT/Primer/Invader | CACGGTCCAGGAACTAT | Requires Stacker 2343-67-34 |
| 258 | 2343-67-22 | Primary Probe | GACGCGGAGTACATCTAC/3AmM/ | |
| 259 | 2343-67-23 | Primary Probe | CCACGGACGTACAATCT/3AmM/ | |
| 260 | 2343-67-24 | RT/Primer/Invader | GGCTACCAAGACACGTAGCCCTACCT | Hairpin Forming |
| 261 | 2343-67-25 | RT/Primer/Invader | CACGGGTCCAGGGCTACCT | Requires Stacker 2343-67-34 |
| 262 | 2343-67-26 | Primary Probe | GACGCGGAGTGCACTATAA/3AmM/ | |
| 263 | 2343-67-27 | Primary Probe | CCACGGACGTGACACTAT/3AmM/ | |
| 264 | 2343-67-28 | RT/Primer/Invader | GGCTACCAAGACACGTAGCCATGCCC | Hairpin Forming |
| 265 | 2343-67-29 | RT/Primer/Invader | CACGGGTCCAGGATGCC | Requires Stacker 2343-67-34 |
| 266 | 2343-67-30 | PCR F. Primer | GTGCTCAGCCAGGAAGTGCTT | |
| 267 | 2343-67-31 | Primary Probe | GACGCGGAGCAAAACAGGA/3AmM/ | |
| 268 | 2343-67-32 | Primary Probe | CCACGGACGCAAAACAG/3AmM/ | |
| 269 | 2343-67-33 | PCR F. Primer | GTGCTCAGCCAGGTAAGTGCT | |
| 270 | 2343-67-34 | Stacker | mCmGmCmUmGmGmAmCmCmGmUmG | m=2'-O-Methyl |
| 271 | 2343-67-35 | Stacker | mCmGmCmUmGmGmAmCmCmGmUmG | m=2'-O-Methyl |
| 272 | 23-755 | FRET Cassette | YTCTXAGCCGGTTTCCGGCTGAGACTCCGCGTCCGT | Y=RED, X=Z28 |
| 273 | 23-755 | FRET Cassette | TTCTXAGCCGGTTTCCGGCTGAGACTCCGCGTCCGT | |
| 274 | Let-7a | Target | UGAGGUAGUAGGUUGUAUAGUU | |
| 275 | Let-7a | Target | /5Phos/rUrGrArGrGrUrArGrUrArGrGrUrUrGrUrArUrArGrUrU | r=ribose (RNA) |
| 276 | Let-7c | Target | /5Phos/rUrGrArGrGrUrArGrUrArGrGrUrUrGrUrArUrGrUrU | r=ribose (RNA) |
| 277 | Let-7e | Target | /5Phos/rUrGrArGrGrUrArGrGrArGrGrUrUrGrUrArUrArGrUrU | r=ribose (RNA) |
| 278 | Let-7f | Target | /5Phos/rUrGrArGrGrUrArGrUrArGrArUrUrGrUrArUrArGrUrU | r=ribose (RNA) |
| 279 | miR-125b | Target | /5Phos/rUrCrCrCrUrGrArGrArCrCrCrUrArArCrUrUrGrUrGrA | r=ribose (RNA) |
| 280 | miR-155 | Target | /5Phos/rUrUrArArUrGrCrUrArArUrCrGrUrGrArUrArGrGrGrU | r=ribose (RNA) |
| 281 | miR-15a | Target | /5Phos/rUrArGrCrArGrCrArCrArUrArArUrGrGrUrUrUrGrUrG | r=ribose (RNA) |
| 282 | miR-16 | Target | /5Phos/rUrArGrCrArGrCrArCrGrUrArArArUrArUrUrGrGrCrG | r=ribose (RNA) |
| 283 | miR-20a | Target | /5Phos/rUrArArArGrUrGrCrUrUrArUrArGrUrGrCrArGrGrUrArG | r=ribose (RNA) |
| 284 | miR-427 | Target | /5Phos/rArArArGrUrGrCrUrGrAnUrArGrUrGrCrArU | r=ribose (RNA) |

FIGURE 43E

| SEQ ID NO: | Code Number | Function | Sequence 5'- | Notes |
|---|---|---|---|---|
| 285 | U6 | Target | GUUCUUCCGAGAACAUAUACUAAAAUUGGAACAAUACAGAGAAGAUUAGCAUGGCCCCUGCGCAAGG | |
| 286 | Let-7a | Target amplicon | AUGACACGCAAAUUCGUGAAGCGUUCCAAUUUU | |
| 287 | 1716-94-4 | PCR Primer | CCAGTGCCGATGAGAGTAGTTGGTGTATAGTTCCTGACCGTG | |
| 288 | miR-15a | Target | CCAGTGCCGATGAGGTAGT | |
| 289 | miR-16 | Target | TAGCAGCACATAATGGTTTGTG | |
| 290 | miR-20a | Target | TAGCAGCACGTAAATATTGGCG | |
| 291 | miR-125b | Target | TAAAGTGCTTATAGTGCAGGTAG | |
| 292 | miR-155 | Target | TCCCTGAGACCCTAACTTGTGA | |
| 293 | miR-427 | Target | TTAATGCTAATCGTGATAGGGG | |
| 294 | Let-7a | Target | AAAGTGCTTCCTGTTTTGGGCAT | |
| 295 | Let-7e | Target | TGAGGTAGTAGGTTGTATAGTT | |
| 296 | Let-7f | Target | TGAGGTAGTAGATTGTATAGTT | |
| 297 | Let-7c | Target | TGAGGTAGTAGGTTGTATGGTT | |
| 298 | 2343-67-15 | Primary Probe | CCACGGACGTACAACCT | |

DETECTION OF NUCLEIC ACIDS

This application is a Continuation-in-Part of co-pending U.S. patent application Ser. No. 10/740,256, filed Feb. 18, 2003, which claims priority to U.S. Provisional Application Ser. No. 60/434,518, filed Dec. 18, 2002, and U.S. Application Ser. No. 60/443,814, filed Jan. 30, 2003. This application is also a Continuation-in-Part of co-pending U.S. patent application Ser. No. 11/266,723, filed on Nov. 3, 2005, which claims priority to U.S. Provisional Application 60/624,626, filed Nov. 3, 2004. This application claims priority to Provisional Patent Application Ser. No. 60/810,078, filed Jun. 1, 2006. Each of these applications is incorporated herein by reference in its entirety.

FIELD OF THE INVENTION

The present invention relates to compositions and methods for the detection and characterization of nucleic acid molecules (e.g., RNA (e.g., small RNAs such as micro RNAs (miRNAs) and small interfering RNAs (siRNAs)) and other short nucleic acid molecules). More particularly, the present invention relates to methods for the detection and quantification of RNA expression. The present invention further provides for the detection of miRNA and siRNA mutants (e.g., deletion mutants) and variants.

BACKGROUND OF THE INVENTION

MicroRNAs (miRNAs) are a new class of noncoding RNAs, which are encoded as short inverted repeats in the genomes of invertebrates and vertebrates (Ambros, (2001) Cell 107, 823-826; Moss (2002) Curr. Biol. 12, R138-R140). miRNAs are modulators of target mRNA translation and stability, although most target mRNAs remain to be identified. miRNAs sequence-specifically control translation of target mRNAs by binding to sites of antisense complementarity in 3' untranslated regions (UTRs) (Ambros, supra; Moss, supra; Lagos-Quintana et al., (2001) Science 294, 853-858; Lau et al., (2001) Science 294, 858-862; Lee et al., (2001) Science 294, 862-864). mRNAs may also inhibit gene expression by other mechanisms (See, e.g., Pillai et al., Science 309, 1573-1576 (2005); Humphreys et al., Proc Natl Acad Sci USA 102, 16961-16966 (2005)).

Several miRNAs, such as let-7 RNA, miR-1, miR-34, miR-60, and miR-87, are highly conserved between invertebrates and vertebrates, implicating that they may recognize multiple sites and/or multiple targets of presumably conserved function (Lagos-Quintana et al., supra; Lau et al., supra; Lee et al., supra; Pasquinelli et al., (2000) Nature 408:86). The small temporal RNAs (stRNAs) lin-4 and let-7 represent a subclass of miRNAs identified by genetic analysis in *Caenorhabditis elegans*, which are developmentally regulated and themselves control developmental programs, such as timing of neuronal rewiring, Dauer larva formation, vulva formation, and the terminal differentiation of hypodermal cells.

miRNAs are typically excised from 60- to 70-nucleotide foldback RNA precursor structures, which are sometimes detected at the onset of miRNA precursor expression (Grishok et al., (2001) Cell 106, 23-34; Hutvagner et al. (2001) Science 93, 834-838; Ketting et al., (2001) Genes Dev. 15, 2654-2659) or during expression of very abundant miRNAs (Lagos-Quintana et al., supra; Lau et al., supra; Lee et al., supra). Generally, only one of the strands of the hairpin precursor molecule is excised and accumulates, presumably because it is protected by associated proteins from RNA degradation. These putative proteins may mediate the translational suppression. The miRNA precursor processing reaction requires Dicer RNase III and Argonaute family members (Grishok et al., supra; Hutvagner et al., supra; Ketting et al., supra).

In addition to their impact on gene expression, small RNAs, (e.g., siRNAs or miRNAs in the range of 18-25 nucleotides), may find utility in areas of therapeutics and drug discovery (e.g. as drug targets or as pharmaceutical agents). Thus, in some circumstances, it is important to know approximately how much of each miRNA exists in cells (e.g., before, during or after therapy).

Furthermore, deletions and downregulation of miRNA genes have been associated with cancer (e.g., B-cell chronic lymphocytic leukemia (CLL)), providing a need in the art to be able to detect and characterize miRNA expression (See, e.g., Calin et al., Proc Natl Acad Sci USA, 99, 15524-15529 (2002). In some cases, it may also be important to compare levels of miRNA in different tissue types or before and after application of a stimulus, e.g. a chemical or physical intervention.

Because related siRNAs and miRNAs may be present in low amounts in cells, it is desirable that methods of detection be both sensitive and specific. Moreover, for certain applications, it may be beneficial to identify methods suitable for high throughput screening, e.g. homogeneous methods, multiplexed methods, or those suitable to highly parallel automated manipulation and limited temperature changes.

Although miRNAs play important roles in the regulation of gene expression, effective techniques for the detection and quantitation of miRNA expression are lacking. Methods used for quantitation of miRNAs have been based on gel electrophoresis. The miRNAs are detected either by Northern blotting or by the presence of radioactive RNase-resistant duplexes. Northern blotting and chip hybridization methods have relatively low analytical sensitivity (Krichevsky et al. 2003), so microgram quantities of RNA are needed for analyses; moreover, transfer of small RNAs to filters can introduce problems with reproducibility of quantitation and is not typically amendable to high-throughput. Moreover, detection methods based on RNase resistance require highly radioactive probes. Further, assays based solely on probe hybridization may not provide adequate discrimination between isotypes closely related in sequence. Alternative approaches involve cloning the miRNAs and then sequencing the inserts. While this approach may be suitable for discriminating single-base differences between closely related miRNA species, it is time consuming and laborious.

Like miRNAs, small interfering RNAs (siRNAs) are small RNA molecules involved in cell defense, e.g. against viral RNA, via a response termed RNA interference (RNAi) (Cullen, B. R., Nature Immunology, 3: 597-599 (2002)). One class of siRNAs is produced through the action of the Dicer enzyme and RNA-induced silencing complex (RISC) protein complex as part of the RNAi response to the presence of double stranded RNA in cells (Khvorova, A. et al., Cell 115: 209-216 (2003)). Another class of siRNAs is synthetic and encompasses short duplexes, usually 21-23 nt with characteristic dinucleotide overhangs (Elbashir, S. M. et al., EMBO J. 20: 6877-6888 (2001)) introduced directly into cells via transfection or expression from an introduced vector (Paul, C. P. et al., Nature Biotechnology 20: 505-508 (2002), US Patent Application Publication No. 2003/0148519A1, herein incorporated by reference in its entirety for all purposes). In some cases, siRNAs appear to persist as defined sequences, making them analogous in function and composition to miRNAs (Elbashir, S. M. et al., supra). Efficient and accurate methods of detecting and characterizing (e.g., quantitating) miRNA and siRNA levels are needed.

SUMMARY OF THE INVENTION

The present invention relates to compositions and methods for the detection and characterization of nucleic acid molecules (e.g., RNA (e.g., small RNAs such as micro RNAs (miRNAs) and small interfering RNAs (siRNAs)) and other short nucleic acid molecules. More particularly, the present invention relates to improved methods for the detection and characterization (e.g., quantification) of RNA expression.

For example, the present invention provides a method, comprising: hybridizing at least one nucleic acid (e.g., that contains sequence that is not complementary to the interfering RNA) to a interfering RNA target to generate a detection structure and detecting the detection structure. In some embodiments, the interfering RNA target is an miRNA. In other embodiments, the interfering RNA target is an siRNA. In some embodiments, the siRNA is double stranded.

In some embodiments, the detection structure comprises an invasive cleavage structure. For example, in some embodiments, the nucleic acid comprises first and second oligonucleotides configured to form an invasive cleavage structure in combination with the miRNA. In some embodiments, the nucleic acid comprises a first oligonucleotide configured to form an invasive cleavage structure in combination with said miRNA. In some embodiments, the first oligonucleotide comprises a 5' portion and a 3' portion, wherein said 3' portion is configured to hybridize to said target sequence, and wherein said 5' portion is configured to not hybridize to said target sequence. In some embodiments employing a second oligonucleotide, the second oligonucleotide comprises a 5' portion and a 3' portion, wherein said 5' portion is configured to hybridize to said target sequence, and wherein said 3' portion is configured to not hybridize to said target sequence. In some embodiments, the detecting step comprises use of an INVADER assay.

In some embodiments, the detection structure comprises a circular oligonucleotide hybridized to said small RNA to generate a circular detection structure. In some embodiments, the detecting step comprises use of a rolling circle replication assay.

In some embodiments, the detection structure comprises a nucleic acid molecule with a free 3'-OH group that is extended by a polymerase (e.g., template dependent extension) and the extended sequence is directly or indirectly detected.

In some embodiments, the detecting step(s) comprises use of a detection assay including, but not limited to, sequencing assays, polymerase chain reaction assays, hybridization assays, hybridization assays employing a probe complementary to a mutation, microarray assays, bead array assays, primer extension assays, enzyme mismatch cleavage assays, branched hybridization assays, NASBA assays, molecular beacon assays, cycling probe assays, ligase chain reaction assays, invasive cleavage structure assays, ARMS assays, and sandwich hybridization assays. In some preferred embodiments, the detecting step is carried out in cell lysate.

In some embodiments, the methods of the present invention comprise detecting a second nucleic acid target. In some preferred embodiments, the second nucleic acid target is RNA. In some particularly preferred embodiments, the second nucleic acid target is U6 RNA or GAPDH mRNA.

In some embodiments, the nucleic acid used to form the detection structure comprises a template with one or more sites sufficiently complementary to the small RNA so as to allow the RNA to hybridize to the template and be extended in an extension reaction. In some embodiments, the extension reaction is a polymerase chain reaction wherein one or more RNAs are used as primers in the polymerase chain reaction. In some such embodiments, a single type of RNA binds to two locations on the template to provide the polymerase chain reaction primers. In other embodiments, two or more RNAs are used as primers. In such embodiments, the detection of an amplification product signifies the presence of the two or more RNAs in the sample (i.e., an miRNA multiplex assay). Similar methods may be employed in a ligase chain reaction where the miRNAs are used as the ligated oligonucleotide(s). In some embodiments, the RNA is used as a template for modification of a detection complex by extension of a primer across at least part of the RNA template.

In some embodiments, the method comprises detection of a plurality of miRNAs. In some such embodiments, the plurality of miRNAs comprises polymorphisms of the same miRNA. In other embodiments, the plurality of miRNAs comprises different miRNAs (e.g., Let-7, miR-1, miR-1d, miR-135, miR-15, miR-16, miR-124a, or miR125b).

The present invention also provides kits for conducting any of the above methods. For example, in some embodiments, the present invention provides kits comprising a nucleic acid configured for forming a detection structure when hybridized to an RNA target sequence. In some embodiments, the kits are configured to detect an miRNA. In some preferred embodiments, kits are configured to detect a Let-7, miR-1, miR-135, miR-15, miR-16, miR-1b, miR-124a, or miR125b miRNA. In some preferred embodiments, kits are configured to co-detect a second RNA target with an miRNA target.

The present invention also provides a method for detecting a miRNA target, comprising providing (i) a miRNA target; (ii) a first unlabeled oligonucleotide; (iii) a second unlabeled oligonucleotide; (iv) a reverse transcriptase; (v) a polymerase; and (vi) a probe oligonucleotide; incubating (i) through (vi) under conditions such that a detection structure forms; and detecting the detection structure. In some embodiments, the first unlabeled oligonucleotide comprises a first region that is complementary to the miRNA target and a second region that is not complementary to the miRNA target. In some embodiments, the second unlabeled oligonucleotide comprises a first region that is complementary to a second region of the miRNA target and a second region that is not complementary to the second region of the miRNA target. In some embodiments, detecting comprises forming an invasive cleavage structure, cleaving the invasive cleavage structure, and detecting the cleavage of the invasive cleavage structure. In some embodiments, said incubating further comprises incubating with an enzyme capable of cleaving a detection structure and lacking polymerase activity. In some embodiments, the enzyme is a 5' nuclease, while in some embodiments, the enzyme comprises a FEN-1 nuclease. In some embodiments, cleaving the invasive cleavage structure occurs at a temperature of between 45° C. and 60° C. In some embodiments, cleaving the invasive cleavage structure occurs at a temperature of approximately 50° C. In some embodiments, the first unlabled oligonucleotide is used as a primer for reverse transcription. In some embodiments, the first unlabled oligonucleotide is used as an INVADER oligonucleotide in an invasive cleavage reaction. In some embodiments, (i) through (vi) are present within the same reaction vessel. In some embodiments, the method further comprises providing (vii) a second probe oligonucleotide. In some embodiments, the first unlabeled oligonucleotide and the reverse transcriptase reverse transcribe the miRNA target. In some embodiments, the reverse transcribed miRNA target (i.e., an miRNA cDNA target) is amplified by the first unlabeled oligonucleotide and the second unlabeled oligonucleotide and the DNA polymerase in a polymerase chain reaction. In some embodiments, the amplified reverse transcribed miRNA target forms a detection structure in the presence of the probe oligonucleotide. In some embodiments, the first unlabeled oligonucleotide comprises nucleic acid sequence such that a duplex of about 6-7 base pairs is formed between the oligonucleotide and the miRNA target. The present invention is capable of detecting miRNA present in very small copy numbers. For example, in some embodiments, less than 200 copies of miRNA in a sample are detected. In some embodiments, less than 100 copies of miRNA in a sample are detected. In some embodiments, the second unlabeled oligonucleotide comprises nucleic acid sequence such that a duplex of about 9 base-pairs is formed between the oligonucleotide and the miRNA target. In some embodiments, the probe oligonucleotide comprises nucleic acid sequence such that a duplex of about 8-10 base-pairs is formed between the oligonucleotide and the miRNA target or the amplified copy of the miRNA target. In some embodiments, the second region of the first unlabeled oligonucleotide probe comprises a first portion and a second portion, wherein the first portion and the second portion can hybridize to each other. In some embodiments, a hairpin structure is formed in the first unlabeled oligonucleotide probe when the first portion and the second portion hybridize to each other. In some embodiments, the second region of the second unlabeled oligonucleotide probe comprises a first portion and a second portion, wherein the first portion and the second portion can hybridize to each other. In some embodiments, a hairpin structure is formed in the second unlabeled oligonucleotide probe when the first portion and the second portion hybridize to each other. In some embodiment, the method further comprises providing (vii) an oligonucleotide complementary to a region of the first unlabeled oligonucleotide probe. In some embodiment, the method further comprises providing (vii) an oligonucleotide complementary to a region of the second unlabeled oligonucleotide probe. In some embodiments, cleaving the invasive cleavage structure at a temperature of approximately 50° C. permits high fidelity discrimination of target sequences, although other temperatures may be selected based on sequence, buffer components, etc. for optimum performance. In some embodiments, the target sequences comprise variant miRNAs of a single species. In some embodiments, increasing the concentration of the probe oligonucleotide increases the sensitivity of detecting the miRNA target. In some embodiments, two or more miRNAs are detected. In some embodiments, detecting comprises use of a labeled probe. In some embodiments, the labeled probe is fluorescently labeled. In some embodiments, the labeled probe is configured for FRET detection. In some embodiments, the labeled probe has a first conformation when not hybridized in a duplex and a second conformation when hybridized in a duplex. In some embodiments, the labeled probe exhibits increased fluorescence when hybridized in a duplex. The present invention is not limited by the miRNA detected. Indeed, a variety of miRNAs can be detected using the compositions and methods of the present invention including, but not limited to, Let-7, miR-1, miR-135, miR-15, miR-16, miR125b, miR-1d, and miR124a.

The present invention also provides a kit comprising one or more of a first unlabeled oligonucleotide that comprises a first region that is complementary to a miRNA target and a second region that is not complementary to the miRNA target; a second unlabeled oligonucleotide that comprises a first region that is complementary to a second region of the miRNA target and a second region that is not complementary to the second region of the miRNA target; a reverse transcriptase; a DNA polymerase; a probe oligonucleotide; and an enzyme capable of cleaving a detection structure. In some embodiments, the detection structure comprises an invasive cleavage structure. In some embodiments, the kit is configured to detect a miRNA target and at least one other RNA target. In some embodiments, the kit is configured to detect the miRNA target sequence in a cell lysate.

DESCRIPTION OF THE DRAWINGS

FIG. 4 shows a third exemplary detection structure used in some embodiments of the present invention.

FIG. 5 shows exemplary oligonucleotides for use with the present invention. Bases of the target miRNA are underlined in lower case. DNA residues in probe or INVADER oligonucleotides are in regular type. Lower case type indicates 2'-O-methyl residues.

FIG. 9 shows the results of cross reactivity experiments using let-7 miRNA.

FIG. 11 shows the results of CLEAVASE enzymes IX and XII comparisons using let-7 miRNA.

FIG. 12 shows a partial sequence alignment of U6 RNA sequences from various organisms.

FIG. 18 shows the results of temperature optimization experiments using the assay designs described in FIG. 16.

FIG. 19 shows the results of temperature optimization experiments using the 10-mer probe and 12-mer INVADER oligonucleotide designs.

FIG. 22 shows the results of invasive cleavage assays to detect miR-124a.

FIG. 24 shows results of experiments testing the effect on miRNA detection of altering probe and oligonucleotide length.

FIG. 31 shows various oligonucleotides generated during development of the present invention for the detection and characterization of miRNAs associated with cancer. Let-7a is SEQ ID NO:275; Let-7f is SEQ ID NO:278; Let-7c is SEQ ID NO:276; Let-7e is SEQ ID NO:277; miR-15 is SEQ ID NO:288; miR-16 is SEQ ID NO:289; miR-125b is SEQ ID NO:291; miR-20a (2343-28-19) is SEQ ID NO:283; miR-155 is SEQ ID NO:280; miR-427 RNA is SEQ ID NO:284; miR0427 DNA is SEQ ID NO:293; 1544-82-01 is SEQ ID NO:146; 1581-63-01 is SEQ ID NO:148; 2343-28-01 is SEQ ID NO:202; 2343-28-02 is SEQ ID NO:203; 2343-28-03 is SEQ ID NO:204; 2343-28-04 is SEQ ID NO:205; 2343-28-05 is SEQ ID NO:206; 2343-28-06 is SEQ ID NO:207; 2343-28-07 is SEQ ID NO:208; 2343-28-08 is SEQ ID NO:209; 2343-28-09 is SEQ ID NO:210; 2343-28-10 is SEQ ID NO:211; 2343-28-11 is SEQ ID NO:212; 2343-28-12 is SEQ ID NO:213; 2343-28-13 is SEQ ID NO:214; 2343-28-14 is SEQ ID NO:215; 2343-28-15 is SEQ ID NO:216; 2343-28-16 is SEQ ID NO:217; 2343-28-17 is SEQ ID NO:218; 2343-28-18 is SEQ ID NO:219; 2343-28-20 is SEQ ID NO:220; 2343-28-21 is SEQ ID NO:221; 2343-28-22 is SEQ ID NO:222; 2343-32-01 is SEQ ID NO:228; 2343-32-02 is SEQ ID NO:229; 2343-32-03 is SEQ ID NO:230; 2343-32-04 is SEQ ID NO:231.

FIG. 41 shows oligonucleotides generated for the detection of miRNAs associated with cancer designed according to guidelines listed in Example 19(M). miR-15a is SEQ ID NO:288; miR-16 is SEQ ID NO:289; miR-155 is SEQ ID NO:292; Let-7c is SEQ ID NO:297; Let-7e is SEQ ID NO:295; Let-7f is SEQ ID NO:296; miR-20a is SEQ ID NO:290; miR-427 is SEQ ID NO:293; 2343-67-01 is SEQ ID NO:238; 2343-67-02 is SEQ ID NO:239; 2343-67-03 is SEQ ID NO:240; 2343-67-04 is SEQ ID NO:241; 2343-67-05 is SEQ ID NO:242; 2343-67-06 is SEQ ID NO:243; 2343-67-07 is SEQ ID NO:244; 2343-67-08 is SEQ ID NO:245; 2343-67-09 is SEQ ID NO:246; 2343-67-10 is SEQ ID NO:247; 2343-67-11 is SEQ ID NO:248; 2343-67-12 is SEQ ID NO:249; 2343-67-13 is SEQ ID NO:250; 2343-67-14 is SEQ ID NO:21; 2343-67-15 is SEQ ID NO:298; 2343-67-16 is SEQ ID NO:252; 2343-67-17 is SEQ ID NO:253; 2343-67-18 is SEQ ID NO:254; 2343-67-19 is SEQ ID NO:255; 2343-67-20 is SEQ ID NO:256; 2343-67-21 is SEQ ID NO:257; 2343-67-22 is SEQ ID NO:258; 2343-67-23 is SEQ ID NO:259; 2343-67-24 is SEQ ID NO:260; 2343-67-25 is SEQ ID NO:261; 2343-67-26 is SEQ ID NO:262; 2343-67-27 is SEQ ID NO:263; 2343-67-28 is SEQ ID NO:264; 2343-67-29 is SEQ ID NO:265; 2343-67-30 is SEQ ID NO:266; 2343-67-31 is SEQ ID NO:267; 2343-67-32 is SEQ ID NO:268; 2343-67-33 is SEQ ID NO:269; 2343-67-34 is SEQ ID NO:270; 2343-67-35 is SEQ ID NO:271.

FIG. 43A-E provides a table listing all oligonucleotides, SEQ ID NOs: 144-285, respectively, used in Example 19.

DEFINITIONS

Figure 1:
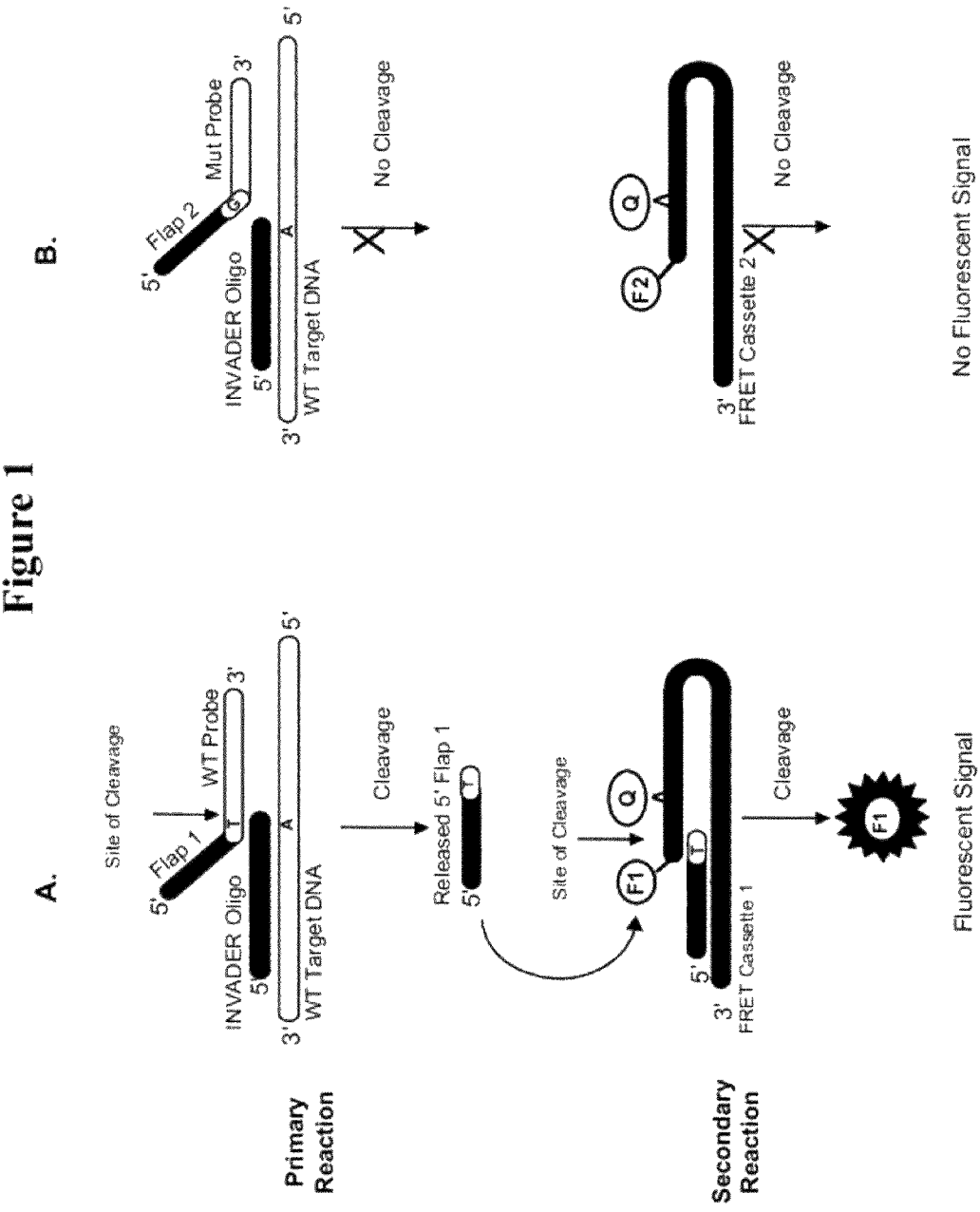
FIG. 1 shows a schematic diagram of INVADER oligonucleotides, probe oligonucleotides and FRET cassettes for detecting two different alleles (e.g., differing by a single nucleotide) in a single reaction.

To facilitate an understanding of the present invention, a number of terms and phrases are defined below:

As used herein, the term "miRNA" refers to micro RNA. As used herein, the term "miRNA target sequence" refers to a miRNA that is to be detected (e.g., in the presence of other nucleic acids). In some embodiments, a miRNA target sequence is a variant of a miRNA.

As used herein, the terms "RNA detection structure" and "detection structure" refer to a structure formed by hybridizing a nucleic acid (e.g., an oligonucleotide) to an RNA target, e.g., an miRNA or siRNA. In some embodiments, the nucleic acid is a single nucleic acid (e.g., a larger nucleic acid with a small region (or regions) of homology to the miRNA). In other embodiments, the nucleic acid comprises two nucleic acids (e.g., that hybridize to the miRNA to form a hairpin (e.g., single or double hairpin) structure). In preferred embodiments, miRNA detection structures are capable of detection using known nucleic acid detection methods, including, but not limited to, those disclosed herein.

In some embodiments, RNA detection structures are further modified following the hybridization step. For example, in some embodiments, one or more components of the detection structure provides a template for extension by a nucleic acid polymerase. In other embodiments, one or more components of the detection structure is contacted with a ligase and ligated to an additional nucleic acid.

The term "siRNAs" refers to short interfering RNAs. In some embodiments, siRNAs comprise a duplex, or double-stranded region, where each strand of the double-stranded region is about 18 to 25 nucleotides long; the double-stranded region can be as short as 16, and as long as 29, base pairs long, where the length is determined by the antisense strand. Often siRNAs contain from about two to four unpaired nucleotides at the 3' end of each strand. siRNAs appear to function as key intermediates in triggering RNA interference in invertebrates and in vertebrates, and in triggering sequence-specific RNA degradation during posttranscriptional gene silencing in plants. At least one strand of the duplex or double-stranded region of a siRNA is substantially homologous to or substantially complementary to a target RNA molecule. The strand complementary to a target RNA molecule is the "antisense" strand; the strand homologous to the target RNA molecule is the "sense" strand and is also complementary to the siRNA antisense strand. One strand of the double stranded region need not be the exact length of the opposite strand, thus, one strand may have at least one fewer nucleotides than the opposite complementary strand, resulting in a "bubble" or at least one unmatched base in the opposite strand. One strand of the double-stranded region need not be exactly complementary to the opposite strand; thus, the strand, preferably the sense strand, may have at least one mismatched base pair.

siRNAs may also contain additional sequences; non-limiting examples of such sequences include linking sequences, or loops, which connect the two strands of the duplex region. This form of siRNAs may be referred to "si-like RNA", "short hairpin siRNA" where the short refers to the duplex region of the siRNA, or "hairpin siRNA". Additional non-limiting examples of additional sequences present in siRNAs include stem and other folded structures. The additional sequences may or may not have known functions; non-limiting examples of such functions include increasing stability of an siRNA molecule, or providing a cellular destination signal.

As used herein, the terms "subject" and "patient" refer to any organisms including plants, microorganisms and animals (e.g., mammals such as dogs, cats, livestock, and humans).

As used herein, the term "INVADER assay reagents" or "invasive cleavage assay reagents" refers to one or more reagents for detecting target sequences, said reagents comprising oligonucleotides capable of forming an invasive cleavage structure in the presence of the target sequence. In some embodiments, the INVADER assay reagents further comprise an agent for detecting the presence of an invasive cleavage structure (e.g., a cleavage agent). In some embodiments, the oligonucleotides comprise first and second oligonucleotides, said first oligonucleotide comprising a 5' portion complementary to a first region of the target nucleic acid and said second oligonucleotide comprising a 3' portion and a 5' portion, said 5' portion complementary to a second region of the target nucleic acid downstream of and contiguous to the first portion. In some embodiments, the 3' portion of the second oligonucleotide comprises a 3' terminal nucleotide not complementary to the target nucleic acid. In preferred embodiments, the 3' portion of the second oligonucleotide consists of a single nucleotide not complementary to the target nucleic acid. In some embodiments, the first and second oligonucleotides are covalently coupled to one another (e.g., through a linker).

In some embodiments, the INVADER assay reagents further comprise a solid support. For example, in some embodiments, the one or more oligonucleotides of the assay reagents (e.g., first and/or second oligonucleotide, whether bridging or non-bridging) is attached to the solid support. In some embodiments, the INVADER assay reagents further comprise a buffer solution. In some preferred embodiments, the buffer solution comprises a source of divalent cations (e.g., $Mn^{2+}$ and/or $Mg^{2+}$ ions). Individual ingredients (e.g., oligonucleotides, enzymes, buffers, target nucleic acids) that collectively make up INVADER assay reagents are termed "INVADER assay reagent components."

In some embodiments, the INVADER assay reagents further comprise a third oligonucleotide complementary to a third portion of the target nucleic acid upstream of the first portion of the first target nucleic acid. In yet other embodiments, the INVADER assay reagents further comprise a target nucleic acid. In some embodiments, the INVADER assay reagents further comprise a second target nucleic acid. In yet other embodiments, the INVADER assay reagents further comprise a third oligonucleotide comprising a 5' portion complementary to a first region of the second target nucleic acid. In some specific embodiments, the 3' portion of the third oligonucleotide is covalently linked to the second target nucleic acid. In other specific embodiments, the second target nucleic acid further comprises a 5' portion, wherein the 5' portion of the second target nucleic acid is the third oligonucleotide. In still other embodiments, the INVADER assay reagents further comprise an ARRESTOR molecule (e.g., ARRESTOR oligonucleotide).

The inclusion of 2' O-methylated ARRESTOR oligonucleotides, which are base-paired fully to each probe's target-specific region and partially to its 5'-flap region, sequesters uncleaved probes and prevents X-structure formation in the secondary reaction, as described in Eis et al., Nature Biotechnology, 19:673-676 (2001), herein incorporated by reference in its entirety for all purposes.

In some preferred embodiments, the INVADER assay reagents further comprise reagents for detecting a nucleic acid cleavage product. In some embodiments, one or more oligonucleotides in the INVADER assay reagents comprise a label. In some preferred embodiments, said first oligonucleotide comprises a label. In other preferred embodiments, said third oligonucleotide comprises a label. In particularly preferred embodiments, the reagents comprise a first and/or a third oligonucleotide labeled with moieties that produce a fluorescence resonance energy transfer (FRET) effect.

In some embodiments one or more the INVADER assay reagents may be provided in a predispensed format (i.e., premeasured for use in a step of the procedure without re-measurement or re-dispensing). In some embodiments, selected INVADER assay reagent components are mixed and predispensed together. In preferred embodiments, predispensed assay reagent components are predispensed and are provided in a reaction vessel (including but not limited to a reaction tube or a well, as in, e.g., a microtiter plate). In particularly preferred embodiments, predispensed INVADER assay reagent components are dried down (e.g., desiccated or lyophilized) in a reaction vessel.

In some embodiments, the INVADER assay reagents are provided as a kit. As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

In some embodiments, the present invention provides INVADER assay reagent kits comprising one or more of the components necessary for practicing the present invention. For example, the present invention provides kits for storing or delivering the enzymes and/or the reaction components necessary to practice an INVADER assay. The kit may include any and all components necessary or desired for assays including, but not limited to, the reagents themselves, buffers, control reagents (e.g., tissue samples, positive and negative control target oligonucleotides, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure specific cleavage enzyme in a suitable storage buffer and container), while a second box may contain oligonucleotides (e.g., INVADER oligonucleotides, probe oligonucleotides, control target oligonucleotides, etc.).

The term "label" as used herein refers to any atom or molecule that can be used to provide a detectable (preferably quantifiable) effect, and that can be attached to a nucleic acid or protein. Labels include, but are not limited to, dyes; radiolabels such as $^{32}P$; binding moieties such as biotin; haptens such as digoxygenin; luminogenic, phosphorescent or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry; fluorescence polarization), and the like. A label may be a charged moiety (positive or negative charge) or alternatively, may be charge neutral. Labels can include or consist of nucleic acid or protein sequence, so long as the sequence comprising the label is detectable.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the terms "complementary" or "complementarity" are used in reference to polynucleotides (i.e., a sequence of nucleotides such as an oligonucleotide or a target nucleic acid) related by the base-pairing rules. For example, the sequence "5'-A-G-T-3'" is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands.

Several equations for calculating the $T_m$ of nucleic acids are well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (see e.g., Anderson and Young, Quantitative Filter Hybridization, in Nucleic Acid Hybridization (1985). Other references (e.g., Allawi and SantaLucia, Biochemistry 36: 10581-94 (1997) include more sophisticated computations which take structural and environmental, as well as sequence characteristics into account for the calculation of $T_m$.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified," "mutant," or "polymorphic" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant DNA vector" as used herein refers to DNA sequences containing a desired heterologous sequence. For example, although the term is not limited to the use of expressed sequences or sequences that encode an expression product, in some embodiments, the heterologous sequence is a coding sequence and appropriate DNA sequences necessary for either the replication of the coding sequence in a host organism, or the expression of the operably linked coding sequence in a particular host organism. DNA sequences necessary for expression in prokaryotes include a promoter, optionally an operator sequence, a ribosome binding site and possibly other sequences. Eukaryotic cells are known to utilize promoters, polyadenlyation signals and enhancers.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "cleavage structure" as used herein, refers to a structure that is formed by the interaction of at least one probe oligonucleotide and a target nucleic acid, forming a structure comprising a duplex, the resulting structure being cleavable by a cleavage means, including but not limited to an enzyme. The cleavage structure is a substrate for specific cleavage by the cleavage means in contrast to a nucleic acid molecule that is a substrate for non-specific cleavage by agents such as phosphodiesterases, which cleave nucleic acid molecules without regard to secondary structure (i.e., no formation of a duplexed structure is required).

The term "cleavage means" or "cleavage agent" as used herein refers to any means that is capable of cleaving a cleavage structure, including but not limited to enzymes. "Structure-specific nucleases" or "structure-specific enzymes" are enzymes that recognize specific secondary structures in a nucleic molecule and cleave these structures. The cleavage means of the invention cleave a nucleic acid molecule in response to the formation of cleavage structures; it is not necessary that the cleavage means cleave the cleavage structure at any particular location within the cleavage structure.

The cleavage means may include nuclease activity provided from a variety of sources including the CLEAVASE enzymes (Third Wave Technologies, Madison, Wis.), the FEN-1 endonucleases (including RAD2 and XPG proteins, and FEN-1 endonucleases derived from archaeabacteria), Taq DNA polymerase and E. coli DNA polymerase I. The cleavage means may include enzymes having 5' nuclease activity (e.g., Taq DNA polymerase (DNAP), E. coli DNA polymerase I). The cleavage means may also include modified DNA polymerases having 5' nuclease activity but lacking synthetic activity. Examples of cleavage means suitable for use in the methods and kits of the present invention are provided in U.S. Pat. Nos. 5,614,402; 5,795,763; 5,843,669; PCT Appln. Nos WO 98/23774; WO 02/070755A2; and WO0190337A2, each of which is herein incorporated by reference it their entireties.

The term "thermostable" when used in reference to an enzyme, such as a 5' nuclease, indicates that the enzyme is functional or active (i.e., can perform catalysis) at an elevated temperature, i.e., at about 55° C. or higher (e.g., including, but not limited to, 60° C., 65° C., 70° C., 75° C., 80° C., 85° C. or 90° C.).

The term "cleavage products" as used herein, refers to products generated by the reaction of a cleavage means with a cleavage structure (i.e., the treatment of a cleavage structure with a cleavage means).

The term "non-target cleavage product" refers to a product of a cleavage reaction that is not derived from the target nucleic acid. As discussed above, in some of the methods of the present invention, cleavage of the cleavage structure generally occurs within the probe oligonucleotide. The fragments of the probe oligonucleotide generated by this target nucleic acid-dependent cleavage are "non-target cleavage products."

The term "probe oligonucleotide", in the context of an INVADER assay reaction, refers to an oligonucleotide that interacts with a target nucleic acid to form a cleavage structure in the presence or absence of an INVADER oligonucleotide. When annealed to the target nucleic acid, the probe oligonucleotide and target form a cleavage structure and cleavage occurs within the probe oligonucleotide.

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide-whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "ARRESTOR molecule" refers to an agent added to or included in an invasive cleavage reaction in order to stop one or more reaction components from participating in a subsequent action or reaction. This may be done by sequestering or inactivating some reaction component (e.g., by binding or base-pairing a nucleic acid component, or by binding to a protein component). The term "ARRESTOR oligonucleotide" refers to an oligonucleotide included in an invasive cleavage reaction in order to stop or arrest one or more aspects of any reaction (e.g., the first reaction and/or any subsequent reactions or actions; it is not intended that the ARRESTOR oligonucleotide be limited to any particular reaction or reaction step). This may be done by sequestering some reaction component (e.g., base-pairing to another nucleic acid, or binding to a protein component). However, it is not intended that the term be so limited as to just situations in which a reaction component is sequestered.

The term "cassette" as used herein refers to an oligonucleotide or combination of oligonucleotides configured to generate a detectable signal in response to cleavage of a probe oligonucleotide in an INVADER assay. In preferred embodiments, the cassette hybridizes to a non-target cleavage product from cleavage of the probe oligonucleotide to form a second invasive cleavage structure, such that the cassette can then be cleaved.

Secondary cleavage reactions in some preferred embodiments of the present invention include the use of FRET cassettes. Such molecules provide both a secondary target (Secondary Reaction Target or SRT) and a FRET labeled cleavable sequence, allowing homogeneous detection (i.e., without product separation or other manipulation after the reaction) of the sequential invasive cleavage reaction. Other preferred embodiments use a secondary reaction system in which the FRET probe and synthetic target are provided as separate oligonucleotides. The cleaved 5'-flaps from a primary reaction act as invasive oligonucleotides in a secondary reaction, in which they bind to the appropriate secondary-reaction target (SRT).

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label. In particularly preferred embodiments, cassette comprises labeled moieties that produce a fluorescence resonance energy transfer (FRET) effect.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

As used herein, the phrase "non-amplified oligonucleotide detection assay" refers to a detection assay configured to detect the presence or absence of a particular target sequence (e.g., miRNA, SNP, repeat sequence, etc.) that has not been amplified (e.g., by PCR), without creating copies of the target sequence. A "non-amplified oligonucleotide detection assay" may, for example, amplify a signal used to indicate the presence or absence of a particular target sequence or polymorphism within a target sequence, so long as the target sequence is not copied.

As used herein, the phrase "non-amplifying oligonucleotide detection assay" refers to a detection assay configured to detect the presence or absence of a target sequence (e.g., miRNA, SNP, repeat sequence, etc.), without creating copies of the target sequence. A "non-amplifying oligonucleotide detection assay" may, for example, amplify a signal used to indicate the presence or absence of a particular target sequence or polymorphism in a target sequence, so long as the target sequence is not copied.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "liberating" as used herein refers to the release of a nucleic acid fragment from a larger nucleic acid fragment, such as an oligonucleotide, by the action of, for example, a 5' nuclease such that the released fragment is no longer covalently attached to the remainder of the oligonucleotide.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner and herein incorporated by reference); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872; each of which is herein incorporated by reference); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include nucleotides having modification on the sugar moiety, such as dideoxy nucleotides and 2'-O-methyl nucleotides. Nucleotide analogs include modified forms of deoxyribonucleotides as well as ribonucleotides.

The term "polymorphic locus" is a locus present in a population that shows variation between members of the population (e.g., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagomorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA (e.g., miRNA) or DNA). Particularly preferred sources of target nucleic acids are biological samples including, but not limited to blood, saliva, cerebral spinal fluid, pleural fluid, milk, lymph, sputum and semen.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present in at least a 100-fold molar excess; typically at least 1 pmole of each probe oligonucleotide would be used when the target nucleic acid sequence was present at about 10 fmoles or less.

A sample "suspected of containing" a first and a second target nucleic acid may contain either, both or neither target nucleic acid molecule.

The term "reactant" is used herein in its broadest sense. The reactant can comprise, for example, an enzymatic reactant, a chemical reactant or light (e.g., ultraviolet light, particularly short wavelength ultraviolet light is known to break oligonucleotide chains). Any agent capable of reacting with an oligonucleotide to either shorten (e.g., cleave) or elongate the oligonucleotide is encompassed within the term "reactant."

As used herein, the term "purified" or "to purify" refers to the removal of contaminants from a sample. For example, in some embodiments, recombinant CLEAVASE nucleases are expressed in bacterial host cells and the nucleases are purified by the removal of host cell proteins; the percent of these recombinant nucleases is thereby increased in the sample.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , n–1).

The term "nucleic acid sequence" as used herein refers to an oligonucleotide, nucleotide or polynucleotide, and fragments or portions thereof, and to DNA or RNA of genomic or synthetic origin, which may be single or double stranded, and represent the sense or antisense strand. Similarly, "amino acid sequence" as used herein refers to peptide or protein sequence.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

DESCRIPTION OF THE INVENTION

The present invention relates to compositions and methods for the detection and characterization of nucleic acid molecules (e.g., RNA (e.g., small RNAs such as micro RNAs (miRNAs) and small interfering RNAs (siRNAs)) and other short nucleic acid molecules). The present invention provides methods of detecting, characterizing and quantitating miRNA expression. In some embodiments, the present invention provides methods of detecting miRNA expression comprising adding a nucleic acid to a miRNA to aid in detection. The resulting "miRNA detection structure" is then detected using any suitable method including, but not limited to, those disclosed herein. While the following description focuses on the detection and quantitation of miRNAs, it should be understood that the invention also finds use with other short nucleic acid molecules (e.g., DNA and RNA of less than, for example, 50, 40, 30, or 20 nucleotides in length).

Various embodiments are illustrated below using miRNA as an example. However, it should be understood that the methods may be applied to other small nucleic acid molecules.

I. Formation of a miRNA Detection Structure

In some embodiments, the present invention provides methods of generating miRNA detection structures to aid in the detection of miRNAs. miRNAs are small in size (approximately 21 nucleotides (e.g., around 18-25 nucleotides)) and are thus difficult to detect using standardized hybridization methods. In some embodiments, the methods of the present invention comprise adding a nucleic acid molecule to an miRNA (e.g., via hybridization, extension, or ligation) to generate a detection structure. Such detection structures can then be detected using any suitable method.

Figure 2:
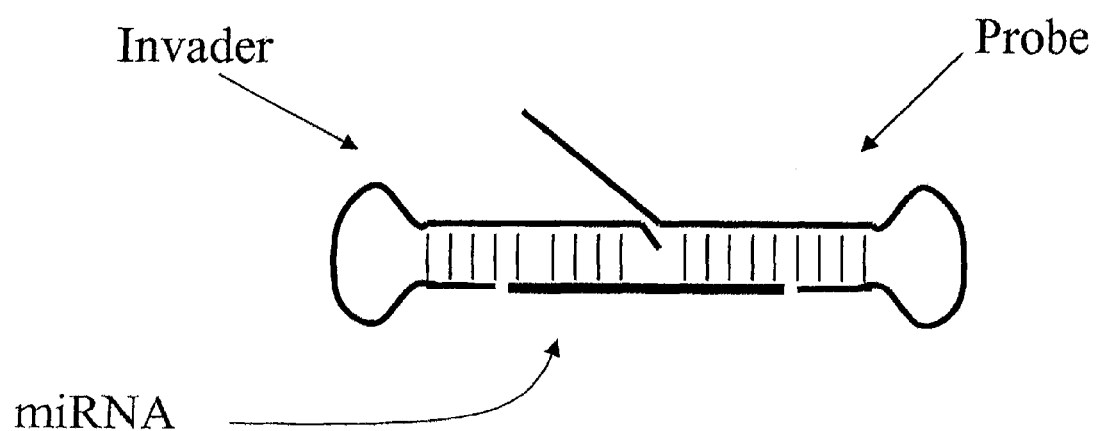
FIG. 2 shows an exemplary detection structure utilized in some embodiments of the present invention.

In one particular embodiment, the detection structure described in FIG. 2 is generated for detection of miRNAs. In this embodiment, two oligonucleotides are annealed to the miRNA to form a double loop or "dumbbell" like structure. The dumbbell structure creates a larger region of double-stranded nucleic acid by extending the ends of the miRNA with a double-stranded region of oligonucleotide. In some embodiments, each end of the miRNA is extended between 2 and 5 nucleotides. In some embodiments, the ends of the oligonucleotides comprise additional nucleic acid sequences that do not hybridize to the miRNA. In some embodiments, these additional sequences form invasive cleavage structures (e.g., INVADER assay invasive cleavage structures). In some embodiments, invasive cleavage structures are detected by the INVADER assay (See e.g., below description). For example, in some embodiments, oligonucleotides described in Example 18 (See, e.g., FIG. 31) are utilized to detect miRNAs associated with cancer (e.g., that form an invasive cleavage structure that can be detected by INVADER assay).

Figure 3:
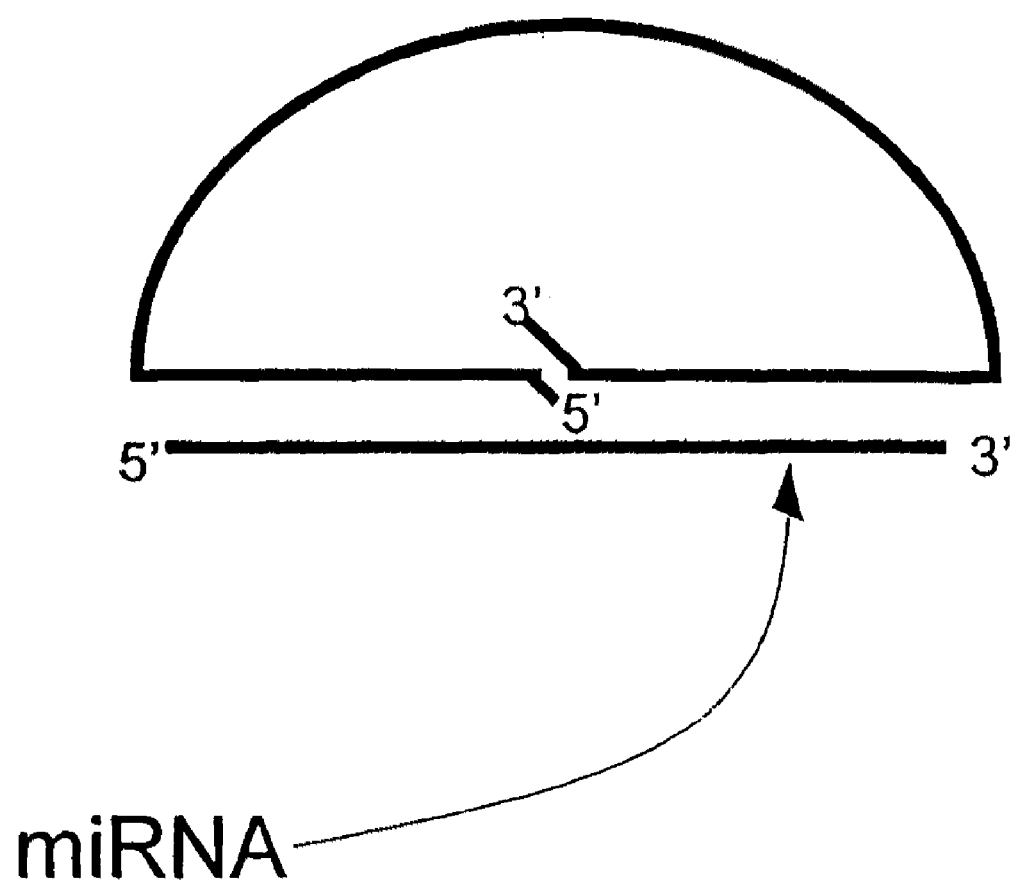
FIG. 3 shows a second exemplary detection structure utilized in some embodiments of the present invention.

In other embodiments, the detection structure described in FIG. 3 is generated for the detection of miRNAs. In this embodiment, one oligonucleotide is annealed to the miRNA to generate an arched structure. The miRNA brings the ends of the oligonucleotide together with greater efficiency than in the absence of the miRNA. In some embodiments, the ends of the oligonucleotide comprise additional sequences that extend beyond the miRNA and do not hybridize to the miRNA. In some embodiments, these additional sequences form invasive cleavage structures (e.g., INVADER assay invasive cleavage structures). In some embodiments, invasive cleavage structures are detected by the INVADER assay (See e.g., below description). In other embodiments, following cleavage of an INVADER assay invasive cleavage structure, the resulting ends are ligated to form a circular structure. In other embodiments, one oligonucleotide is hybridized to a miRNA such that the ends of the oligonucleotide are brought in close proximity (e.g., hybridized to adjacent nucleotides of the miRNA) and are then ligated.

Figure 25:
FIG. 25 shows exemplary invasive cleavage oligonucleotide designs for detection of an siRNA. Lower case residues indicate 2'-O-methyl.

In still further embodiments, the detection structures described in FIGS. 24 and 25 are generated. In this embodiment, either probe or INVADER oligonucleotides are extended to create a single hairpin loop or "half dumbbell" structure. For example, in some embodiments, oligonucleotides described in Example 18 (See, e.g., FIG. 31) are utilized to detect miRNAs associated with cancer (e.g., that form an invasive cleavage structure that can be detected by INVADER assay).

In some embodiments, the ends of the oligonucleotides comprise additional nucleic acid sequences that do not hybridize to the miRNA (See, e.g., Examples 19G and 19H). In some embodiments, these additional sequences form invasive cleavage structures (e.g., INVADER assay invasive cleavage structures). In some embodiments, invasive cleavage structures are detected by the INVADER assay (See e.g., below description).

In other embodiments, these additional sequences are complementary to additional oligonucleotides added to reaction mixtures to stabilize a cleavage structure, e.g. an INVADER assay invasive cleavage structure (FIG. 4).

In some embodiments, circular structures generated as described above are detected using a rolling circle replication assay (See e.g., below description of rolling circle replication).

In still further embodiments, detection structures are generated from long oligonucleotides (e.g., greater than 50, 100, 1000 or more nucleotides) with short region(s) of homology to miRNAs. One or more miRNAs are hybridized to the oligonucleotides to generate detection structures. In some embodiments, these detection structures are detected by extension of miRNAs (e.g., via ligation or polymerization reactions such as RT-PCR). In some embodiments, these detection structures are further detected by hybridization to oligonucleotides conjugated to solid supports, such as microspheres, or other surfaces or structures. In some embodiments, the non-miRNA component is extended or ligated to another nucleic acid and directly or indirectly detected.

In some embodiments, oligonucleotides used to form detection structures comprise one or more nucleotide analogs. For example, in some embodiments, 2'-O-methyl nucleotides are utilized. The present invention is not limited to a particular mechanism. Indeed, an understanding of the mechanism is not necessary to practice the present invention. Nonetheless, it is contemplated that the presence of 2'-O-methyl bases increases the stability of the hybridized detection structure and aids in further detection methods.

II. Detection of Nucleic Acids (e.g., Interfering RNAs)

In some embodiments, the present invention provides methods of detecting miRNAs. The present invention is not limited to a particular detection assay. Any suitable method may be utilized including, but not limited to, those disclosed herein.

In some preferred embodiments of the present invention, miRNA detection methods are quantitative. The present invention is not limited to a particular mechanism. Indeed, an understanding of the mechanism is not necessary to practice the present invention. Nonetheless, it is contemplated that levels of a particular miRNA in the body are associated with a level of gene expression from their cognate genes. The present invention thus provides methods of correlated miRNAs with gene expression of particular genes (e.g., genes involved in disease states (e.g., cancer) or metabolism). For example, in some embodiments, the methods of the present invention are utilized to determine the presence of abnormal (e.g., high or low) levels of a particular miRNA (e.g., miRNA expression associated with cancer (See, e.g., Calin et al., Proc Natl Acad Sci USA, 99, 15524-15529 (2002), e.g., using oligonucleotides described in Example 18 and FIG. 31) or to determine the effect of an intervention (e.g., drug) on miRNA expression. In other embodiments, heterologous miRNAs (e.g., from expression vectors, transgenic constructs, transfection, etc.) are detected to characterize the efficiency of miRNA expression systems.

In some embodiments, the present invention provides methods of detecting a particular miRNA (e.g., a miRNA such as mir-1 or mir-135). In other embodiments, the methods of the present invention are used to distinguish between variants (e.g., polymorphisms or mutations) in a particular miRNA. In still further embodiments, the present invention provides methods of lysing cells to be tested for the presence of miRNAs.

A. INVADER Assay

In some embodiments, the INVADER assay is used for the detection of miRNAs. In some embodiments, the INVADER assay comprises forming a nucleic acid cleavage structure that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products or the cleavage of the cleavage structure is indicative of the presence of specific target nucleic acid sequences in the sample. When one or two (or more) strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay (Third Wave Technologies) and are described in U.S. Pat. Nos. 5,846,717, 5,985,557, 5,994,069, 6,001,567, 6,090,543, 6,348,314, and 6,458,535, WO 97/27214 WO 98/42873, Lyamichev et al., Nat. Biotech., 17:292 (1999), Hall et al., PNAS, USA, 97:8272 (2000), each of which is herein incorporated by reference in its entirety for all purposes).

The INVADER assay detects hybridization of probes to a target by enzymatic cleavage of specific structures by structure specific enzymes (See, INVADER assays, Third Wave Technologies; See e.g., U.S. Pat. Nos. 5,846,717; 6,090,543; 6,001,567; 5,985,557; 5,994,069; 6,090,543; 6,348,314; 6,458,535; U.S. Patent App. Nos. 20030186238 (Ser. No. 10/084,839); 20030104378A1 (Ser. No. 09/864,636); Lyamichev et al., Nat. Biotech., 17:292 (1999), Hall et al., PNAS, USA, 97:8272 (2000), WO97/27214 and WO98/42873, each of which is herein incorporated by reference in its entirety for all purposes).

The INVADER assay detects specific DNA and RNA sequences by using structure-specific enzymes (e.g. FEN endonucleases) to cleave a complex formed by the hybridization of overlapping oligonucleotide probes (See, e.g. FIG. 1). Elevated temperature and an excess of one of the probes enable multiple probes to be cleaved for each target sequence present without temperature cycling. In some embodiments, these cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific sequences, mutations, and SNPs in unamplified, as well as amplified (See, e.g., Example 19, FIG. 32), RNA and DNA, including genomic DNA. In the embodiments shown schematically in FIG. 1, the INVADER assay uses two cascading steps (a primary and a secondary reaction) both to generate and then to amplify the target-specific signal. For convenience, the alleles in the following discussion are described as wild-type (WT) and mutant (MT), even though this terminology does not apply to all genetic variations. In the primary reaction (FIG. 1, panel A), the WT primary probe and the INVADER oligonucleotide hybridize in tandem to the target nucleic acid to form an overlapping structure. An unpaired "flap" is included on the 5' end of the WT primary probe. A structure-specific enzyme (e.g. the CLEAVASE enzyme, Third Wave Technologies) recognizes the overlap and cleaves off the unpaired flap, releasing it as a target-specific product. In the secondary reaction, this cleaved product serves as an INVADER oligonucleotide on the WT fluorescence resonance energy transfer (WT-FRET) probe to again create the structure recognized by the structure specific enzyme (panel A). When the two dyes on a single FRET probe are separated by cleavage (indicated by the arrow in FIG. 1), a detectable fluorescent signal above background fluorescence is produced. Consequently, cleavage of this second structure results in an increase in fluorescence, indicating the presence of the WT allele (or mutant allele if the assay is configured for the mutant allele to generate the detectable signal). In some embodiments, FRET probes having different labels (e.g. resolvable by difference in emission or excitation wavelengths, or resolvable by time-resolved fluorescence detection) are provided for each allele or locus to be detected, such that the different alleles or loci can be detected in a single reaction. In such embodiments, the primary probe sets and the different FRET probes may be combined in a single assay, allowing comparison of the signals from each allele or locus in the same sample.

If the primary probe oligonucleotide and the target nucleotide sequence do not match perfectly at the cleavage site (e.g., as with the MT primary probe and the WT target, FIG. 1, panel B), the overlapped structure does not form and cleavage is suppressed. The structure specific enzyme (e.g., CLEAVASE VIII enzyme, Third Wave Technologies) used cleaves the overlapped structure more efficiently (e.g. at least 340-fold) than the non-overlapping structure, allowing excellent discrimination of the alleles.

The probes turn over without temperature cycling to produce many signals per target (i.e., linear signal amplification). Similarly, each target-specific product can enable the cleavage of many FRET probes.

The primary INVADER assay reaction is directed against the target DNA (or RNA) being detected. The target DNA is the limiting component in the first invasive cleavage, since the INVADER and primary probe are supplied in molar excess. In the second invasive cleavage, it is the released flap that is limiting. When these two cleavage reactions are performed sequentially, the fluorescence signal from the composite reaction accumulates linearly with respect to the target DNA amount.

In certain embodiments, the INVADER assay, or other nucleotide detection assays, are performed with accessible site-designed oligonucleotides and/or bridging oligonucleotides. Such methods, procedures and compositions are described in U.S. Pat. Nos. 6,194,149, 6,358,691, 6,355,437, U.S. patent application Ser. No. 09/882,945, and PCT Applications WO9850403, and WO0198537, all of which are specifically incorporated by reference in their entireties.

In some preferred embodiments, the exposing of the sample (e.g., nucleic acid sequence (e.g., interfering RNA (e.g., miRNA or siRNA))) to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some embodiments, the target sequence (e.g. miRNA) comprises a first region and a second region, the second region downstream of and contiguous to the first region, and the oligonucleotides comprise first and second oligonucleotides, wherein at least a portion of the first oligonucleotide is completely complementary to the first portion of the target sequence and wherein the second oligonucleotide comprises a 3' portion and a 5' portion, wherein the 5' portion is completely complementary to the second portion of the target nucleic acid.

In some preferred embodiments, the exposing of the sample to the oligonucleotides and the agent comprises exposing the sample to the oligonucleotides and the agent under conditions wherein an invasive cleavage structure is formed between the target sequence and the oligonucleotides if the target sequence is present in the sample, wherein the invasive cleavage structure is cleaved by the cleavage agent to form a cleavage product.

In some particularly preferred embodiments, the target sequence comprises a first region and a second region, said second region downstream of and contiguous to said first region, and said oligonucleotides comprise first and second oligonucleotides, wherein at least a portion of said first oligonucleotide is completely complementary to said first portion of said target sequence and wherein said second oligonucleotide comprises a 3' portion and a 5' portion, wherein said 5' portion is completely complementary to said second portion of said target nucleic acid.

In certain embodiments, the present invention provides kits for assaying a pooled sample (e.g., a pooled blood sample or pooled cell lysates) using INVADER detection reagents (e.g. primary probe, INVADER probe, and FRET cassette). In preferred embodiments, the kit further comprises instructions on how to perform the INVADER assay, and in some embodiments, how to apply the INVADER detection assay to pooled samples from many individuals, or to "pooled" samples from many cells (e.g., from a biopsy sample) from a single subject.

The present invention further provides assays in which the target nucleic acid is reused or recycled during multiple rounds of hybridization with oligonucleotide probes and cleavage of the probes without the need to use temperature cycling (i.e., for periodic denaturation of target nucleic acid strands) or nucleic acid synthesis (i.e., for the polymerization-based displacement of target or probe nucleic acid strands). When a cleavage reaction is run under conditions in which the probes are continuously replaced on the target strand (e.g. through probe-probe displacement or through an equilibrium between probe/target association and disassociation, or through a combination comprising these mechanisms, (Reynaldo et al., J. Mol. Biol. 97: 511-520 (2000)), multiple probes can hybridize to the same target, allowing multiple cleavages, and the generation of multiple cleavage products.

The INVADER Assay Reaction:

In preferred embodiments of the INVADER DNA assay, two oligonucleotides (a discriminatory primary probe and an INVADER Oligo) hybridize in tandem to the target DNA to form an overlapping structure. The 5'-end of the primary probe includes a 5'-flap that does not hybridize to the target DNA (FIG. 1). The 3'-nucleotide of the bound INVADER oligonucleotide overlaps the primary probe, but need not hybridize to the target DNA (See, e.g., Examples 15 and 16). The CLEAVASE enzyme recognizes this overlapping structure and cleaves off the unpaired 5'-flap of the primary probe, releasing it as a target-specific product. The primary probe is designed to have a melting temperature close to the reaction temperature. Thus, under the isothermal assay conditions, primary probes, which are provided in excess, cycle on the target DNA. This allows for multiple rounds of primary probe cleavage for each target DNA, and amplification of the number of released 5'-flaps.

In the secondary reaction, each released 5'-flap can serve as an INVADER oligonucleotide on a fluorescence resonance energy transfer (FRET) Cassette to create another overlapping structure that is recognized and cleaved by the CLEAVASE enzyme (FIG. 1). When the FRET Cassette is cleaved, the fluorophore (F) and quencher (Q) are separated, generating detectable fluorescence signal. Similar to the initial reaction, the released 5'-flap and the FRET Cassette cycle, resulting in amplified fluorescence signal. The initial and secondary reactions run concurrently in the same well.

The biplex format of the INVADER DNA Assay enables simultaneous detection of two DNA sequences in a single well (See, e.g., Examples 17 and 19(L)). Most often, this involves detection of two variants of a particular polymorphism (e.g., in a miRNA). The biplex format uses two different discriminatory Primary Probes, each with a unique 5'-flap, and two different FRET Cassettes, each with a spectrally distinct fluorophore. By design, the released 5'-flaps will bind only to their respective FRET Cassettes to generate a target-specific signal.

In some embodiments, the present invention provides kits comprising one or more of the components necessary for practicing the present invention. For example, the present invention provides kits for storing or delivering the enzymes of the present invention and/or the reaction components necessary to practice a cleavage assay (e.g., the INVADER assay). By way of example, and not intending to limit the kits of the present invention to any particular configuration or combination of components, the following section describes one embodiment of a kit for practicing the present invention:

In some embodiments, the kits of the present invention provide the following reagents:

| | |
|---|---|
| CLEAVASE enzyme | Primary Probe Oligos |
| DNA Reaction Buffer 1 | INVADER Oligo |
| | FRET Cassette 1 (e.g., F) |
| | FRET Cassette 2 (e.g., R) |
| | Mutant DNA controls |
| | Wild type DNA controls |
| | "No Target" Blank control |

In other embodiments, the kits of the present invention are configured for direct detection of RNA. These kits may provide the following reagents:

| | |
|---|---|
| CLEAVASE enzyme | Primary Probe oligonucleotides |
| DNA Reaction Buffer 1 | INVADER Oligo |
| | FRET Probe 1 (e.g., F) |
| | FRET Probe 2 (e.g., R) |
| | Secondary Reaction Target 1 |
| | Secondary Reaction Target 2 |
| | ARRESTOR oligonucleotide 1 |
| | ARRESTOR oligonucleotide 2 |
| | Mutant DNA controls |
| | Wild type DNA controls |
| | "No Target" Blank control |

An additional consideration has to do with undesired effects resulting from particular combinations of oligonucleotides in a single reaction. One such effect is target-independent generation of background signal. Certain oligonucleotides in combination with others may generate signal in the INVADER assay in the absence of the particular target being detected. Separation of these oligonucleotide combinations into different pools can be used to alleviate this effect. Similarly, certain oligonucleotide combinations can artificially repress signal generation from a desired target. Again, separation of these combinations into different pools can alleviate this effect.

The designs of the probes sets (e.g., the oligonucleotides and/or their sequences) are adapted for use in miRNA detection assays using the guidelines for reaction design and optimization provided herein (See e.g., the Experimental Section). For example, in some embodiments, the reaction temperature is reduced (e.g., to 50-60° C.) to account for the smaller region of hybridization.

In some embodiments, a kit of the present invention provides a list of additional components (e.g., reagents, supplies, and/or equipment) to be supplied by a user in order to perform the methods of the invention. For example, and without intending to limit such additional components lists to any particular components, one embodiment of such a list comprises the following:

Clear CHILLOUT-14 liquid wax (MJ Research) or RNase-free, optical grade mineral oil (Sigma, Cat. No. M-5904)

96-well polypropylene microplate (MJ Research, Cat. No. MSP-9601)

Sterile 1.5-ml or 2.0-ml microcentrifuge tubes

Sterile, DNase/RNase free disposable aerosol barrier pipet tips

Multichannel pipets (0.5-10 µl, 2, 5-20 µl)

Thermal cycler or other heat source (e.g., lab oven or heating block).

Miscellaneous laboratory equipment (tube racks, micropipetors, multichannel pipet, microcentrifuge, vortex mixer).

Fluorescence microplate reader (a preferred plate reader is top-reading and equipped with light filters have the following characteristics:

| Excitation (Wavelength/Bandwidth) | Emission (Wavelength/Bandwidth) |
|---|---|
| 485 nm/20 nm | 530 nm/25 nm |
| 560 nm/20 nm | 620 nm/40 nm |

In some embodiments, a kit of the present invention provides a list of optional components (e.g., reagents, supplies, and/or equipment) to be supplied by a user to facilitate performance of the methods of the invention. For example, and without intending to limit such optional components lists to any particular components, one embodiment of such a list comprises the following:

Sterile 8-tube strip or microplate (optional)

Disposable plastic trough (optional)

Plate sealing tape (optional)

In some embodiments, a kit of the present invention provides a list of required components to be supplied by a user to facilitate performance of the methods of the invention for which multiple alternatives are acceptable (e.g. sample preparation kits). For example, and without intending to limit such optional components lists to any particular components, one embodiment of such a list comprises the following:

QIAGEN QIAAMP Blood Kit

Gentra Systems PUREGENE Kit

Gentra Systems GENERATION Products

In some embodiments of a kit, detailed protocols are provided. In preferred embodiments, protocols for the assembly of INVADER assay reactions (e.g., formulations and preferred procedures for making reaction mixtures) are provided. In particularly preferred embodiments, protocols for assembly of reaction mixtures include computational or graphical aids to reduce risk of error in the performance of the methods of the present invention (e.g., tables to facilitate calculation of volumes of reagents needed for multiple reactions, and plate-layout guides to assist in configuring multi-well assay plates to contain numerous assay reactions).

In some embodiments, supplementary documentation, such as protocols for ancillary procedures, e.g., for the preparation of additional reagents, or for preparation of samples for use in the methods of the present invention, are provided. In preferred embodiments, supplementary documentation includes guidelines and lists of precautions provided to facilitate successful use of the methods and kits by unskilled or inexperienced users. In particularly preferred embodiments, supplementary documentation includes a troubleshooting guide, e.g., a guide describing possible problems that may be encountered by users, and providing suggested solutions or corrections to intended to aid the user in resolving or avoiding such problems.

In preferred embodiments, samples are diluted to concentrations that correspond to a 10-µl addition per reaction. The concentration of a 100-ng sample should be 15 ng/µl.

B. Rolling Circle Replication

In other embodiments, rolling circle replication methods (Amersham Biosciences, Piscataway, N.J.) are utilized for detection of miRNA detection structures (See e.g., U.S. Pat. Nos. 6,344,329; 6,143,495; 6,316,229; 6,210,884, 6,183,960 and 6,235,502; each of which is herein incorporated by reference). In some embodiments, rolling circle replication is used to detect circular miRNA detection structures generated from the annealing of the ends of a single oligonucleotide annealed to a miRNA. In some embodiments, the ends of the oligonucleotide hybridize to the miRNA with no overlap. This oligonucleotide can be ligated in the presence or absence of miRNA. However, the ligation reaction is more efficient in the presence of the miRNA. In such embodiments, the level of circular molecules detected over time is compared to a control reaction lacking miRNA.

In other embodiments, the ends of the oligonucleotide hybridize to the miRNA with overlapping ends to generate an invasive cleavage structure. Such structures are cleaved prior to ligation, thus improving the specificity of the generation of the circular detection structure.

Rolling circle amplification (RCA) involves replication of circular single-stranded DNA molecules. In RCA, a rolling circle replication primer hybridizes to circular nucleic acid molecules followed by rolling circle replication of the nucleic acid molecules using a strand-displacing DNA polymerase. Amplification takes place during rolling circle replication in a single reaction cycle. Rolling circle replication results in large DNA molecules containing tandem repeats of the nucleic acid sequence. This DNA molecule is referred to as a tandem sequence DNA (TS-DNA).

In some embodiments, ligation-mediated rolling circle amplification (LM-RCA), which involves a ligation operation prior to replication, is utilized. In the ligation operation, an probe hybridizes to its cognate target nucleic acid sequence, if present, followed by ligation of the ends of the hybridized probe to form a covalently closed, single-stranded nucleic acid. After ligation, a rolling circle replication primer hybridizes to probe molecules followed by rolling circle replication of the circular molecules using a strand-displacing DNA polymerase. Generally, LM-RCA comprises mixing an open circle probe with a target sample, resulting in an probe-target sample mixture, and incubating the probe-target sample mixture under conditions promoting hybridization between the open circle probe and a target sequence, mixing ligase with the probe-target sample mixture, resulting in a ligation mixture, and incubating the ligation mixture under conditions promoting ligation of the open circle probe to form an amplification target circle (ATC), mixing a rolling circle replication primer (RCRP) with the ligation mixture, resulting in a primer-ATC mixture, and incubating the primer-ATC mixture under conditions that promote hybridization between the amplification target circle and the rolling circle replication primer, mixing DNA polymerase with the primer-ATC mixture, resulting in a polymerase-ATC mixture, and incubating the polymerase-ATC mixture under conditions promoting replication of the amplification target circle, where replication of the amplification target circle results in formation of tandem sequence DNA (TS-DNA).

C. Additional Detection Methods

The present invention is not limited to INVADER assay or rolling circle assay detection. Any method that allows for the detection of miRNA detection structures may be utilized. Exemplary, non-limiting detection assay that find use in the methods of the present invention are described below.

1. Hybridization Assays

In some embodiments of the present invention, detection structures are detected using a hybridization assay. In a hybridization assay, the presence of absence of a given nucleic acid sequence is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Detection of Hybridization Using "DNA Chip" Assays

In some embodiments of the present invention, sequences are detected using a DNA chip hybridization assay. In this assay, a series of oligonucleotide probes are affixed to a solid support. The oligonucleotide probes are designed to be unique to a given target sequence (e.g., component of a detection complex). The sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given target sequence are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target sequences by determining which of the DNA capture probes hybridize, with target sequences. An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or non-specifically bound DNA from each site, the polarity or charge of the site is reversed to negative, thereby forcing any unbound or nonspecifically bound DNA back into solution away from the capture probes. A laser-based fluorescence scanner is used to detect binding.

In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction sites. For example, the A amidite is delivered only to the sites where amidite A is to be coupled during that synthesis step and so on. Common reagents and washes are delivered by flooding the entire surface and then removing them by spinning.

DNA probes unique for the target sequence (e.g., component of a detection complex) of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., nucleic acid sample). Hybridization is detected using any suitable method.

b. Enzymatic Detection of Hybridization

In some embodiments of the present invention, hybridization is detected by enzymatic cleavage of specific structures.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the target sequence location. Incorporation of the label into the DNA can be detected by any suitable method (e.g., if the nucleotide contains a biotin label, detection is via a fluorescently labeled antibody specific for biotin).

2. Other Detection Assays

Additional detection assays useful in the detection of miRNA detection structures include, but are not limited to, enzyme mismatch cleavage methods (e.g., Variagenics, U.S. Pat. Nos. 6,110,684, 5,958,692, 5,851,770, herein incorporated by reference in their entireties); polymerase chain reaction (See, e.g., Example 19 and FIG. 32); branched hybridization methods (e.g., Chiron, U.S. Pat. Nos. 5,849,481, 5,710,264, 5,124,246, and 5,624,802, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110, 677, 5,914,230, 5,882,867, and 5,792,614, herein incorporated by reference in their entireties); ligase chain reaction (Barnay Proc. Natl. Acad. Sci. USA 88, 189-93 (1991)); and sandwich hybridization methods (e.g., U.S. Pat. No. 5,288, 609, herein incorporated by reference in its entirety).

EXPERIMENTAL

The following examples are provided in order to demonstrate and further illustrate certain preferred embodiments and aspects of the present invention and are not to be construed as limiting the scope thereof.

Example 1

Materials and Methods

The following final concentrations were used for all reactions in Examples 1-18, (unless noted otherwise herein):
Probe=1 µM
INVADER=1 µM
ARRESTOR=2.67 µM
CLEAVASE XII enzyme=30 ng All synthetic miRNA oligonucleotides were purchased from Dharmacon and gel purified on 20% denaturing acrylamide. Synthetic miRNAs were used to determine temperature optima (see below) and LOD.

INVADER, probe, and ARRESTOR oligonucleotides were synthesized either by Integrated DNA Technologies (IDT) or Third Wave Technologies and purified on 20% denaturing acrylamide, unless otherwise indicated.

The following 2.5× primary reaction buffer was used (unless otherwise noted) for all reactions:

25 mM MOPS pH 7.5

62.5 mM KCl 0.125% Tween 20

0.125% Nonidet NP40

62.5 mM $MgSO_4$

5% PEG

Unless otherwise noted, all reactions were overlaid with 10 µl mineral oil prior to the first thermal incubation.

Unless otherwise noted, synthetic miRNAs contained a 5'OH. Experiments comparing detection of 5' phosphorylated vs. unphosphorylated synthetic miRNA targets indicated that there was no significant difference in the ability of the INVADER assay to detect these two different types of synthetic molecules.

Example 2

Temperature Optimization Experiments for let-7 and mir-1

The oligonucleotide design for let-7 is shown in FIG. 5. The oligonucleotide design for mir-1 is shown in FIG. 5. The following primary mixes were made and incubated at 50° C.±10° C. in a 96 well plate for 30 minutes. In addition, a no target master mix was prepared (addition of $H_2O$ in place of RNA). All reactions were covered with mineral oil to prevent evaporation.

| Primary Reaction Components | Stock Concentration | Amount Added |
| --- | --- | --- |
| Primary Reaction Buffer | 2.5 X | 4 µl |
| Probe oligonucleotide (SEQ ID NOs: 2, 6, or 9 for let 7; SEQ ID NOs: 12, 16, or 19 for miR-1) | 10 µM | 1 µl |
| INVADER oligonucleotide (SEQ ID NOs: 1, 5, or 8 for let 7; SEQ ID NOs: 11, 15, or 18 for miR-1) | 10 µM | 1 µl |
| CLEAVASE IX or XII enzyme | 40 ng/µl CLEAVASE IX enzyme or 60 ng/µl CLEAVASE XII enzyme | 0.5 µl |
| tRNA | 20 ng/µl | 1.5 µl |
| Synthetic miRNA (SEQ ID NO: 4 for let-7a; SEQ ID NO: 14 for miR-1) | 100 pM | 2 µl |
| Total | | 10 µl |

After completion of the primary reaction, 5 µl of the following secondary reaction mix were added and the reaction was then incubated at 60° C. for 10-15 minutes.

| Secondary Reaction Components | Stock Concentration | Amount Added |
| --- | --- | --- |
| $H_2O$ (or buffer for CLEAVASE IX enzyme assays) | | 2 µl |
| FAM FRET probe (SEQ ID NO: 21) | 10 µM | 1 µl |
| Secondary Reaction Target (SEQ ID NO: 22 for let-7; SEQ ID NO: 40 for miR-1) | 1.5 µM | 1 µl |
| ARRESTOR Oligonucletide (SEQ ID NOs: 3, 7, or 10 for let-7; SEQ ID NOs: 13, 17, or 20 for miR-1) | 40 µM | 1 µl |
| Total | | 5 µl |

Figure 6A:
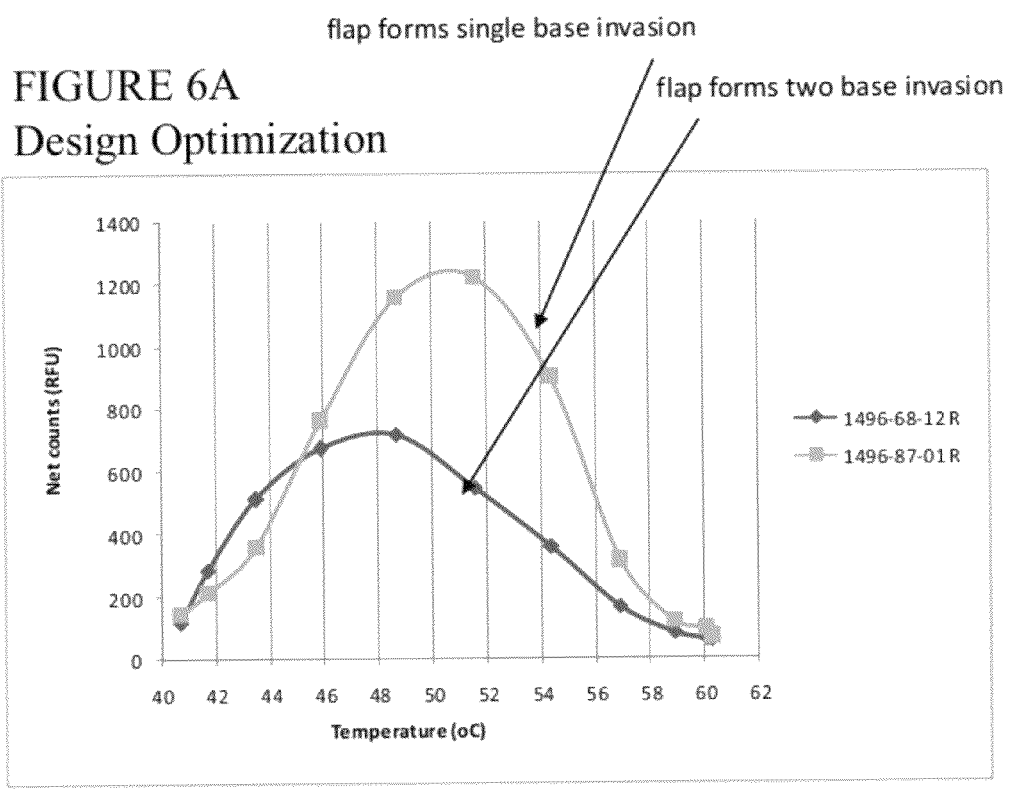
FIG. 6 shows the results of temperature optimization experiments for let-7.
Figure 6B:
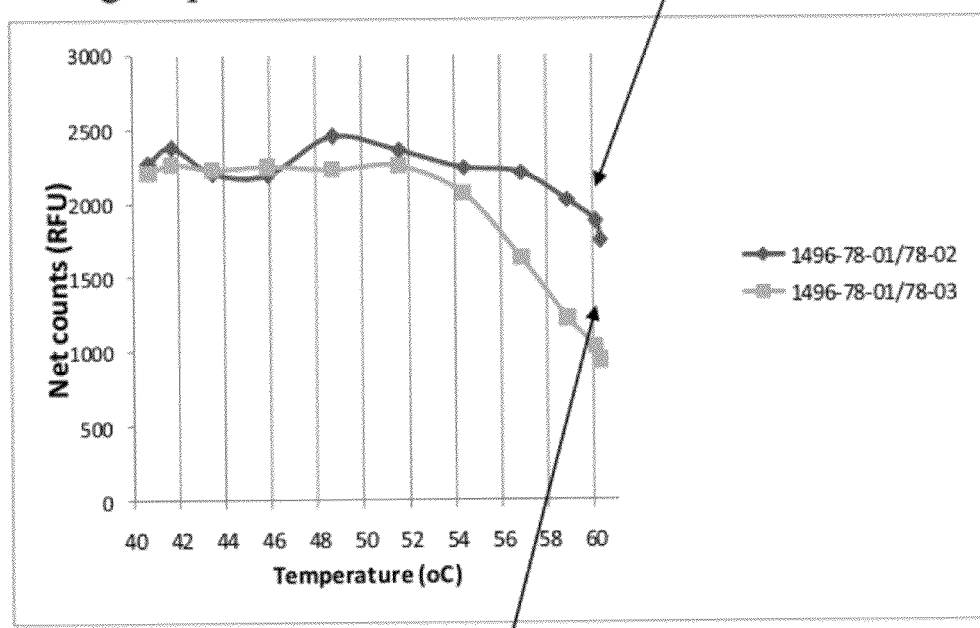
Figure 7:
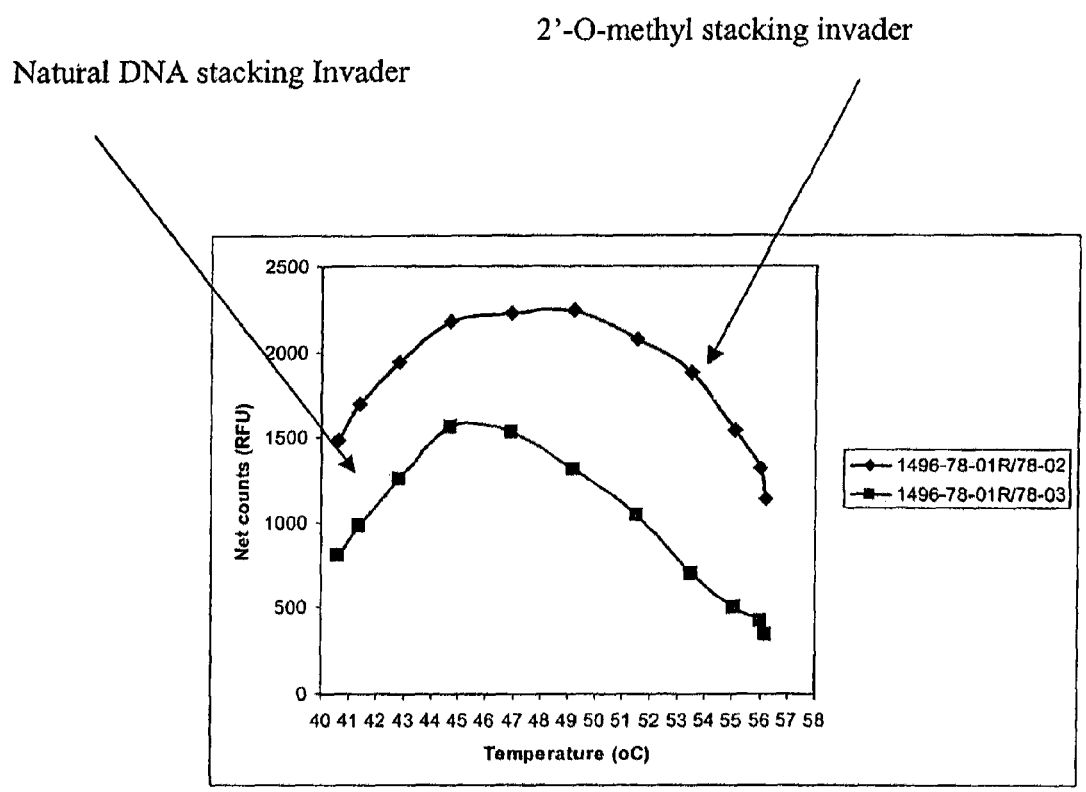
FIG. 7 shows the results of temperature optimization experiments for let-7.

After completion of the reaction, the plate was read in a CYTOFLUOR 4000 fluorescence microplate reader using an excitation wavelength of 485 nm and emission wavelength of 530 nm. Results are shown in FIGS. 6 and 7. Stacking of the 5'-end of the INVADER oligonucleotide to the 3'-end of the miRNA is enhanced when the 3'-end of the INVADER oligonucleotide is 2'-O-methylated. In addition, 2'-O-methylation of the 5'-end of the INVADER oligonucleotide increases the reaction temperature. Extending the 2'-O-methylated bases of the INVADER oligonucleotide so that they base pair with the first two bases of the miRNA (SEQ ID NO: 8 (1496-96-02) vs. SEQ ID NO: 23 (1496-96-03) in design SEQ ID NO: 9 (1496-96-01R) of let-7a) increases the temperature optimum of the described reaction but does not enhance the detection.

Example 3

LOD Experiments for let-7 and miR-1

After determining the optimal reaction temperature for each set of probe and INVADER oligonucleotides and determining the best working design (from the temperature optimization net signal), the following experiment was set up to determine the LOD of the design using synthetic RNA. The following reaction mix was aliquoted into a 96-well plate (see plate setup below) with each well containing:

| Component | Stock conc. | Amount Added |
| --- | --- | --- |
| Primary reaction buffer | 2.5 X | 4 µl |
| Probe SEQ ID NO: 6 for let 7 SEQ ID NO: 16 or 19 for miR-1 | 10 µM | 1 µl |
| INVADER oligo SEQ ID NO: 5 for let 7 SEQ ID NO: 15 or 18 for miR-1 | 10 µM | 1 µl |
| CLEAVASE XII enzyme | 60 ng/µl | 0.5 µl |
| TRNA | 20 ng/µl | 1 µl |
| TOTAL | | 7.5 µl |

2.5 µl of the following miRNA concentrations were added in triplicates or quadruplicates using the following setup:

|  |  | 10 nM<br>1 | 1 nM<br>2 | 100 pM<br>3 | 10 pM<br>4 | 1 pM<br>5 | 100 fM<br>6 | 10 fM<br>7 | H2O<br>8 |
|---|---|---|---|---|---|---|---|---|---|
| Let 7 A | A | | | | | | | | |
| Let 7 A | B | | | | | | | | |
| Let 7 C | C | | | | | | | | |
| Let 7 C | D | | | | | | | | |
| Let 7 E | E | | | | | | | | |
| Let 7 E | F | | | | | | | | |
| Let 7 F | G | | | | | | | | |
| Let 7 F | H | | | | | | | | |

|  | (miRNA) | | | | | |
|---|---|---|---|---|---|---|
|  | 1 nM | 100 pM | 10 pM | 1 pM | 100 fM | 10 fM | H2O |
| A | | | | | | | |
| B | | | | | | | |
| C | | | | | | | |
| D | | | | | | | |

The plate was overlayed with mineral oil (10 µl) and incubated at 50° C. for 2 hrs. After completion of the primary reaction, 5 µl of the following was added to each well and the plates were incubated at 60° C. for 1.5 hrs. The plate was read using the settings described above (see Example 2).

| Secondary Reaction Components | Stock Conc. | Amount Added |
|---|---|---|
| H₂O (or buffer for CLEAVASE IX enzyme assays) | | 2 µl |
| FAM FRET Probe (SEQ ID NO: 21) | 10 µM | 1 µl |
| Secondary Target (SEQ ID NO: 22 for let-7; SEQ ID NO: 40 for miR-1) | 1.5 µM | 1 µl |
| ARRESTOR oligonucleotide (SEQ ID NO: 7 for let 7; SEQ ID NOs: 17 or 20 for miR-1) | 40 µM | 1 µl |
| Total | | 5 µl |

Figure 8:
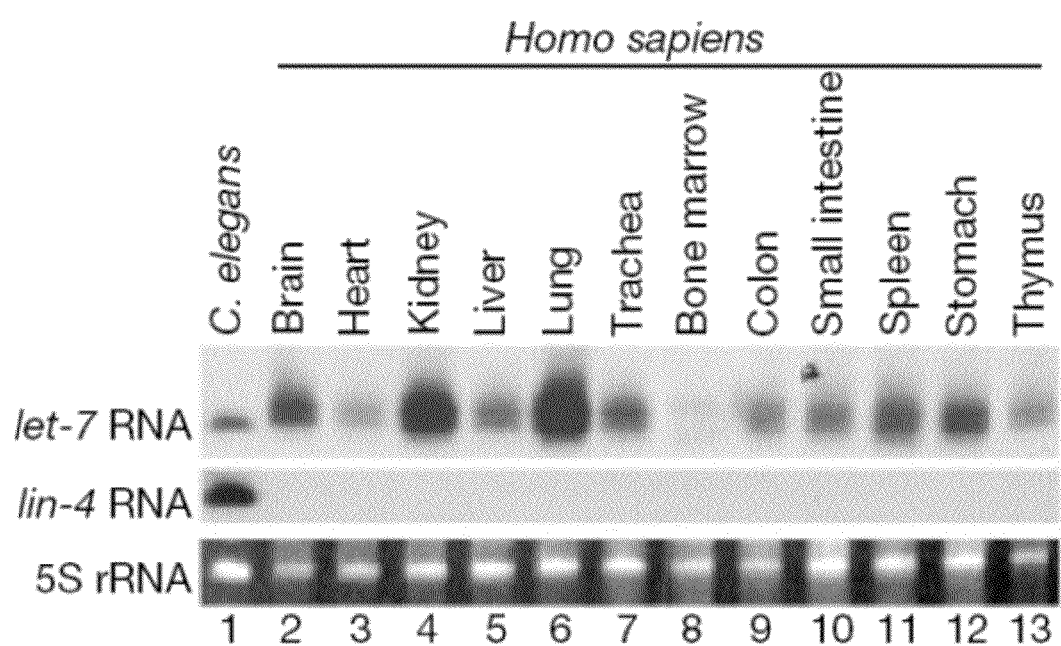
FIG. 8 shows the results of limit of detection (LOD) experiments for let-7.
Figure 10:
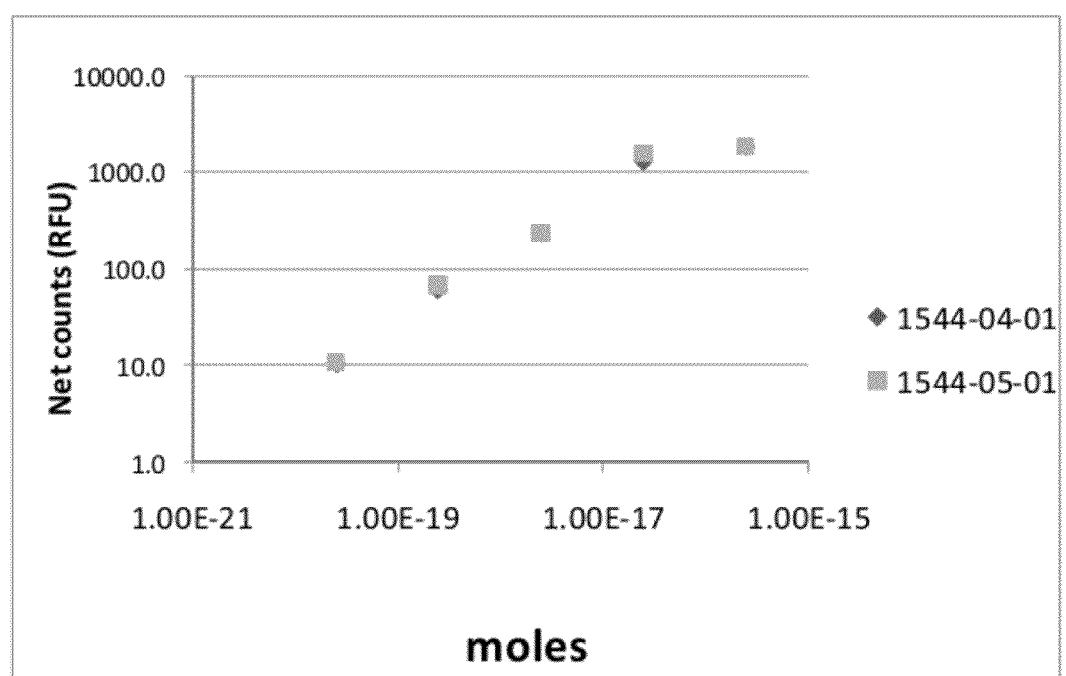
FIG. 10 shows the results of LOD experiments for miR-1.

The LOD for let-7 and mir-1 was next tested on human RNA samples. The protocol described above was utilized. 50-100 ng of tissue specific total human RNA samples (Clonetech, Palo Alto, Calif.) was used. Results are shown in FIGS. 8 and 10. Using total RNA the let-7a INVADER assay detects the same tissue expression profile as seen before for let-7a expression levels depending on the source of tissue (Pasquinelli et al., 408:86 (2000)).

Example 4

Cross Reactivity Experiments for let-7 a, c, e, and f

This Example describes an analysis of the cross reactivity of probe and/or INVADER oligonucleotides directed against one sub-type of let-7 for another sub-type. The protocol for synthetic let-7a miRNA setup described in Example 3 was utilized. FIG. 5 shows the oligonucleotide designs. The following plate setup was used:

The results are shown in FIG. 9. For let-7a design, cross reactivity is maximum when the miRNA is of the same length with a one base change away from the cleavage site. In other words, mismatches at the INVADER oligonucleotide/miRNA hybridizing regions result in high cross reactivity when the mismatch is furthest from the cleavage site (let-7c). Cross reactivity is the lowest when base changes are opposite (or close to) the cleavage site. For let-7a, the worst cross reactivity is with let-7c, which results in 25% of the signal. This Example demonstrates that the INVADER assay is able to differentiate between very similar miRNAs.

Example 5

CLEAVASE IX Enzyme vs CLEAVASE XII Enzyme

This Example describes the optimization of CLEAVASE enzymes for use in miRNA assays. The protocol for temperature optimization described above was utilized. Either 20 ng of the CLEAVASE IX enzyme (Third Wave Technologies, Madison, Wis.) or 30 ng of the CLEAVASE XII enzyme (Third Wave Technologies, Madison, Wis.) was used. The following buffer was used for the CLEAVASE 1x enzyme:

2.5x primary reaction buffer: 25 mM MOPS pH 7.5, 250 mM KCl, 0.125% Tween 20, 0.125% Nonidet NP40, 31.25 mM MgSO₄, 10% PEG.

7.5x secondary reaction buffer: 87.5 mM MgSO₄

The following buffer was used for the CLEAVASE XII enzyme:

2.5x primary reaction buffer: 25 mM MOPS pH 7.5, 62.5 mM KCl, 0.125% Tween 20, 0.125% Nonidet NP40, 62.5 mM MgSO₄, 5% PEG.

7.5x secondary reaction buffer: H₂O

The LOD experimental protocol was used with either the CLEAVASE IX or XII enzymes. The LOD was determined for both enzymes. The results are shown in FIG. 11.

Signal increased linearly with increasing amounts of the let-7 miRNA when assayed with either the CLEAVASE IX enzyme or the CLEAVASE XII enzyme. However, $R^2$ values were greater in the CLEAVASE XII enzyme, indicating greater linearity. Moreover, the LOD was lower with the CLEAVASE XII enzyme. The net signal for the detection of 2.5 amoles was 20 counts with the CLEAVASE IX enzyme and 66.75 with the CLEAVASE XII enzyme.

Example 6 miR-135, GAPDH and U6 RNA

A. Design of Oligonucleotides to Detect miR135

Figure 13:
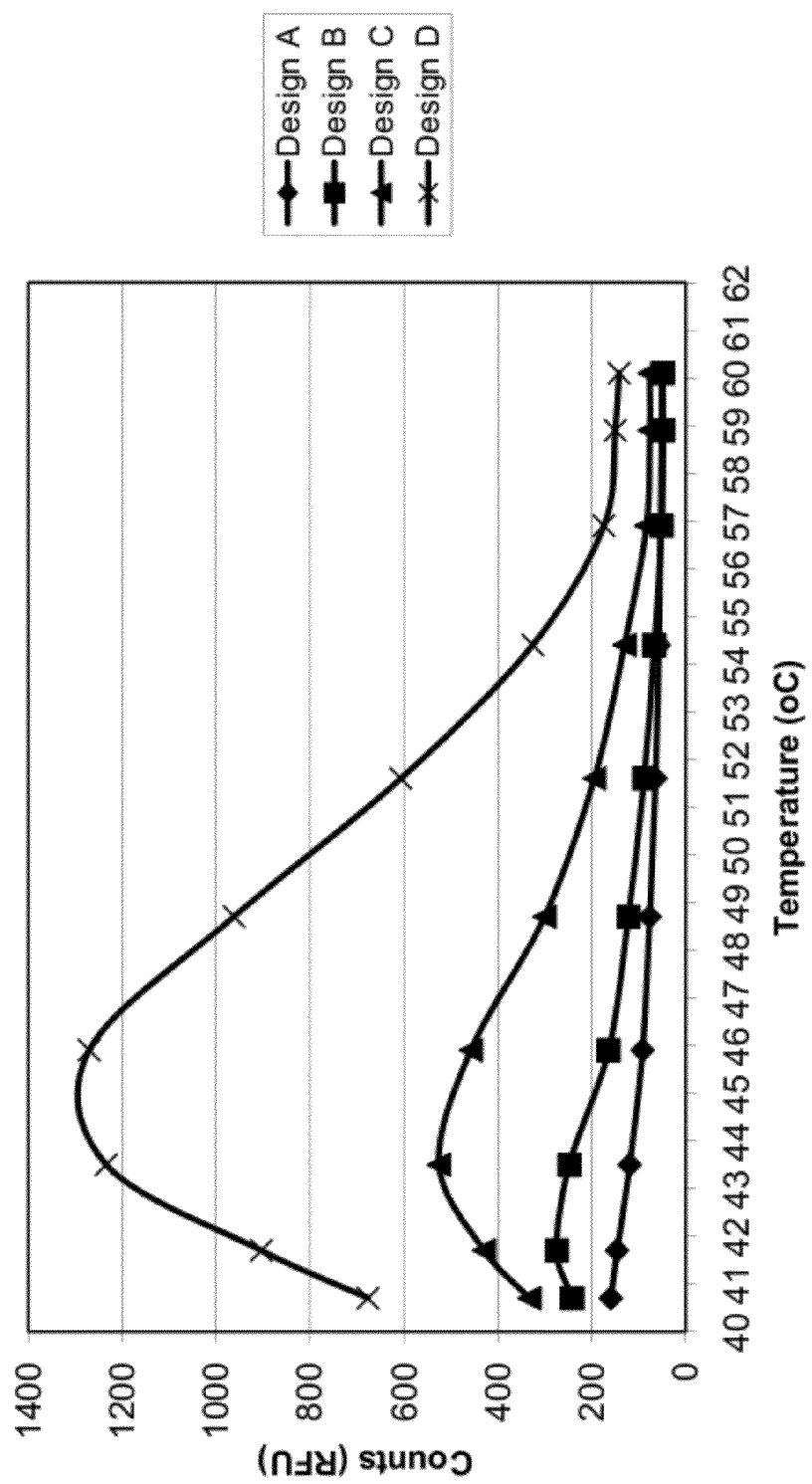
FIG. 13 shows the results of temperature optimization experiments for mir-135.
Figure 14:
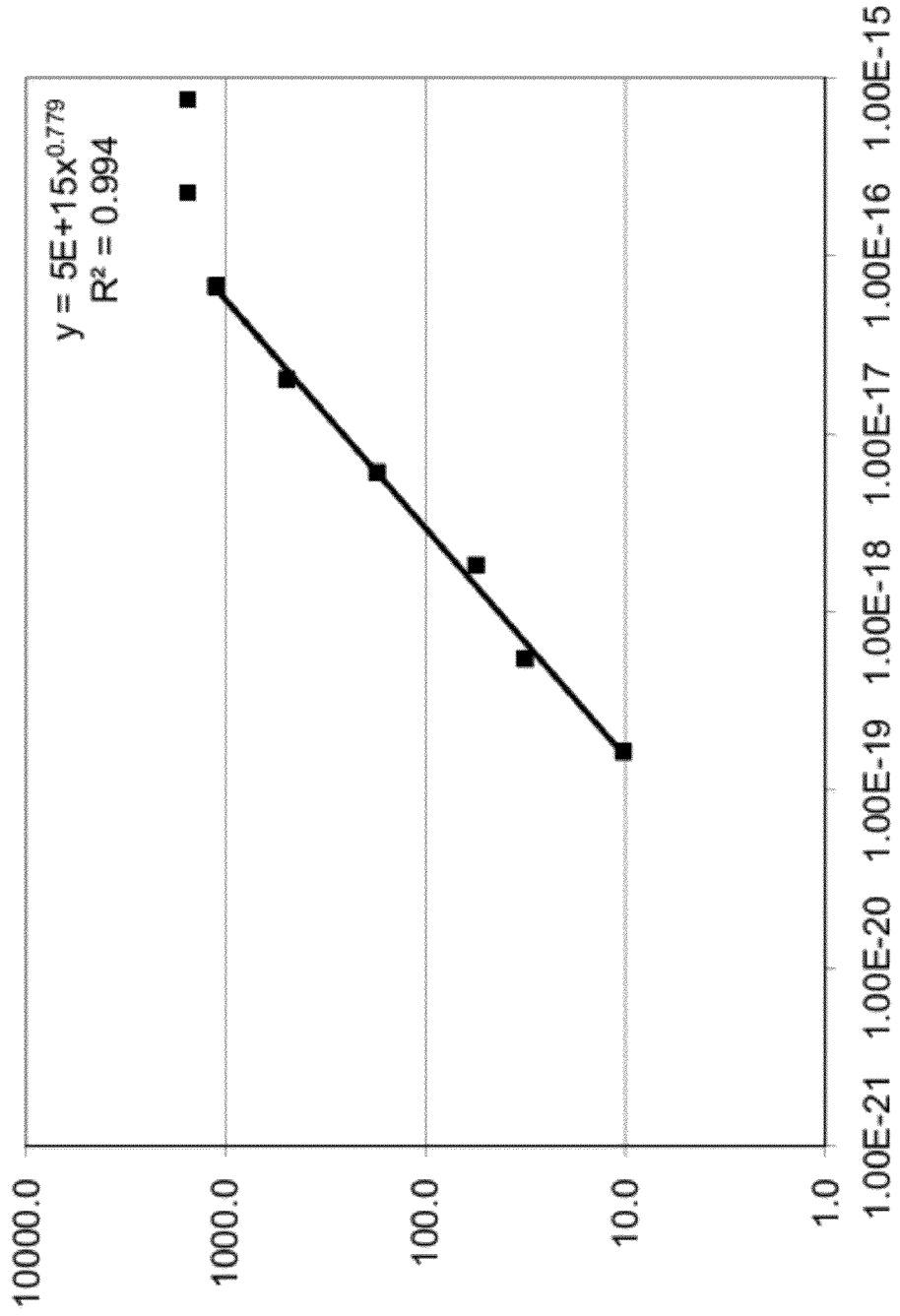
FIG. 14 shows the results of LOD experiments for mir-135.

This example describes assay design and LOD determination for miRNA miR135. Experiments were performed as described in Examples 2 and 3 for miR-1. The oligonucleotide designs are described in FIG. 5. Each of the designs (A-D) utilizes different INVADER and probe oligonucleotides for the detection of mir-135 miRNA. Results of the temperature optimization experiments comparing performance of all of the designs are shown in FIG. 13. Design D gave the highest signal. Results of LOD experiments using assay design D are shown in FIG. 14.

FIG. 14A presents the raw counts generated from four replicate assays at each of the indicated target concentrations. The average counts obtained with each target concentration are indicated as are the net signal and fold-over-zero (FOZ). The limit of detection of the miR-135 target in this experiment was 164 zmoles, equivalent to 98,743 molecules. FIG. 14B contains a graphical representation of the average counts obtained at each concentration and indicates that the INVADER assay is linear throughout much of the concentration range tested.

B. Design of Oligonucleotides to Detect GAPDH and U6 RNA

In some circumstances, it may be desirable to co-detect, e.g. in a biplex assay, an RNA generally present in all cells at constant levels along with one or more miRNA species, which may be expressed in a tissue-specific manner. INVADER assays were therefore designed to two distinct RNAs generally found in all cell types: human glyceraldehydes-3-phosphate dehydrogenase (hGAPDH) and U6 RNA.

In the case of hGAPDH, the following oligonucleotides have been used in biplex miRNA detection assays: INVADER oligonucleotide (SEQ ID NO: 41); probe (SEQ ID NO: 42); ARRESTOR oligonucleotide (SEQ ID NO: 43); SRT oligonucleotide (SEQ ID NO:49), FRET oligonucleotide (red dye) (SEQ ID NO: 48).

Figure 12:
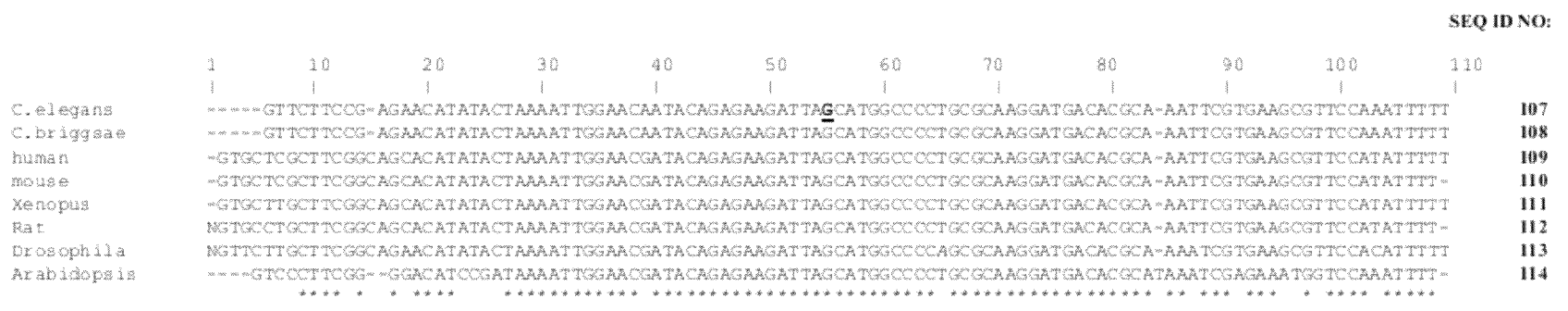

In the case of U6, sequence alignments of the U6 RNAs of 8 diverse species from *C. elegans* to mouse to *arabidopsis* to humans to identify a region suitable for the design of a "universal" INVADER assay. The alignment is shown in FIG. 12; the oligonucleotide sequences created to detect this sequence are SEQ ID NOs: 93-95.

Initial experiments carried out with these oligonucleotides on cell lysates using SEQ ID NOs: 45-47 demonstrated that signal from U6 reactions reached saturation well before miRNA signal, possibly owing to large quantities of U6 RNA in cells. Therefore, titration reactions were carried out to determine whether diluting the probe and INVADER oligonucleotide concentrations would render this probe set suitable for use in biplex miRNA detection assays with INVADER and probe final concentrations ranging from 1 μM to 12.5 nM. Final concentrations of the INVADER and probe oligonucleotides between 12.5-50 nM were suitable for biplex miRNA detection for miR-1d and let-7a. ARRESTOR, SRT, and FRET probe concentrations were as described in the previous examples. Further experiments demonstrate that detection of U6 RNA with the "universal" U6 RNA oligonucleotides (SEQ ID NOs: 93-95) is comparable to detection with SEQ ID NOs: 45-47.

Example 7

Detection of let-7, GAPDH, and U6 RNA in Cell Lysates

A. Detection of let 7a in Cell Lysates

This example describes detection of the let-7 miRNA directly in total cell RNA as well as in uninduced fibroblast cells from a human osteosarcoma cell line, MG63 (Third Wave Technologies, Madison, Wis.; catalog number CRL-1427). Total cell RNA was extracted using TRIZOL (Gibco-BRL), as previously described (Chomczynski et al., Anal. Biochem. 162: 156-156 (1987)), and cell lysates were prepared as described by Eis et al., Nature Biotechnology, 19: 673-6 (2001); both publications are herein incorporated by reference.

Reactions were set up as follows. Aliquots of 5 μl of either cell lysate, synthetic miRNA target in lysis buffer (Eis et al., Nature Biotechnology, 19: 673-6 (2001)) at the indicated concentrations, or 5 μl of 20 ng/μl of tRNA (for the no target controls) were pipetted into the appropriate wells of a microtiter plate. A primary reaction master mix was made for 96 reactions containing the following reagents.

| Reagent | Stock concentration | Amount per reaction (μl) | Total added to Master Mix (μl) |
|---|---|---|---|
| Mixture of Probe oligonucleotide 1496-78-01 R (SEQ ID NO: 6) and INVADER oligonucleotide 1496-78-02 (SEQ ID NO: 5) | Probe 20 μM/ INVADER oligonucleotide 200 μM | 0.5 | 45 |
| CLEAVASE XII enzyme | 60 ng/μl | 0.5 | 45 |
| Primary Buffer | 2.5 X | 4 | 360 |
| TOTAL | | 5 | 450 |

Aliquots of 5 μl of the primary reaction master mix were added to the wells containing the appropriate target or control. The plate was overlayed with mineral oil (10 μl) and incubated at 53° C. for 2 hrs. After completion of the primary reaction, 5 μl of the following was added to each well, and the plates were incubated at 60° C. for 1.5 hrs. The plate was read using the settings described above (see Example 2).

| Secondary Reaction Components | Stock Conc. | Amount Added |
|---|---|---|
| H2O (or buffer for CLEAVASE IX enzyme assays) | | 2 μl |
| FAM FRET probe (SEQ ID NO: 21) | 10 μM | 1 μl |
| Secondary Reaction Target (SRT) SEQ ID NO: 22 | 1.5 μM | 1 μl |
| ARRESTOR oligonucleotide SEQ ID NO: 7 | 40 μM | 1 μl |
| Total | | 5 μl |

Figure 15:
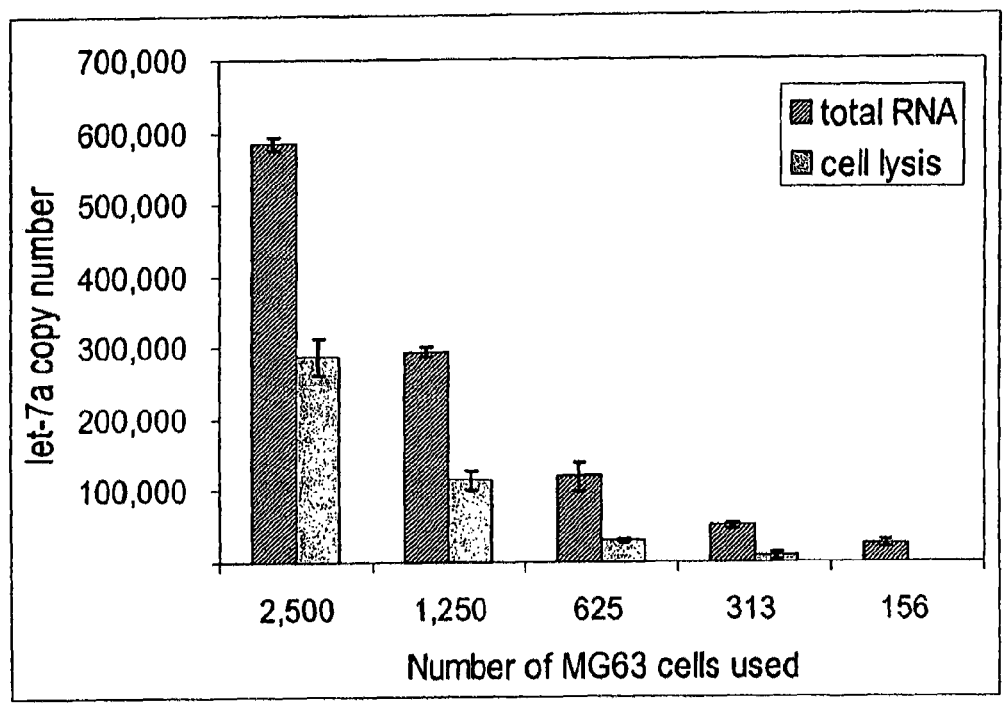
FIG. 15 contains a graphical representation of average counts obtained for the detection of let-7 in cell lysates.

All targets were assayed in quadruplicate. The average counts obtained for the different numbers of cells assayed for both total RNA and cell lysates were plotted in FIG. 15. A standard curve obtained from INVADER assays on known quantities of synthetic let-7a miRNA was used to extrapolate the let-7a copy number per cell. The number of cells from which cell lysates were generated was determined during the seeding procedure prior to cell lysis as described in Eis et al., Nature Biotechnology, 19: 673-6 (2001), herein incorporated by reference. In this experiment, the limit of detection in cell lysates was reached in the total RNA extracts obtained from 156 cells.

B. Lysis in Absence of $Mg^{++}$

An alternative lysis procedure was developed as follows. It had been noted that when the above lysis procedure was used, long mRNAs, i.e. from GAPDH, were not being detected in the quantities expected. Experiments were carried out to examine the effect of $Mg^{++}$ on extraction of RNA in lysates. Extracts lysed in the presence or absence of $MgCl_2$ were compared to total cell RNA extracts prepared using TRIZOL as described above in this example.

Hela cells ($7.5\times10^6$ cells) were suspended in 100 μl of a solution of 10 mM MOPS buffer, pH 7.5, with 100 mM KCl. Aliquots of 10 μl were added to separate tubes and lysed with 100 μl of two different lysis buffers prepared as follows:

| MOPS lysis w/$Mg^{++}$ | MOPS lysis w/out $Mg^{++}$ |
|---|---|
| 180 μl 11 μg/ml tRNA | 180 μl 11 μg/ml tRNA |
| 0.5 ml NP40 | 0.5 ml NP40 |
| 4 ml 0.5 M MOPS | 4 ml 0.5 M MOPS |
| 0.5 ml 1 M $MgCl_2$ | N/A |
| 4.82 ml $H_2O$ | 5.32 mls $H_2O$ |
| 10 mls | 10 mls |

All tubes were then incubated at 80° C. for 15 minutes to lyse the cells, and then centrifuged to pellet debris. Aliquots of 5 μl of the various lysates were added to INVADER reactions as follows.

Primary INVADER reactions were as described above for let-7a; PI oligonucleotide mixes were also made for GAPDH (SEQ ID NOs: 41-43) and for U6 (SEQ ID NOs: 45-47 at 50 nM final concentration).

| Component | Amount added per reaction | Final concentration |
|---|---|---|
| PI oligonucleotide mix* | 0.25 μl | 1 μM each* |
| $H_2O$ | 0.25 μl | 0.25 μl |
| CLEAVASE XII enzyme 60 ng/μl | 0.5 μl | 0.5 μl |
|  | 4 μl | 4 μl |
| Total | 5 μl | 5 μl |

*Primary INVADER reactions were as described above for let-7a; PI oligonucleotide mixes were also made for GAPDH (SEQ ID NOs: 41-43) and for U6 (SEQ ID NOs: 45-47 at 50 nM final concentration).

Primary reaction mixtures were incubated at 49° C. for 1 hour. Aliquots of the following secondary reaction mixture were then added:

| Component | Amount added per reaction |
|---|---|
| Secondary reaction mixture* | 1.5 μl |
| $H_2O$ | 3.5 μl |
| Total | 5 μl |

Secondary reaction mixture included SRTs (SEQ ID NO: 22 for let-7; SEQ ID NO: 49 for GAPDH and U6) target, FRET oligonucleotides (SEQ ID NO: 21 for let-7; SEQ ID NO: 48 for GAPDH and U6), ARRESTORs (SEQ ID NO:7 for let-7, SEQ ID NO:43 for GAPDH, and SEQ ID NO: 47 for U6) at the concentrations indicated in Example 7A.

Secondary reactions were run at 60° C. for 1 hour. Reactions were read on a CYTOFLUOR microplate reader as described in Example 2. The results are presented in FIG. 16 and indicate that presence of the GAPDH signal is dependent on the absence of Mg++ from the lysis buffer, whereas U6 RNA signal remains relatively constant regardless of the presence of Mg++. Additional experiments confirmed that all RNAs were detectable in total cell RNA at levels comparable to those obtained from lysis in the absence of Mg++.

Example 8

Alternative INVADER Assay Designs for Detection of Various miRNAs

A. Alternative Designs for Detection of let-7A

This example describes the creation and testing of alternative oligonucleotide designs for detection of the let-7a miRNA. In one series of experiments, a set of alternative designs was created in which the target specific regions of both the INVADER oligonucleotide and the probe oligonucleotide were eleven nucleotides long. A second set of designs was created in which the target specific regions of the probe oligonucleotides were 10 nucleotides long and the target specific regions of the INVADER oligonucleotides were 12 nucleotides long.

1. Oligonucleotide Designs a. 11-mer Probe and INVADER Oligonucleotide Designs

FIG. 5 shows sets of alternative oligonucleotide designs for detection of the let-7a miRNA in which the target specific regions of both the probe and INVADER oligonucleotides are 11 nucleotides long. SEQ ID NOs: 50-51 provide a design in which both the INVADER and probe oligonucleotides are linear. SEQ ID NO: 6 contains a probe oligonucleotide that forms a stem-loop structure); SEQ ID NO: 5, an INVADER oligonucleotide that forms a stem-loop structure); SEQ ID NOs: 5-6, both probe and INVADER oligonucleotides with stem-loops.

b. 10-mer Probe and 12-mer INVADER Oligonucleotide Designs

FIG. 5 shows a set of alternative oligonucleotide designs for detection of the let-7a miRNA in which the target specific regions of the probe comprise 10 nucleotides, and those of the INVADER oligonucleotides, 12 nucleotides. SEQ ID NOs: 52-53 provide a design in which both the INVADER and probe oligonucleotides are linear. SEQ ID NO: 2 contains a probe oligonucleotide that forms a stem-loop structure); SEQ ID NO: 1, an INVADER oligonucleotide that forms a stem-loop structure).

2. Temperature Optimization Profiles of Alternative Oligonucleotide Designs for Detection of the let-7a miRNA Temperature optimization experiments were carried out as follows. A master mix was made for 24 reactions. Each reaction contained the following:

| Stock concentration | Volume per reaction | Final concentration |
|---|---|---|
| 2.5 X Primary reaction buffer for the CLEAVASE XII enzyme (as described in Example 5) | 4 μl | 1 X |
| 10 μM probe* | 1 μl | 1 μM |
| 100 μM INVADER oligonucleotide* | 1 μl | 10 μM |
| 60 ng/μl CLEAVASE 12 | 0.5 μl | 30 ng |
| H$_2$O | 2.5 μl | N/A |
| 30 pM miRNA (for the 11-mer temperature optimizations) OR 10 nM miRNA (for the 10-mer probe/12-mer INVADER oligonucleotide temperature optimizations) | 1 μl | 3 pM OR 1 nM |
| 20 ng/μl tRNA (for no target controls only) | 1 μl | 2 ng |
| TOTAL | 10 μl | |

Figure 16:
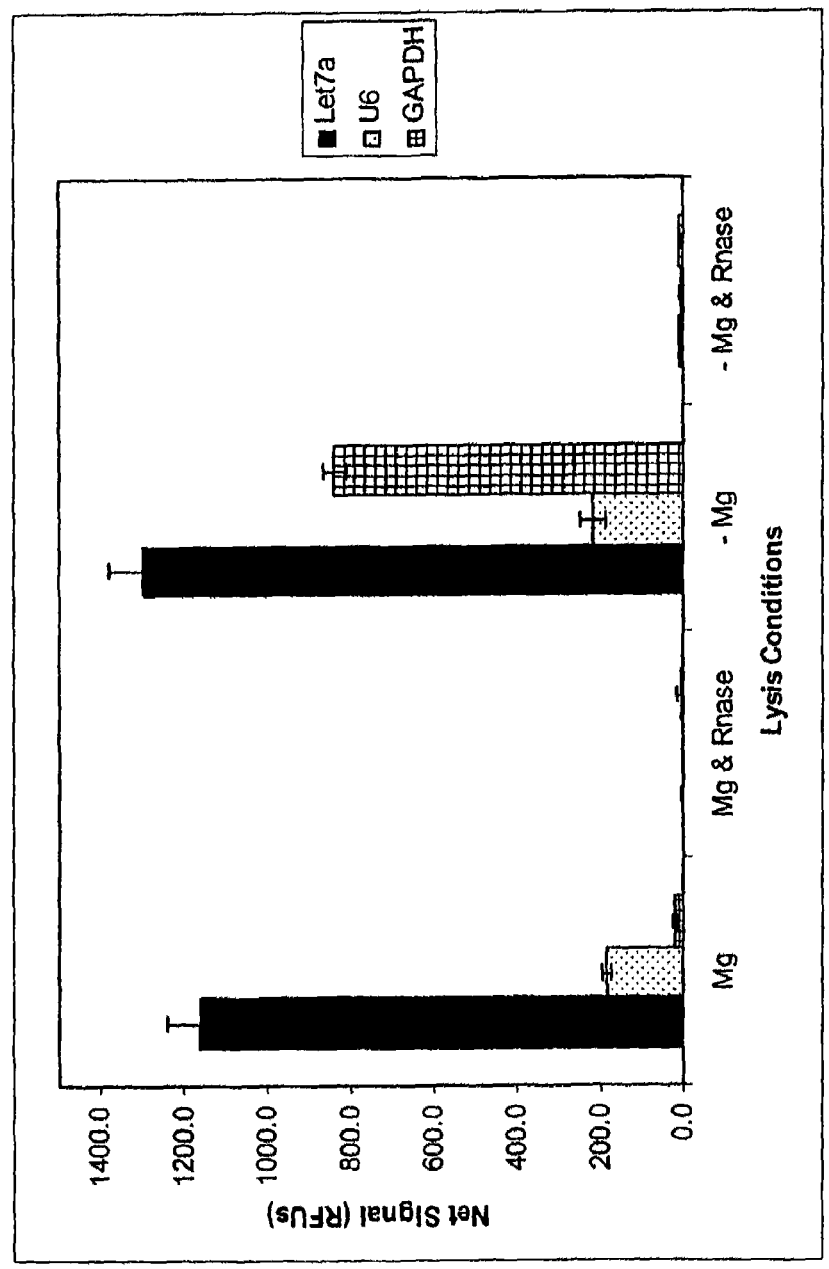
FIG. 16 shows the results of miRNA and mRNA in cell lysates with and without RNAse A treatment.
Figure 17:
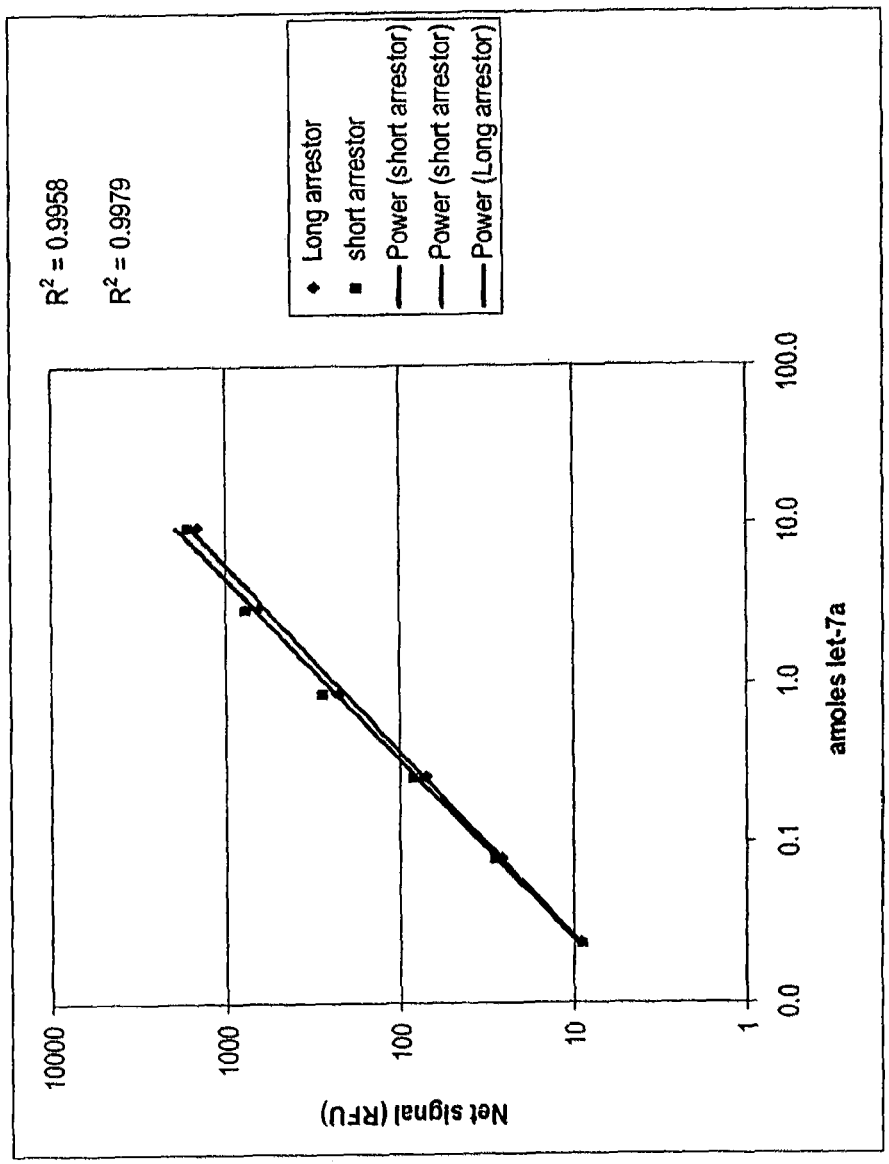
FIG. 17 shows results of invasive cleavage assays comparing the effects of including full-length vs. shortened ARRESTOR oligonucleotides.

*Various combinations of probe and INVADER oligonucleotides were used in this experiment as indicated in FIGS. 16-17.

Secondary reaction mixes were as described in Example 3 for let-7. Where appropriate, ARRESTOR sequences were made to compliment the entire loop and target specific regions of the probe and extending 6 bases toward the 5' end of the probe.

In the case of the 11-mer temperature optimization experiment, the primary reactions were run at 50±9° C. for 1 hour followed by a 15 minute secondary reaction at 60° C. as described in Example 2. As for the 10-mer probe, with the 12-mer INVADER oligo, the primary reactions were run at 50±9° C. for 15 minutes followed by a 15 minute secondary reaction at 60° C.

Results for the designs in which the target specific portions of the INVADER and probe oligonucleotides were 11 nucleotides long are presented in FIG. 18. FIG. 18A shows the temperature optimization profiles of each design. FIG. 18B shows the normalized maximum performance of each design, including the optimum temperature for each. Results for the designs in which the target specific portion of the probe oligonucleotide was 10 bases and that of the INVADER oligonucleotide was 12 are presented in FIG. 19. FIG. 19 A shows the temperature optimization profiles, and FIG. 19 B, the normalized maximum performance of each design.

Examination of these results suggests that which design results in maximum performance varies depending on both reaction conditions and the relative stability of the miRNA-oligonucleotide hybrid formed. For example, when the target specific regions of both oligonucleotides are 11 bases long, the probe target specific region has a predicted Tm of 49° C. and that of the INVADER, of 37° C. In this case, stabilization of the INVADER oligonucleotide-miRNA interaction confers improved assay performance on this design. However, for the let-7a designs in which probes were 10-mers and INVADER oligonucleotides, 12-mers, the target specific regions of the two oligonucleotides have approximately equivalent Tms. In this case, the design in which both oligonucleotides are looped works best.

3. LOD of let-7a Using Two Alternative Designs

Experiments were set up as described in Example 3 to compare the LOD of the double loop design and the single loop design, in which the INVADER oligonucleotide forms a stem-loop structure.

Figure 20:
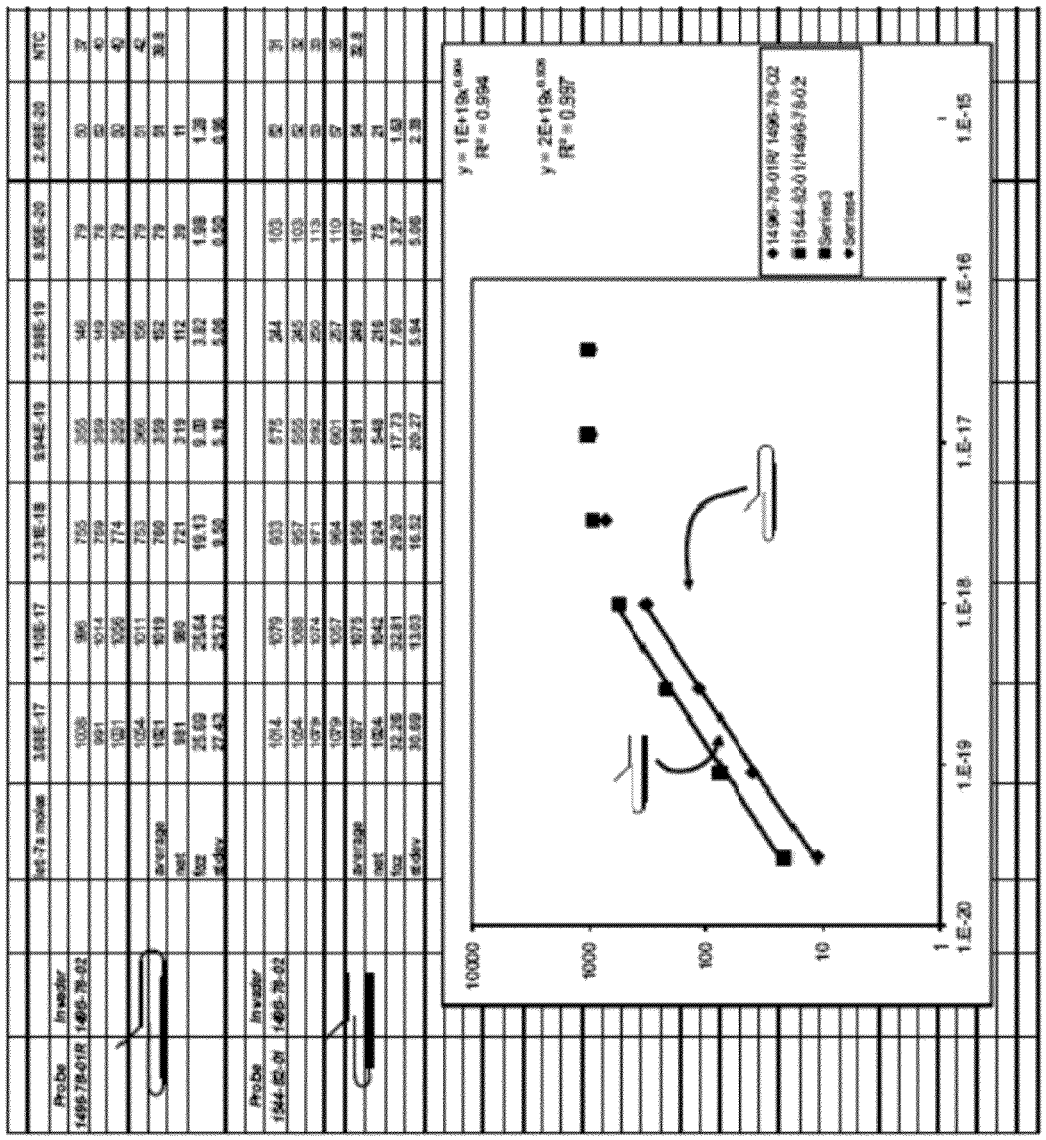
FIG. 20 shows the results of experiments to compare the LODs of two alternative oligonucleotide designs.

Reactions to determine LOD were run in quadruplicate. Reaction mixtures contained the following reagents (final concentrations):

| Stock concentration | Volume per reaction | Final concentration |
|---|---|---|
| 2.5 X Primary reaction buffer for CLEAVASE XII enzyme | 4 μl | 1 X |
| 10 μM probe/200 μM INVADER oligonucleotide mix (sequences as indicated in FIG. 20) | 0.5 μl | 1 μM probe/20 μM INVADER oligonucleotide |
| 60 ng/μl CLEAVASE XII enzyme | 0.5 μl | 30 ng |
| Total | 5 μl | |

Aliquots of 5 μl of miRNA were added to the wells containing the reaction mixtures at the final concentrations indicated in FIG. 20. Primary reactions were run for 1.5 hours at the optimal temperatures for each designed as determined in Example 8B (50° C. for the looped INVADER oligonucleotide design and 53° C. for the double loop design). The secondary reactions were set up as described in Examples 2 and 3 and run for 1 hour at 60° C.

The results in FIG. 20 show net signal produced as a function of moles of miRNA. The linear ranges of the plots indicated that more signal was produced from a given amount of miRNA using the INVADER loop design than from the double loop design. Similarly, an examination of the table in FIG. 20 indicates that the fold-over-zero values at each miRNA level are greater for the single loop design. Both designs resulted in sufficient FOZ at the lowest concentrations tested, 2.68×10$^{-20}$ moles, or 26.8 zeptomoles, equivalent to approximately 16,000 molecules.

4. Full Length vs. Shortened ARRESTOR Oligonucleotides

Experiments were conducted to evaluate the relative performance of full-length ARRESTOR molecules, e.g. as shown in FIGS. 4 and 12, in which the ARRESTOR molecules extend at their 5' ends around the loop, throughout the length of the miRNA-specific region of the probe and into the 5' flap region vs. shortened ARRESTOR molecules that are complementary only to the miRNA-specific region of the probe and part of the 5' flap but do not extend into the loop region or beyond. Reactions were set up as follows to detect synthetic let-7a miRNA:

| Component | Stock concentration | Amount added per reaction |
|---|---|---|
| PI mix (probe SEQ ID NO: 6; INVADER oligonucleotide SEQ ID NO: 5) | 10 μM probe 50 μM INVADER oligo | 1 μl |
| CLEAVASE XII enzyme | (60 ng/μl) | 0.5 μl |
| H$_2$O | | 0.5 μl |
| Primary Reaction Buffer | 2.5 X | 4 μl |
| Total | | 6 μl |

Aliquots of 6 μl of the primary reaction mix were added to the appropriate wells of a microtiter plate followed by aliquots of 4 μl of syntheticlet-7a miRNA or 4 μl of 10 ng/μl tRNA in dH$_2$O at the final concentrations indicated in the table below. Primary INVADER reactions were incubated at 53° C. for 1.5 hours.

Aliquots of secondary reaction mixtures were added as follows:

| Full-length ARRESTOR | | |
|---|---|---|
| Component | Stock concentration | Amount added |
| ARRESTOR SEQ ID NO: 7 for full length ARRESTOR, SEQ ID NO: 54 for shortened ARRESTOR | 40 µM | 1 µl |
| MO5 SRT (SEQ ID NO: 22) | 1.5 µM | 1 µl |
| FRET FAM (SEQ ID NO: 21) | 10 µM | 1 µl |
| H$_2$O | | 2 µl |

Secondary reactions were incubated at 60° C. for 1.5 hours. Microtiter plates were read as described in Example 2. The results were as shown in FIG. 17.

These results indicate that there is no significant different in signal generation or limit of detection when full-length or shortened ARRESTOR oligonucleotides complementary to the miRNA-specific portion of the probe are used in the secondary INVADER reaction.

B. Alternative Designs Using Linear Probe and INVADER Oligonucleotides

Alternative designs were tested in which both the probe and INVADER oligonucleotides contain a universal sequence, and neither oligonucleotide forms a hairpin. A schematic of the design is presented in FIG. 4. The universal sequence is present on the 5' end of the INVADER oligonucleotide and on the 3' end of the probe oligo. A short, complementary "capture" oligonucleotide is added and is comprised of 2'-O-methyl residues, allowing it to promote co-axial stacking in the presence of the miRNA (e.g. SEQ ID NO: 60). Designs were created for both miR-15 (SEQ ID NOs: 58-59 and 61) and mir-135 (SEQ ID NOs: 63-65). Initial designs, while leading to high non-specific background signal in the absence of miRNA target, nonetheless indicate that it is feasible to detect miRNAs with such universal capture oligonucleotides.

Example 9

Effect of 2'-O-methylation of Nucleotide Residues in the Loops

This example describes experiments aimed at assessing the effect of substituting 2'-deoxy residues for some or all of the 2'-O-methyl residues incorporated in the probe and INVADER oligonucleotides used for detecting miRNAs. All of the designs presented in the preceding examples include 2'-O-methyl residues in the loop regions as described in Example 2. Experiments were conducted to test the effect of substituting 2' deoxy residues for some or all of the 2'-O-methyl residues in the INVADER and probe oligonucleotides designed to detect the let-7a miRNA.

FIG. 5 shows the modified let-7a designs. SEQ ID NOs: 5-6 contain 2'-O-methyl residues as described in Example 2. The design in SEQ ID NOs: 73-74 contain 2'deoxy residues at all positions; and those in SEQ ID NOs: 75-76, 2'-O-methyl residues in the portions of the stems adjacent to the target.

INVADER reactions were set up to compare the signal generation and temperature optima of the three different designs. Reactions were as described in the LOD experiments in Example 8 and included 100 pM synthetic miRNA, 1 µM probe, and 10 µM INVADER oligonucleotide. Primary reactions were run for 15 minutes at the temperatures indicated; secondary reactions were run for 5 minutes at 60° C.

Figure 21:
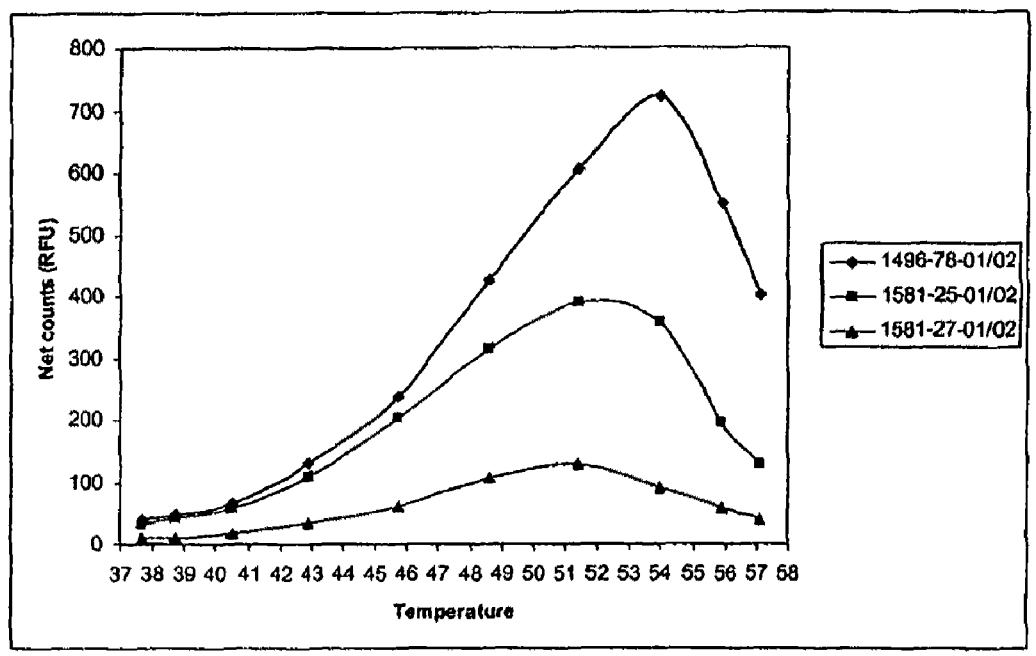
FIG. 21 shows results comparing the effects of substituting 2'-deoxy residues for some or all of the 2'-O-methyl residues in the probe and INVADER oligonucleotides.

The results of the INVADER assays are shown in FIG. 21 and indicate that the design in which the stem loop structures are comprised of 2'-O-methyl residues yields the most signal, followed by the design in which the bases adjacent to the target are comprised of 2'-O-methyl residues. The oligonucleotides comprised entirely of 2'-deoxy residues generated the lowest levels of signal.

A further set of experiments was designed to test additional design variations as follows: probe and INVADER oligonucleotides with shorter hairpins, probe and INVADER oligonucleotides with more stable loops or, alternatively with shorter loops, probe and INVADER oligonucleotides with only three 2'-O-methyl residues. Primary reactions were set up to test detection of miR-15 as follows.

The following probe/INVADER oligonucleotide combinations were tested.

| Probe | | INVADER oligo | |
|---|---|---|---|
| 1544-71-01 | SEQ ID NO: 55 | 1544-71-02 | SEQ ID NO: 56 |
| 1544-71-01 | SEQ ID NO: 55 | 1796-43-02 | SEQ ID NO: 68 |
| 1544-71-01 | SEQ ID NO: 55 | 1796-43-04 | SEQ ID NO: 70 |
| 1544-71-01 | SEQ ID NO: 55 | 1796-43-06 | SEQ ID NO: 72 |
| 1796-43-01 | SEQ ID NO: 67 | 1544-71-02 | SEQ ID NO: 56 |
| 1796-43-03 | SEQ ID NO: 69 | 1544-71-02 | SEQ ID NO: 56 |
| 1796-43-05 | SEQ ID NO: 71 | 1544-71-02 | SEQ ID NO: 56 |
| 1796-43-03 | SEQ ID NO: 69 | 1796-43-04 | SEQ ID NO: 70 |

Primary reaction mixes were made as follows.

| Primary Reaction Component | Stock Concentration | Amount Added |
|---|---|---|
| Probe oligonucleotide (as indicated in above table) | 40 µM | 0.25 µl |
| INVADER oligo | 40 µM | 0.25 µl |
| CLEAVASE XII enzyme | 60 ng/µl | 0.5 µl |
| Primary Reaction Buffer | 2.5 X | 4 µl |
| Total | | 5 µl |

Aliquots of 5 µl of Primary reaction mix were added to 5 µl of synthetic miR-15 RNA at the following final amounts: 0, 0.1 amole, 0.33 amole, 1.09 amole. Primary reactions were incubated at 52.5° C. for 2 hours.

Secondary reaction mixes were made as follows.

| Secondary reaction component | Concentration | Amount Added |
|---|---|---|
| FAM FRET oligonucleotide (SEQ ID NO: 21) and Secondary Reaction Target (SRT) (SEQ ID NO: 40) | 13.4 µl FAM FRET 2 µM SRT | 0.75 µl |
| ARRESTOR oligonucleotide (SEQ ID NO: 66) | 54 µM | 0.75 µl |
| H$_2$O | | 3.5 µl |
| Total | | 5 µl |

Aliquots of 5 µl were added and the reactions incubated at 60° C. for 45 minutes. The results, in relative fluorescent units (RFUs) are presented below.

| Probe<br>INVADER | 1544-71-01<br>1544-71-02 | | | NET | FOZ | | 1544-71-01<br>1796-43-02 | | | NET | FOZ |
|---|---|---|---|---|---|---|---|---|---|---|---|
| 1.09 amole | 655 | 658 | 662 | 566 | 7.13 | 1.09 amole | 706 | 738 | 777 | 636 | 7.12 |
| 0.33 amole | 314 | 262 | 256 | 185 | 3.00 | 0.33 amole | 281 | 287 | 290 | 182 | 2.75 |
| 0.10 amole | 122 | 138 | 134 | 39 | 1.42 | 0.10 amole | 149 | 150 | 153 | 47 | 1.45 |
| 0 amole | 88 | 93 | 96 | | | 0 amole | 104 | 101 | 107 | | |
| Probe<br>INVADER | 1796-43-01<br>1544-71-02 | | | NET | FOZ | | 1796-43-03<br>1544-71-02 | | | NET | FOZ |
| 1.09 amole | 1689 | 1744 | 1895 | 146 | 1.09 | 1.09 amole | 882 | 869 | 847 | 702 | 5.27 |
| 0.33 amole | 1655 | 1717 | 1817 | 99 | 1.06 | 0.33 amole | 335 | 341 | 341 | 175 | 2.06 |
| 0.10 amole | 1692 | 1693 | 1695 | 63 | 1.04 | 0.10 amole | 196 | 209 | 196 | 36 | 1.22 |
| 0 amole | 1636 | 1601 | 1654 | | | 0 amole | 169 | 165 | 159 | | |
| | 1544-71-01<br>1796-43-04 | | | NET | FOZ | | 1544-71-01<br>1796-43-06 | | | NET | FOZ |
| 1.09 amole | 676 | 688 | 693 | 579 | 6.43 | 1.09 amole | 625 | 562 | 579 | 501 | 6.69 |
| 0.33 amole | 274 | 275 | 264 | 164 | 2.54 | 0.33 amole | 229 | 215 | 204 | 128 | 2.45 |
| 0.10 amole | 153 | 137 | 143 | 38 | 1.35 | 0.10 amole | 126 | 121 | 112 | 32 | 1.36 |
| 0 amole | 111 | 107 | 102 | | | 0 amole | 94 | 87 | 83 | | |
| | 1796-43-05<br>1544-71-02 | | | NET | FOZ | | 1796-43-05<br>1796-43-06 | | | NET | FOZ |
| 1.09 amole | 806 | 824 | 773 | 708 | 8.64 | 1.09 amole | 772 | 752 | 704 | 631 | 6.65 |
| 0.33 amole | 280 | 280 | 262 | 181 | 2.96 | 0.33 amole | 260 | 252 | 251 | 143 | 2.28 |
| 0.10 amole | 144 | 145 | 139 | 50 | 1.54 | 0.10 amole | 140 | 142 | 139 | 29 | 1.26 |
| 0 amole | 91 | 95 | 92 | | | 0 amole | 115 | 109 | 111 | | |

These results suggest that the designs in which the probe oligonucleotide contained a shortened hairpin and a highly stable tetra-loop comprised of 2'-O-methyl residues in combination with the original INVADER oligonucleotide design (2'-O-methyl residues, TTTT loop, long hairpin) may generate a somewhat higher FOZ value. Otherwise, none of the alternative design oligonucleotide sets offered any improvement over the original designs. It is noteworthy that the combination of an all-DNA INVADER oligonucleotide with the original chimeric probe oligonucleotide gave FOZ values approximately equivalent to those obtained with both chimeric probe and INVADER oligonucleotides. In some applications, substitution of an all DNA INVADER oligonucleotide may be desirable to reduce oligonucleotide synthesis costs and may be made without sacrificing limit of detection.

Further experiments demonstrated that it is possible to compensate for sub-optimal signal generation with particular oligonucleotide sets by adding more RNA (e.g. lysate, purified total RNA, synthetic miRNA) to the reaction. Similarly, additional experiments in which various oligonucleotides (i.e. probe, INVADER, ARRESTOR, or various combinations thereof) were gel purified as described in Example 1 indicated that standard gel purification of all three types of oligonucleotides gives maximal signal. It is possible to achieve signal levels approximately equal to the maximal levels with gel purified probes if the other oligonucleotides, i.e. the INVADER and ARRESTOR oligonucleotides, are desalted following synthesis.

Example 10

Detection of miRNA Expression in Total RNA from Multiple Tissue Types

This example describes experiments carried out to test the suitability of the INVADER assay to detect different miRNA species in total RNA extracted from diverse tissue types. In order to evaluate tissue specific gene expression, temperature optima and LODs were first determined for each design.

1. INVADER and Probe Oligonucleotide Designs

INVADER assay oligonucleotides were designed to detect the miR-15, miR-16, and miR-125b miRNA species. The designs for these assays are presented in FIG. 5. The designs for let-7a and miR-135 are described in Examples 2 and 6, respectively.

2. Determination of Temperature Optima and LODs

Temperature optimization experiments were conducted for each of these oligonucleotide sets as described in Example 8. Each primary reaction included 1 nM of the targeted miRNA and was carried out for 15 minutes at temperatures ranging from 50±9° C. Secondary reactions were as described in Example 2 and were run for 1 to 1.5 hours at 60° C. Optimum temperatures were as follows:

| | |
|---|---|
| let-7a | 53° C. |
| miR-15 | 53° C. |
| miR-16 | 56° C. |
| MiR-125b | 52° C. |
| MiR-135 | 45° C. |

Once the temperature optima were obtained, LODs were determined for each miRNA species as described in Example 8. All LODs were ≦30 zeptomoles.

3. Gene Expression Profiling

Gene expression profiling was carried out on total RNA extracted from 20 different tissue types. Total RNA was purchased from Clontech (Palo Alto, Calif., catalog number K4008-1, Human Total RNA Master Panel II). For let-7a, 50 ng of total RNA was tested in each reaction; for the other miRNA species, 100 ng of total RNA was tested. All reactions were set up as described in Example 8; primary reactions were run at the temperature optima for 1.5 hours; secondary reactions were as described above. The gene expression profiles for each miRNA species are presented in FIG. 23. These results indicate that the INVADER assay can be used to examine miRNA expression in different tissue types. These data further suggest that let-7a and miR-125b are expressed in a wide variety of tissues; the other miRNA species appear to be more specific to a limited number of tissue types.

Example 11

Effects of Variable Oligonucleotide Length on INVADER Assay Detection of miRNA

This example describes the impact of alterations in probe and INVADER oligonucleotide length on detection of the let-7a 22-nt miRNA. In particular, these experiments compare detection of an miRNA that forms perfect stacking interactions between the ends of the probe and INVADER oligonucleotides to detection of an miRNA that forms both 5' and 3' overlaps as well as to one that results in a single nucleotide gap at both the 5' and 3' ends.

FIG. 24 shows the results of analyzing three different types of designs. SEQ ID NOs: 5-6 shows a perfect stack between the 22-nt target and the flanking ends of the looped probe and INVADER oligonucleotides. In SEQ ID NOs: 83-84, both the probe and INVADER oligonucleotides are extended by a single base, resulting in both 5' and 3' overlaps. In SEQ ID NOs: 85-86, both the probe and INVADER oligonucleotides are shortened by a single base, relative to the designs in SEQ ID NOs: 5-6, resulting in a single nucleotide gap at both ends.

INVADER assays were set up to test the performance of these oligonucleotide sets for detection of synthetic let-7a miRNAs. Reactions were carried out as described in Example 8 and included 100 pM synthetic let-7a miRNA, 1 μM probe and 10 μM INVADER oligonucleotide. Primary reactions were run for 15 minutes at 53° C.; secondary reactions, for 5 minutes at 60° C., as described in Example 2. The results are presented in FIG. 24.

These data indicate that in this experiment, a single nucleotide overlap at both ends of the miRNA target resulted in an approximately 30% decrease in signal generation as well as a reduction of 2° C. in optimal temperature. A one nucleotide gap at both ends of the target, however, did not reduce signal generation, though it did reduce the optimal reaction temperature by 5° C.

Example 12

Discrimination of miRNA from Precursor RNA and from Encoding DNA

Experiments were carried out to determine whether the INVADER miRNA assay discriminated the miRNA target itself from both its precursor RNA and from the DNA encoding the miRNA.

A. Precursor Cross-reactivity Test

Precursor let-7 RNA (SEQ ID NO: 87) was transcribed in vitro and analyzed by capillary electrophoresis to determine whether it contained any fragments that might mimic the let-7a miRNA. The shortest contaminating fragment was estimated to be approximately 45 nt. LOD reactions were run essentially as described in Example 3 at precursor or synthetic 5' P let-7a mi-RNA concentrations as indicated in the table below. PI mixes contained 10 μM probe SEQ ID NO: 6 and 100 μM INVADER oligonucleotide SEQ ID NO: 5. Primary reactions were run at 53° C. for 1 hour; secondary reactions were run at 58° C. for 1 hour with secondary reaction mixes essentially as described in Example 3 (FRET probe SEQ ID NO: 21, SRT SEQ ID NO: 22, and ARRESTOR SEQ ID NO: 7). The results of this experiment indicated that this miRNA assay is approximately 4% cross reactive vs. the precursor RNA.

B. Discrimination of RNA vs. DNA Signal

Reactions were run to detect let-7a miRNA in cell lysates as described in Example 7. Prior to detection with the INVADER assay, aliquots 1 μl of 8 μg/μl RNAse A (Qiagen, Inc.) were added to 80 μl of cell lysate and incubated at 37° C. for 2.25 hours. The RNAse A treated samples failed to generate any signal above background, indicating that signal generated in assays lacking RNAse A arises from detection of the miRNA target and not the encoding DNA (FIG. 16). Further experiments were carried out in which RNAse A was added either prior to the primary reaction or prior to the secondary reaction. When RNAse A was added prior to the primary reaction, no signal was generated, consistent with the previous results. When RNAse A was added subsequent to the primary reaction, no loss of signal was observed, further indicating that the signal being detected is due to RNA and that there is no adverse effect of RNAse on other reaction components, e.g. the CLEAVASE enzyme.

Example 13

Detection of a Dual Form miRNA

Oligonucleotide designs were created for miR-124a. These oligonucleotides can be used to detect two naturally occurring miRNAs—one 21 nt in length and the other, 22 nt.

Figure 22:
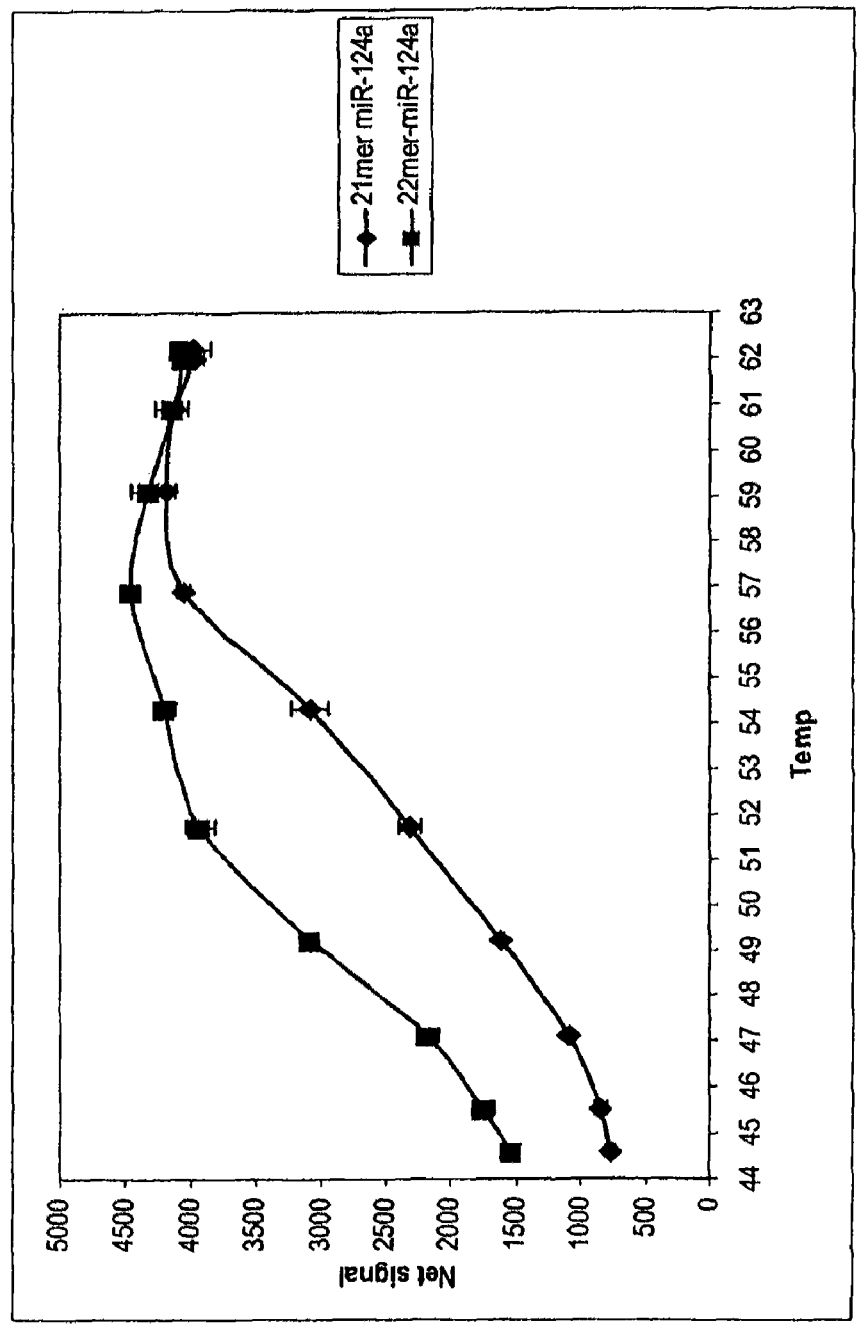
Figure 23A:
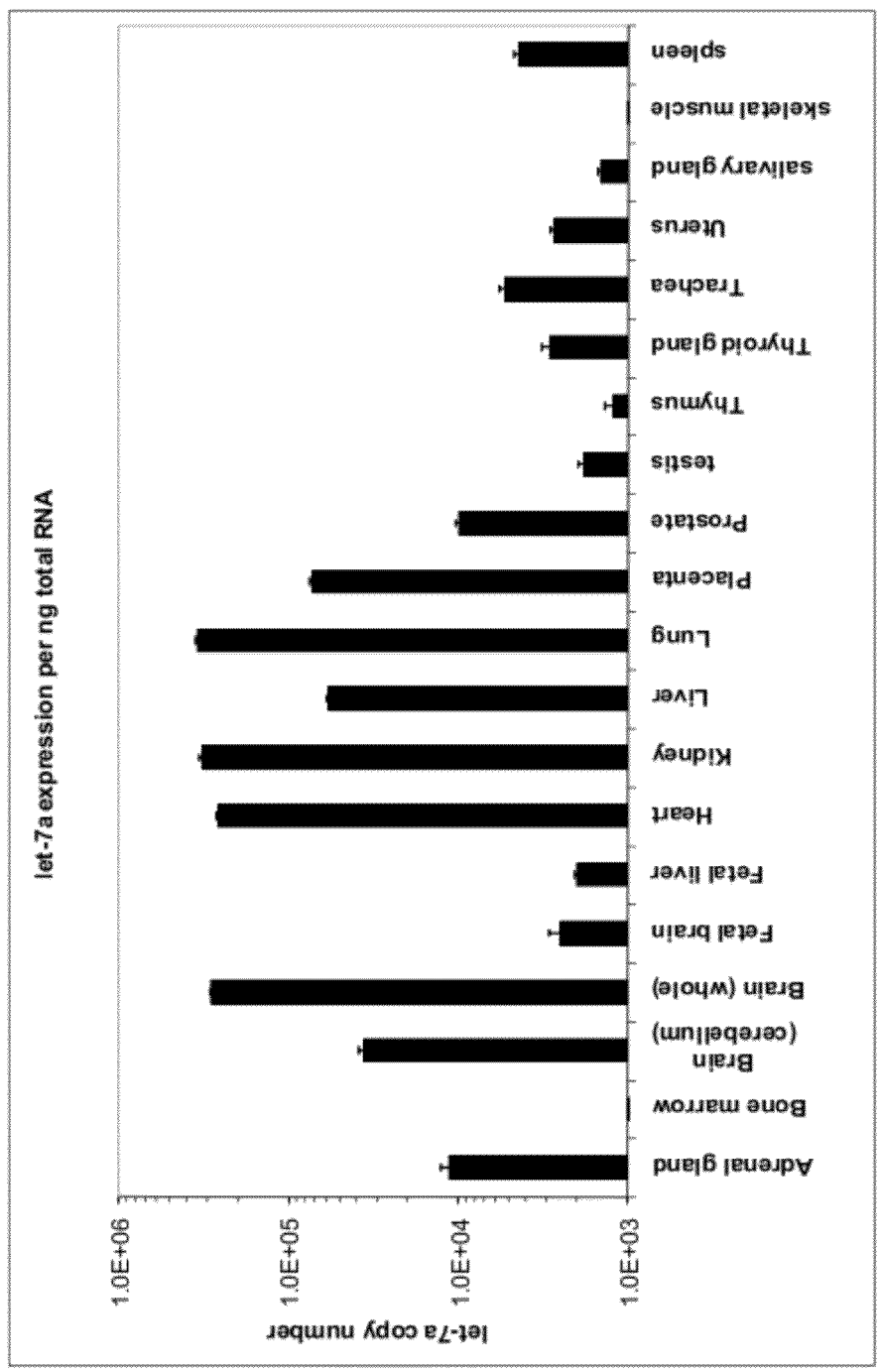
FIG. 23 shows the results of experiments to detect five different miRNA species in total RNA isolated from 20 different tissue types.
Figure 23B:
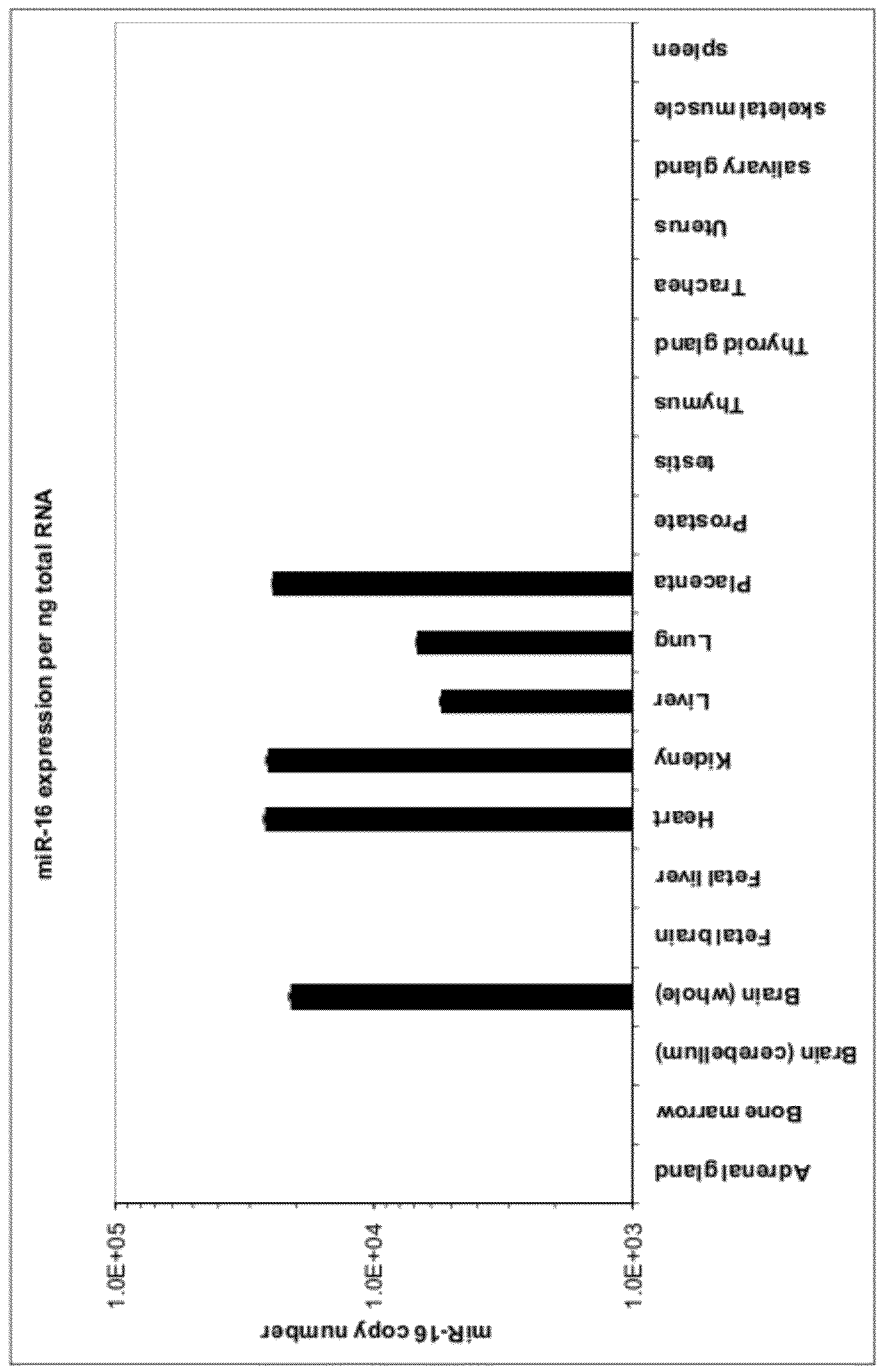
Figure 23C:
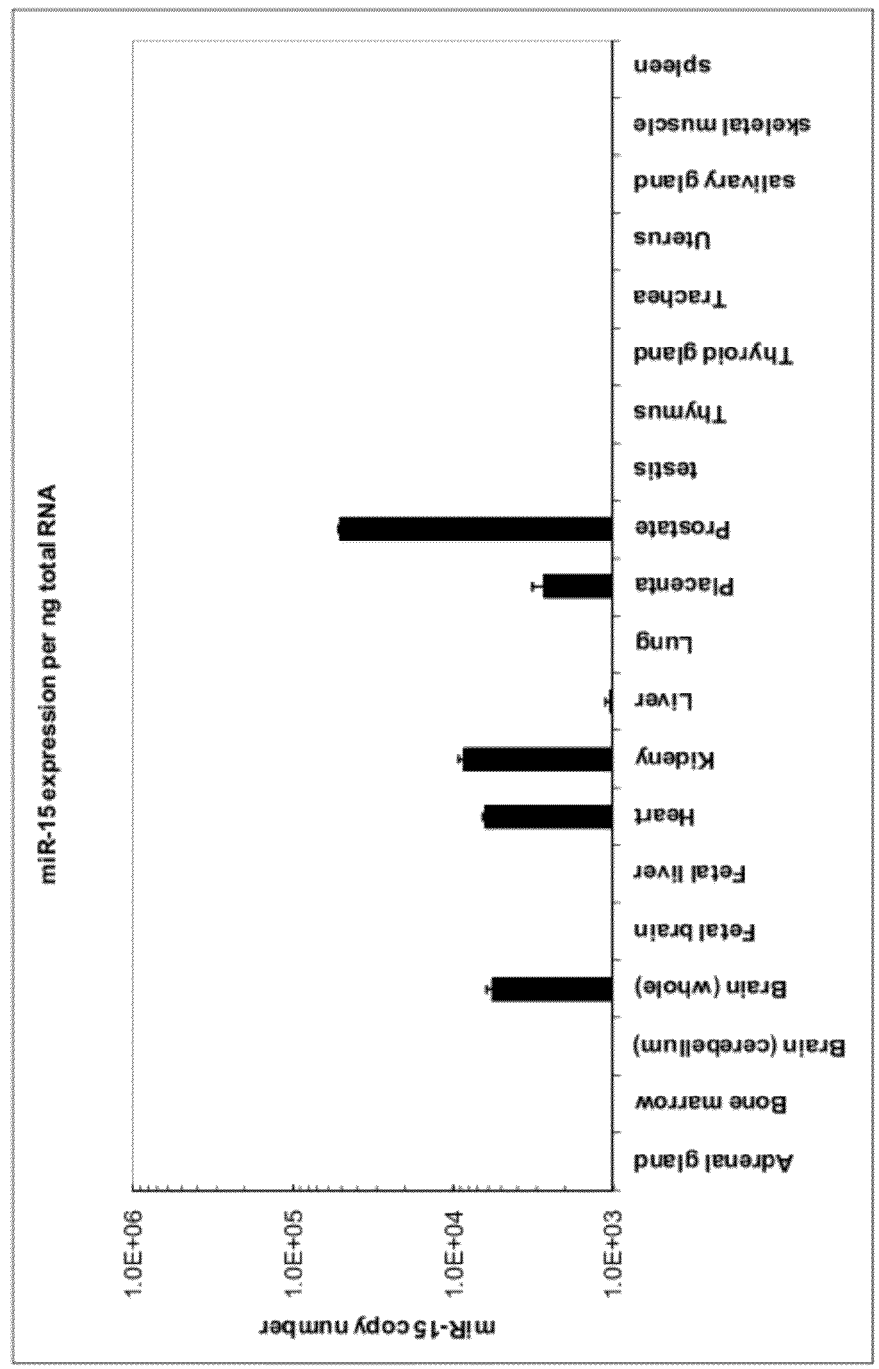
Figure 23D:
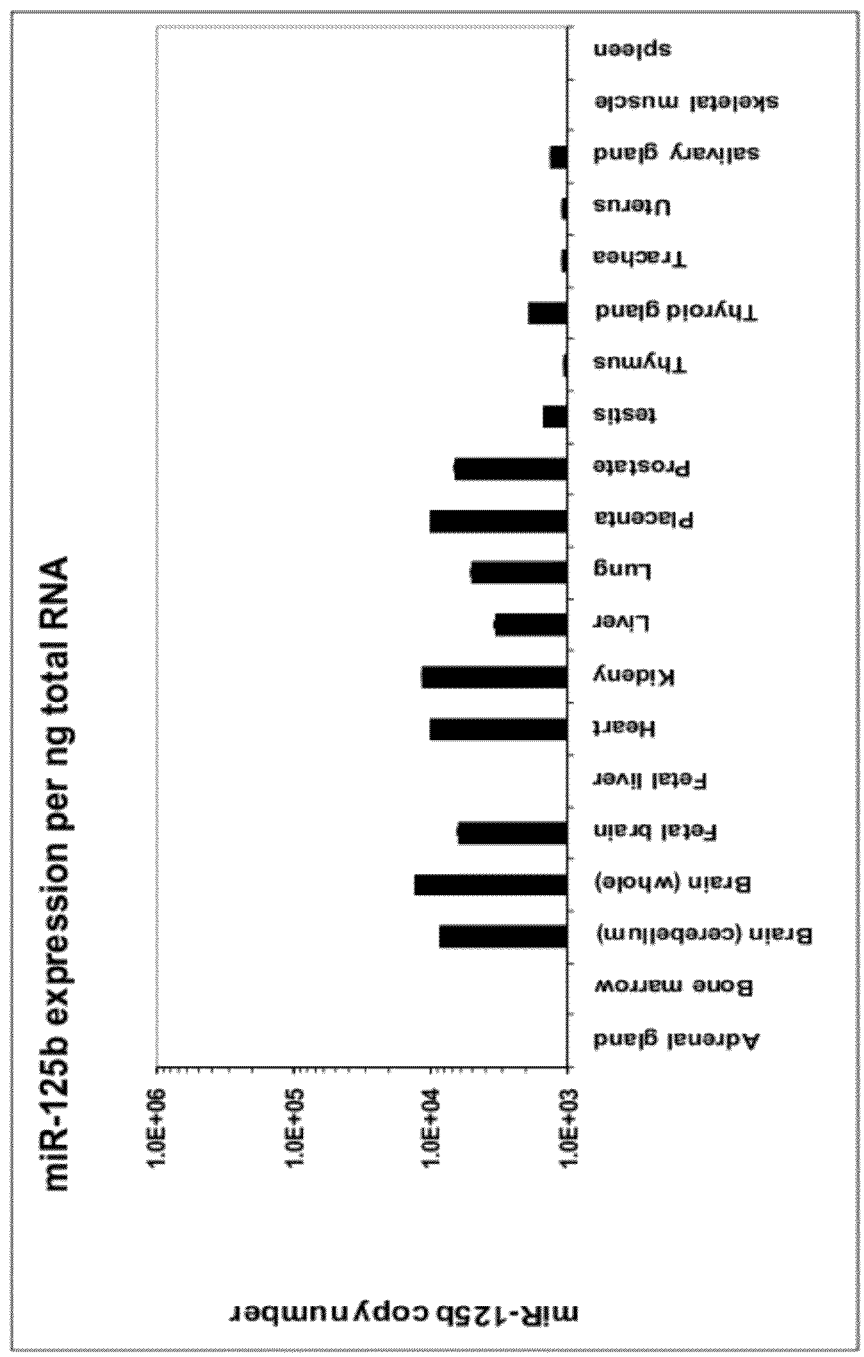

Temperature optimization reactions were set up, essentially as described in Example 3, using 1 nM of synthetic miRNA target, 25 primary reaction and a 15 minute secondary reaction. The oligonucleotides used in these reactions are listed in FIG. 5 (SEQ ID NOs: 90-92). Temperature profiles for the two different length miRNA targets are shown in FIG. 22 and indicate that the same oligonucleotide designs can be used to detect both targets.

Example 14

Oligonucleotide Designs for Detection of an siRNA

Approaches similar to those described in the preceding examples may similarly be used to detect siRNAs. FIG. 25 illustrates two alternative INVADER assay designs for detection of a β-actin siRNA. This siRNA is described in Harborth, J. et al., Journal of Cell Science, 114: 4557-4565 (2001). One design is presented for each the sense and antisense strands; exemplary oligonucleotides for detecting this siRNA are listed in FIG. 26, SEQ ID Nos: 101-106.

Example 15

Optimization to Extend the Dynamic Range of let-7a miRNA Detection

In an attempt to extend the dynamic range of let-7a miRNA INVADER assay detection, two oligonucleotide probes with the same let-7a hybridizing-region were designed, but with different 5'-flap "arm" sequences. The different 5'-flaps or arms report to FRET cassettes that are designed to generate FAM signal upon cleavage. The oligonucleotide sequences were as follows ("Z28" refers to the ECLIPSE quencher, Nanogen, Inc., San Diego, Calif.):

Primary Let-7a INVADER reactions were setup in 10 uL reactions for a total of nine probe concentration conditions. The nine probe concentration conditions tested were: (i) 1 µM of probe 1544-82-01, (ii) 1 µM of probe 2343-25-01, (iii) 1 µM or both probes 1544-82-01 and 2343-25-01, (iv) 100 nM of probe 2343-25-01, (v) 1 µM of probe 1544-82-01 and 100 nM of 2343-25-01, (vi) 10 nM of 2343-25-01, (vii) 1 µM of 1544-82-01 and 10 mM of 2343-25-01, (vii) 4 nM of 2343-25-01, and (ix) 1 µM of 1544-82-01 and 4 nM of 2343-25-01. In addition to these probe oligo concentrations, the reactions contained 1 µM of INVADER oligo 1496-78-02, 30 ng of CLEAVASE XII enzyme, and 10 mM MOPS pH 7.5, 25 mM KCl, 0.05% Tween 20, 0.05% Nonidet P40, 25 mM MgSO4, and 2% PEG.

For each probe concentration conditions, Let-7a synthetic RNA were added to the reaction mix at final concentrations of $6\times10^9$, $6\times10^8$, $6\times10^7$, $6\times10^6$, $6\times10^5$, $6\times10^4$, $6\times10^3$, and 0 copies per reaction. Let-7a RNA dilutions were made in a solution of 20 ng/µl tRNA diluted in Rnase-free water. The

Figure 26:
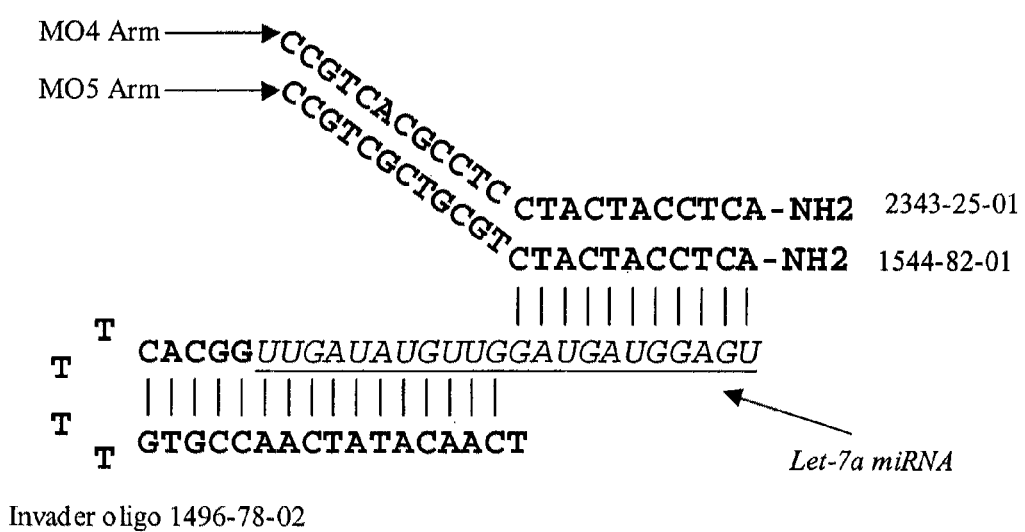
FIG. 26 shows two probes with the same let-7a hybridizing-region but with different 5'-flap "arm" sequences. Let-7a is SEQ ID NO:275; 1496-78-02 is SEQ ID NO:145; 2343-25-01 is SEQ ID NO:196; 1544-82-01 is SEQ ID NO:146.

| Sequence Number | Description | Sequence 5'-3' | Notes |
|---|---|---|---|
| 1544-82-01 (SEQ ID NO: 124) | Probe MO5 Arm | CCGTCGCTGCGTCTACTACCTCA-NH2 | |
| 2343-25-01 (SEQ ID NO: 125) | Probe MO4 Arm | CCGTCACGCCTCCTACTACCTCA-NH2 | |
| 1496-78-02 (SEQ ID NO: 126) | INVADER oligo | mGmGmCmAmCmUmUmUmUmGmUmGmCmCAACTATACAACT | m = 2'-O-methyl |
| 1581-63-01 (SEQ ID NO: 127) | Arrestor for MO5-arm probe | mUmGmAmGmGmUmAmGmUmAmGmAmCmGmCmAmG | m = 2'-O-methyl |
| 2343-25-02 (SEQ ID NO: 128) | Arrestor for MO4-arm probe | mUmGmAmGmGmUmAmGmUmAmGmGmAmGmGmCmG | m = 2'-O-methyl |
| 23-182 (SEQ ID NO: 129) | FAM FRET probe for MO5 SRT | YCACXTGCTTCGTGG | Y = 6FAM, X = Z28 quencher |
| 2343-23-01 (SEQ ID NO: 130) | FAM FRET probe for MO4 SRT | YCACXTCGAACGTCG | Y = 6FAM, X = Z28 quencher |
| 2343-23-02 (SEQ ID NO: 131) | MO4 SRT | CGAGGTTCGAAGTGGAGGCGTGACmGmGmU | |
| 1107-10-02 (SEQ ID NO: 132) | MO5 SRT | CCAGGAAGCAAGTGACGCAGCGACmGmGmU | |
| Let-7a (SEQ ID NO: 133) | Let-7a synthetic RNA | UGAGGUAGUAGGUUGUAUAGUU | | and are shown in FIG. 26. Reaction conditions tested were as follows:

| | |
|---|---|
| 2.5 X Reaction Buffer | 25 mM MOPS pH 7.5, 62.5 mM KCl, 0.125% Tween 20, 0.125% Nonidet P40, 62.5 mM MgSO4, 5% PEG. |
| tRNA Carrier | 20 ng/ul tRNA yeast in RNase free water |
| CLEAVASE XII enzyme | 60 ng/ul CLEAVASE XII enzyme diluted in 20 mM Tris pH 8.0, 50 mM KCl, 0.5% Tween 20, 0.5% Nonidet P40, 50% glycerol, 0.1 mg/ml BSA. | reactions were assembled in a 96-well plate and 10 µl of clear mineral oil were added to each well to prevent evaporation. The plate was then transferred to a thermal-block and incubated at 49° C. for 90 minutes.

After incubation was complete, 5 µL of a secondary reaction mix containing 0.3 µM of secondary reaction templates 1107-10-02 and 2343-23-01, 8 µM of ARRESTOR oligonucleotides 1581-63-01 and 2343-25-$O_2$, and 2 µM of FRET probes 23-182 and 2343-23-01 were added and the reaction plate incubated at 60° C. for 90 minutes. After completion of the reaction, the plate was transferred to a fluorescent plate reader (Cytofluor) and data was acquired by reading the fluorescence using the an excitation and emission wavelengths of 485 nm and 535 nm, respectively with a gain setting of 43.

The raw and processed date generated was as follows:

| 1- Raw data | | | | | | | | | |
|---|---|---|---|---|---|---|---|---|---|
| Let-7a | | | | Probe conc Mix # | | | | | |
| copies | i | ii | iii | iv | v | vi | vii | viii | ix |
| $6 \times 10^9$ | 21731 | 16970 | 35383 | 18062 | 36419 | 19680 | 33594 | 19297 | 28291 |
| $6 \times 10^8$ | 20369 | 14201 | 29797 | 16429 | 35792 | 18103 | 28532 | 18419 | 25425 |
| $6 \times 10^7$ | 19752 | 3772 | 7247 | 15969 | 32775 | 15128 | 22546 | 10576 | 21604 |
| $6 \times 10^6$ | 11535 | 997 | 1452 | 4548 | 13603 | 3419 | 11830 | 1998 | 10654 |
| $6 \times 10^5$ | 3500 | 726 | 787 | 1254 | 2941 | 1084 | 2759 | 923 | 2540 |
| $6 \times 10^4$ | 1415 | 638 | 675 | 751 | 1053 | 750 | 972 | 726 | 1050 |
| $6 \times 10^3$ | 840 | 652 | 665 | 666 | 841 | 671 | 770 | 690 | 756 |
| $6 \times 10^0$ | 638 | 635 | 637 | 661 | 800 | 658 | 731 | 694 | 698 |

Figure 27:
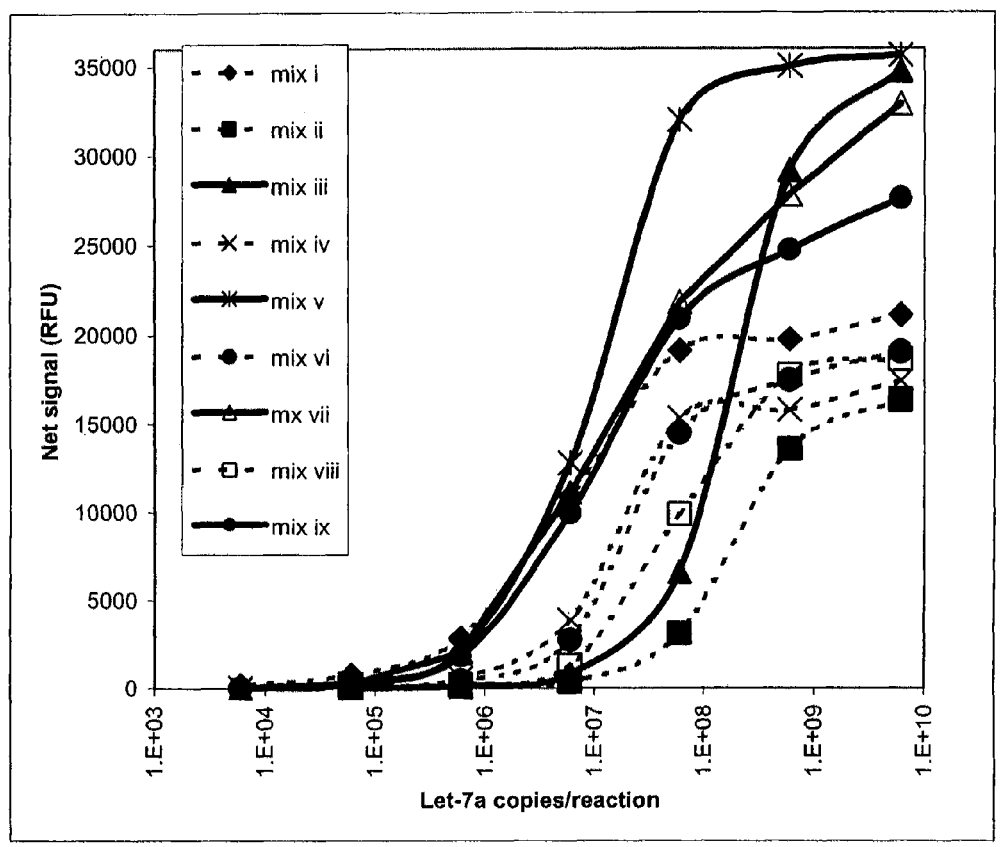
FIG. 27 shows a chart depicting copy number versus net signal for probes 1544-82-01 and 2343-25-01 are mixed at a 1 µM and 10 nM (mix vii) and 1 µM and 4 nM mix (ix), respectively.

| 2- Processed data | | | | | | | | | |
|---|---|---|---|---|---|---|---|---|---|
| Let-7a | | | | Probe conc Mix # | | | | | |
| copies | i | ii | iii | iv | v | vi | vii | viii | ix |
| $6 \times 10^9$ | 21093 | 16335 | 34746 | 17401 | 35619 | 19022 | 32863 | 18603 | 27593 |
| $6 \times 10^8$ | 19731 | 13566 | 29160 | 15768 | 34992 | 17445 | 27801 | 17725 | 24727 |
| $6 \times 10^7$ | 19114 | 3137 | 6610 | 15308 | 31975 | 14470 | 21815 | 9882 | 20906 |
| $6 \times 10^6$ | 10897 | 362 | 815 | 3887 | 12803 | 2761 | 11099 | 1304 | 9956 |
| $6 \times 10^5$ | 2862 | 91 | 150 | 593 | 2141 | 426 | 2028 | 229 | 1842 |
| $6 \times 10^4$ | 777 | 3 | 38 | 90 | 253 | 92 | 241 | 32 | 352 |
| $6 \times 10^3$ | 202 | 17 | 28 | 10 | 41 | 13 | 39 | −4 | 58 | and is presented in FIG. 27.

Results demonstrate that a dynamic range of >6 logs was achieved when probes 1544-82-01 and 2343-25-01 are mixed at a 1 mM and 10 nM (mix vii) and 1 mM and 4 nM mix (ix), respectively.

Example 16

Optimization to Extend the Dynamic Range of U6 RNA Detection

In an attempt to extend the dynamic range of U6 RNA detection using the INVADER assay, two oligonucleotide probes with the same U6 RNA hybridizing-region, but with different 5'-flap "arm" sequences were designed. The different 5'-flaps or arms report to FRET cassettes that are designed to generate RED signal upon cleavage. The oligonucleotide sequences were as follows (RED dye refers to REDMOND RED, Nanogen Inc, San Diego, Calif.):

| Sequence Number | Description | Sequence 5'-3' | Notes |
|---|---|---|---|
| 1796-53-01 (SEQ ID NO: 134) | Probe 562-86B Arm | ccgccgagatcacCTAATCTTCTCTGTAT-NH2 | |
| 2343-30-01 (SEQ ID NO: 135) | Probe ER4 arm | AAGCACGCAGCACCTAATCTTCTCTGTAT-NH2 | |
| 1796-59-01 (SEQ ID NO: 136) | U6 synthetic target | rUrUrUrArUrArCrArGrArGrArArGrArUrUrArGrCrArUrGrGrCrCrCrUrG rCrGrCrArArGrGrArUrGrUrUrU | |
| 1796-53-02 (SEQ ID NO: 137) | INVADER oligo | CATCCTTGCGCAGGGGCCATGA | |
| 1796-53-03 (SEQ ID NO: 138) | Arrestor for probe 1796-53-01 | mAmUmAmCmAmGmAmGmAmAmGmAmUmUmAmGmGmumGmA mUmC | m = 2'-O-methyl |
| 2343-30-04 (SEQ ID NO: 139) | Arrestor for probe 2343-30-01 | mAmUmAmcmAmGmAmGmAmAmGmAmUmUmAmGmGmUmGmC mUmG | m = 2'-O-methyl |

-continued

Figure 28:
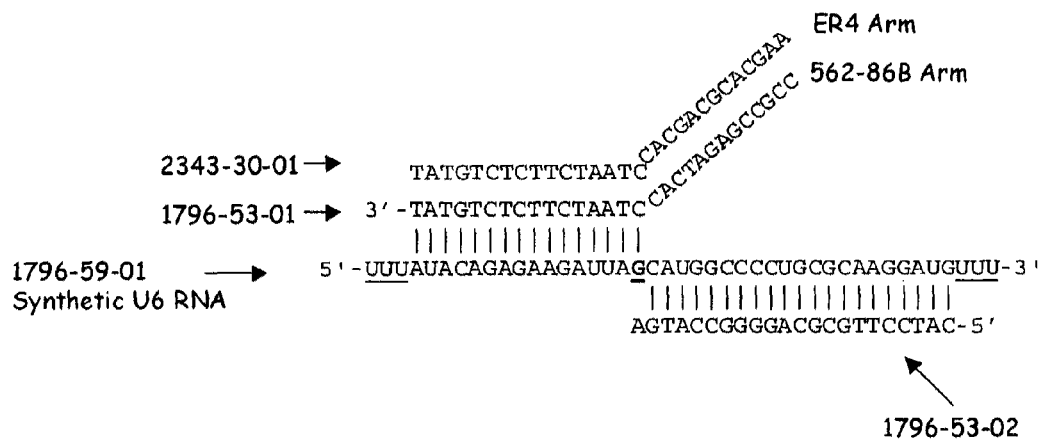
FIG. 28 shows two oligonucleotide probes with the same U6 RNA hybridizing-region but with different 5'-flap "arm" sequences. 1796-59-01 is SEQ ID NO:164; 2343-30-01 is SEQ ID NO:223; 1796-53-01 is SEQ ID NO:161; 1796-53-02 is SEQ ID NO:162.

| Sequence Number | Description | Sequence 5'-3' | Notes |
|---|---|---|---|
| 23-181 (SEQ ID NO: 140) | RED FRET probe for 562-86B arm | YCTCXTTCTCAGTGCG | y = Red dye and x = Z28 |
| 2343-30-02 (SEQ ID NO: 141) | RED FRET probe for ER4 arm | YCTCXTGCATAGTCCG | y = Red dye and x = Z28 |
| 23-183 (SEQ ID NO: 142) | 562-86B SRT | CGCAGTGAGAATGAGGTGATCTCGGCmGmGmU | |
| 2343-30-03 (SEQ ID NO: 143) | ER4 SRT | CGGAGTATGCATGAGGTGCTGCGTGCmUmUmU | | and are shown in FIG. 28.

The reaction conditions were as follows:

| | Reagents: |
|---|---|
| Reaction Buffer | 25 mM MOPS pH 7.5, 62.5 mM KCl, 0.125% Tween 20, 0.125% Nonidet P40, 62.5 mM MgSO4, 5% PEG. |
| tRNA Carrier | 20 ng/ul tRNA yeast in RNase free water |
| CLEAVASE XII enzyme | 60 ng/ul CLEAVASE XII enzyme diluted in 20 mM Tris pH 8.0, 50 mM KCl, 0.5% Tween 20, 0.5% Nonidet P40, 50% glycerol, 0.1 mg/ml BSA. |

Primary INVADER reactions were setup in 10 µL volumes containing probe concentrations of 1 µM of 1796-53-01, 4 nM of probe 2343-30-01, or 1 µM and 4 nM of 1796-53-01 and 2343-30-01, respectively. In addition, these reactions contained 1 µM of INVADER oligo 1796-53-02, 30 ng of CLEAVASE XII enzyme, and 10 mM MOPS pH 7.5, 25 mM KCl, 0.05% Tween 20, 0.05% Nonidet P40, 25 mM MgSO4, and 2% PEG.

For each probe concentration conditions, U6 synthetic RNA were added to the reaction mix at final concentrations of $102 \times 10^9$, $102 \times 10^8$, $102 \times 10^7$, $102 \times 10^6$, $102 \times 10^5$, $102 \times 10^4$, $102 \times 10^3$, 10,200, 5,100, 2,550, and 0 copies per reaction. U6 synthetic RNA dilutions were made in a solution of 20 ng/ul tRNA diluted in Rnase-free water. Reactions were assembled in a 96-well plate and 10 ul of clear mineral oil were added to each well to prevent evaporation. The plate was then transferred to a thermal-block at incubated at 50° C. for 90 minutes.

After incubation is complete, 5 µL of a secondary reaction mix containing 0.3 µM of secondary reaction templates 23-183 and 2343-30-02, 7.5 µM of ARRESTOR oligonucleotides 1796-53-03 and 2343-30-04, and 1.5 µM of FRET probes 23-181 and 2343-30-02 and the reaction plate was then incubated at 60° C. for 90 minutes. After completion of the reaction, the plate was transferred to a fluorescent plate reader (Cytofluor) and data was acquired by reading the fluorescence using the an excitation and emission wavelengths of 560 nm and 620 nm, respectively with a gain setting of 45.

Figure 29:
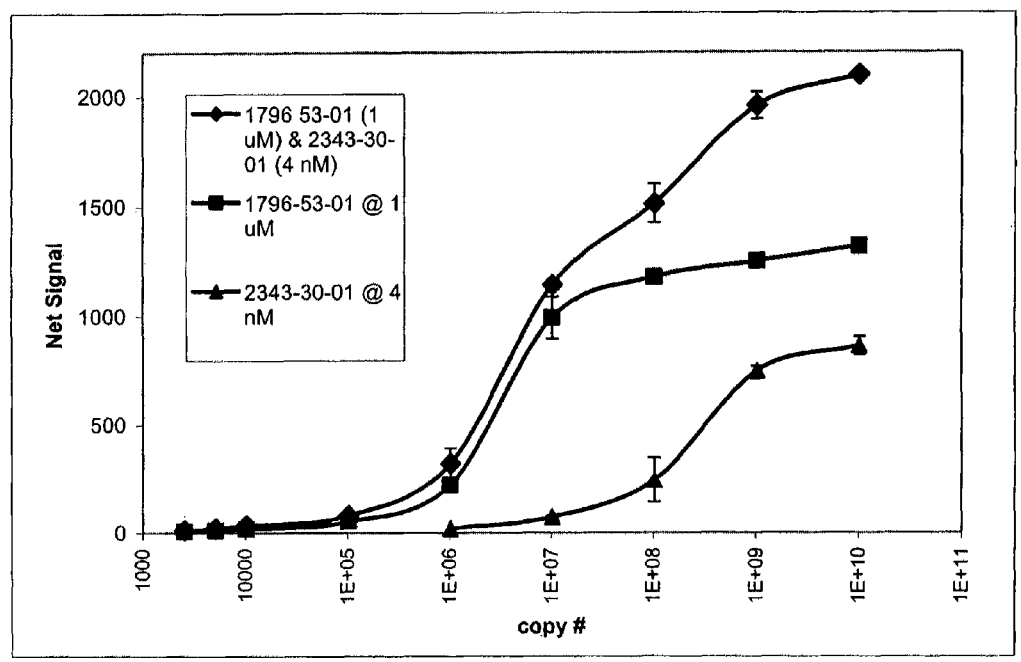
FIG. 29 shows a chart depicting copy number versus net signal plots for probes 1796-53-01 and 2343-30-01 are mixed at a 1 µM and 4 nM mix, respectively.

The data generated was as follows:

| Probe | conc | U6 copies/ rxn | $102 \times 10^9$ | $102 \times 10^8$ | $102 \times 10^7$ | $102 \times 10^6$ | $102 \times 10^5$ | $102 \times 10^4$ | $102 \times 10^3$ | 10,200 | 5,100 | 2,550 | 0 | 0 |
|---|---|---|---|---|---|---|---|---|---|---|---|---|---|---|
| 1796-53-01 | 1 uM | | 1174 | 1343 | 1282 | 1205 | 958 | 235 | 77 | 51 | 45 | 40 | 31 | 31 |
| | | | 1347 | 1359 | 1286 | 1219 | 1094 | 280 | 95 | 50 | 47 | 42 | 36 | 33 |
| | | Average | 1260.5 | 1351 | 1284 | 1212 | 1026 | 257.5 | 86 | 50.5 | 46 | 41 | 33.5 | 32 |
| | | Net | 1227.75 | 1318.25 | 1251.25 | 1179.25 | 993.25 | 224.75 | 53.25 | 17.75 | 13.25 | 8.25 | | |
| 2343.30-01 | 4 nM | | 838 | 865 | 762 | 348 | 101 | 48 | 43 | 40 | 38 | 36 | 32 | 29 |
| | | | 819 | 924 | 794 | 204 | 110 | 55 | 49 | 41 | 42 | 36 | 35 | 28 |
| | | Average | 828.5 | 894.5 | 778 | 276 | 105.5 | 51.5 | 46 | 40.5 | 40 | 36 | 33.5 | 28.5 |
| | | Net | 797.5 | 863.5 | 747 | 245 | 74.5 | 20.5 | 15 | 9.5 | 9 | 5 | | |
| 1796-53-01 and 2343-30-01 | 1 uM 4 nM | | 1934 | 2142 | 2033 | 1608 | 1523 | 404 | 115 | 68 | 57 | 47 | 32 | 30 |
| | | | 1685 | 2113 | 1947 | 1483 | 1174 | 304 | 110 | 66 | 48 | 41 | 34 | 29 |
| | | Average | 1809.5 | 2127.5 | 1990 | 1545.5 | 1174 | 354 | 112.5 | 67 | 52.5 | 44 | 33 | 29.5 |
| | | Net | 1778.25 | 2096.25 | 1958.75 | 1514.25 | 1142.75 | 322.75 | 81.25 | 35.75 | 21.25 | 12.75 | | | and is shown in FIG. 29 as copy number versus net signal plots.

Results demonstrate that a dynamic range of >6 logs was achieved when probes 1796-53-01 and 2343-30-01 are mixed at a 1 µM and 4 nM mix, respectively.

Example 17

Optimization to Extend the Dynamic Range of Let-7a and U6 Detection in a Single Reaction Vessel In an attempt to extend the dynamic range of both let-7a miRNA and U6 RNA detection in a biplex INVADER assay, several parameters were tested and evaluated.

Primary INVADER reactions were setup in 10 uL volumes containing probe concentrations of 1 µM of 1796-53-01, 1 µM of 1544-82-01, 4 nM of 2343-30-01, 4 nM of 2343-25-01, 1 µM of INVADER oligos 1796-53-02 and 1496-78-02, 30 ng of CLEAVASE XII enzyme, and 10 mM MOPS pH 7.5, 25 mM KCl, 0.05% Tween 20, 0.05% Nonidet P40, 25 mM MgSO4, and 2% PEG. Duplicate reactions were setup at U6 RNA and Let-7a miRNA concentrations of $6\times10^9$, $1.2\times10^9$, $2.4\times10^8$, $4.8\times10^7$, $9.6\times10^6$, $1.92\times10^6$, 384,000, 76,800, 15,360, 3,072, and 0 copies per reaction. Reactions were assembled in a 96-well plate and 10 µl of clear mineral oil were added to each well to prevent evaporation. The plate was then transferred to a thermal-block at incubated at 49° C. for 90 minutes After incubation was complete, 5 µL of a secondary reaction mix containing 0.3 µM of secondary reaction templates 1107-10-02, 2343-30-02, 23-183 and 2343-30-03, 7.5 µM of ARRESTORs 1796-53-03 and 1581-63-01, and 30 nM of ARRESTORs 2343-30-04 and 2343-25-02, 1.5 µM of FRET probes 23-181, 2343-30-02, 23-182, and 2343-23-01 were added. The reaction plate was then incubated at 60° C. for 90 minutes. After completion of the reaction, the plate was transferred to a fluorescent plate reader (Cytofluor) and data was acquired by reading the fluorescence using the excitation and emission wavelengths of 560 nm and 620 nm, respectively, with a gain setting of 45 for Red dye and excitation and emission wavelengths of 485 nm and 530, respectively, with a gain setting of 43 for FAM dye.

Figure 30:
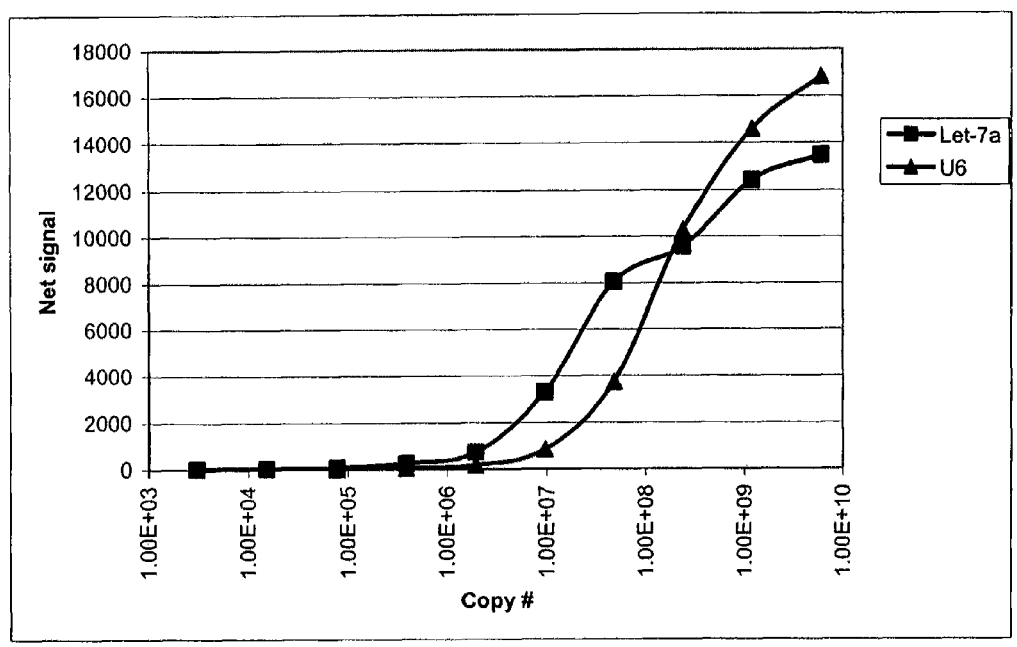
FIG. 30 shows a chart depicting copy number versus net signal plots for biplex U6 and Let-7a detection.

The data generated was as follows:

| Dye channel | Let-7a/ U6 copies/rxn | 6.00E * 09 | 1.20E * 09 | 2.40E * 08 | 4.80E807 | 9.60E * 06 | 1.92E * 06 | 3.84E * 05 | 7.68E * 04 | 1.54E * 04 | 3.07E * 03 | 0 |
|---|---|---|---|---|---|---|---|---|---|---|---|---|
| FAM | | 14133 | 13249 | 9947 | 9102 | 4204 | 1177 | 701 | 466 | 427 | 397 | 389 |
| | | 13569 | 12336 | 9942 | 7759 | 3159 | 1020 | 577 | 447 | 422 | 397 | 364 |
| | Average | 13851 | 12793 | 9945 | 8431 | 3682 | 1099 | 639 | 457 | 425 | 397 | 377 |
| | Net | 13474 | 12416 | 9568 | 8054 | 3305 | 722 | 262 | 80 | 48 | 20 | |
| Red | | 17353 | 15351 | 10722 | 4140 | 1219 | 429 | 322 | 257 | 237 | 235 | 237 |
| | | 16785 | 14299 | 10317 | 3780 | 936 | 378 | 285 | 245 | 217 | 234 | 226 |
| | Average | 17069 | 14825 | 10520 | 3960 | 1078 | 404 | 304 | 251 | 227 | 235 | 232 |
| | Net | 16837 | 14593 | 10288 | 3728 | 846 | 172 | 72 | 19 | −5 | 3 | | and is shown in FIG. 30 as copy number versus net signal plots.

Results demonstrate that a dynamic range of >6 logs was achieved for biplex U6 and Let-7a detection.

Example 18

Compositions for the Detection of miRNAs Associated with and Prognostic for Cancer Deletions and downregulation of miRNA genes have been associated with cancer (e.g., B-cell chronic lymphocytic leukemia (CLL)) (See, e.g., Calin et al., Proc Natl Acad Sci USA, 99, 15524-15529 (2002). Thus, various oligonucleotides were designed herein for the detection and characterization of miRNAs associated with cancer. These oligonucleotides are depicted in FIG. 31 (where m=2'-O-Methyl; r=ribose (to indicate RNA instead of DNA)).

Figure 32:
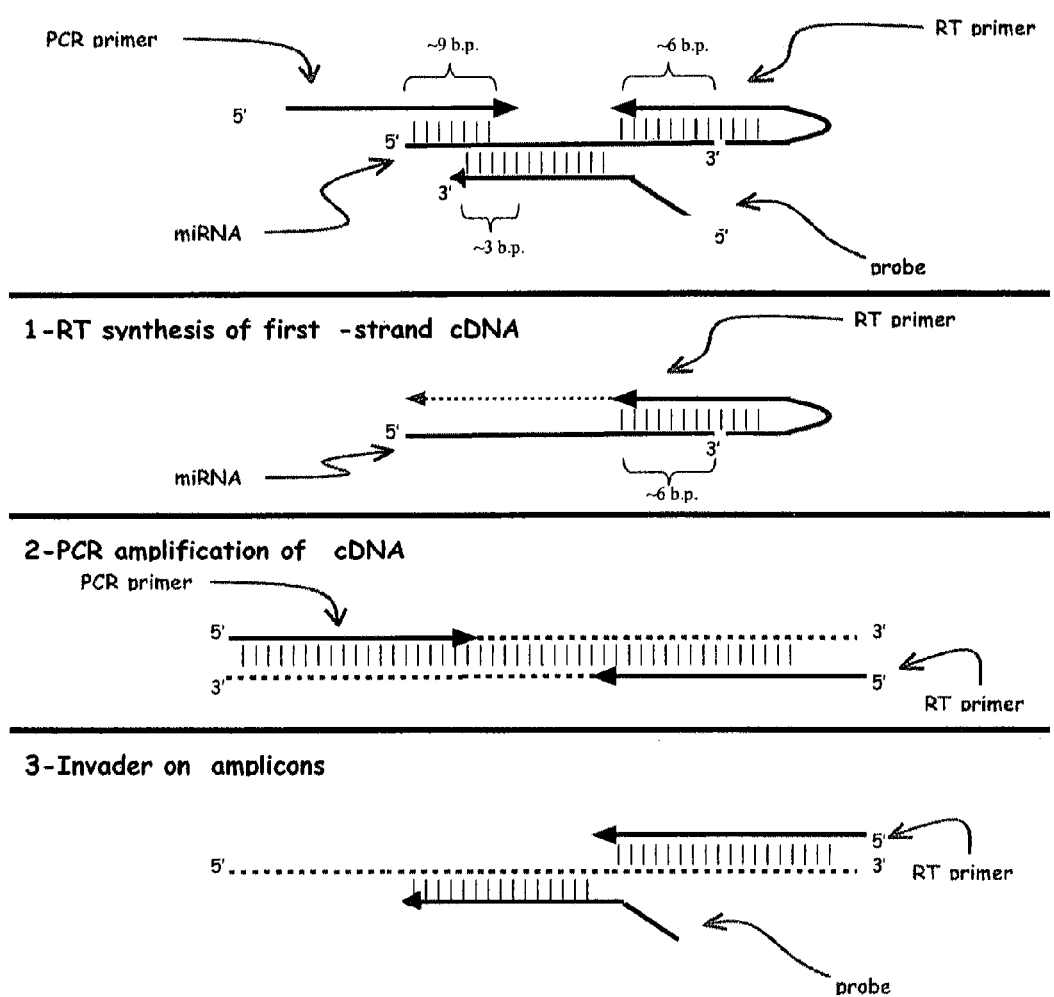
FIG. 32 depicts the general design for detection of miRNA using an assay comprising a reverse transcription reaction, a polymerase chain reaction and an invasive cleavage assay reaction.
Figure 33:
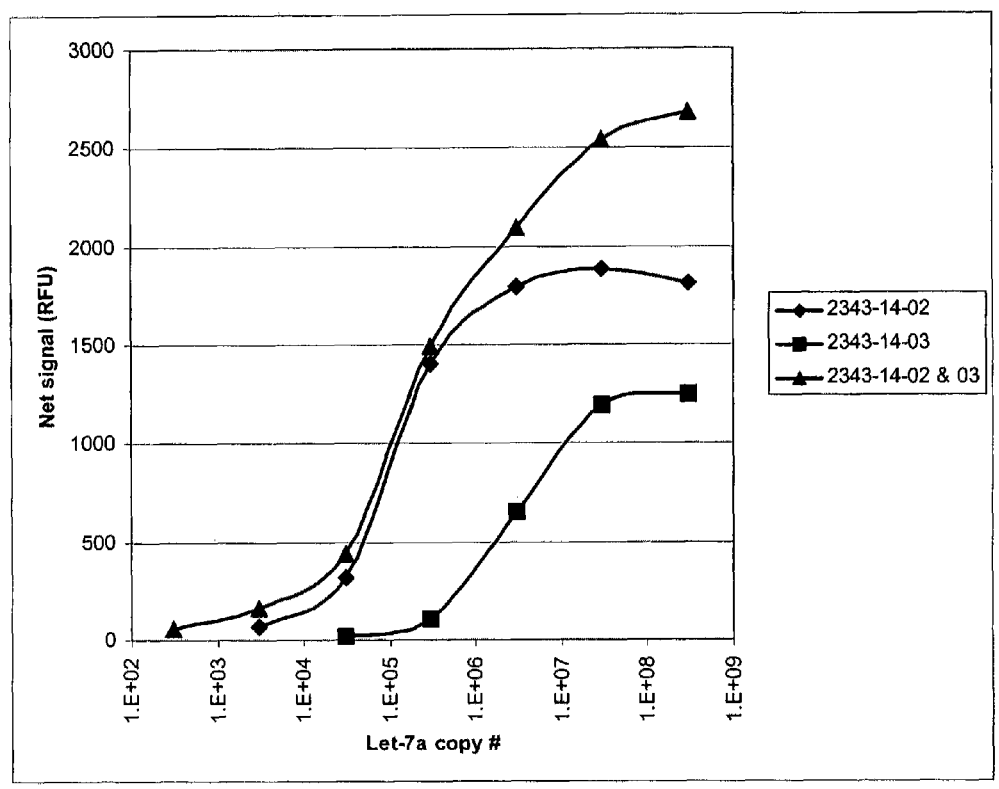
FIG. 33 shows net signal versus the copy number of Let-7a per reaction.

Example 19 miRNA Detection Using an Assay Comprising a Reverse Transcription Reaction, a Polymerase Chain Reaction and an Invasive Cleavage Assay Reaction Experiments were conducted in order to detect and characterize miRNAs using reverse transcription (RT), polymerase chain reaction (PCR) and invasive cleavage reaction assay (e.g., in a two-step or single-step reaction (e.g., in a single tube)). Chemistries utilized for these assays (e.g., single-step RT, PCR and invasive cleavage reactions) are described, for example, in U.S. Pat. Nos. 6,913,881; 6,875,572, 6,872,816, and 7,011,944, and U.S. patent application Ser. No. 11/266,723, filed Nov. 3, 2005, each of which is hereby incorporated by reference in its entirety. The general design for detection of miRNA using this methodology is shown in FIG. 32. Briefly, a reverse transcription (RT) primer oligonucleotide (that, in preferred embodiments, also serves as the INVADER oligonucleotide in an invasive cleavage reaction assay) and a reverse transcriptase are used to reverse transcribe (into cDNA) a target RNA (e.g., miRNA), and, subsequently (e.g., in a two-step assay) or concurrently (e.g., in a one-step assay (e.g., in a single tube)), a polymerase chain reaction (PCR) primer oligonucleotide and DNA polymerase are used for amplification of the cDNA product in the presence of primary probe thereby enabling formation of a detection structure (e.g., that can be detected by an invasive cleavage reaction assay).

During development of the present invention, multiple factors were examined and characterized in order to optimize miRNA detection capability and sensitivity using an assay that comprises a reverse transcription reaction, a polymerase chain reaction and an invasive cleavage assay reaction. These include the length (e.g., through oligonucleotide design) of the RT primer/miRNA duplex formed (e.g., between 4 and 10 (e.g., between 6 and 7) base-pairs); the copy number of miRNA available in a sample for detection; the length (e.g., through oligonucleotide design) of the PCR forward primer/miRNA duplex formed (e.g., between 4 and 10 (e.g., between 7 and 9) base-pairs); concentration of oligonucleotides used; reaction temperature at which assays could be conducted; the influence of stacker oligonucleotides (e.g., oligonucleotides that bind to the RT primer/INVADER oligo or PCR primer); use of oligonucleotides that form hairpin structures; the use of a single-step or two-step assay configuration; the effect of INVADER primary probe length (e.g., between 8 and 10) base pairs; the ability of the assay to discriminate between variants (e.g., mutants) of a single miRNA species; and the ability of the assay to detect more than one miRNA in a single reaction (e.g., biplex assay).

A) Length of RT-primer/miRNA Duplexes

Various lengths of RT-primer/miRNA duplexes were tested and characterized. To test the effect of RT primer-miRNA duplex length with the ability to detect miRNA, oligonucleotides were designed for use as RT primers such that duplexes of 6 or 7 base pairs formed between the RT primer and miRNA. These primers were tested for performance in triplicate using varying levels of let-7a miRNA molecules per reaction (e.g., 300,000, 50,000, 8,333, 1,389, 231, 39, and 0). Reactions were performed in 25 uL volumes containing 0.5 µM of forward PCR primer 2343-16-01, 0.034 units/µL native Taq polymerase, 2 units/µl of MMLV reverse transcriptase, and 6.67 ng/ul of CLEAVASE VIII enzyme in a buffer containing 10 mM MOPS, pH 7.5, 7.5 mM MgCl$_2$, and 25 uM dNTPs. For the 6 base pair duplex length, 0.5 µM of RT primer 2343-14-01, 0.5 µM probe 2343-14-05, 0.25 µM FRET probe 23-211 were added to the reaction mix. For the 7 base pair duplex length, 0.5 µM of RT primer 2343-03-01, 0.5 µM probe 2343-14-08, 0.25 µM FRET probe 23-755 were added to the reaction mix. Reactions were assembled in a 96-well skirted plate, covered with 10 uL of mineral oil. The plate was then subjected to single steps of 42° C. for 30 minutes followed by 95° C. for 2 minutes, and 30 cycles of 95° C. for 15 seconds, 60° C. for 15 seconds, 72° C. for 45 seconds. After completion of the cycles, the reaction plate was heated to 99° C. for 10 minutes then cooled down to 50° C. for 15 minutes then read on a Cytofluor plate reader using excitation and emission wavelengths of 560 nm and 620 nm, respectively with a gain setting of 45.

Data generated using a RT oligonucleotide primer configured to provide a 7 base-pair duplex with miRNA target was as follows:

| 7mer RT primer Let-7a duplex | | | | | |
|---|---|---|---|---|---|
| copies/rxn | | | | Average | Net counts |
| 300,000 | 1307 | 1257 | 1191 | 1252 | 1147 |
| 50,000 | 549 | 520 | 538 | 536 | 431 |
| 8,333 | 178 | 178 | 174 | 177 | 72 |
| 1,389 | 121 | 118 | 114 | 118 | 13 |
| 231 | 108 | 110 | 110 | 109 | 4 |
| 39 | 105 | 106 | 107 | 106 | 1 |
| — | 102 | 108 | 109 | 105 | |
| — | 104 | 102 | 105 | | |

Data generated using a RT oligonucleotide primer configured to provide a 6 base-pair duplex with miRNA target was as follows:

| 6mer RT primer Let-7a duplex | | | | | |
|---|---|---|---|---|---|
| copies/rxn | | | | Average | Net counts |
| 300,000 | 1006 | 958 | 757 | 907 | 813 |
| 50,000 | 436 | 413 | 358 | 402 | 308 |
| 8,333 | 143 | 151 | 139 | 144 | 50 |
| 1,389 | 103 | 101 | 102 | 102 | 8 |
| 231 | 100 | 94 | 95 | 96 | 2 |
| 39 | 95 | 91 | 92 | 93 | −2 |
| — | 97 | 93 | 92 | 94 | |
| — | 99 | 92 | 92 | | |

Thus, the present invention provides that, when comparing the same copy number of let-7a per reaction, the net signal is higher for 7 base-pair RT primer-miRNA duplex than for the 6 base-pair RT primer-miRNA duplex, although a shorter duplex provides levels of signal sufficient for detection. Accordingly, in some embodiments, assays of the present invention (e.g., comprising a reverse transcription reaction, a polymerase chain reaction, and an invasive cleavage assay reaction and a detection structure) are able to detect miRNA targets when oligonucleotides with short (e.g., less than 10 nucleotides; less than 8 nucleotides; or less than 7 nucleotides) regions of homology between RT primer/INVADER oligonucleotides and miRNA target are used. In some embodiments, the RT primer/INVADER oligonucleotide comprises other sequence that does not form a duplex (e.g., that is not complementary) with the target miRNA. In some embodiments, the other sequence that does not form a duplex forms a hairpin structure (e.g., sequence within the sequence that does not form a duplex with the target RNA is able to fold back and bind with itself).

Accordingly, in some embodiments, RT primer/INVADER oligonucleotides are designed such that a 6 base-pair duplex is formed between the oligonucleotide and the miRNA target. In some embodiments, RT primer oligonucleotides are designed such that a 7 base-pair duplex is formed between the oligonucleotide and the miRNA target. Although an understanding of the mechanism is not necessary to practice the present invention and the present invention is not limited to any particular mechanism of action, an increased length of duplex formation between the RT primer and miRNA target provides a more readily formable detection structure (e.g., when the RT primer oligonucleotide is also used as the primary INVADER oligonucleotide as described in FIG. 32) that in turn provides a higher net signal compared to shorter duplexes.

B) Detection of Low Levels of miRNA

Experiments to determine the scope of the level of detection utilized various levels of miR-16 miRNA ranging from 3×10$^6$ to 2 copies per reaction tested using 25 µL reaction volumes. Reactions were setup with 0.5 µM of primers 2343-03-05 and 2343-03-06, 0.67 µM of probe 2343-03-07, 0.25 µM of FRET probe 23-210, 0.034 units/µL native Taq polymerase, 2 units/µl of MMLV reverse transcriptase, and 6.67 ng/ul of CLEAVASE VIII enzyme in a buffer containing 10 mM MOPS, pH 7.5, 7.5 mM MgCl$_2$, and 25 uM dNTPs. Reactions were assembled in a 96-well skirted plate and covered with 10 µL of mineral oil. The plate was then subjected to single steps of 42° C. for 45 minutes followed by 95° C. for 2 minutes, and 30 cycles of 95° C. for 15 seconds, 60° C. for 30 seconds, 72° C. for 60 seconds. After completion of the cycles, the reaction plate was heated to 99° C. for 10 minutes then cooled down to 50° C. for 30 minutes then read on a Cytofluor plate reader using excitation and emission wavelengths of 485 nm and 535 nm, respectively, with a gain setting of 43.

Data generated was as follows:

| miR-16 copies/rxn | 3,000,000 | 600,000 | 120,000 | 24,000 | 4,800 | 960 | 192 | 38 | 8 | 2 | tRNA |
|---|---|---|---|---|---|---|---|---|---|---|---|
|  | 2039 | 2040 | 2128 | 2134 | 2319 | 2359 | 2014 | 1073 | 1040 | 918 | 275 |
|  | 2087 | 2161 | 2254 | 2236 | 2391 | 2327 | 2203 | 1185 | 309 | 297 | 301 |
|  | 2070 | 2099 | 2212 | 2260 | 2364 | 2315 | 2311 | 310 | 983 | 294 | 292 |
|  | 1953 | 2140 | 2240 | 2257 | 2311 | 2236 | 2121 | 1496 | 295 | 309 | 295 |
| Net counts | 1746 | 1819 | 1918 | 1931 | 2055 | 2018 | 1871 | 725 | 366 | 164 |  |

Thus, using compositions and methods of the present invention (e.g., using an assay (e.g., single-step or two-step assay) comprising a reverse transcription reaction, a polymerase chain reaction and an invasive cleavage assay reaction and a detection structure), it is possible to measure miRNA species whose copy numbers are as low as about 38-192 copies. Thus, in some embodiments, the present invention provides compositions and methods for detecting and characterizing miRNAs that are present in low copy numbers (e.g., less than 500 copies; less than 400 copies; less than 300 copies; less than 200 copies; less than 100 copies; less than 50 copies). Although an understanding of the mechanism is not necessary to practice the present invention and the present invention is not limited to any particular mechanism of action, in some embodiments, the use of a RT primer oligonucleotide that is also used as the INVADER oligonucleotide (e.g., in an assay comprising a reverse transcription reaction, a polymerase chain reaction and an invasive cleavage assay reaction) provides the proper amount of association for extension (e.g., from an miRNA template) as well as for recognition by a invasive cleavage enzyme (e.g., CLEAVASE enzyme) involved in the generation and detection of a detection structure capable of detecting of very low copy numbers (e.g., less than 100 (e.g., less than 50)) of a target miRNA.

C) Optimization of Length of PCR Forward Primer/miRNA Duplex (7, 8, and 9 Base-pairs)

Various levels of miR-16 miRNA ranging from 3,000 to 47 molecules per reaction were used to test the optimal miRNA and PCR forward primer hybridizing length. Hybridizing region lengths of 7, 8, and 9 base pairs (b.p.) were tested using 0.5 µM of each of the following primers 2343-03-06 (9 b.p.), 2343-10-05 (8 b.p.), 2343-10-06 (7 b.p.), mixed with 0.5 µM of RT primer 2343-03-05, 0.67 µM or probe 2343-03-07, 0.25 µM of FRET probe 23-210, in a 25 µL reaction containing 0.034 units/µL native Taq polymerase, 2 units/µl of MMLV reverse transcriptase, and 6.67 ng/ul of CLEAVASE VIII enzyme and a buffer of 10 mM MOPS, pH 7.5, 7.5 mM MgCl$_2$, and 25 uM dNTPs. Reactions were assembled in a 96-well skirted plate, covered with 10 µL of mineral oil. The plate was then subjected to single steps of 42° C. for 45 minutes followed by 95° C. for 2 minutes, and 30 cycles of 95° C. for 15 seconds, 60° C. for 15 seconds, 72° C. for 60 seconds. After completion of the cycles, the reaction plate was heated to 99° C. for 10 minutes then cooled down to 50° C. for 15 minutes then read on a Cytofluor plate reader using excitation and emission wavelengths of 485 nm and 535 nm, respectively with a gain setting of 43.

Results were as follows:

Raw data:

| miR-16 | Primer-miRNA length (b.p.) | | | | | | | | |
|---|---|---|---|---|---|---|---|---|---|
| (molecules/rxn) | 9 | 9 | 9 | 8 | 8 | 8 | 7 | 7 | 7 |
| 3,000 | 1608 | 1662 | 1634 | 560 | 1206 | 843 | 230 | 225 | 219 |
| 1,500 | 1453 | 1490 | 1578 | 735 | 221 | 231 | 240 | 231 | 222 |
| 750 | 948 | 1277 | 1035 | 490 | 259 | 365 | 236 | 230 | 231 |
| 375 | 970 | 959 | 1374 | 347 | 224 | 226 | 238 | 238 | 232 |
| 188 | 669 | 859 | 612 | 218 | 233 | 383 | 214 | 240 | 222 |
| 94 | 594 | 728 | 894 | 338 | 227 | 233 | 238 | 242 | 230 |
| 47 | 511 | 561 | 437 | 225 | 230 | 247 | 241 | 241 | 240 |
| 0 | 686 | 189 | 519 | 223 | 227 | 221 | 228 | 228 | 227 |

Processed data:

| | Primer-miRNA length (b.p.) | | | | | |
|---|---|---|---|---|---|---|
| | 9 | | 8 | | 7 | |
| miR-16 (molecules/rxn) | Average | Net counts (RFU) | Average | Net counts (RFU) | Average | Net counts (RFU) |
| 3,000 | 1635 | 1170 | 870 | 646 | 225 | −3 |
| 1,500 | 1507 | 1042 | 396 | 172 | 231 | 3 |
| 750 | 1087 | 622 | 371 | 147 | 232 | 4 |
| 375 | 1101 | 636 | 266 | 42 | 236 | 8 |
| 188 | 713 | 248 | 278 | 54 | 225 | −3 |
| 94 | 739 | 274 | 266 | 42 | 237 | 9 |
| 47 | 503 | 38 | 234 | 10 | 241 | 13 |
| 0 | 465 | | 224 | | 228 | |

Thus, the present invention demonstrates that the performance of detection assays for miRNA (e.g., comprising a reverse transcription reaction, a polymerase chain reaction and a invasive cleavage assay reaction and a detection structure) decreases as the PCR primer-miRNA duplex length decreases from 9 to 7 base pairs. Thus, in some embodiments, PCR primer oligonucleotides are designed such that a duplex of about 9 base-pairs is formed between the primer oligonucleotide and the target miRNA. In some embodiments, the primer oligonucleotide comprises other sequence that does not form a duplex (e.g., that is not complementary) with the target miRNA or cDNA generated therefrom. In some embodiments, the other sequence that does not form a duplex forms a hairpin structure (e.g., sequence within the sequence that does not form a duplex with the target sequence or cDNA generated therefrom is able to fold back and bind with itself).
D) Detection of Let-7a miRNA Using Single or Multiple Probes Levels of Let-7a miRNA ranging from $3 \times 10^8$ to 3 molecules per reaction were tested employing the following two probes 2343-14-02 at 0.5 µM and 2343-14-03 at 40 nM in reactions where one of the probes was present or both. For all reactions, individual or combined probes at the above stated concentrations were mixed in 25 µL volumes containing the appropriate level of Let-7a, 0.5 µM of primers 2343-14-01 and 2343-16-01, and 0.25 µM of FRET probes 23-210 and 23-204 in a buffer containing 0.034 units/µL native Taq polymerase, 2 units/µl of MMLV reverse transcriptase, and 6.67 ng/ul of CLEAVASE VIII enzyme, 10 mM MOPS, pH 7.5, 7.5 mM MgCl$_2$, and 25 uM dNTPs. Reactions were assembled in a 96-well skirted plate, covered with 10 µL of mineral oil. The plate was then subjected to single steps of 42° C. for 45 minutes followed by 95° C. for 2 minutes, and 29 cycles of 95° C. for 15 seconds, 60° C. for 15 seconds, 72° C. for 45 seconds. After completion of the cycles, the reaction plate was heated to 99° C. for 10 minutes then cooled down to 50° C. for 30 minutes then read on a Cytofluor plate reader using excitation and emission wavelengths of 485 nm and 535 nm, respectively, with a gain setting of 43.

Fluorescence data generated was as follows:

with short regions of target hybridization. Two primary probes, with 10 and 11 bases of target hybridization were examined across a range of incubation temperatures from 45° C. to 60° C.

1. Oligonucleotides for the INVADER assay:

| 1716-94-1 (SEQ ID NO: 149) | Primary Probe | 5'-GACGCGGAGTACAACCTAC-HEX |
| 1716-94-2 (SEQ ID NO: 152) | Primary Probe | 5'-GACGCGGAGATACAACCTAC-HEX |
| 1716-94-3 (SEQ ID NO: 153) | RT/Primer/ INVADER | 5'-CACGGTCCAGCGAACTAT |
| 1716-94-5 (SEQ ID NO: 156) | RT/Primer/ INVADER | 5'-CACGGTCCAGCGAACTA |
| 1716-94-6 (SEQ ID NO: 155) | PCR Primer | 5'-CCAGTGCCGATGAGGTAGTA |
| 1716-94-8 (SEQ ID NO: 156) | Stacker | 5'-CGCTGGACCGTG-HEX-3' |

| Probe | Let-7a (molec/rxn) | 3.E+08 | 3.E+07 | 3.E+06 | 3.E+05 | 3.E+04 | 3.E+03 | 3.E+02 | 3.E+01 | 3 | 0 |
|---|---|---|---|---|---|---|---|---|---|---|---|
| 2343-14-02 | | 2056 | 2129 | 2035 | 1643 | 599 | 315 | 266 | 281 | 255 | 262 |
| 0.5 uM | | 2071 | 2144 | 2061 | 1681 | 548 | 323 | 233 | 250 | 295 | 252 |
| | Average | 2064 | 2137 | 2048 | 1662 | 574 | 319 | 250 | 266 | 275 | 257 |
| | Net counts | 1807 | 1880 | 1791 | 1405 | 317 | 62 | −8 | 9 | 18 | |
| 2343-14-03 | | 1425 | 1357 | 822 | 289 | 205 | 190 | 191 | 190 | 188 | 188 |
| 40 nM | | 1448 | 1393 | 858 | 303 | 205 | 198 | 199 | 196 | 192 | 188 |
| | Average | 1437 | 1375 | 840 | 296 | 205 | 194 | 195 | 193 | 190 | 188 |
| | Net counts | 1249 | 1187 | 652 | 108 | 17 | 6 | 7 | 5 | 2 | |
| 2343-14-02 | | 3203 | 3022 | 2563 | 1931 | 851 | 604 | 442 | 343 | 415 | 400 |
| (0.5 uM) & | | 2973 | 2889 | 2450 | 1872 | 848 | 540 | 489 | 472 | 437 | 417 |
| 2343-14-03 | Average | 3088 | 2956 | 2507 | 1902 | 850 | 572 | 466 | 408 | 426 | 409 |
| (40 nM) | Net counts | 2679 | 2547 | 2098 | 1493 | 441 | 163 | 57 | −2 | 17 | | and is shown in FIG. 32.

Thus, the present invention provides that a combination of probes 2343-14-02 (0.5 µM) and 2343-14-03 (40 nM) results in an extended dynamic range of >6 orders of magnitudes for miRNA detection. Accordingly, in some embodiments, a miRNA detection assay of the present invention (e.g., the comprises a reverse transcription reaction, a polymerase chain reaction and an invasive cleavage assay reaction) utilizes more than one (e.g., two, three or more) probe oligonucleotides in order to increase the sensitivity of detection (e.g., of low copy number miRNAs).
E) Effect of Reaction Temperature Using Primary Probes with Short Regions of Target Hybridization Experiments were conducted to determine the temperature sensitivity (or lack thereof) of assays using primary probes -continued

| Let-7a RNA Target (SEQ ID NO: 275) | 5'-UGAGGUAGUAGGUUGUAUAGUU |

2. Let-7a amplicon generation: let-7a amplicon was generated in RT-PCR reaction including 0.4 µM 1716-94-3, 0.4 µM 1716-94-6, 0.4 µM 1716-94-8, 0.5 fM let-7a RNA, 2 unit/µl MMLV, 0.033 unit/µl TaqPol in 20 µl 10 mM MOPS pH 7.5, 7.5 mM MgCl$_2$, 0.25 mM dNTP each. PCR cycling profile: 37 C for 30 min followed by 28 cycles of 95 C for 30 s and 60 C for 1 min.

3. Schematic of the Let-7a amplicon RT-PCR

```
          let-7a 5'-UGAGGUAGUACGUUGUAUAGUU 1716-94-6 5'-CCAGTGCCGATGAGGTAGTA    3'-TATCAAGCGACCTGGCAC 1716-94-3

CGCTGGACCGTG-HEX-3' 1716-94-8
```

(let-7a is SEQ ID NO:275; 1716-94-6 is SEQ ID NO:155; 1716-94-3 is SEQ ID NO:153; 1716-94-8 is SEQ ID NO:156)

4. INVADER assays: INVADER reactions with 1716-94-1 probe were performed in 18 µl 10 mM MOPS pH 7.5, 7.5 mM MgCl$_2$, 0.25 mM each dNTP including 0.67 µM 1716-94-1, 0.4 µM 1716-94-3, 1 µl of 10-fold diluted let-7a amplicon used as a target, 2 unit/µl MMLV, 0.033 unit/µl TaqPol, 6.7 ng/ul CLEAVASE VIII enzyme at 99 C for 10 min then at 45-60 C temperature gradient for 1 h. After this, 2 µl 23-210 arm 3-FAM FRET cassette was added to the tube and reaction was continued at 95 C for 1 min and then at 54 C for 10 min.

5. Schematic of the INVADER assay with 1716-94-1 probe

```
                   3'-HEX-CATCCAACAT-GAGGCGCAG-5'
                             1716-94-1

5'-CCAGTGCCGATGAGGTAGTAGGTTGTATAGTTCGCTGGACCGTG
let-7a amplicon
                                      3'-TATCAAGCGACCTGGCAC
                                             1716-94-3
```

(let-7a amplicon is SEQ ID NO:286; 1716-94-1 is SEQ ID NO:149; 1716-94-3 is SEQ ID NO:153)

6. INVADER reactions with 1716-94-2 probe were performed in 18 µl 10 mM MOPS pH 7.5, 7.5 mM MgCl$_2$, 0.25 mM each dNTP including 0.67 µM 1716-94-2, 0.4 µM 1716-94-5, 1 µl of 10-fold diluted let-7a amplicon used as a target, 2 unit/µl MMLV, 0.033 unit/µl TaqPol, 6.7 ng/µl CLEAVASE VIII enzyme at 99 C for 10 min then at 45-60 C temperature gradient for 1 h. After this, 2 µl 23-210 arm 3-FAM FRET cassette was added to the tube and reaction was continued at 95 C for 1 min and then at 54 C for 10 min. For 'no target control' 2 µl H$_2$O was used instead of the amplicon.

7. Schematic of the INVADER assay with 1716-94-2 probe

```
                   3'-HEX-CATCCAACATA-GAGGCGCAG-5'
                             1716-94-2

5'-CCAGTGCCGATGAGGTAGTAGGTTGTATAGTTCGCTGGACCGTG
let-7a amplicon
                                      3'-ATCAAGCGACCTGGCAC
                                             1716-94-5
```

(let-7a amplicon is SEQ ID NO:286; 1716-94-2 is SEQ ID NO:152; 1716-94-5 is SEQ ID NO:154)

Figure 34:
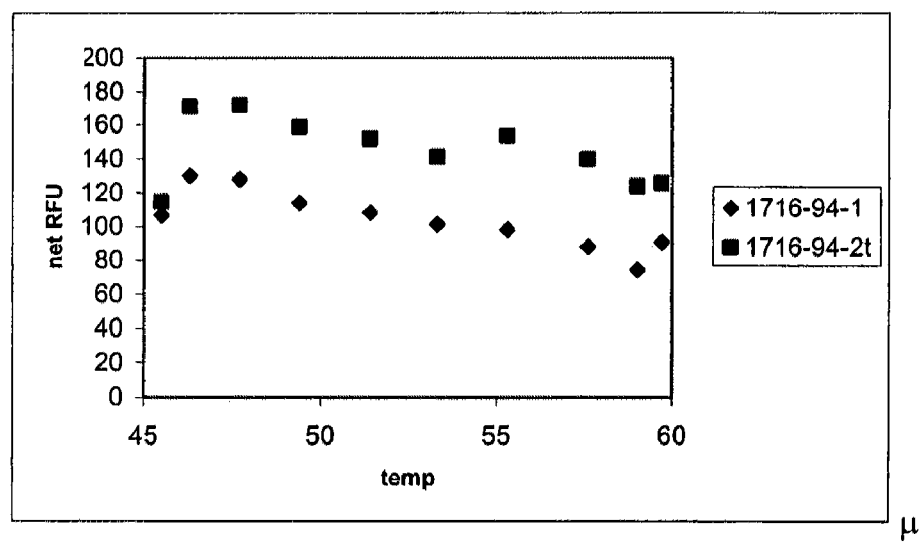
FIG. 34 shows net signal as a function of temperature.

The net signal of the INVADER reactions with probes 1716-94-1 and 1716-94-2 plotted as a function of temperature are shown in FIG. 34.

Thus, the present invention provides that use of primary probes with target hybridization regions of 10 or 11 bases functions well across a broad range of temperatures. Accordingly, in some embodiments, the present invention provides that assays for detecting miRNA (e.g., comprising a reverse transcription reaction, a polymerase chain reaction and an invasive cleavage assay reaction, and a detection structure) comprise incubation with an invasive cleavage enzyme (e.g., CLEAVASE enzyme) at a temperature between 45 and 60° C. (e.g., in some preferred embodiments, at 50° C., in other preferred embodiments at 49° C., in still other preferred embodiments at 48° C., and in further preferred embodiments at 47° C.).

F) Effect of Stacker Oligonucleotides on RT-primer and PCR Forward Primer Oligonucleotides Experiments were designed and conducted to test the effect of a stacker oligonucleotide on both the RT primer/invader oligonucleotide and the PCR forward oligonucleotide primer oligonucleotides.

Oligonucleotides for the let-7a assay:

```
     1716-94-9    Stacker    5'-TCGGCACTGG-HEX
```

1. Schematic of the let-7a assay

```
                   3'-HEX-CATCCAACAT-GAGGCGCAG 1716-94-1 let-7a 5'-UGAGGUAGUAGGUUGUAUAGUU 1716-94-6 5'-CCAGTGCCGATGAGGTAGTA    3'-TATCAAGCGACCTGGCAC 1716-94-3

3'-HEX-GGTCACGGCT                      CGCTGGACCGTG-HEX-3' 1716-94-8 Stacker

Stacker 1716-94-9
```

(let-7a is SEQ ID NO:275; 1716-94-1 is SEQ ID NO:149; 1716-94-6 is SEQ ID NO:155; 1716-94-3 is SEQ ID NO:153; 1716-94-9 is SEQ ID NO:157; 1716-94-8 is SEQ ID NO:156)

2. Let-7a assay was carried out in 20 µl 10 mM MOPS pH 7.5, 7.5 mM MgCl$_2$, 0.25 mM each dNTP including 0.67 uM 1716-94-1, 0.4 uM 1716-94-3, 0.4 uM 1716-94-6, 2 unit/ul MMLV, 0.033 unit/µl TaqPol, 6.7 ng/ul CLEAVASE VIII enzyme; 0.25 µM 23-210 arm 3-FAM FRET cassette; 60,000, 6,000, 600 or none copies of let-7a RNA in the presence of both 1716-94-8 and 1716-94-9 stackers (8+9), 1716-94-8 stacker (8), 1716-94-9 stacker (9), or none of the stackers (none). Temperature profile was 37 C for 30 min; 95 C for 1 min; 28 cycles of 95 C for 30 s then 60 C for 1 min; 99 C for 10 min; 49 C for 30 min.

Figure 35:
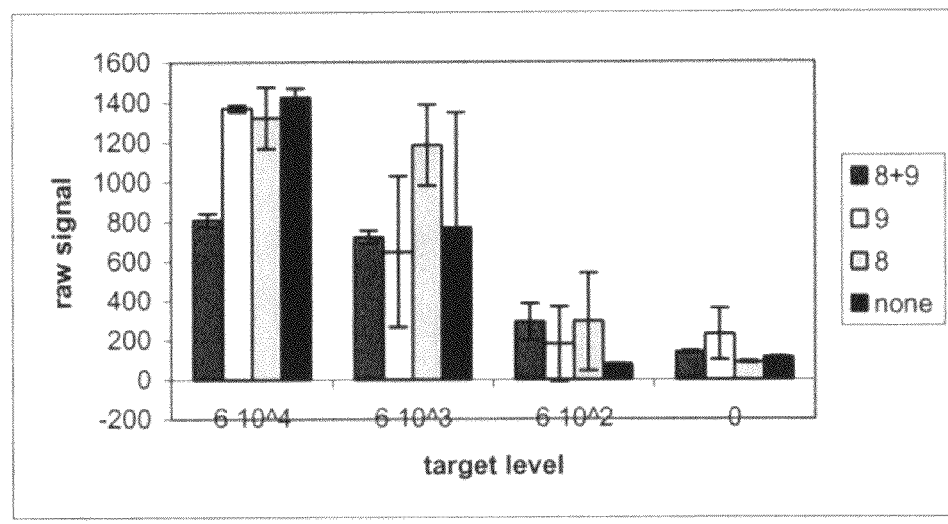
FIG. 35 shows the raw signal of let-7a reactions plotted as a function of let-7a copy number.

Raw signal of the let-7a reactions plotted as a function of let-7a RNA copy number are shown in FIG. 35.

Thus, the present invention provides that, in some embodiments, use of any stackers is preferable to no stacker (e.g., at low levels (e.g., copy number) of target miRNA). In some embodiments, at higher levels (e.g., copy number) of target nucleic acid (e.g., miRNA), use of a stacker results in higher signal. The use of a stacker oligonucleotide on the PCR forward oligonucleotide primer did not appear to confer any positive benefit on the reaction, and may actually reduce signal in some instances. In contrast, the use of a stacker of the RT primer/invader oligonucleotide provided an enhanced sensitivity for the assay.

G) Comparison of Stacker Oligonucleotide vs. Use of a Hairpin-forming RT-primer

Experiments were designed and conducted to compare the use of a hairpin-forming region of the 5' end of the RT/primer/ invader oligonucleotide versus the use of a stacker oligonucleotide in the same region.

1. Oligonucleotides for the INVADER assay:

```
2343-03-    RT/Primer/    5'-GCTACCAAGACACGTAGCCAACTAT
1 (SEQ      INVADER
ID NO:
171)
```

2. Schematic of the stacker design for the let-7a assay:

```
                   3'-HEX-CATCCAACAT-GAGGCGCAG 1716-94-1 let-7a 5'-UGAGGUAGUAGGUUGUAUAGUU 1716-94-6 5'-CCAGTGCCGATGAGGTAGTA    3'-TATCAAGCGACCTGGCAC 1716-94-3

CGCTGGACCGTG-HEX-3' 1716-94-8
```

(let-7a is SEQ ID NO:275; 1716-94-1 is SEQ ID NO:149; 1716-94-6 is SEQ ID NO:155; 1716-94-3 is SEQ ID NO:153; 1716-94-8 is SEQ ID NO:156)

3. Schematic of the hairpin design for the let-7a assay:

```
                   3'-HEX-CATCCAACAT-GAGGCGCAG 1716-94-1
              let-7a 5'-UGAGGUAGUAGGUUGUAUGUU
1716-94-6 5'-CCAGTGCCGATGAGGTAGTA    3'-TATCAACCGATGCACA
                                        ||||||  ) 2343-3-1
                                    5'-GGCTACCAAG
```

(let-7a is SEQ ID NO:275; 1716-94-1 is SEQ ID NO:149; 1716-94-6 is SEQ ID NO:155; 2343-3-1 is SEQ ID NO:171)

4. Let-7a stacker assay was carried out in 20 μl 10 mM MOPS pH 7.5, 7.5 mM MgCl$_2$, 0.25 mM each dNTP including 0.67 μM 1716-94-1, 0.4 μM 1716-94-3, 0.4 μM 1716-94-6, 2 unit/μl MMLV, 0.033 unit/μl TaqPol, 6.7 ng/μl CLEAVASE VIII enzyme; 0.25 uM 23-210 arm 3-FAM FRET cassette; 60,000, 6,000, 600 or no copies of let-7a RNA in the presence of 1716-94-8 stacker. Temperature profile was 37 C for 30 min; 95 C for 1 min; 28 cycles of 95 C for 30 s then 60 C for 1 min; 99 C for 10 min: 49 C for 30 min.

Let-7a hairpin assay was carried as described for the stacker assay except 0.4 μM 2343-03-1 was used instead of 1716-94-3 and 1716-94-8.

Figure 36:
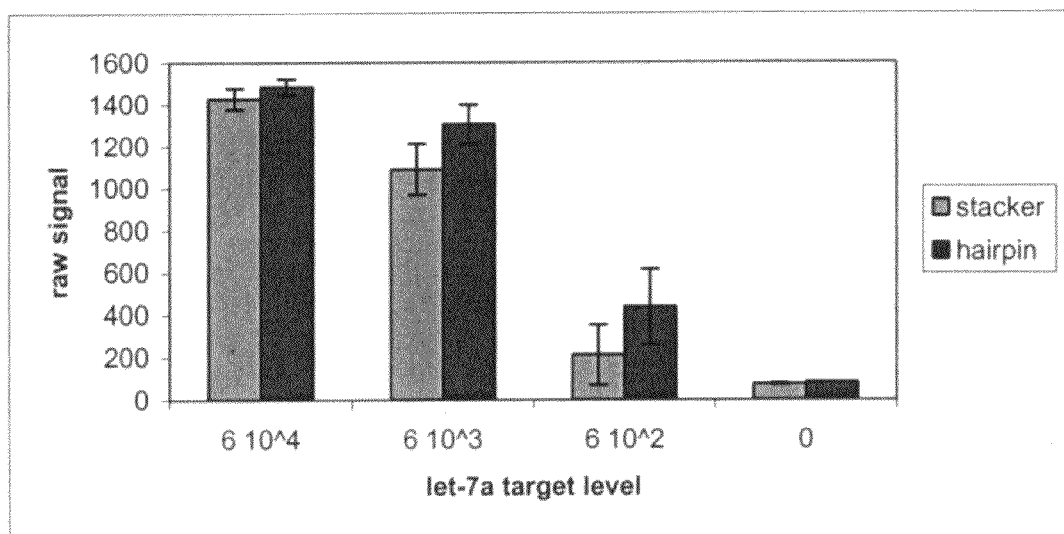
FIG. 36 shows the raw signal of the let-7a stacker and hairpin assays plotted as a function of let-7a RNA copy number.

The raw signal of the let-7a stacker and hairpin assays plotted as a function of let-7a RNA copy number is shown in FIG. 36.

Thus, the present invention provides that no significant difference in detection capability (e.g., sensitivity) is observed between using a stacker versus a hairpin-forming oligonucleotide.

H) Comparison of 1-step vs. 2-step Reaction Configurations

Experiments were designed and conducted to compare 1-step vs. 2-step reaction configurations. In the 1-step configuration, each of the reverse transcription reaction, polymerase chain reaction, and invasive cleavage assay reaction is performed in sequence, with no reagent additions to the reaction vessel. By contrast, in the 2-step configuration, following the reverse transcription reaction step, $\frac{1}{10}^{th}$ of the reverse transcription reaction volume is added to a reaction vessel containing the reagents for polymerase chain reaction and invasive cleavage assay reaction.

1. One-step let-7a assay. Let-7a 1-step assay was carried out in 20 μl 10 mM MOPS pH 7.5, 7.5 mM MgCl$_2$, 0.25 mM each dNTP including 0.67 μM 1716-94-1, 0.4 μM 1716-94-3, 0.4 μM 1716-94-6, 0.4 μM 1716-94-8, 2 unit/μl MMLV, 0.033 unit/μl TaqPol, 6.7 ng/μl CLEAVASE VIII enzyme; 0.25 μM 23-210 arm 3-FAM FRET cassette with 60,000, 6,000, 600 or none copies of let-7a RNA. Temperature profile was 37 C for 30 min; 95 C for 1 min; 27 cycles of 95 C for 30 s then 60 C for 1 min; 99 C for 10 min: 49 C for 30 min.

Two-step let-7a assay. First step was performed in 20 μl MMLV reaction buffer (Promega) including 0.25 mM each dNTP, 0.4 μM 1716-94-3, 0.4 μM 1716-94-8, 5 unit/μl MMLV with 60,000, 6,000, 600 or none copies of let-7a RNA at 37 C for 30 min. MMLV was inactivated at 95 C for 1 min. Second step was carried out in 20 μl 10 mM MOPS pH 7.5, 7.5 mM MgCl$_2$, 0.25 mM each dNTP including 0.67 μM 1716-94-1, 0.4 μM 1716-94-3, 0.4 μM 1716-94-6, 0.4 μM 1716-94-8, 0.033 unit/μl TaqPol, 6.7 ng/ul CLEAVASE VIII enzyme; 0.25 μM 23-210 arm 3-FAM FRET cassette with 2 μl of the first step reaction sample. Temperature profile was 95 C for 1 min; 27 cycles of 95 C for 30 s then 60 C for 1 min; 99 C for 10 min; 49 C for 30 min.

Figure 37:
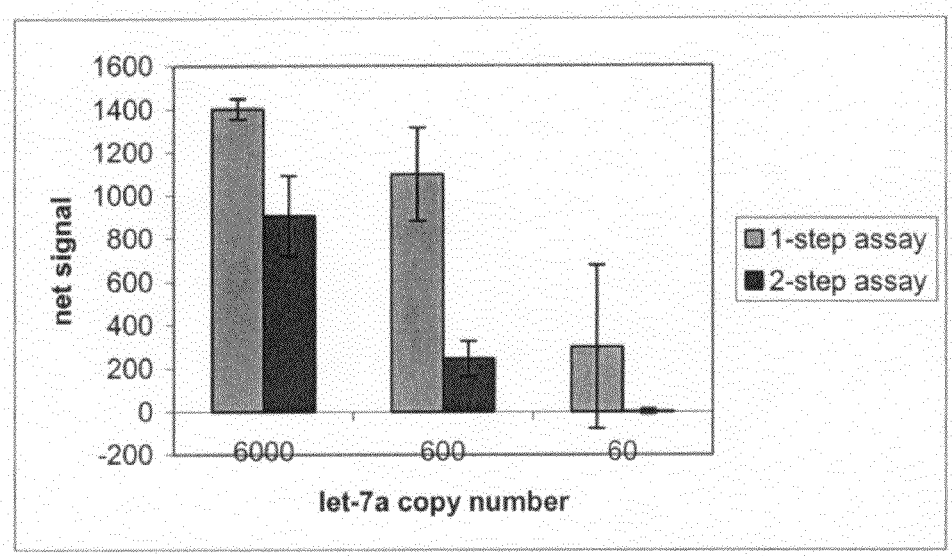
FIG. 37 shows the net signal generated by the 1-step and 2-step let-7a assays as a function of let-7a copy number.

The net signal generated by the 1-step and 2-step let-7a assays as a function of let-7a copy number is shown in FIG. 37.

Thus, the present invention provides that, when correcting for the $\frac{1}{10}^{th}$ dilution of template in the 2-step configuration, there is no significant difference in signal strength, limit of detection, or dynamic range, when using either the 1-step or 2-step assay configuration. Thus, in some embodiments, the present invention provides detection of a target nucleic acid (e.g., RNA (e.g., miRNA)) using an assay that comprises a reverse transcription reaction, a polymerase chain reaction, and an invasive cleavage assay reaction all in a single step (e.g., in a single tube), thereby saving time and expense and reducing the potential for sample contamination and/or mishandling. In some embodiments, the present invention provides detection of a target nucleic acid (e.g., RNA (e.g., miRNA)) using an assay that comprises a reverse transcription reaction, a polymerase chain reaction, and an invasive cleavage assay reaction in a two step reaction, wherein a portion of nucleic acid (e.g., cDNA) obtained from a reverse transcription reaction step is used in a subsequent step that comprises a polymerase chain reaction and an invasive cleavage reaction assay.

I) Primary Probes in a Low Temperature Invasive Cleavage Assay Reactions

Experiments were designed and conducted to test the effect of different primary probe lengths in a low-temperature reaction. Primary probes having target hybridization regions of 8, 9 and 10 base-pairs in length were tested in a 50° C. INVADER reaction.

1. Oligonucleotides for the INVADER assay:

```
1716-94-10   Primary Probe 5'-CCACGGACGTACAACCTA-NH2
(SEQ ID
NO: 150)

1716-94-11   Primary Probe 5'-CCACGGACGTACAACCT-NH2
(SEQ ID
NO: 151)
```

2. Schematic of the let-7a assay with probes of different length

```
                     3'-HEX-CATCCAACAT-GAGGCGCAG  1716-94-1

3'-NH2-ATCCAACAT-GCAGGCACC   1716-94-10

3'-NH2-TCCAACAT-GCAGGCACC    1716-94-11 let-7a 5'-UGAGGUAGUAGGUUGUAUAGUU 1716-94-4 5'-CCAGTGCCGATGAGGTAGT    3'-TATCAAGCGACCTGGCAC        1716-94-3

CGCTGGACCGTG-HEX-3'  1716-94-8
```

(let-7a is SEQ ID NO:275; 1716-94-1 is SEQ ID NO:149; 1716-94-10 is SEQ ID NO:150; 1716-94-11 is SEQ ID NO:151; 1716-94-4 is SEQ ID NO:287; 1716-94-3 is SEQ ID NO:153; 1716-94-8 is SEQ ID NO:156)

3. Let-7a assay with 1716-94-1 probe was carried out in 20 µl 10 mM MOPS pH 7.5, 7.5 mM MgCl$_2$, 0.25 mM each dNTP including 0.67 µM 1716-94-1, 0.4 µM 1716-94-3, 0.4 µM 1716-94-4, 0.4 µM 1716-94-8, 2 unit/µl MMLV, 0.033 unit/µl TaqPol, 6.7 ng/µl CLEAVASE VIII enzyme; 0.25 µM 23-210 arm 3-FAM FRET cassette with 6 10$^6$, 6 10$^5$, 6 10$^4$, 6,000, 600, 60, or none copies of let-7a RNA. Temperature profile was 42 C for 30 min; 95 C for 1 min; 25 cycles of 95 C for 20 s then 60 C for 1 min; 99 C for 6 min; 50 C for 30 min.

4. Let-7a assay with probes 1716-94-10 or 1716-94-11 was carried out in 20 µl 10 mM MOPS pH 7.5, 7.5 mM MgCl$_2$, 0.25 mM each dNTP including 0.67 µM 1716-94-10 or 1716-94-11, 0.4 µM 1716-94-3, 0.4 µM 1716-94-4, 0.4 µM 1716-94-8, 2 unit/µl MMLV, 0.033 unit/µl TaqPol, 6.7 ng/ul CLEAVASE VIII enzyme; 0.25 µM 23-204 arm 4-FAM FRET cassette with 6 10$^6$, 6 10$^5$, 6 10$^4$, 6,000, 600, 60, or none copies of let-7a RNA. Temperature profile was 42 C for 30 min; 95 C for 1 min; 25 cycles of 95 C for 20 then 60 C for 1 min; 99 C for 6 min; 50 C for 30 min.

Figure 38:
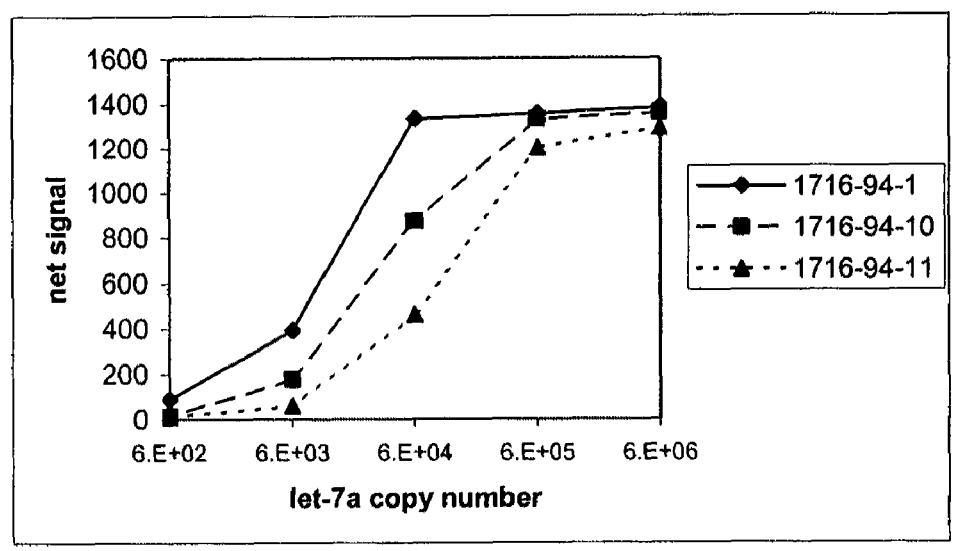
FIG. 38 shows the net signal generated by the let-7a assays with probes 1716-94-1, 1717-94-10 or 1716-94-11 as a function of let-7a copy number.

The net signal generated by the let-7a assays with 1716-94-1, 1716-94-10, or 1716-94-11 probes as a function of let-7a copy number is shown in FIG. 38.

Thus, the present invention provides that primary probes having target hybridization regions (e.g., that associate with target nucleic acid (e.g., miRNA)) of 8-10 base-pairs in length function at different levels in the assays. Specifically, as the length of the primary probe increases, the signal strength also increases (See, e.g., FIG. 38, probe 1716-94-1), and when the primary probe length decreases there is also a decrease in the signal strength (See, e.g., FIG. 38, probe 1716-94-11).

J) Probe Length and Concentration

Experiments were conducted to determine whether the dynamic range of the assay could be expanded through the use of primary probes having different lengths of target hybridizing region. In this case, 8 vs. 10 bp was tested. In addition, the concentration of the 10 bp containing primary probe was varied.

1. Let-7a assay with extended dynamic range was carried out in 20 µl 10 mM MOPS pH 7.5, 7.5 mM MgCl$_2$, 0.25 mM each dNTP including 0.67 µM 1716-94-1; 0.067, 0.167, or 0.33 µM 1716-94-11; 0.4 µM 1716-94-3, 0.4 µM 1716-94-4, 0.4 µM 1716-94-8, 2 unit/µl MMLV, 0.033 unit/µl TaqPol, 6.7 ng/µl CLEAVASE VIII enzyme; 0.25 µM 23-210 arm 3-FAM and 0.25 µM 23-204 arm 4-FAM FRET cassettes with 6 10$^6$, 6 10$^5$, 6 10$^4$, 6,000, 600, 60, or none copies of let-7a RNA. Temperature profile was 42 C for 30 min; 95 C for 1 min; 25 cycles of 95 C for 20 s then 60 C for 1 min; 99 C for 6 min; 50 C for 30 min.

Figure 39:
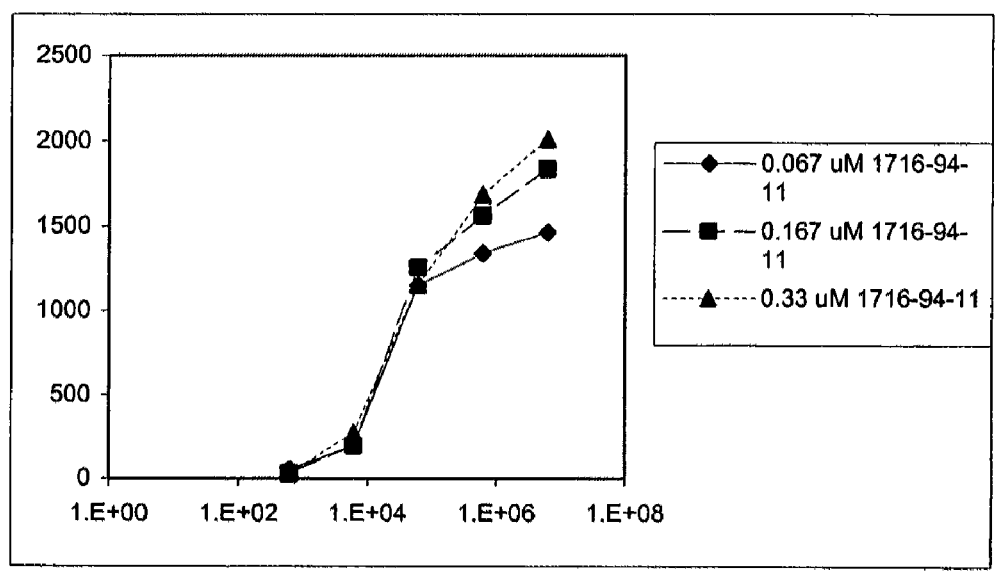
FIG. 39 shows the net signal generated by the let-7a assays with probes 1716-94-1 and 1717-94-11 at different ratios as a function of let-7a copy number.

The net signal generated by the let-7a assays with 1716-94-1 and 1716-94-11 probes taken at different ratio as a function of let-7a copy number is shown in FIG. 39.

Accordingly, the present invention provides that concentrations of primary probe from 0.067 µM-0.33 µM function in the assays of the present invention, where, in some embodiments, using a higher concentration of probe (e.g., 0.33 µM) provides an increase in the sensitivity of the assay compared to using a lower concentration (e.g., 0.067 µM). Thus, in some embodiments, altering (e.g., increasing) the concentration of a primary probe in a detection assay (e.g., comprising a reverse transcription reaction, a polymerase chain reaction, and an invasive cleavage assay reaction and a detection structure) of the present invention alters (e.g., increases) the sensitivity of the reaction.

K) Specific Discrimination of Let-7 Isoforms

Experiments were designed and conducted to test the ability of a Let-7a assay to discriminate between closely related isoforms of Let-7 (e.g., Let-7 variants).

The let-7 variants used were:

```
let-7 species
let-7a       UGAGGUAGUAGGUUGUAUAGUU    (let-7a is
                                        SEQ ID NO:
                                        275)

let-7c       ------------------G--- let-7e       --------G------------- let-7f       ----------A-----------
```

Figure 40:
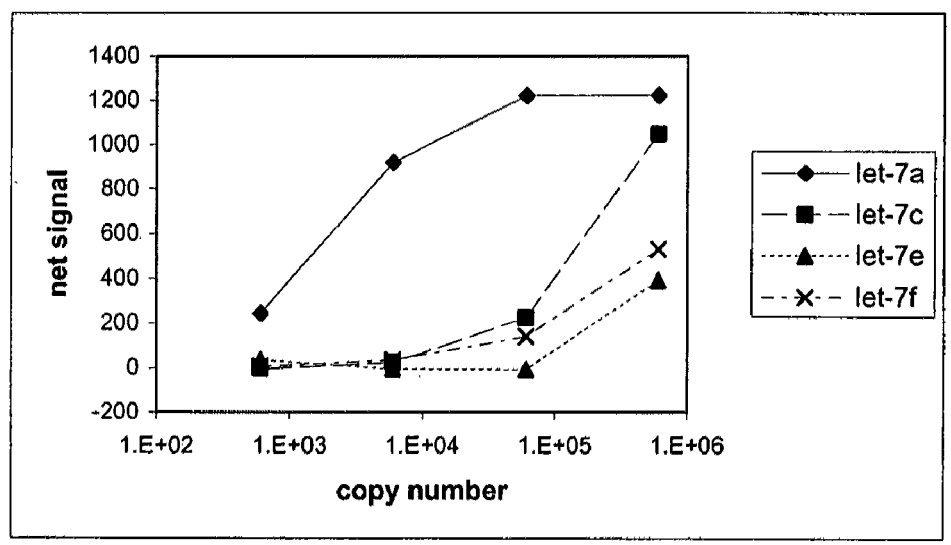
FIG. 40 shows the net signal generated by the let-7a assays as a function of let-7a, let-7c, let-7e, or let-7f copy number.

Let-7a assays were carried out in 20 µl 10 mM MOPS pH 7.5, 7.5 mM MgCl$_2$, 0.25 mM each dNTP including 0.67 µM 1716-94-1, 0.4 µM 1716-94-3, 0.4 µM 1716-94-4, 0.4 µM 1716-94-8, 2 unit/μl MMLV, 0.033 unit/μl TaqPol, 6.7 ng/μl CLEAVASE VIII enzyme; 0.25 μM 23-210 arm 3-FAM FRET cassette with 6 10$^5$, 6 10$^4$, 6,000, 600, 60, or none copies of let-7a RNA. Temperature profile was 42 C for 30 min; 95 C for 1 min; 25 cycles of 95 C for 20 s then 60 C for 1 min; 99 C for 6 min; 49 C for 30 min The net signal generated by the let-7a assays as a function of let-7a, let-7c, let-7e, or let-7f copy number is shown in FIG. 40.

Thus, the present invention provides that nucleic acid (e.g., RNA (e.g., miRNA)) detection assays (e.g., comprising a reverse transcription reaction, a polymerase chain reaction, and an invasive cleavage assay reaction and a detection structure) described herein display a 100-fold specificity for target nucleic acid (e.g., Let-7a) compared to variant sequences thereof (e.g., Let-7c).

L) Biplex Assay for let-7a miRNA and U6 RNA as an Internal Standard.

Experiments were designed and conducted to test detection of two fluorescent signals, each corresponding to a separate miRNA, in the same reaction vessel.

1. Schematic of the let-7a assay with extended range reporting to FAM dye and U6 RNA assay reporting to RED dye.

3. Let-7a and U6 specific signals generated by let-7a/U6 biplex assay are shown below:

| let-7a standard | Net let-7a signal | U6 standard | Net U6 signal |
|---|---|---|---|
| 6.0E+06 | 1101 | 6.0E+08 | 952 |
| 1.2E+06 | 432 | 1.2E+08 | 942 |
| 2.4E+05 | 93 | 2.4E+07 | 878 |
| 4.8E+04 | 24 | 4.8E+06 | 600 |
| 9.6E+03 | 1 | 9.6E+05 | 210 |
| 1.9E+03 | 1 | 1.9E+05 | 71 |
| 3.8E+02 | −2 | 3.8E+04 | 12 |
| Clontech samples | | Clontech samples | |
| heart | 1064 | heart | 840 |
| kidney | 1212 | kidney | 842 |
| liver | 467 | liver | 597 |
| lung | 1150 | lung | 774 |
| trachea | 73 | trachea | 158 |
| bone marrow | 9 | bone marrow | 48 |
| thymus | 17 | thymus | 514 |
| prostate | 168 | prostate | 95 |
| skeletal muscle | 4 | skeletal muscle | 52 |
| testis | 45 | testis | 324 |
| uterus | 33 | uterus | 288 |
| fetal liver | 41 | fetal liver | 265 |
| adrenal gland | 19 | adrenal gland | 266 |

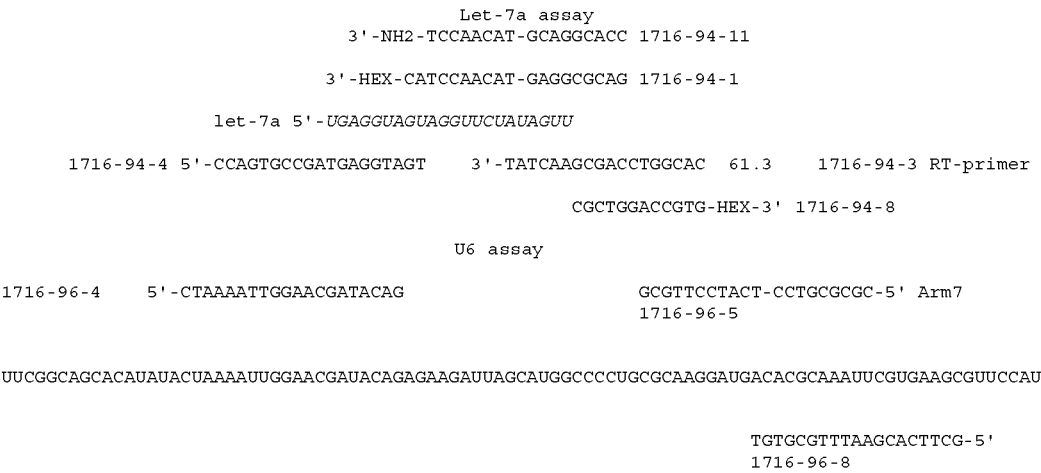

(let-7a is SEQ ID NO:275; U6 is SEQ ID NO:285; 1716-94-11 is SEQ ID NO:151; 1716-94-1 is SEQ ID NO:149; 1716-94-4 is SEQ ID NO:287; 1716-94-3 is SEQ ID NO:153; 1716-94-8 is SEQ ID NO:156; 1716-96-4 is SEQ ID NO:158; 1716-96-5 is SEQ ID NO:159; 1716-96-8 is SEQ ID NO:160)

2. Let-7a assay biplexed with U6 was carried out in 20 μl 10 mM MOPS pH 7.5, 7.5 mM MgCl$_2$, 0.25 mM each dNTP including 0.67 μM 1716-94-1; 0.33 μM 1716-94-11; 0.4 μM 1716-94-3, 0.4 μM 1716-94-4, 0.4 μM 1716-94-8, 0.4 μM 1716-96-5; 0.04 μM 1716-96-4; 0.04 μM 1716-96-8; 2 unit/μl MMLV, 0.033 unit/μl TaqPol, 6.7 ng/μl CLEAVASE VIII enzyme; 0.25 μM 23-210 arm 3-FAM, 0.25 μM 23-204 arm 4-FAM FRET and 0.25 μM arm 7-RED cassettes. Aliquots containing known amount of let-7a and U6 RNA or total RNA from different tissues (Clontech) were used as samples. Temperature profile was 42 C for 30 min; 95 C for 1 min; 20 cycles of 95 C for 20 s then 60 C for 1 min; 99 C for 6 min; 50 C for 10 min.

-continued

| salivary gland | 27 | salivary gland | 257 |
|---|---|---|---|
| thyroid | 30 | thyroid | 273 |

As shown in the data above, the present invention provides that two distinct miRNAs can be simultaneously amplified and detected in a single-step reaction (e.g., in a single reaction vessel).

M) Designs for the Detection of a miRNAs Associated with Cancer

Several oligonucleotides were generated during development of the present invention that are capable of detecting a variety of miRNAs associated with cancer. The oligonucleotides were designed according to the following guidelines:
1) RT primer-miRNA hybridizing region of 6 base pairs.
2) RT primer form a co-axial stack when hybridized to the targeted miRNA using three methods:
 a. 5'-end of RT primer folds back on itself to form a hairpin that stacks to the 3'-end of the miRNA.
 b. A DNA oligonucleotide is added to hybridize the RT primer forming a co-axial stack with miRNA once hybridized to it.

c. A 2'-O-methylated oligonucleotide is added to hybridize the RT primer forming a co-axial stack with miRNA once hybridized to it.
3) PCR primer cDNA hybridizing region of 9 base pairs. INVADER probe of 10 and 8 base pairs complementaries to the miRNA using arm 3 and 4, respectively.

Oligonucleotides designed according to these guidelines are depicted in FIG. 41.

Figure 42:
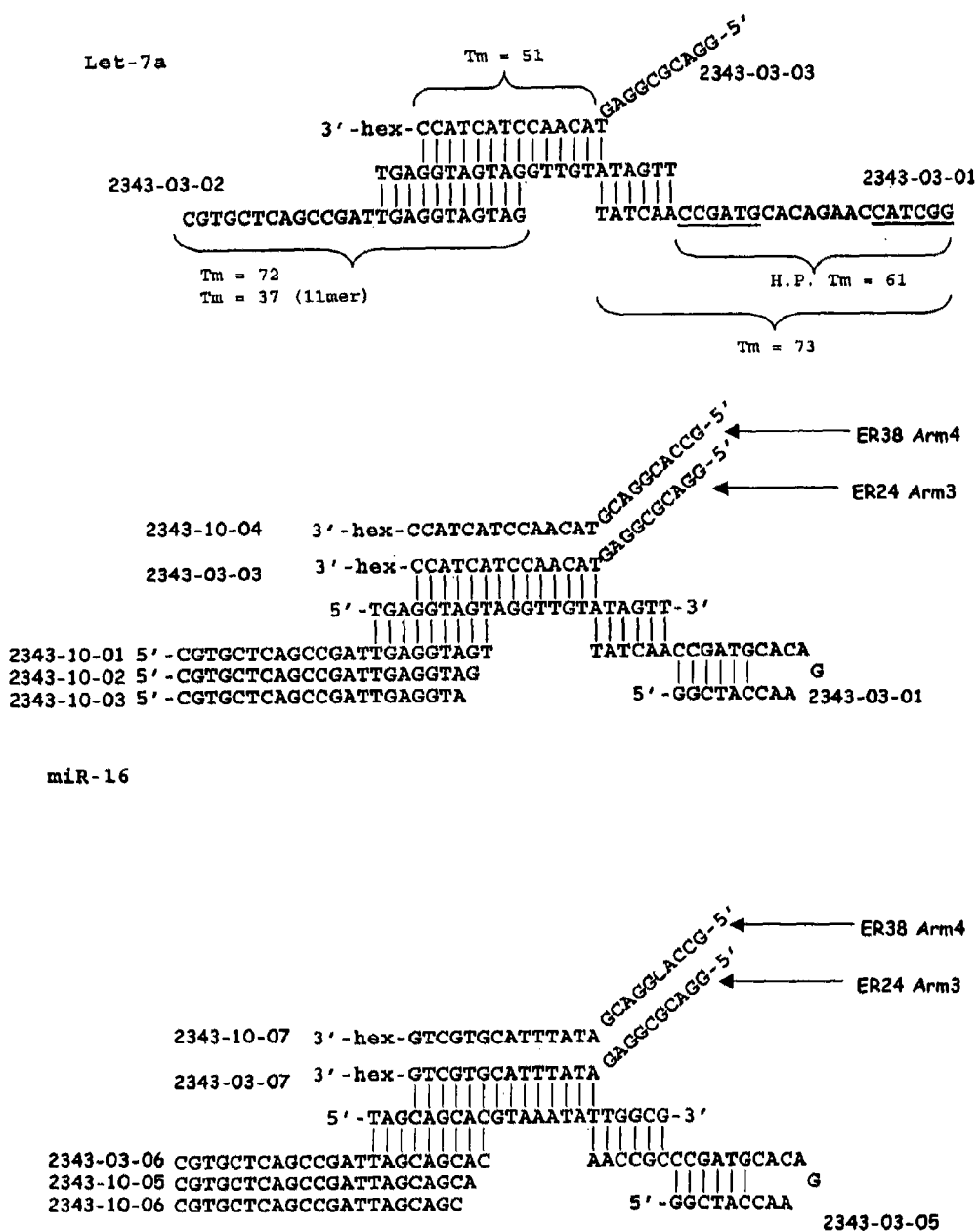
FIG. 42 shows additional designs for let-7a and miR-16 with varying lengths of primary probe and PCR primer hybridizing regions. Let-7a is SEQ ID NO:294; miR-16 is SEQ ID NO:289; 2343-03-01 is SEQ ID NO:171; 2343-03-02 is SEQ ID NO:172; 2343-03-03 is SEQ ID NO:173; 2343-03-05 is SEQ ID NO:174; 2343-03-06 is SEQ ID NO:175; 2343-03-07 is SEQ ID NO:176; 2343-10-01 is SEQ ID NO:177; 2343-10-02 is SEQ ID NO:178; 2343-10-03 is SEQ ID NO:179; 2343-10-04 is SEQ ID NO:180; 2343-10-05 is SEQ ID NO:181; 2343-10-06 is SEQ ID NO:182; 2343-10-07 is SEQ ID NO:183; 2343-14-01 is SEQ ID NO:184; 2343-14-02 is SEQ ID NO:185; 2343-14-03 is SEQ ID NO:186; 2343-14-04 is SEQ ID NO:187; 2343-14-05 is SEQ ID NO:188; 2343-14-06 is SEQ ID NO:189; 2343-14-07 is SEQ ID NO:190; 2343-14-08 is SEQ ID NO:191; 2343-14-09 is SEQ ID NO:192.

Additional designs for Let-7a and miR-16 with varying lengths of primary probe and PCR primer hybridizing regions are shown in FIG. 42.

A list of all oligonucleotides used in this Example are depicted in FIG. 43.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

We claim:

1. A method for detecting an miRNA target, comprising:
   a) providing:
      i) a sample suspected of containing an miRNA target, said miRNA target comprising a first region, a second region, and a third region, wherein said first region is downstream of and contiguous to said second region, and wherein said second region is downstream of and contiguous to said third region;
      ii) a first oligonucleotide that comprises a 3' portion that is complementary to said first region of said miRNA target, and a 5' portion that is not complementary to said miRNA target;
      iii) a second oligonucleotide that comprises a 3' portion that is substantially homologous to a said third region of said miRNA target and a 5' portion that is not homologous to said third region of said miRNA target;
      iv) a reverse transcriptase;
      v) a DNA polymerase;
      vi) a 5' nuclease;
      vii) a probe oligonucleotide, wherein at least a portion of said probe oligonucleotide is complementary to at least a portion of said second region of said miRNA target; and
      viii) a first stacker oligonucleotide comprising a 5' terminal portion, wherein at least the 5' terminal portion of said stacker oligonucleotide is complementary to a region in said 5' portion of said first oligonucleotide adjacent to said 3' portion of said first oligonucleotide;
   b) incubating components (i) through (viii) under conditions such that an invasive cleavage structure forms and is cleaved, wherein under said conditions:
      1) said first oligonucleotide hybridizes to said miRNA target and said first stacker oligonucleotide and is extended by said reverse transcriptase to produce a first extended product complementary to said miRNA target;
      2) said first extended product is amplified by polymerase chain reaction using said first oligonucleotide and said second oligonucleotide as primers to form an miRNA cDNA target;
      3) said probe oligonucleotide and said first oligonucleotide hybridize to said miRNA cDNA target to form an invasive cleavage structure; and
      4) said probe oligonucleotide in said invasive cleavage structure is cleaved by said 5' nuclease to produce non-target cleavage product;
      and
   c) detecting cleavage of said probe oligonucleotide, wherein cleavage of said probe oligonucleotide is indicative of the presence of said miRNA target.

2. The method of claim 1, wherein components (i) through (viii) are combined in the same reaction vessel prior to said incubating.

3. The method of claim 1, wherein said 5' nuclease is thermostable.

4. The method of claim 1, wherein said probe oligonucleotide is unlabeled and contains a 5' and 3' region, wherein said 3' region is complementary to said second region of said miRNA target; and wherein said 5' region is non-complementary to said miRNA target and forms a 5' flap.

5. The method of claim 1, wherein said 3' portion of said first oligonucleotide forms a duplex of about 6-10 base pairs with said miRNA target during said incubating.

6. The method of claim 1, further comprising providing a second stacker oligonucleotide comprising a 5' terminal portion, wherein at least the 5' terminal portion of said second stacker oligonucleotide is complementary to a region of said 5' portion said second oligonucleotide adjacent to said 3' portion of said second oligonucleotide.

7. The method of claim 1, wherein said detecting comprises use of a labeled probe that is configured for FRET detection.

8. The method of claim 1, wherein said miRNA is selected from the group consisting of Let-7, miR-1, miR-135, miR-15, miR-16, miR125b, miR-1d, and miR124a.

9. The method of claim 1, wherein said 5' nuclease comprises a modified DNA polymerase, wherein said modified DNA polymerase has 5' nuclease activity but lacks synthetic activity.

10. The method of claim 4, further comprising providing an oligonucleotide cassette, wherein a portion of said oligonucleotide cassette is complementary to said 5' region of said probe oligonucleotide, wherein said oligonucleotide cassette is configured to form an invasive cleavage structure with said non-target cleavage product from said cleavage of said probe oligonucleotide.

11. A method for detecting an miRNA target, comprising:
    a) providing:
        i) a sample suspected of containing an miRNA target, said miRNA target comprising a first region, a second region, and a third region, wherein said first region is downstream of and contiguous to said second region, and wherein said second region is downstream of and contiguous to said third region;
        ii) a first oligonucleotide that comprises a 3' portion that is complementary to said first region of said miRNA target, and a 5' portion that is not complementary to said miRNA target;
        iii) a second oligonucleotide that comprises a 3' portion that is substantially homologous to a said third region of said miRNA target and a 5' portion that is not homologous to said third region of said miRNA target;
        iv) a reverse transcriptase;
        v) a DNA polymerase;
        vi) a FEN-1 endonuclease;
        vii) a probe oligonucleotide, wherein at least a portion of said probe oligonucleotide is complementary to at least a portion of said second region of said miRNA target; and
        viii) a first stacker oligonucleotide comprising a 5' terminal portion, wherein at least the 5' terminal portion of said stacker oligonucleotide is complementary to a region in said 5' portion of said first oligonucleotide adjacent to said 3' portion of said first oligonucleotide;
    b) incubating components (i) through (viii) under conditions such that an invasive cleavage-structure forms and is cleaved, wherein under said conditions:
        1) said first oligonucleotide hybridizes to said miRNA target and said first stacker oligonucleotide and is extended by said reverse transcriptase to produce a first extended product complementary to said miRNA target;
        2) said first extended product is amplified by polymerase chain reaction using said first oligonucleotide and said second oligonucleotide as primers to form an miRNA cDNA target;
        3) said probe oligonucleotide and said first oligonucleotide hybridize to said miRNA cDNA target to form an invasive cleavage structure; and
        4) said probe oligonucleotide in said invasive cleavage structure is cleaved by said FEN-1 endonuclease to produce non-target cleavage product; and
    c) detecting cleavage of said probe oligonucleotide, wherein cleavage of said probe oligonucleotide is indicative of the presence of said miRNA target.

12. The method of claim 11, wherein components (i) through (viii) are combined in the same reaction vessel prior to said incubating.

13. The method of claim 11, wherein said FEN-1 endonuclease comprises a thermostable FEN-1.

14. The method of claim 13, wherein said FEN-1 endonuclease is from an archaebacterium.

15. The method of claim 14, wherein said archaebacterium species is selected from the group consisting of: *Pyrococcus furiosus, Methanococcus jannaschii, Archaeoglobus venefi-cus* and *Archaeoglobus fulgidus*.

16. The method of claim 11, wherein said probe oligonucleotide is unlabeled and contains a 5' and 3' region, wherein said 3' region is complementary to said second region of said miRNA target; and said 5' region is non-complementary to said second region of said miRNA target and forms a 5' flap.

17. The method of claim 16, further comprising an oligonucleotide cassette, wherein a portion of said oligonucleotide cassette is complementary to said 5' region of said probe oligonucleotide, wherein said oligonucleotide cassette is configured to form an invasive cleavage structure with said non-target cleavage product from said cleavage of said probe oligonucleotide.

18. The method of claim 11, further comprising providing a second stacker oligonucleotide comprising a 5' terminal portion, wherein at least the 5' terminal portion of said second stacker oligonucleotide is complementary to a region of said 5' portion said second oligonucleotide adjacent to said 3' portion of said second oligonucleotide.

19. The method of claim 11, wherein said detecting comprises use of a labeled probe that is configured for FRET detection.

20. The method of claim 11, wherein said miRNA is selected from the group consisting of Let-7, miR-1, miR-135, miR-15, miR-16, miR125b, miR-1d, and miR124a.

* * * * *

SEQUENCE LISTING

```
<160> NUMBER OF SEQ ID NOS: 298

<210> SEQ ID NO 1
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(14)
<223> OTHER INFORMATION: 2'-O-methyl

<400> SEQUENCE: 1
ggcacuuuug ugccaactat acaaccg                                       27

<210> SEQ ID NO 2
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (23)..(36)
<223> OTHER INFORMATION: 2'-O-methyl

<400> SEQUENCE: 2
ccgtcgctgc gttactacct cacgacguuu ucgucg                             36

<210> SEQ ID NO 3
<211> LENGTH: 30
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(30)
<223> OTHER INFORMATION: 2'-O-methyl

<400> SEQUENCE: 3
cgacgaaaac gucgugaggu aguaacgcag                                    30

<210> SEQ ID NO 4
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(20)
```

```
<400> SEQUENCE: 4
ugagguagua gguuguauag uu                                              22

<210> SEQ ID NO 5
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(14)
<223> OTHER INFORMATION: 2'-O-methyl

<400> SEQUENCE: 5
ggcacuuuug ugccaactat acaact                                          26

<210> SEQ ID NO 6
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(37)
<223> OTHER INFORMATION: 2'-O-methyl

<400> SEQUENCE: 6
ccgtcgctgc gtctactacc tcacgacguu uucgucg                              37

<210> SEQ ID NO 7
<211> LENGTH: 31
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(31)
<223> OTHER INFORMATION: 2'-O-methyl

<400> SEQUENCE: 7
cgacgaaaac gucgugaggu aguagacgca g                                    31

<210> SEQ ID NO 8
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(14)
<223> OTHER INFORMATION: 2'-O-methyl

<400> SEQUENCE: 8
ggcacuuuug ugccaactat acaat                                           25

<210> SEQ ID NO 9
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(38)
<223> OTHER INFORMATION: 2'-O-methyl
```

```
<400> SEQUENCE: 9
aacgaggcgc accctactac ctcacgacgu uuucgucg                                  38

<210> SEQ ID NO 10
<211> LENGTH: 32
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(32)
<223> OTHER INFORMATION: 2'-O-methyl

<400> SEQUENCE: 10
cgacgaaaac gucgugaggu aguagggugc gc                                       32

<210> SEQ ID NO 11
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 11
ggcagcuuuu gcugccctcc atacttctc                                           29

<210> SEQ ID NO 12
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (23)..(38)
<223> OTHER INFORMATION: 2'-O-methyl

<400> SEQUENCE: 12
aacgaggcgc acttacattc cacgagccuu uuggcucg                                 38

<210> SEQ ID NO 13
<211> LENGTH: 32
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(32)
<223> OTHER INFORMATION: 2'-O-methyl

<400> SEQUENCE: 13
cgagccaaaa ggcucgugga auguaagugc gc                                       32

<210> SEQ ID NO 14
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl
```

-continued

```
<400> SEQUENCE: 14
uggaauguaa agaaguaugg ag                                              22

<210> SEQ ID NO 15
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 15
ggcagcuuuu gcugccctcc atacttcc                                        28

<210> SEQ ID NO 16
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(39)
<223> OTHER INFORMATION: 2'-O-methyl

<400> SEQUENCE: 16
aacgaggcgc actttacatt ccacgagccu uuuggcucg                            39

<210> SEQ ID NO 17
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(33)
<223> OTHER INFORMATION: 2'-O-methyl

<400> SEQUENCE: 17
cgagccaaaa ggcucgugga auguaaagug cgc                                  33

<210> SEQ ID NO 18
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 18
ggcagcuuuu gcugccctcc atacttt                                         27

<210> SEQ ID NO 19
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(40)
<223> OTHER INFORMATION: 2'-O-methyl
```

-continued

```
<400> SEQUENCE: 19
aacgaggcgc acctttacat tccacgagcc uuuuggcucg                           40

<210> SEQ ID NO 20
<211> LENGTH: 34
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(34)

<400> SEQUENCE: 20
cgagccaaaa ggcucgugga auguaaaggu gcgc                                 34

<210> SEQ ID NO 21
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(13)
<223> OTHER INFORMATION: 2'-o-methyl
<220> FEATURE:
<221> NAME/KEY: misc_feature
<222> LOCATION: (3)..(3)
<223> OTHER INFORMATION: The residue at this position is linked to a
      quencher moiety

<400> SEQUENCE: 21
cactgcttcg tgg                                                        13

<210> SEQ ID NO 22
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(27)
<223> OTHER INFORMATION: 2'-O-methyl

<400> SEQUENCE: 22
ccaggaagca agtgacgcag cgacggu                                         27

<210> SEQ ID NO 23
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 23
ggcacuuuug ugccaactat acaat                                           25

<210> SEQ ID NO 24
<211> LENGTH: 22
<212> TYPE: RNA
<213> ORGANISM: Artificial Sequence
<220> FEATURE:
<223> OTHER INFORMATION: Synthetic
<220> FEATURE:
```

```
<221> NAME/KEY: modified_base
<222> LOCATION: (1)..(22)
<223> OTHER INFORMATION: 2'-O-methyl

<400> SEQUENCE: 24
uugguauguu ggaugaugga gu                                              22

<210> SEQ ID NO 25
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(21)
<223> OTHER INFORMATION: 2'-O-methyl

<400> SEQUENCE: 25
ugguacguug gaugauggag u                                               21

<210> SEQ ID NO 26
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 26
uugauauguu agaugaugga gu                                              22

<210> SEQ ID NO 27
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 27
ccgagcgaaa gcucggttca cataggaatc                                      30

<210> SEQ ID NO 28
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(39)
<223> OTHER INFORMATION: 2'-O-methyl

<400> SEQUENCE: 28
aacgaggcgc acaaaaagcc atacgagccg aaaggcucg                            39

<210> SEQ ID NO 29
<211> LENGTH: 33
<212> TYPE: RNA
<213> ORGANISM: Artificial Sequence
<220> FEATURE:
<223> OTHER INFORMATION: Synthetic
<220> FEATURE:
```

```
<221> NAME/KEY: modified_base
<222> LOCATION: (1)..(33)
<223> OTHER INFORMATION: 2'-O-methyl

<400> SEQUENCE: 29
cgagccuuuc ggcucguaug gcuuuugug cgc                              33

<210> SEQ ID NO 30
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 30
ccgagcgaaa gcucggttca cataggaac                                  29

<210> SEQ ID NO 31
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(40)
<223> OTHER INFORMATION: 2'-O-methyl

<400> SEQUENCE: 31
aacgaggcgc actaaaaagc catacgagcc gaaaggcucg                      40

<210> SEQ ID NO 32
<211> LENGTH: 34
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(34)
<223> OTHER INFORMATION: 2'-O-methyl

<400> SEQUENCE: 32
cgagccuuuc ggcucguaug gcuuuuuagu gcgc                            34

<210> SEQ ID NO 33
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 33
ccgagcgaaa gcucggttca cataggac                                   28

<210> SEQ ID NO 34
<211> LENGTH: 41
<212> TYPE: DNA
<213> ORGANISM: Artificial Sequence
<220> FEATURE:
<223> OTHER INFORMATION: Synthetic
<220> FEATURE:
```

-continued

```
<221> NAME/KEY: modified_base
<222> LOCATION: (26)..(41)
<223> OTHER INFORMATION: 2'-O-methyl

<400> SEQUENCE: 34
aacgaggcgc acataaaaag ccatacgagc cgaaaggcuc g                           41

<210> SEQ ID NO 35
<211> LENGTH: 35
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(35)
<223> OTHER INFORMATION: 2'-O-methyl

<400> SEQUENCE: 35
cgagccuuuc ggcucguaug gcuuuuuaug ugcgc                                 35

<210> SEQ ID NO 36
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 36
ccgagcgaaa gcucggttca cataggc                                          27

<210> SEQ ID NO 37
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (27)..(42)
<223> OTHER INFORMATION: 2'-O-methyl

<400> SEQUENCE: 37
aacgaggcgc acaataaaaa gccatacgag ccgaaaggcu cg                         42

<210> SEQ ID NO 38
<211> LENGTH: 36
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(36)
<223> OTHER INFORMATION: 2'-O-methyl

<400> SEQUENCE: 38
cgagccuuuc ggcucguaug gcuuuuuauu gugcgc                                36

<210> SEQ ID NO 39
<211> LENGTH: 22
<212> TYPE: DNA
<213> ORGANISM: Artificial Sequence
<220> FEATURE:
<223> OTHER INFORMATION: Synthetic
<220> FEATURE:
```

```
<221> NAME/KEY: modified_base
<222> LOCATION: (1)..(22)
<223> OTHER INFORMATION: 2'-O-methyl

<400> SEQUENCE: 39
uagcagcacg taaauauugg cg                                            22

<210> SEQ ID NO 40
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(27)
<223> OTHER INFORMATION: 2'-O-methyl

<400> SEQUENCE: 40
ccaggaagca agtggaggcg tgacggu                                       27

<210> SEQ ID NO 41
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(11)
<223> OTHER INFORMATION: 2'-O-methyl

<400> SEQUENCE: 41
ggaaucauau uggaacatgt aaaccatc                                      28

<210> SEQ ID NO 42
<211> LENGTH: 25
<212> TYPE: DNA
<213> ORGANISM: Artificial Sequence
<220> FEATURE:
<223> OTHER INFORMATION: Synthetic

<400> SEQUENCE: 42
ccgccgagat cacgtagttg aggtc                                         25

<210> SEQ ID NO 43
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(18)
<223> OTHER INFORMATION: 2'-O-methyl

<400> SEQUENCE: 43
gaccucaacu acgugauc                                                 18

<210> SEQ ID NO 44
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl
```

```
<400> SEQUENCE: 44
ucccugagac cuaacuugu ga                                              22

<210> SEQ ID NO 45
<211> LENGTH: 17
<212> TYPE: DNA
<213> ORGANISM: Artificial Sequence
<220> FEATURE:
<223> OTHER INFORMATION: Synthetic

<400> SEQUENCE: 45
ggccatgcta atcttca                                                   17

<210> SEQ ID NO 46
<211> LENGTH: 25
<212> TYPE: DNA
<213> ORGANISM: Artificial Sequence
<220> FEATURE:
<223> OTHER INFORMATION: Synthetic

<400> SEQUENCE: 46
ccgccgagat cactctgtat cgttc                                          25

<210> SEQ ID NO 47
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(18)
<223> OTHER INFORMATION: 2'-O-methyl

<400> SEQUENCE: 47
gaacgauaca gagugauc                                                  18

<210> SEQ ID NO 48
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(14)
<223> OTHER INFORMATION: 2'-O-methyl
<220> FEATURE:
<221> NAME/KEY: misc_feature
<222> LOCATION: (3)..(3)
<223> OTHER INFORMATION: The residue at this position is linked to a
      quencher moiety

<400> SEQUENCE: 48
ctcttctcag tgcg                                                      14

<210> SEQ ID NO 49
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (26)..(28)
<223> OTHER INFORMATION: 2'-O-methyl

<400> SEQUENCE: 49
ccagcaagca agtggtgatc tcggcggu                                       28
```

```
<210> SEQ ID NO 50
<211> LENGTH: 23
<212> TYPE: DNA
<213> ORGANISM: Artificial Sequence
<220> FEATURE:
<223> OTHER INFORMATION: Synthetic

<400> SEQUENCE: 50
ccgtcgctgc gtctactacc tca                                           23

<210> SEQ ID NO 51
<211> LENGTH: 12
<212> TYPE: DNA
<213> ORGANISM: Artificial Sequence
<220> FEATURE:
<223> OTHER INFORMATION: Synthetic

<400> SEQUENCE: 51
aactatacaa ct                                                       12

<210> SEQ ID NO 52
<211> LENGTH: 22
<212> TYPE: DNA
<213> ORGANISM: Artificial Sequence
<220> FEATURE:
<223> OTHER INFORMATION: Synthetic

<400> SEQUENCE: 52
ccgtcgctgc gttactacct ca                                            22

<210> SEQ ID NO 53
<211> LENGTH: 13
<212> TYPE: DNA
<213> ORGANISM: Artificial Sequence
<220> FEATURE:
<223> OTHER INFORMATION: Synthetic

<400> SEQUENCE: 53
aactatacaa ccg                                                      13

<210> SEQ ID NO 54
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-O-methyl

<400> SEQUENCE: 54
ugagguagua gacgcag                                                  17

<210> SEQ ID NO 55
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(39)
<223> OTHER INFORMATION: 2'-O-methyl

<400> SEQUENCE: 55
aacgaggcgc acatgtgctg ctacgagccu uuuggcucg                          39
```

```
<210> SEQ ID NO 56
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (17)..(28)
<223> OTHER INFORMATION: 2'-O-methyl

<400> SEQUENCE: 56
ggcagcuuuu gcugcccaca aaccattc                                           28

<210> SEQ ID NO 57
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(33)
<223> OTHER INFORMATION: 2'-O-methyl

<400> SEQUENCE: 57
cgagccaaaa ggcucguagc agcacaugug cgc                                     33

<210> SEQ ID NO 58
<211> LENGTH: 36
<212> TYPE: DNA
<213> ORGANISM: Artificial Sequence
<220> FEATURE:
<223> OTHER INFORMATION: Synthetic

<400> SEQUENCE: 58
aacgaggcgc acatgtgctg ctagctcgcc acgccg                                  36

<210> SEQ ID NO 59
<211> LENGTH: 25
<212> TYPE: DNA
<213> ORGANISM: Artificial Sequence
<220> FEATURE:
<223> OTHER INFORMATION: Synthetic

<400> SEQUENCE: 59
gctcgccacg ccgcacaaac cattc                                              25

<210> SEQ ID NO 60
<211> LENGTH: 13
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(13)

<400> SEQUENCE: 60
cggcguggcg agc                                                           13

<210> SEQ ID NO 61
<211> LENGTH: 30
<212> TYPE: RNA
<213> ORGANISM: Artificial Sequence
<220> FEATURE:
<223> OTHER INFORMATION: Synthetic
<220> FEATURE:
```

```
<221> NAME/KEY: modified_base
<222> LOCATION: (1)..(30)
<223> OTHER INFORMATION: 2'-O-methyl

<400> SEQUENCE: 61
cggcguggcg agcuagcagc acaugugcgc                                    30

<210> SEQ ID NO 62
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 62
uagcagcaca uaaugguuug ug                                            22

<210> SEQ ID NO 63
<211> LENGTH: 39
<212> TYPE: DNA
<213> ORGANISM: Artificial Sequence
<220> FEATURE:
<223> OTHER INFORMATION: Synthetic

<400> SEQUENCE: 63
aacgaggcgc acaataaaaa gccatagctc gccacgccg                          39

<210> SEQ ID NO 64
<211> LENGTH: 24
<212> TYPE: DNA
<213> ORGANISM: Artificial Sequence
<220> FEATURE:
<223> OTHER INFORMATION: Synthetic

<400> SEQUENCE: 64
gctcgccacg ccgttcacat aggc                                          24

<210> SEQ ID NO 65
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(33)
<223> OTHER INFORMATION: 2'-O-methyl

<400> SEQUENCE: 65
cggcguggcg agcuauggcu uuuuauugug cgc                                33

<210> SEQ ID NO 66
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-O-methyl

<400> SEQUENCE: 66
uagcagcaca ugugcgc                                                  17
```

```
<210> SEQ ID NO 67
<211> LENGTH: 32
<212> TYPE: DNA
<213> ORGANISM: Artificial Sequence
<220> FEATURE:
<223> OTHER INFORMATION: Synthetic

<400> SEQUENCE: 67
aacgaggcgc acatgtgctg ctaggcgaag cc                                    32

<210> SEQ ID NO 68
<211> LENGTH: 21
<212> TYPE: DNA
<213> ORGANISM: Artificial Sequence
<220> FEATURE:
<223> OTHER INFORMATION: Synthetic

<400> SEQUENCE: 68
ggcgaagccc acaaaccatt c                                                21

<210> SEQ ID NO 69
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (30)..(32)
<223> OTHER INFORMATION: 2'-O-methyl

<400> SEQUENCE: 69
aacgaggcgc acatgtgctg ctaggcgaag cc                                    32

<210> SEQ ID NO 70
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(3)
<223> OTHER INFORMATION: 2'-O-methyl

<400> SEQUENCE: 70
ggcgaagccc acaaaccatt c                                                21

<210> SEQ ID NO 71
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(33)
<223> OTHER INFORMATION: 2'-O-methyl

<400> SEQUENCE: 71
aacgaggcgc acatgtgctg ctaggcuucg gcc                                   33

<210> SEQ ID NO 72
<211> LENGTH: 22
<212> TYPE: DNA
<213> ORGANISM: Artificial Sequence
<220> FEATURE:
<223> OTHER INFORMATION: Synthetic
<220> FEATURE:
```

```
<221> NAME/KEY: modified_base
<222> LOCATION: (1)..(10)
<223> OTHER INFORMATION: 2'-O-methyl

<400> SEQUENCE: 72
ggcuucggcc cacaaaccat tc                                            22

<210> SEQ ID NO 73
<211> LENGTH: 26
<212> TYPE: DNA
<213> ORGANISM: Artificial Sequence
<220> FEATURE:
<223> OTHER INFORMATION: Synthetic

<400> SEQUENCE: 73
ggcacttttg tgccaactat acaact                                        26

<210> SEQ ID NO 74
<211> LENGTH: 37
<212> TYPE: DNA
<213> ORGANISM: Artificial Sequence
<220> FEATURE:
<223> OTHER INFORMATION: Synthetic

<400> SEQUENCE: 74
ccgtcgctgc gtctactacc tcacgacgtt ttcgtcg                            37

<210> SEQ ID NO 75
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: 2'-O-methyl

<400> SEQUENCE: 75
ggcacttttg tgccaactat acaact                                        26

<210> SEQ ID NO 76
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (33)..(37)
<223> OTHER INFORMATION: 2'-O-methyl

<400> SEQUENCE: 76
ccgtcgctgc gtctactacc tcacgacgtt ttcgucg                            37

<210> SEQ ID NO 77
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 77
ggcagcuuuu gcugcccgcc aatattg                                       27
```

```
<210> SEQ ID NO 78
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(40)
<223> OTHER INFORMATION: 2'-O-methyl

<400> SEQUENCE: 78
aacgaggcgc actacgtgct gctacgagcc uuuuggcucg                              40

<210> SEQ ID NO 79
<211> LENGTH: 34
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(34)
<223> OTHER INFORMATION: 2'-O-methyl

<400> SEQUENCE: 79
cgagccaaaa ggcucguagc agcacguagu gcgc                                    34

<210> SEQ ID NO 80
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 80
ggcagcuuuu gctgcctcac aagttaga                                           28

<210> SEQ ID NO 81
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(39)
<223> OTHER INFORMATION: 2'-O-methyl

<400> SEQUENCE: 81
aacgaggcgc acggtctcag ggacgagccu uuuggcucg                               39

<210> SEQ ID NO 82
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(33)
<223> OTHER INFORMATION: 2'-O-methyl

<400> SEQUENCE: 82
cgagccaaaa ggcucguccc ugagaccgug cgc                                     33
```

```
<210> SEQ ID NO 83
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(38)
<223> OTHER INFORMATION: 2'-O-methyl

<400> SEQUENCE: 83
ccgtcgctgc gtctactacc tcacgacguu uucgucgu                                    38

<210> SEQ ID NO 84
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(15)
<223> OTHER INFORMATION: 2'-O-methyl

<400> SEQUENCE: 84
uggcacuuuu gugccaacta tacaact                                                27

<210> SEQ ID NO 85
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(36)
<223> OTHER INFORMATION: 2'-O-methyl

<400> SEQUENCE: 85
ccgtcgctgc gtctactacc tcacgacguu uucguc                                      36

<210> SEQ ID NO 86
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(13)
<223> OTHER INFORMATION: 2'-O-methyl

<400> SEQUENCE: 86
gcacuuuugu gccaactata caact                                                  25

<210> SEQ ID NO 87
<211> LENGTH: 85
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(85)
<223> OTHER INFORMATION: 2'-O-methyl

<400> SEQUENCE: 87
gggcuuuggg gugagguagu agguuguaua guuuggaaua uuaccaccgg ugaacuaugc            60
```

-continued aauuuucuac cuuuccugaa guccc                                                   85

<210> SEQ ID NO 88
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(21)
<223> OTHER INFORMATION: 2'-O-methyl

<400> SEQUENCE: 88
uaaggcacgc ggugaaugcc a                                                       21

<210> SEQ ID NO 89
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 89
uuaaggcacg cggugaaugc ca                                                      22

<210> SEQ ID NO 90
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(39)
<223> OTHER INFORMATION: 2'-O-methyl

<400> SEQUENCE: 90
ccgtcgctgc gtcgcgtgcc ttacgagccu uuuggcucg                                    39

<210> SEQ ID NO 91
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-O-methyl

<400> SEQUENCE: 91
uaaggcacgc gacgcag                                                            17

<210> SEQ ID NO 92
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 92

```
ggcagcuuuu gcugccuggc attcaca                                            27

<210> SEQ ID NO 93
<211> LENGTH: 29
<212> TYPE: DNA
<213> ORGANISM: Artificial Sequence
<220> FEATURE:
<223> OTHER INFORMATION: Synthetic

<400> SEQUENCE: 93
ccgccgagat cacctaatct tctctgtat                                          29

<210> SEQ ID NO 94
<211> LENGTH: 22
<212> TYPE: DNA
<213> ORGANISM: Artificial Sequence
<220> FEATURE:
<223> OTHER INFORMATION: Synthetic

<400> SEQUENCE: 94
catccttgcg caggggccat ga                                                 22

<210> SEQ ID NO 95
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 95
auacagagaa gauuagguga uc                                                 22

<210> SEQ ID NO 96
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(24)
<223> OTHER INFORMATION: 2'-O-methyl

<400> SEQUENCE: 96
uauggcuuuu uauccuaug ugaa                                                24

<210> SEQ ID NO 97
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 97
uggaauguaa agaaguaugu au                                                 22

<210> SEQ ID NO 98
<211> LENGTH: 39
<212> TYPE: DNA
<213> ORGANISM: Artificial Sequence
<220> FEATURE:
```

```
<223> OTHER INFORMATION: Synthetic
<220> FEATURE:
<221> NAME/KEY: modified_base
<222> LOCATION: (24)..(39)
<223> OTHER INFORMATION: 2'-O-methyl

<400> SEQUENCE: 98
aacgaggcgc actttacatt ccacgagccu uuuggcucg                         39

<210> SEQ ID NO 99
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 99
ggcagcuuuu gcugccatac atacttcc                                    28

<210> SEQ ID NO 100
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(33)
<223> OTHER INFORMATION: 2'-O-methyl

<400> SEQUENCE: 100
cgagccaaaa ggcucgugga auguaaagug cgc                              33

<210> SEQ ID NO 101
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(33)
<223> OTHER INFORMATION: 2'-O-methyl

<400> SEQUENCE: 101
aacgaggcgc acaagatcat tgcggcuucg gcc                              33

<210> SEQ ID NO 102
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-O-methyl

<400> SEQUENCE: 102
ggcuucggcc aatgaagatc c                                           21

<210> SEQ ID NO 103
<211> LENGTH: 17
<212> TYPE: RNA
<213> ORGANISM: Artificial Sequence
<220> FEATURE:
```

```
<223> OTHER INFORMATION: Synthetic
<220> FEATURE:
<221> NAME/KEY: modified_base
<222> LOCATION: (1)..(17)
<223> OTHER INFORMATION: 2'-O-methyl

<400> SEQUENCE: 103
gcaaugaucu ugugcgc                                                    17

<210> SEQ ID NO 104
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(33)
<223> OTHER INFORMATION: 2'-O-methyl

<400> SEQUENCE: 104
aacgaggcgc accttgatct tcaggcuucg gcc                                  33

<210> SEQ ID NO 105
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-O-methyl

<400> SEQUENCE: 105
ggcuucggcc aagcaatgat a                                               21

<210> SEQ ID NO 106
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-O-methyl

<400> SEQUENCE: 106
ugaagaucaa ggugcgc                                                    17

<210> SEQ ID NO 107
<211> LENGTH: 102
<212> TYPE: DNA
<213> ORGANISM: Caenorhabditis elegans

<400> SEQUENCE: 107
gttcttccga gaacatatac taaaattgga acaatacaga gaagattagc atggcccctg     60
cgcaaggatg acacgcaaat tcgtgaagcg ttccaaattt tt                       102

<210> SEQ ID NO 108
<211> LENGTH: 102
<212> TYPE: DNA
<213> ORGANISM: Caenorhabditis briggsae

<400> SEQUENCE: 108
gttcttccga gaacatatac taaaattgga acaatacaga gaagattagc atggcccctg     60
```

```
cgcaaggatg acacgcaaat tcgtgaagcg ttccaaattt tt              102
```

<210> SEQ ID NO 109
<211> LENGTH: 107
<212> TYPE: DNA
<213> ORGANISM: Homo sapiens

<400> SEQUENCE: 109

```
gtgctcgctt cggcagcaca tatactaaaa ttggaacgat acagagaaga ttagcatggc   60
ccctgcgcaa ggatgacacg caaattcgtg aagcgttcca tattttt              107
```

<210> SEQ ID NO 110
<211> LENGTH: 106
<212> TYPE: DNA
<213> ORGANISM: Mus musculus

<400> SEQUENCE: 110

```
gtgctcgctt cggcagcaca tatactaaaa ttggaacgat acagagaaga ttagcatggc   60
ccctgcgcaa ggatgacacg caaattcgtg aagcgttcca tatttt               106
```

<210> SEQ ID NO 111
<211> LENGTH: 107
<212> TYPE: DNA
<213> ORGANISM: Xenopus sp.

<400> SEQUENCE: 111

```
gtgcttgctt cggcagcaca tatactaaaa ttggaacgat acagagaaga ttagcatggc   60
ccctgcgcaa ggatgacacg caaattcgtg aagcgttcca tattttt              107
```

<210> SEQ ID NO 112
<211> LENGTH: 107
<212> TYPE: DNA
<213> ORGANISM: Rattus norvegicus
<220> FEATURE:
<221> NAME/KEY: misc_feature
<222> LOCATION: (1)..(1)
<223> OTHER INFORMATION: n is a, c, g, or t

<400> SEQUENCE: 112

```
ngtgcctgct tcggcagcac atatactaaa attggaacga tacagagaag attagcatgg   60 ccctgcgca aggatgacac gcaaattcgt gaagcgttcc atatttt               107
```

<210> SEQ ID NO 113
<211> LENGTH: 108
<212> TYPE: DNA
<213> ORGANISM: Drosophila melanogaster
<220> FEATURE:
<221> NAME/KEY: misc_feature
<222> LOCATION: (1)..(1)
<223> OTHER INFORMATION: n is a, c, g, or t

<400> SEQUENCE: 113

```
ngttcttgct tcggcagaac atatactaaa attggaacga tacagagaag attagcatgg   60
ccccagcgca aggatgacac gcaaaatcgt gaagcgttcc acatttttt              108
```

<210> SEQ ID NO 114
<211> LENGTH: 102
<212> TYPE: DNA
<213> ORGANISM: Arabidopsis thaliana

<400> SEQUENCE: 114

```
gtcccttcgg ggacatccga taaaattgga acgatacaga gaagattagc atggcccctg   60
```

```
cgcaaggatg acacgcataa atcgagaaat ggtccaaatt tt                        102
```

<210> SEQ ID NO 115
<211> LENGTH: 85
<212> TYPE: DNA
<213> ORGANISM: Artificial Sequence
<220> FEATURE:
<223> OTHER INFORMATION: Synthetic

<400> SEQUENCE: 115

```
ccgtcgctgc gtctactacc tcacgacgtt ttcgtcguga gguaguaggu uguauaguug     60
gcacttttgt gccaactata caact                                           85
```

<210> SEQ ID NO 116
<211> LENGTH: 87
<212> TYPE: DNA
<213> ORGANISM: Artificial Sequence
<220> FEATURE:
<223> OTHER INFORMATION: Synthetic

<400> SEQUENCE: 116

```
ccgtcgctgc gtctactacc tcacgacgtt ttcgtcgtug agguaguagg uuguauaguu     60
tggcactttt gtgccaacta tacaact                                         87
```

<210> SEQ ID NO 117
<211> LENGTH: 83
<212> TYPE: DNA
<213> ORGANISM: Artificial Sequence
<220> FEATURE:
<223> OTHER INFORMATION: Synthetic

<400> SEQUENCE: 117

```
ccgtcgctgc gtctactacc tcacgacgtt ttcgtcugag guaguagguu guauaguugc     60
acttttgtgc caactataca act                                             83
```

<210> SEQ ID NO 118
<211> LENGTH: 21
<212> TYPE: DNA
<213> ORGANISM: Artificial Sequence
<220> FEATURE:
<223> OTHER INFORMATION: Synthetic

<400> SEQUENCE: 118

```
ugaagaucaa gaucauugct t                                               21
```

<210> SEQ ID NO 119
<211> LENGTH: 21
<212> TYPE: DNA
<213> ORGANISM: Artificial Sequence
<220> FEATURE:
<223> OTHER INFORMATION: Synthetic

<400> SEQUENCE: 119

```
gcaaugaucu ugaucuucat t                                               21
```

<210> SEQ ID NO 120
<211> LENGTH: 75
<212> TYPE: DNA
<213> ORGANISM: Artificial Sequence
<220> FEATURE:
<223> OTHER INFORMATION: Synthetic

<400> SEQUENCE: 120

```
aacgaggcgc acaagatcat tgcggcuucg gccgcaauga ucuugaucuu cattggcuuc     60
```
ggccaatgaa gatcc                                                75

<210> SEQ ID NO 121
<211> LENGTH: 75
<212> TYPE: DNA
<213> ORGANISM: Artificial Sequence
<220> FEATURE:
<223> OTHER INFORMATION: Synthetic

<400> SEQUENCE: 121
aacgaggcgc accttgatct tcaggcuucg gccugaagau caagaucauu gcttggcuuc    60
ggccaagcaa tgata                                                75

<210> SEQ ID NO 122
<211> LENGTH: 17
<212> TYPE: DNA
<213> ORGANISM: Artificial Sequence
<220> FEATURE:
<223> OTHER INFORMATION: Synthetic

<400> SEQUENCE: 122
gcaaugaucu ugugcgc                                              17

<210> SEQ ID NO 123
<211> LENGTH: 17
<212> TYPE: DNA
<213> ORGANISM: Artificial Sequence
<220> FEATURE:
<223> OTHER INFORMATION: Synthetic

<400> SEQUENCE: 123
ugaagaucaa ggugcgc                                              17

<210> SEQ ID NO 124
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: The residue at this position is linked to NH2

<400> SEQUENCE: 124
ccgtcgctgc gtctactacc tca                                       23

<210> SEQ ID NO 125
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: The residue at this position is linked to NH2

<400> SEQUENCE: 125
ccgtcacgcc tcctactacc tca                                       23

<210> SEQ ID NO 126
<211> LENGTH: 26
<212> TYPE: DNA
<213> ORGANISM: Artificial Sequence
<220> FEATURE:
<223> OTHER INFORMATION: Synthetic
<220> FEATURE:

```
<221> NAME/KEY: modified_base
<222> LOCATION: (1)..(14)
<223> OTHER INFORMATION: 2'-o-methyl

<400> SEQUENCE: 126
ggcacuuuug ugccaactat acaact                                          26

<210> SEQ ID NO 127
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-o-methyl

<400> SEQUENCE: 127
ugagguagua gacgcag                                                    17

<210> SEQ ID NO 128
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-o-methyl

<400> SEQUENCE: 128
ugagguagua ggaggcg                                                    17

<210> SEQ ID NO 129
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
<220> FEATURE:
<221> NAME/KEY: misc_feature
<222> LOCATION: (4)..(4)
<223> OTHER INFORMATION: The residue at this position is linked to a
      quencher moiety

<400> SEQUENCE: 129
cactgcttcg tgg                                                        13

<210> SEQ ID NO 130
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
<220> FEATURE:
<221> NAME/KEY: misc_feature
<222> LOCATION: (4)..(4)
<223> OTHER INFORMATION: The residue at this position is linked to a
      quencher moiety
```

```
<400> SEQUENCE: 130
cactcgaacg tcg                                                          13

<210> SEQ ID NO 131
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(27)
<223> OTHER INFORMATION: 2'-o-methyl

<400> SEQUENCE: 131
cgaggttcga agtggaggcg tgacggu                                           27

<210> SEQ ID NO 132
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(27)
<223> OTHER INFORMATION: 2'-o-methyl

<400> SEQUENCE: 132
ccaggaagca agtgacgcag cgacggu                                           27

<210> SEQ ID NO 133
<211> LENGTH: 22
<212> TYPE: RNA
<213> ORGANISM: Artificial Sequence
<220> FEATURE:
<223> OTHER INFORMATION: Synthetic

<400> SEQUENCE: 133
ugagguagua gguuguauag uu                                                22

<210> SEQ ID NO 134
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(29)
<223> OTHER INFORMATION: The residue at this position is linked to NH2

<400> SEQUENCE: 134
ccgccgagat cacctaatct tctctgtat                                         29

<210> SEQ ID NO 135
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(29)
<223> OTHER INFORMATION: The residue at this position is linked to NH2

<400> SEQUENCE: 135
aagcacgcag cacctaatct tctctgtat                                         29
```

```
<210> SEQ ID NO 136
<211> LENGTH: 43
<212> TYPE: RNA
<213> ORGANISM: Artificial Sequence
<220> FEATURE:
<223> OTHER INFORMATION: Synthetic

<400> SEQUENCE: 136
uuuauacaga gaagauuagc auggccccug cgcaaggaug uuu            43

<210> SEQ ID NO 137
<211> LENGTH: 22
<212> TYPE: DNA
<213> ORGANISM: Artificial Sequence
<220> FEATURE:
<223> OTHER INFORMATION: Synthetic

<400> SEQUENCE: 137
catccttgcg cagggccat ga                                    22

<210> SEQ ID NO 138
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-o-methyl

<400> SEQUENCE: 138
auacagagaa gauuagguga uc                                   22

<210> SEQ ID NO 139
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-o-methyl

<400> SEQUENCE: 139
auacagagaa gauuaggugc ug                                   22

<210> SEQ ID NO 140
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
<220> FEATURE:
<221> NAME/KEY: misc_feature
<222> LOCATION: (4)..(4)
<223> OTHER INFORMATION: The residue at this position is linked to a
      quencher moiety

<400> SEQUENCE: 140
ctcttctcag tgcg                                            14

<210> SEQ ID NO 141
```

```
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
<220> FEATURE:
<221> NAME/KEY: misc_feature
<222> LOCATION: (4)..(4)
<223> OTHER INFORMATION: The residue at this position is linked to a
      quencher moiety

<400> SEQUENCE: 141
ctctgcatag tccg                                                         14

<210> SEQ ID NO 142
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (27)..(29)
<223> OTHER INFORMATION: 2'-o-methyl

<400> SEQUENCE: 142
cgcagtgaga atgaggtgat ctcggcggu                                         29

<210> SEQ ID NO 143
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (27)..(29)
<223> OTHER INFORMATION: 2'-o-methyl

<400> SEQUENCE: 143
cggagtatgc atgaggtgct gcgtgcuuu                                         29

<210> SEQ ID NO 144
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(27)
<223> OTHER INFORMATION: 2'-o-methyl

<400> SEQUENCE: 144
ccaggaagca agtgacgcag cgacggu                                           27

<210> SEQ ID NO 145
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(14)
<223> OTHER INFORMATION: 2'-o-methyl
```

```
<400> SEQUENCE: 145
ggcacuuuug ugccaactat acaact                                          26

<210> SEQ ID NO 146
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (23)..(23)
<223> OTHER INFORMATION: The residue at this position is linked to amino

<400> SEQUENCE: 146
ccgtcgctgc gtctactacc tca                                             23

<210> SEQ ID NO 147
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: The residue at this position is linked to NH2

<400> SEQUENCE: 147
ccgtcgctgc gtctactacc tca                                             23

<210> SEQ ID NO 148
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-o-methyl

<400> SEQUENCE: 148
ugagguagua gacgcag                                                    17

<210> SEQ ID NO 149
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: The residue at this position is linked to
      hexanediol

<400> SEQUENCE: 149
gacgcggagt acaacctac                                                  19

<210> SEQ ID NO 150
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: The residue at this position is linked to NH2
```

<400> SEQUENCE: 150
ccacggacgt acaaccta                                                   18

<210> SEQ ID NO 151
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: The residue at this position is linked to NH2

<400> SEQUENCE: 151
ccacggacgt acaacct                                                    17

<210> SEQ ID NO 152
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: The residue at this position is linked to
      hexanediol

<400> SEQUENCE: 152
gacgcggaga tacaacctac                                                 20

<210> SEQ ID NO 153
<211> LENGTH: 18
<212> TYPE: DNA
<213> ORGANISM: Artificial Sequence
<220> FEATURE:
<223> OTHER INFORMATION: Synthetic

<400> SEQUENCE: 153
cacggtccag cgaactat                                                   18

<210> SEQ ID NO 154
<211> LENGTH: 17
<212> TYPE: DNA
<213> ORGANISM: Artificial Sequence
<220> FEATURE:
<223> OTHER INFORMATION: Synthetic

<400> SEQUENCE: 154
cacggtccag cgaacta                                                    17

<210> SEQ ID NO 155
<211> LENGTH: 20
<212> TYPE: DNA
<213> ORGANISM: Artificial Sequence
<220> FEATURE:
<223> OTHER INFORMATION: Synthetic

<400> SEQUENCE: 155
ccagtgccga tgaggtagta                                                 20

<210> SEQ ID NO 156
<211> LENGTH: 12
<212> TYPE: DNA
<213> ORGANISM: Artificial Sequence
<220> FEATURE:

```
<223> OTHER INFORMATION: Synthetic
<220> FEATURE:
<221> NAME/KEY: misc_feature
<222> LOCATION: (12)..(12)
<223> OTHER INFORMATION: The residue at this position is linked to
      hexanediol

<400> SEQUENCE: 156
cgctggaccg tg                                                            12

<210> SEQ ID NO 157
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: The residue at this position is linked to
      hexanediol

<400> SEQUENCE: 157
tcggcactgg                                                               10

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
ctaaaattgg aacgatacag                                                    20

<210> SEQ ID NO 159
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: The residue at this position is linked to NH2

<400> SEQUENCE: 159
cgcgcgtcct catccttgcg                                                    20

<210> SEQ ID NO 160
<211> LENGTH: 19
<212> TYPE: DNA
<213> ORGANISM: Artificial Sequence
<220> FEATURE:
<223> OTHER INFORMATION: Synthetic

<400> SEQUENCE: 160
gcttcacgaa tttgcgtgt                                                     19

<210> SEQ ID NO 161
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(29)
<223> OTHER INFORMATION: The residue at this position is linked to NH2
```

-continued

<400> SEQUENCE: 161
ccgccgagat cacctaatct tctctgtat                                                29

<210> SEQ ID NO 162
<211> LENGTH: 22
<212> TYPE: DNA
<213> ORGANISM: Artificial Sequence
<220> FEATURE:
<223> OTHER INFORMATION: Synthetic

<400> SEQUENCE: 162
catccttgcg cagggccat ga                                                        22

<210> SEQ ID NO 163
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-o-methyl

<400> SEQUENCE: 163
auacagagaa gauuagguga uc                                                       22

<210> SEQ ID NO 164
<211> LENGTH: 43
<212> TYPE: RNA
<213> ORGANISM: Artificial Sequence
<220> FEATURE:
<223> OTHER INFORMATION: Synthetic

<400> SEQUENCE: 164
uuuauacaga gaagauuagc auggcccug cgcaaggaug uuu                                 43

<210> SEQ ID NO 165
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
<220> FEATURE:
<221> NAME/KEY: misc_feature
<222> LOCATION: (4)..(4)
<223> OTHER INFORMATION: The residue at this position is linked to a
      quencher moiety

<400> SEQUENCE: 165
ctcttctcag tgcg                                                                14

<210> SEQ ID NO 166
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
<220> FEATURE:
<221> NAME/KEY: misc_feature

```
<222> LOCATION: (4)..(4)
<223> OTHER INFORMATION: The residue at this position is linked to a
      quencher moiety

<400> SEQUENCE: 166
cactgcttcg tgg                                                          13

<210> SEQ ID NO 167
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (27)..(29)
<223> OTHER INFORMATION: 2'-o-methyl

<400> SEQUENCE: 167
cgcagtgaga atgaggtgat ctcggcggu                                         29

<210> SEQ ID NO 168
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
<220> FEATURE:
<221> NAME/KEY: misc_feature
<222> LOCATION: (4)..(4)
<223> OTHER INFORMATION: The residue at this position is linked to a
      quencher moiety

<400> SEQUENCE: 168
tctagccggt tttccggctg agacgtccgt ggcct                                  35

<210> SEQ ID NO 169
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
<220> FEATURE:
<221> NAME/KEY: misc_feature
<222> LOCATION: (4)..(4)
<223> OTHER INFORMATION: The residue at this position is linked to a
      quencher moiety

<400> SEQUENCE: 169
tctagccggt tttccggctg agactccgcg tccgt                                  35

<210> SEQ ID NO 170
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
```

```
<220> FEATURE:
<221> NAME/KEY: misc_feature
<222> LOCATION: (4)..(4)
<223> OTHER INFORMATION: The residue at this position is linked to a
      quencher moiety

<400> SEQUENCE: 170
tcttcggcct tttggccgag agacgtccgt ggcct                      35

<210> SEQ ID NO 171
<211> LENGTH: 26
<212> TYPE: DNA
<213> ORGANISM: Artificial Sequence
<220> FEATURE:
<223> OTHER INFORMATION: Synthetic

<400> SEQUENCE: 171
ggctaccaag acacgtagcc aactat                                26

<210> SEQ ID NO 172
<211> LENGTH: 25
<212> TYPE: DNA
<213> ORGANISM: Artificial Sequence
<220> FEATURE:
<223> OTHER INFORMATION: Synthetic

<400> SEQUENCE: 172
cgtgctcagc cgattgaggt agtag                                 25

<210> SEQ ID NO 173
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: The residue at this position is linked to
      hexanediol

<400> SEQUENCE: 173
ggacgcggag tacaacctac tacc                                  24

<210> SEQ ID NO 174
<211> LENGTH: 26
<212> TYPE: DNA
<213> ORGANISM: Artificial Sequence
<220> FEATURE:
<223> OTHER INFORMATION: Synthetic

<400> SEQUENCE: 174
ggctaccaag acacgtagcc cgccaa                                26

<210> SEQ ID NO 175
<211> LENGTH: 23
<212> TYPE: DNA
<213> ORGANISM: Artificial Sequence
<220> FEATURE:
<223> OTHER INFORMATION: Synthetic

<400> SEQUENCE: 175
cgtgctcagc cgattagcag cac                                   23

<210> SEQ ID NO 176
<211> LENGTH: 24
<212> TYPE: DNA
<213> ORGANISM: Artificial Sequence
```

```
<220> FEATURE:
<223> OTHER INFORMATION: Synthetic

<400> SEQUENCE: 176
ggacgcggag atatttacgt gctg                                              24

<210> SEQ ID NO 177
<211> LENGTH: 23
<212> TYPE: DNA
<213> ORGANISM: Artificial Sequence
<220> FEATURE:
<223> OTHER INFORMATION: Synthetic

<400> SEQUENCE: 177
cgtgctcagc cgattgaggt agt                                               23

<210> SEQ ID NO 178
<211> LENGTH: 22
<212> TYPE: DNA
<213> ORGANISM: Artificial Sequence
<220> FEATURE:
<223> OTHER INFORMATION: Synthetic

<400> SEQUENCE: 178
cgtgctcagc cgattgaggt ag                                                22

<210> SEQ ID NO 179
<211> LENGTH: 22
<212> TYPE: DNA
<213> ORGANISM: Artificial Sequence
<220> FEATURE:
<223> OTHER INFORMATION: Synthetic

<400> SEQUENCE: 179
acgtgctcag ccgattgagg ta                                                22

<210> SEQ ID NO 180
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: The residue at this position is linked to
      hexanediol

<400> SEQUENCE: 180
gccacggacg tacaacctac tacc                                              24

<210> SEQ ID NO 181
<211> LENGTH: 22
<212> TYPE: DNA
<213> ORGANISM: Artificial Sequence
<220> FEATURE:
<223> OTHER INFORMATION: Synthetic

<400> SEQUENCE: 181
cgtgctcagc cgattagcag ca                                                22

<210> SEQ ID NO 182
<211> LENGTH: 21
<212> TYPE: DNA
<213> ORGANISM: Artificial Sequence
<220> FEATURE:
<223> OTHER INFORMATION: Synthetic
```

-continued

```
<400> SEQUENCE: 182
cgtgctcagc cgattagcag c                                              21

<210> SEQ ID NO 183
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: The residue at this position is linked to
      hexanediol

<400> SEQUENCE: 183
gccacggacg atatttacgt gctg                                           24

<210> SEQ ID NO 184
<211> LENGTH: 27
<212> TYPE: DNA
<213> ORGANISM: Artificial Sequence
<220> FEATURE:
<223> OTHER INFORMATION: Synthetic

<400> SEQUENCE: 184
ggctaccaag acacgtagcc aactata                                        27

<210> SEQ ID NO 185
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: The residue at this position is linked to
      hexanediol

<400> SEQUENCE: 185
gacgcggaga caacctacta                                                20

<210> SEQ ID NO 186
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: The residue at this position is linked to
      hexanediol

<400> SEQUENCE: 186
ccacggacga caacctacta                                                20

<210> SEQ ID NO 187
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: The residue at this position is linked to
      hexanediol
```

-continued

<400> SEQUENCE: 187
gacgcggaga caacctact                                              19

<210> SEQ ID NO 188
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: The residue at this position is linked to
      hexanediol

<400> SEQUENCE: 188
ccacggacga caacctact                                              19

<210> SEQ ID NO 189
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: The residue at this position is linked to
      hexanediol

<400> SEQUENCE: 189
gacgcggagt acaacctact                                             20

<210> SEQ ID NO 190
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: The residue at this position is linked to
      hexanediol

<400> SEQUENCE: 190
ccacggacgt acaacctact                                             20

<210> SEQ ID NO 191
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: The residue at this position is linked to
      hexanediol

<400> SEQUENCE: 191
gacgcggagt acaacctac                                              19

<210> SEQ ID NO 192
<211> LENGTH: 19
<212> TYPE: DNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: (19)..(19)
<223> OTHER INFORMATION: The residue at this position is linked to
      hexanediol

<400> SEQUENCE: 192
ccacggacgt acaacctac                                                    19

<210> SEQ ID NO 193
<211> LENGTH: 22
<212> TYPE: DNA
<213> ORGANISM: Artificial Sequence
<220> FEATURE:
<223> OTHER INFORMATION: Synthetic

<400> SEQUENCE: 193
gtgctcagcc aggtgaggta gt                                                22

<210> SEQ ID NO 194
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
<220> FEATURE:
<221> NAME/KEY: misc_feature
<222> LOCATION: (4)..(4)
<223> OTHER INFORMATION: The residue at this position is linked to a
      quencher moiety

<400> SEQUENCE: 194
cactcgaacg tcg                                                          13

<210> SEQ ID NO 195
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(27)
<223> OTHER INFORMATION: 2'-o-methyl

<400> SEQUENCE: 195
cgaggttcga agtggaggcg tgacggu                                           27

<210> SEQ ID NO 196
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: The residue at this position is linked to NH2

<400> SEQUENCE: 196
ccgtcacgcc tcctactacc tca                                               23

<210> SEQ ID NO 197
<211> LENGTH: 17
<212> TYPE: RNA
<213> ORGANISM: Artificial Sequence
```

```
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-o-methyl

<400> SEQUENCE: 197
ugagguagua ggaggcg                                                    17

<210> SEQ ID NO 198
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-o-methyl

<400> SEQUENCE: 198
ugagguagua ggaggcg                                                    17

<210> SEQ ID NO 199
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-o-methyl

<400> SEQUENCE: 199
uagcagcaca ugugcgc                                                    17

<210> SEQ ID NO 200
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(33)
<223> OTHER INFORMATION: 2'-o-methyl

<400> SEQUENCE: 200
ccgtcacgcc tcatgtgctg ctaggcuucg gcc                                  33

<210> SEQ ID NO 201
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-o-methyl

<400> SEQUENCE: 201
uagcagcaca ugaggcg                                                    17

<210> SEQ ID NO 202
<211> LENGTH: 22
<212> TYPE: DNA
<213> ORGANISM: Artificial Sequence
```

```
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-o-methyl

<400> SEQUENCE: 202
ggcuucggcc aactatacaa ct                                              22

<210> SEQ ID NO 203
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-o-methyl

<400> SEQUENCE: 203
ggcuucggcc aactatacaa tt                                              22

<210> SEQ ID NO 204
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-o-methyl

<400> SEQUENCE: 204
ggcuucggcc aaccatacaa ct                                              22

<210> SEQ ID NO 205
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(33)
<223> OTHER INFORMATION: 2'-o-methyl

<400> SEQUENCE: 205
ccgtcgctgc gtctcctacc tcaggcuucg gcc                                  33

<210> SEQ ID NO 206
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-o-methyl

<400> SEQUENCE: 206
ggcuucggcc actatacaac t                                               21

<210> SEQ ID NO 207
<211> LENGTH: 17
<212> TYPE: RNA
<213> ORGANISM: Artificial Sequence
```

```
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-o-methyl

<400> SEQUENCE: 207
ugagguagga gacgcag                                                17

<210> SEQ ID NO 208
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(33)
<223> OTHER INFORMATION: 2'-o-methyl

<400> SEQUENCE: 208
aacgaggcgc acatgtgctg ctaggcuucg gcc                               33

<210> SEQ ID NO 209
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-o-methyl

<400> SEQUENCE: 209
ggcuucggcc cacaaaccat tc                                           22

<210> SEQ ID NO 210
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-o-methyl

<400> SEQUENCE: 210
uagcagcaca ugugcgc                                                 17

<210> SEQ ID NO 211
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(34)
<223> OTHER INFORMATION: 2'-o-methyl

<400> SEQUENCE: 211
aacgaggcgc actacgtgct gctaggcuuc ggcc                              34

<210> SEQ ID NO 212
<211> LENGTH: 21
<212> TYPE: DNA
<213> ORGANISM: Artificial Sequence
```

```
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-o-methyl

<400> SEQUENCE: 212
ggcuucggcc cgccaatatt g                                             21

<210> SEQ ID NO 213
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(18)
<223> OTHER INFORMATION: 2'-o-methyl

<400> SEQUENCE: 213
uagcagcacg uagugcgc                                                 18

<210> SEQ ID NO 214
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (23)..(33)
<223> OTHER INFORMATION: 2'-o-methyl

<400> SEQUENCE: 214
aacgaggcgc acggtctcag ggaggcuucg gcc                                33

<210> SEQ ID NO 215
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-o-methyl

<400> SEQUENCE: 215
ggcuucggcc tcacaagtta ga                                            22

<210> SEQ ID NO 216
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-o-methyl

<400> SEQUENCE: 216
ucccugagac cgugcgc                                                  17

<210> SEQ ID NO 217
<211> LENGTH: 35
<212> TYPE: DNA
<213> ORGANISM: Artificial Sequence
```

```
<220> FEATURE:
<223> OTHER INFORMATION: Synthetic
<220> FEATURE:
<221> NAME/KEY: modified_base
<222> LOCATION: (26)..(35)
<223> OTHER INFORMATION: 2'-o-methyl

<400> SEQUENCE: 217
ccgtcgctgc gttataagca ctttaggcuu cggcc                              35

<210> SEQ ID NO 218
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-o-methyl

<400> SEQUENCE: 218
ggcuucggcc ctacctgcac c                                             21

<210> SEQ ID NO 219
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(19)
<223> OTHER INFORMATION: 2'-o-methyl

<400> SEQUENCE: 219
uaaagugcuu auaacgcag                                                19

<210> SEQ ID NO 220
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(34)
<223> OTHER INFORMATION: 2'-o-methyl

<400> SEQUENCE: 220
ccgtcgctgc gtgattagca ttaaggcuuc ggcc                               34

<210> SEQ ID NO 221
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-o-methyl

<400> SEQUENCE: 221
ggcuucggcc cccctatcac c                                             21

<210> SEQ ID NO 222
<211> LENGTH: 18
<212> TYPE: RNA
<213> ORGANISM: Artificial Sequence
```

```
<220> FEATURE:
<223> OTHER INFORMATION: Synthetic
<220> FEATURE:
<221> NAME/KEY: modified_base
<222> LOCATION: (1)..(18)
<223> OTHER INFORMATION: 2'-o-methyl

<400> SEQUENCE: 222
uuaaugcuaa ucacgcag                                                      18

<210> SEQ ID NO 223
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(29)
<223> OTHER INFORMATION: The residue at this position is linked to amino
<220> FEATURE:
<221> NAME/KEY: misc_feature
<222> LOCATION: (29)..(29)
<223> OTHER INFORMATION: The residue at this position is linked to C6

<400> SEQUENCE: 223
aagcacgcag cacctaatct tctctgtat                                          29

<210> SEQ ID NO 224
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(29)
<223> OTHER INFORMATION: The residue at this position is linked to NH2

<400> SEQUENCE: 224
aagcacgcag cacctaatct tctctgtat                                          29

<210> SEQ ID NO 225
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
<220> FEATURE:
<221> NAME/KEY: misc_feature
<222> LOCATION: (4)..(4)
<223> OTHER INFORMATION: The residue at this position is linked to a
      quencher moiety

<400> SEQUENCE: 225
ctctgcatag tccg                                                          14

<210> SEQ ID NO 226
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (27)..(29)
<223> OTHER INFORMATION: 2'-o-methyl
```

<400> SEQUENCE: 226
cggagtatgc atgaggtgct gcgtgcuuu                                    29

<210> SEQ ID NO 227
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-o-methyl

<400> SEQUENCE: 227
auacagagaa gauuaggugc ug                                           22

<210> SEQ ID NO 228
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(34)
<223> OTHER INFORMATION: 2'-o-methyl

<400> SEQUENCE: 228
ccgtcgctgc gtaggaagca ctttggcuuc ggcc                              34

<210> SEQ ID NO 229
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-o-methyl

<400> SEQUENCE: 229
ggcuucggcc atgcccaaaa cg                                           22

<210> SEQ ID NO 230
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(18)
<223> OTHER INFORMATION: 2'-o-methyl

<400> SEQUENCE: 230
aaagugcuuc cuacgcag                                                18

<210> SEQ ID NO 231
<211> LENGTH: 23
<212> TYPE: RNA
<213> ORGANISM: Artificial Sequence
<220> FEATURE:
<223> OTHER INFORMATION: Synthetic

<400> SEQUENCE: 231
aaagugcuuc cuguuuggg cau                                           23

```
<210> SEQ ID NO 232
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (26)..(36)
<223> OTHER INFORMATION: 2'-o-methyl

<400> SEQUENCE: 232
ccgtcgctgc gtctataagc actttaggcu ucggcc                                36

<210> SEQ ID NO 233
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-o-methyl

<400> SEQUENCE: 233
ggcuucggcc ctacctgcat                                                  20

<210> SEQ ID NO 234
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(20)
<223> OTHER INFORMATION: 2'-o-methyl

<400> SEQUENCE: 234
uaaagugcuu auagacgcag                                                  20

<210> SEQ ID NO 235
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(33)
<223> OTHER INFORMATION: 2'-o-methyl

<400> SEQUENCE: 235
aacgaggcgc acggaagcac tttggcuucg gcc                                   33

<210> SEQ ID NO 236
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-o-methyl

<400> SEQUENCE: 236
ggcuucggcc atgcccaaaa caa                                              23
```

<210> SEQ ID NO 237
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-o-methyl

<400> SEQUENCE: 237
aaagugcuuc cgugcgc                                                  17

<210> SEQ ID NO 238
<211> LENGTH: 26
<212> TYPE: DNA
<213> ORGANISM: Artificial Sequence
<220> FEATURE:
<223> OTHER INFORMATION: Synthetic

<400> SEQUENCE: 238
ggctaccaag acacgtagcc cacaaa                                        26

<210> SEQ ID NO 239
<211> LENGTH: 18
<212> TYPE: DNA
<213> ORGANISM: Artificial Sequence
<220> FEATURE:
<223> OTHER INFORMATION: Synthetic

<400> SEQUENCE: 239
cacggtccag cgcacaaa                                                 18

<210> SEQ ID NO 240
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: The residue at this position is linked to amino

<400> SEQUENCE: 240
gacgcggaga ccattatgt                                                19

<210> SEQ ID NO 241
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: The residue at this position is linked to amino

<400> SEQUENCE: 241
ccacggacga ccattat                                                  17

<210> SEQ ID NO 242
<211> LENGTH: 18
<212> TYPE: DNA
<213> ORGANISM: Artificial Sequence
<220> FEATURE:
<223> OTHER INFORMATION: Synthetic

<400> SEQUENCE: 242
cacggtccag cgcgccaa                                                        18

<210> SEQ ID NO 243
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: The residue at this position is linked to amino

<400> SEQUENCE: 243
gacgcggaga tatttacgt                                                       19

<210> SEQ ID NO 244
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: The residue at this position is linked to amino

<400> SEQUENCE: 244
gacgcggaga tatttac                                                         17

<210> SEQ ID NO 245
<211> LENGTH: 26
<212> TYPE: DNA
<213> ORGANISM: Artificial Sequence
<220> FEATURE:
<223> OTHER INFORMATION: Synthetic

<400> SEQUENCE: 245
ggctaccaag acacgtagcc ccccta                                               26

<210> SEQ ID NO 246
<211> LENGTH: 18
<212> TYPE: DNA
<213> ORGANISM: Artificial Sequence
<220> FEATURE:
<223> OTHER INFORMATION: Synthetic

<400> SEQUENCE: 246
cacggtccag cgcccta                                                         18

<210> SEQ ID NO 247
<211> LENGTH: 22
<212> TYPE: DNA
<213> ORGANISM: Artificial Sequence
<220> FEATURE:
<223> OTHER INFORMATION: Synthetic

<400> SEQUENCE: 247
gtgctcagcc aggttaatgc ta                                                   22

<210> SEQ ID NO 248
<211> LENGTH: 19
<212> TYPE: DNA
<213> ORGANISM: Artificial Sequence
<220> FEATURE:
<223> OTHER INFORMATION: Synthetic

```
<220> FEATURE:
<221> NAME/KEY: misc_feature
<222> LOCATION: (19)..(19)
<223> OTHER INFORMATION: The residue at this position is linked to amino

<400> SEQUENCE: 248
gacgcggaga tcacgatta                                                      19

<210> SEQ ID NO 249
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: The residue at this position is linked to amino

<400> SEQUENCE: 249
gacgcggaga tcacgat                                                        17

<210> SEQ ID NO 250
<211> LENGTH: 26
<212> TYPE: DNA
<213> ORGANISM: Artificial Sequence
<220> FEATURE:
<223> OTHER INFORMATION: Synthetic

<400> SEQUENCE: 250
ggctaccaag acacgtagcc aaccat                                              26

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
cacggtccag cgaaccat                                                       18

<210> SEQ ID NO 252
<211> LENGTH: 26
<212> TYPE: DNA
<213> ORGANISM: Artificial Sequence
<220> FEATURE:
<223> OTHER INFORMATION: Synthetic

<400> SEQUENCE: 252
ggctaccaag acacgtagcc actata                                              26

<210> SEQ ID NO 253
<211> LENGTH: 18
<212> TYPE: DNA
<213> ORGANISM: Artificial Sequence
<220> FEATURE:
<223> OTHER INFORMATION: Synthetic

<400> SEQUENCE: 253
cacggtccag cgactata                                                       18

<210> SEQ ID NO 254
<211> LENGTH: 22
<212> TYPE: DNA
<213> ORGANISM: Artificial Sequence
<220> FEATURE:
<223> OTHER INFORMATION: Synthetic
```

<400> SEQUENCE: 254
gtgctcagcc aggtgaggta gg                                             22

<210> SEQ ID NO 255
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: The residue at this position is linked to amino

<400> SEQUENCE: 255
gacgcggaga caacctcc                                                  18

<210> SEQ ID NO 256
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: The residue at this position is linked to amino

<400> SEQUENCE: 256
ccacggacga caacct                                                    16

<210> SEQ ID NO 257
<211> LENGTH: 18
<212> TYPE: DNA
<213> ORGANISM: Artificial Sequence
<220> FEATURE:
<223> OTHER INFORMATION: Synthetic

<400> SEQUENCE: 257
cacggtccag cgaactat                                                  18

<210> SEQ ID NO 258
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: The residue at this position is linked to amino

<400> SEQUENCE: 258
gacgcggagt acaatctac                                                 19

<210> SEQ ID NO 259
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: The residue at this position is linked to amino

<400> SEQUENCE: 259
ccacggacgt acaatct                                                   17

<210> SEQ ID NO 260
<211> LENGTH: 26
<212> TYPE: DNA
<213> ORGANISM: Artificial Sequence
<220> FEATURE:
<223> OTHER INFORMATION: Synthetic

<400> SEQUENCE: 260
ggctaccaag acacgtagcc ctacct                                          26

<210> SEQ ID NO 261
<211> LENGTH: 18
<212> TYPE: DNA
<213> ORGANISM: Artificial Sequence
<220> FEATURE:
<223> OTHER INFORMATION: Synthetic

<400> SEQUENCE: 261
cacggtccag cgctacct                                                   18

<210> SEQ ID NO 262
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: The residue at this position is linked to amino

<400> SEQUENCE: 262
gacgcggagt gcactataa                                                  19

<210> SEQ ID NO 263
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: The residue at this position is linked to amino

<400> SEQUENCE: 263
ccacggacgt gcactat                                                    17

<210> SEQ ID NO 264
<211> LENGTH: 26
<212> TYPE: DNA
<213> ORGANISM: Artificial Sequence
<220> FEATURE:
<223> OTHER INFORMATION: Synthetic

<400> SEQUENCE: 264
ggctaccaag acacgtagcc atgccc                                          26

<210> SEQ ID NO 265
<211> LENGTH: 18
<212> TYPE: DNA
<213> ORGANISM: Artificial Sequence
<220> FEATURE:
<223> OTHER INFORMATION: Synthetic

<400> SEQUENCE: 265
cacggtccag cgatgccc                                                   18

<210> SEQ ID NO 266
<211> LENGTH: 22
<212> TYPE: DNA
<213> ORGANISM: Artificial Sequence
<220> FEATURE:
<223> OTHER INFORMATION: Synthetic

<400> SEQUENCE: 266
gtgctcagcc aggaaagtgc tt                                              22

<210> SEQ ID NO 267
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(19)
<223> OTHER INFORMATION: The residue at this position is linked to amino

<400> SEQUENCE: 267
gacgcggagc aaaacagga                                                  19

<210> SEQ ID NO 268
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: The residue at this position is linked to amino

<400> SEQUENCE: 268
ccacggacgc aaaacag                                                    17

<210> SEQ ID NO 269
<211> LENGTH: 22
<212> TYPE: DNA
<213> ORGANISM: Artificial Sequence
<220> FEATURE:
<223> OTHER INFORMATION: Synthetic

<400> SEQUENCE: 269
gtgctcagcc aggtaaagtg ct                                              22

<210> SEQ ID NO 270
<211> LENGTH: 12
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(12)
<223> OTHER INFORMATION: 2'-o-methyl

<400> SEQUENCE: 270
cgcuggaccg ug                                                         12

<210> SEQ ID NO 271
<211> LENGTH: 11
<212> TYPE: RNA
<213> ORGANISM: Artificial Sequence
<220> FEATURE:
<223> OTHER INFORMATION: Synthetic

```
<220> FEATURE:
<221> NAME/KEY: modified_base
<222> LOCATION: (1)..(11)
<223> OTHER INFORMATION: 2'-o-methyl

<400> SEQUENCE: 271
cgcuggaccg u                                                              11

<210> SEQ ID NO 272
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
<220> FEATURE:
<221> NAME/KEY: misc_feature
<222> LOCATION: (4)..(4)
<223> OTHER INFORMATION: The residue at this position is linked to a
      quencher moiety

<400> SEQUENCE: 272
tctagccggt tttccggctg agactccgcg tccgt                                    35

<210> SEQ ID NO 273
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a
      dye moiety
<220> FEATURE:
<221> NAME/KEY: misc_feature
<222> LOCATION: (4)..(4)
<223> OTHER INFORMATION: The residue at this position is linked to a
      quencher moiety

<400> SEQUENCE: 273
tctagccggt tttccggctg agactccgcg tccgt                                    35

<210> SEQ ID NO 274
<211> LENGTH: 22
<212> TYPE: RNA
<213> ORGANISM: Artificial Sequence
<220> FEATURE:
<223> OTHER INFORMATION: Synthetic

<400> SEQUENCE: 274
ugagguagua gguuguauag uu                                                  22

<210> SEQ ID NO 275
<211> LENGTH: 22
<212> TYPE: RNA
<213> ORGANISM: Artificial Sequence
<220> FEATURE:
<223> OTHER INFORMATION: Synthetic

<400> SEQUENCE: 275
ugagguagua gguuguauag uu                                                  22

<210> SEQ ID NO 276
<211> LENGTH: 22
```

```
<212> TYPE: RNA
<213> ORGANISM: Artificial Sequence
<220> FEATURE:
<223> OTHER INFORMATION: Synthetic

<400> SEQUENCE: 276
ugagguagua gguuguaugg uu                                              22

<210> SEQ ID NO 277
<211> LENGTH: 21
<212> TYPE: RNA
<213> ORGANISM: Artificial Sequence
<220> FEATURE:
<223> OTHER INFORMATION: Synthetic

<400> SEQUENCE: 277
ugagguagga gguuguauag u                                               21

<210> SEQ ID NO 278
<211> LENGTH: 22
<212> TYPE: RNA
<213> ORGANISM: Artificial Sequence
<220> FEATURE:
<223> OTHER INFORMATION: Synthetic

<400> SEQUENCE: 278
ugagguagua gauuguauag uu                                              22

<210> SEQ ID NO 279
<211> LENGTH: 22
<212> TYPE: RNA
<213> ORGANISM: Artificial Sequence
<220> FEATURE:
<223> OTHER INFORMATION: Synthetic

<400> SEQUENCE: 279
ucccugagac ccuaacuugu ga                                              22

<210> SEQ ID NO 280
<211> LENGTH: 22
<212> TYPE: RNA
<213> ORGANISM: Artificial Sequence
<220> FEATURE:
<223> OTHER INFORMATION: Synthetic

<400> SEQUENCE: 280
uuaaugcuaa ucgugauagg gg                                              22

<210> SEQ ID NO 281
<211> LENGTH: 22
<212> TYPE: RNA
<213> ORGANISM: Artificial Sequence
<220> FEATURE:
<223> OTHER INFORMATION: Synthetic

<400> SEQUENCE: 281
uagcagcaca uaaugguuug ug                                              22

<210> SEQ ID NO 282
<211> LENGTH: 22
<212> TYPE: RNA
<213> ORGANISM: Artificial Sequence
<220> FEATURE:
<223> OTHER INFORMATION: Synthetic

<400> SEQUENCE: 282
uagcagcacg uaaauauugg cg                                              22
```

<210> SEQ ID NO 283
<211> LENGTH: 23
<212> TYPE: RNA
<213> ORGANISM: Artificial Sequence
<220> FEATURE:
<223> OTHER INFORMATION: Synthetic

<400> SEQUENCE: 283
uaaagugcuu auagugcagg uag                                              23

<210> SEQ ID NO 284
<211> LENGTH: 23
<212> TYPE: RNA
<213> ORGANISM: Artificial Sequence
<220> FEATURE:
<223> OTHER INFORMATION: Synthetic

<400> SEQUENCE: 284
aaagugcuuc cuguuugggg cau                                              23

<210> SEQ ID NO 285
<211> LENGTH: 102
<212> TYPE: RNA
<213> ORGANISM: Artificial Sequence
<220> FEATURE:
<223> OTHER INFORMATION: Synthetic

<400> SEQUENCE: 285
guucuuccga gaacauauac uaaaauugga acaauacaga gaagauuagc auggcccug       60 cgcaaggaug acacgcaaau ucgugaagcg uuccaaauuu uu                        102

<210> SEQ ID NO 286
<211> LENGTH: 44
<212> TYPE: DNA
<213> ORGANISM: Artificial Sequence
<220> FEATURE:
<223> OTHER INFORMATION: Synthetic

<400> SEQUENCE: 286
ccagtgccga tgaggtagta ggttgtatag ttcgctggac cgtg                       44

<210> SEQ ID NO 287
<211> LENGTH: 19
<212> TYPE: DNA
<213> ORGANISM: Artificial Sequence
<220> FEATURE:
<223> OTHER INFORMATION: Synthetic

<400> SEQUENCE: 287
ccagtgccga tgaggtagt                                                   19

<210> SEQ ID NO 288
<211> LENGTH: 22
<212> TYPE: DNA
<213> ORGANISM: Artificial Sequence
<220> FEATURE:
<223> OTHER INFORMATION: Synthetic

<400> SEQUENCE: 288
tagcagcaca taatggtttg tg                                               22

<210> SEQ ID NO 289
<211> LENGTH: 22
<212> TYPE: DNA
<213> ORGANISM: Artificial Sequence

```
<220> FEATURE:
<223> OTHER INFORMATION: Synthetic

<400> SEQUENCE: 289
tagcagcacg taaatattgg cg                                      22

<210> SEQ ID NO 290
<211> LENGTH: 23
<212> TYPE: DNA
<213> ORGANISM: Artificial Sequence
<220> FEATURE:
<223> OTHER INFORMATION: Synthetic

<400> SEQUENCE: 290
taaagtgctt atagtgcagg tag                                     23

<210> SEQ ID NO 291
<211> LENGTH: 22
<212> TYPE: DNA
<213> ORGANISM: Artificial Sequence
<220> FEATURE:
<223> OTHER INFORMATION: Synthetic

<400> SEQUENCE: 291
tccctgagac cctaacttgt ga                                      22

<210> SEQ ID NO 292
<211> LENGTH: 22
<212> TYPE: DNA
<213> ORGANISM: Artificial Sequence
<220> FEATURE:
<223> OTHER INFORMATION: Synthetic

<400> SEQUENCE: 292
ttaatgctaa tcgtgatagg gg                                      22

<210> SEQ ID NO 293
<211> LENGTH: 23
<212> TYPE: DNA
<213> ORGANISM: Artificial Sequence
<220> FEATURE:
<223> OTHER INFORMATION: Synthetic

<400> SEQUENCE: 293
aaagtgcttc ctgttttggg cat                                     23

<210> SEQ ID NO 294
<211> LENGTH: 22
<212> TYPE: DNA
<213> ORGANISM: Artificial Sequence
<220> FEATURE:
<223> OTHER INFORMATION: Synthetic

<400> SEQUENCE: 294
tgaggtagta ggttgtatag tt                                      22

<210> SEQ ID NO 295
<211> LENGTH: 22
<212> TYPE: DNA
<213> ORGANISM: Artificial Sequence
<220> FEATURE:
<223> OTHER INFORMATION: Synthetic

<400> SEQUENCE: 295
tgaggtagta ggttgtatgg tt                                      22
```

```
<210> SEQ ID NO 296
<211> LENGTH: 22
<212> TYPE: DNA
<213> ORGANISM: Artificial Sequence
<220> FEATURE:
<223> OTHER INFORMATION: Synthetic

<400> SEQUENCE: 296
tgaggtagta gattgtatag tt                                              22

<210> SEQ ID NO 297
<211> LENGTH: 22
<212> TYPE: DNA
<213> ORGANISM: Artificial Sequence
<220> FEATURE:
<223> OTHER INFORMATION: Synthetic

<400> SEQUENCE: 297
tgaggtagta ggttgtatgg tt                                              22

<210> SEQ ID NO 298
<211> LENGTH: 17
<212> TYPE: DNA
<213> ORGANISM: Artificial Sequence
<220> FEATURE:
<223> OTHER INFORMATION: Synthetic

<400> SEQUENCE: 298
ccacggacgt acaacct                                                    17
```